US008105777B1

(12) United States Patent
Dai et al.

(10) Patent No.: US 8,105,777 B1

(45) Date of Patent: Jan. 31, 2012

(54) METHODS FOR DIAGNOSIS AND/OR PROGNOSIS OF COLON CANCER

(75) Inventors: Hongyue Dai, Kenmore, WA (US); Laura J. Van't Veer, Amsterdam (NL); Yudong He, Kirkland, WA (US)

(73) Assignees: Nederlands Kanker Instituut, Amsterdam (NL); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/370,264

(22) Filed: Feb. 12, 2009

Related U.S. Application Data

(60) Provisional application No. 61/028,468, filed on Feb. 13, 2008.

(51) Int. Cl.
*C12Q 1/68* (2006.01)

(52) U.S. Cl. ........................................................ 435/6.1

(58) Field of Classification Search ........................ None
See application file for complete search history.

(56) References Cited

U.S. PATENT DOCUMENTS

| | | | |
|---|---|---|---|
| 5,510,270 | A | 4/1996 | Fodor et al. |
| 5,539,083 | A | 7/1996 | Cook |
| 5,545,522 | A | 8/1996 | Van Gelder |
| 5,556,752 | A | 9/1996 | Lockhart |
| 5,578,832 | A | 11/1996 | Trulson |
| 5,716,785 | A | 2/1998 | Van Gelder |
| 5,891,636 | A | 4/1999 | Van Gelder |
| 6,028,189 | A | 2/2000 | Blanchard |
| 6,203,987 | B1 | 3/2001 | Friend |
| 6,218,122 | B1 | 4/2001 | Friend |
| 6,271,002 | B1 | 8/2001 | Linsley |
| 6,974,667 | B2 | 12/2005 | Horne |
| 7,108,969 | B1 | 9/2006 | Warrington |
| 7,171,311 | B2 | 1/2007 | Dai |
| 2005/0054826 | A1 | 3/2005 | Mao |
| 2005/0277118 | A1 | 12/2005 | Roth |
| 2006/0074565 | A1 | 4/2006 | Miller |
| 2007/0026405 | A1 | 2/2007 | Alitalo |
| 2007/0065888 | A1 | 3/2007 | Ring |

FOREIGN PATENT DOCUMENTS

| | | | |
|---|---|---|---|
| WO | 00/39339 | A1 | 7/2000 |
| WO | 01/05935 | A2 | 1/2001 |
| WO | 01/06013 | A1 | 1/2001 |
| WO | 02/16650 | A2 | 2/2002 |
| WO | 02/18646 | A2 | 3/2002 |
| WO | 2005/086891 | A3 | 9/2005 |

OTHER PUBLICATIONS

Tockman et al (Cancer Res., 1992, 52:2711s-2718s).*

Alberts et al. (Molecular Biology of the Cell, 3rd edition, 1994, p. 465).*

Greenbaum et al. (Genome Biology, 2003, vol. 4, Issue 9, pp. 117.1-117.8).*

Barrier, A., et al., "Prognosis of Stage II Colon Cancer by Non-Neoplastic Mucosa Gene Expression Profiling," Oncogene 26(18):2642-2648, Apr. 2007.

Blanchard, A.P., et al., "High-Density Oligonucleotide Arrays," Biosensors & Bioelectronics 11(6/7):687-690, 1996.

Blanchard, A., "Synthetic DNA Arrays," Genetic Engineering 20:111-123, 1998.

Bonaldo, M.F., et al., "Normalization and Subtraction: Two Approaches to Facilitate Gene Discovery," Genome Research 6(9):791-806, Sep. 1996.

Dai, H., et al., "A Cell Proliferation Signature is a Marker of Extremely Poor Outcome in a Subpopulation of Breast Cancer Patients," Cancer Research 65(10):4059-4066, May 2005.

Egholm, M., et al., "PNA Hybridizes to Complementary Oligonucleotides Obeying the Watson-Crick Hydrogen-Bonding Rules," Nature 365(6446):566-568, Oct. 1993.

Eschrich, S., et al., "Molecular Staging for Survival Prediction of Colorectal Cancer Patients," Journal of Clinical Oncology 23(15):3526-3535, May 2005.

Ewing, B., and P. Green, "Analysis of Expressed Sequence Tags Indicates 35,000 Human Genes," Nature Genetics 25(2):232-234, Jun. 2000.

Fodor, S.P.A., et al., "Light-Directed, Spatially Addressable Parallel Chemical Synthesis," Science 251 (4995):767-773, Feb. 1991.

Freund, Y., "Boosting a Weak Learning Algorithm by Majority," Information and Computation 121(2):256-285, Sep. 1995.

Froehler, B.C., et al., "Synthesis of DNA via Deoxynucleoside H-phosphonate Intermediates," Nucleic Acids Research 14(13):5399-5407, Jul. 1986.

Hughes, T.R., et al., "Expression Profiling Using Microarrays Fabricated by an Ink-Jet Oligonucleotide Synthesizer," Nature Biotechnology 19(4):342-347, Apr. 2001.

Hughes, T.R., et al., "Functional Discovery via a Compendium of Expression Profiles," Cell 102(1):109-126, Jul. 2000.

Kononen, J., et al., "Tissue Microarrays for High-Throughput Molecular Profiling of Tumor Specimens," Nature Medicine 4(7):844-847, Jul. 1998.

Lockhart, D.J., et al., "Expression Monitoring by Hybridization to High-Density Oligonucleotide Arrays," Nature Biotechnology 14(13):1675-1680, Dec. 1996.

McBride, L.J., and M.H. Caruthers, "An Investigation of Several Deoxynucleoside Phosphoramidites Useful for Synthesizing Deoxyoligonucleotides," Tetrahedron Letters 24(3):245-248, 1983.

Pease, A.C., et al., "Light-Generated Oligonucleotide Arrays for Rapid DNA Sequence Analysis," Proc. Natl. Acad. Sci. USA 91(11):5022-5026, May 1994.

Schena, M., et al., "Parallel Human Genome Analysis: Microarray-Based Expression Monitoring of 1000 Genes," Proc. Natl. Acad. Sci. USA 93(20):10614-10619, Oct. 1996.

Schena, M., et al., "Quantitative Monitoring of Gene Expression Patterns with a Complementary DNA Microarray," Science 270(5235):467-470, Oct. 1995.

Shalon, D., et al., "A DNA Microarray System for Analyzing Complex DNA Samples Using Two-Color Fluorescent Probe Hybridization," Genome Research 6(7):639-645, Jul. 1996.

Van De Vijver, M.J., et al., "A Gene-Expression Signature as a Predictor of Survival in Breast Cancer," New England Journal of Medicine 347(25):1999-2009, Dec. 2002.

Van'T Veer, L.J., "Gene Expression Profiling Predicts Clinical Outcome of Breast Cancer," Nature 415 (6871):530-536, Jan. 2002.

Wang, Y., et al., "Gene Expression Profiles and Molecular Markers to Predict Recurrence of Dukes' B Colon Cancer," Journal of Clinical Oncology 22(9):1564-1571, May 2004.

* cited by examiner

*Primary Examiner* — Sean Aeder

(74) *Attorney, Agent, or Firm* — Christensen O'Connor Johnson Kindness PLLC

(57) ABSTRACT

The present invention relates to genetic markers whose expression is correlated with colon cancer. In one aspect, the invention provides sets of markers whose expression can be used for classifying colon cancer patients into different prognostic categories. In another aspect, the invention provides kits containing marker sets for determining prognosis of colon cancer. In another aspect, the invention provides methods of classifying cancer patients with regard to prognosis.

17 Claims, 6 Drawing Sheets

METHODS FOR DIAGNOSIS AND/OR PROGNOSIS OF COLON CANCER

CROSS REFERENCE TO RELATED APPLICATION

This application claims the benefit of Provisional Application No. 61/028,468, filed Feb. 13, 2008, the disclosure of which is hereby incorporated herein by reference.

FIELD OF THE INVENTION

The invention relates to sets of markers, kits and methods for classifying colon cancer patients into different prognostic categories.

BACKGROUND

The death rate from colorectal cancer has declined over the past 15 years due to improved screening methods and advances in treatment. However, risk estimates for recurrence of disease are not very precise and therefore result in considerable undertreatment, as well as overtreatment, of colorectal cancer patients with adjuvant therapy.

The current prognostication in colorectal cancer is based on classic clinicopathological characteristics such as bowel wall invasion, involvement of lymph nodes, and distant organs in metastatic spread. Although useful to discern different survival likelihoods for groups of patients, current prognostication is not able to assess individual risks. For example, the Dukes Staging system describes the following categories of colon cancer patients. In "Dukes Stage A colon cancer," the cancer has spread beyond the innermost lining of the colon to the second and third layers and involves the inside wall of the colon. The cancer has not spread to the outer wall of the colon or outside the colon. In "Dukes Stage B colon Cancer," the tumor extends through the muscular wall of the colon, but there is no cancer in the lymph nodes (small structures that are found throughout the body that produce and store cells that fight infection). In "Dukes Stage C colon cancer," the cancer has spread outside the colon to one or more lymph nodes. Finally, in "Dukes Stage D colon cancer," the cancer has spread outside the colon to other parts of the body, such as the liver or the lungs. The tumor can be any size and may or may not include affected lymph nodes.

The use of Dukes staging for determination of prognosis and treatment regimen is not optimal for decisions regarding therapy for individual patients, resulting in undertreatment of some colon cancer patients and overtreatment of other colon cancer patients. Dukes staging describes prognosis as follows: Dukes Stage A patients have >90%, Stage B 80%, Dukes C 60% and Dukes D have less than 20% likelihood to remain disease-free 5 years after initial diagnosis. In this regard, the standard of care for node positive patients (Dukes C) is adjuvant chemotherapy using fluorouracil (5-FU) based regimens. However, 50% of these patients would not have developed a recurrence without adjuvant treatment. In patients staged Dukes B (node negative), adjuvant treatment is controversial since the vast majority of the patients are not at risk for recurrence and will thus not benefit from it. Therefore, optimization of treatment would greatly benefit from the ability to accurately classify a patient's prognosis based on the biological potential of a tumor in each individual case.

A marker-based approach to tumor identification and characterization promises improved diagnostic and prognostic reliability. Gene microarrays have been used to identify diagnostic and prognostic biomarkers and to decipher the molecular mechanisms behind the clinical outcome or phenotype in various types of cancers, such as breast cancer. See, e.g., Dai, et al., *Cancer Res* 65(10):4059-4066 (2005). In the colon cancer area, expression studies have also been conducted which shows interesting leads, but have not yet reached a level where these results can be used to improve treatment decisions for patients. See, for examples, Barrier, et al., *Oncogene* 26(18):2642-8 (Apr. 19, 2007); Epub (Oct. 9, 2006); Wang, et al., *J. Clin Oncol* 22(9):1564-71 (May 1, 2004); Epub (Mar. 29, 2004); Eschrich, et al., *J. Clin Oncol* 23(15): 3526-35 (May 20, 2005).

Thus, there exists a need for improved prognostic methods so that appropriate courses of prophylaxis and/or therapy may be provided for colorectal cancer patients.

SUMMARY

In accordance with the foregoing, in one aspect, the invention provides an isolated population of polynucleotide probes comprising a plurality of polynucleotides, each complementary and hybridizable to a sequence of at least five different markers selected from any one of TABLES 1-5. In one embodiment, the polynucleotide probes are immobilized on a solid support, such as, for example, a microarray.

In another aspect, the invention provides a kit for determining whether a sample is derived from a human patient having a good prognosis of colon cancer or a poor prognosis of colon cancer. The kit comprises a plurality of polynucleotide probes, each complementary and hybridizable to a sequence of at least five different markers selected from any one of TABLES 1-5 in a sealed container. In one embodiment, the kit further comprises a computer-readable medium having recorded thereof one or more programs for determining the similarity level of nucleic acid derived from at least five of the markers listed in any of TABLES 1-5 in a sample as compared to a pool of samples derived from a plurality of individual patients having a good outcome of colon cancer and a pool of samples derived from a plurality of individual patients having a poor outcome of colon cancer.

In another aspect, the invention provides a method for classifying a human individual afflicted with colon cancer as having a good prognosis or a poor prognosis where said good prognosis indicates that said individual is expected to have no distant metastasis within three years of initial diagnosis of colon cancer, and wherein said poor prognosis indicates that said individual is expected to have distant metastasis within three years of initial diagnosis of colon cancer. The method according to this aspect of the invention comprises (i) calculating a first measure of similarity between a first expression profile comprising the expression levels of a plurality of genes comprising at least five of the genes for which markers are listed in any of TABLES 1-5 in a cell sample taken from the individual, and a poor outcome template, wherein said poor outcome template comprises expression levels of said plurality of genes that are average expression levels of the respective genes of a plurality of colon cancer patients having distant metastasis within three years of initial diagnosis of colon cancer; (ii) classifying said individual as having said poor prognosis if said first expression profile has a similarity to said poor outcome template that is above a predetermined threshold, or classifying said patient as having said good prognosis if said first expression profile has a similarity to said poor outcome template that is below a predetermined threshold; and (iii) displaying or outputting to a user interface device a computer-readable storage medium, or a local or remote computer system, the classification produced by said classifying step (ii).

In another aspect, the invention provides a method of classifying a human individual afflicted with colon cancer according to prognosis. The method of this aspect of the invention comprises the steps of (a) contacting first nucleic acids derived from a tumor sample taken from a human individual afflicted with colon cancer, and second nucleic acids derived from two or more tumor samples from colon cancer patients who have had no distant metastases within three years of initial diagnosis, with an array under conditions such that hybridization can occur, detecting at each of a plurality of discrete loci on said array a first fluorescent emission signal from said first nucleic acids and a second fluorescent emission signal from said second nucleic acids that are bound to said array under said conditions, wherein said array comprises at least five of the genes for which markers are listed in TABLE 1 and wherein at least 50% of the probes on said array are listed in TABLE 1; (b) calculating the similarity between said first fluorescent emission signals and said second fluorescent emission signals across said at least five genes; and (c) classifying said individual afflicted with colon cancer according to prognosis of his or her colon cancer based on the similarity between said first fluorescent emission signals and said second fluorescent emission signals across said at least five genes.

In another aspect, the invention provides a method of assigning a therapeutic regimen to a colon cancer patient. The method according to this aspect of the invention comprises (a) classifying said patient as having a "poor prognosis," or a "good prognosis" on the basis of the levels of expression of at least five of the genes for which markers are listed in TABLE 1; and (b) assigning said patient a therapeutic regimen, said therapeutic regimen comprising no adjuvant chemotherapy if the patient is classified as having a good prognosis, or comprising chemotherapy if said patient is classified as having a poor prognosis.

The invention thus provides reagents, kits, and methods for classifying a human individual afflicted with colon cancer according to prognosis.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
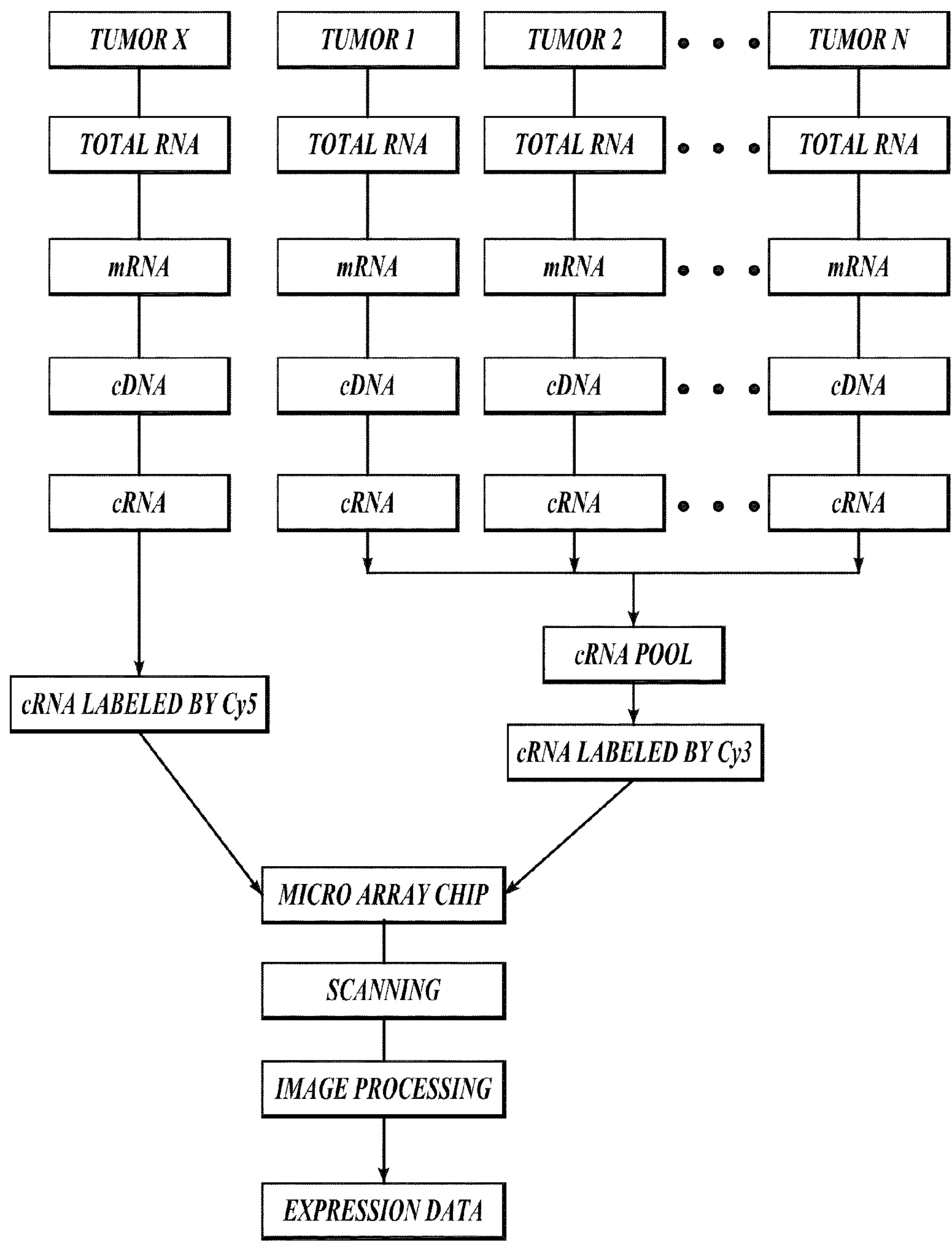
FIG. 1 is a flow diagram illustrating the experimental procedures for measuring differential changes in mRNA transcript abundance in colon cancer tumors used in this study. In each experiment, Cy5-labeled cRNA from one tumor X is hybridized on a 25 k human microarray together with a Cy3-labeled cRNA pool made of cRNA samples from tumors 1, 2, . . . N. The digital expression data were obtained by scanning and image processing. The error modeling allowed for the assignment of a p-value to each transcript ratio measurement, as described in EXAMPLE 1.

In one aspect, the present invention provides sets of markers useful for classifying colon cancer patients into different prognostic categories. In another aspect, the invention provides a method for using these markers to determine whether an individual afflicted with colon cancer will have a good or poor clinical prognosis. In another aspect of the invention, for each of the above classifications, the invention further provides recommended therapeutic regimens.

DEFINITIONS

As used herein, "colon cancer," also called "colorectal cancer" or "bowel cancer," refers to a malignancy that arises in the large intestine (colon) or the rectum (end of the colon), and includes cancerous growths in the colon, rectum, and appendix, including adenocarcinoma, lymphoma, squamous cell carcinoma, carcinoid tumors, melanoma, and sarcoma.

As used herein, the term "absolute amplitude" of correlation expressions means the distance, either positive or negative, from a zero value, i.e., both correlation coefficients −0.50 and 0.50 have an absolute amplitude of 0.50.

As used herein, the term "good prognosis" in the context of colon cancer means that a patient is expected to have no distant metastases of a colon tumor within three years of initial diagnosis of colon cancer.

As used herein, the term "poor prognosis" in the context of colon cancer means that a patient is expected to have distant metastases of a colon tumor within three years of initial diagnosis of colon cancer.

As used herein, the term "distant metastasis" means a recurrence of a primary tumor in other organs or tissues than the primary tumor. For example, a distant metastasis for colon cancer includes cancer spreading to a tissue or organ other than colon (e.g., liver, lung).

As used herein, the term "gene marker" means an entire gene, or portion thereof, such as an EST derived from that gene, the expression or level of which changes between certain conditions. Where the expression of the gene correlates with a certain condition, the gene is a marker for that condition.

As used herein, the term "gene marker-derived polynucleotides" means the RNA transcribed from a marker gene, any cDNA or cRNA produced therefrom, and any nucleic acid derived therefrom, such as synthetic nucleic acid having a sequence derived from the gene corresponding to the marker gene.

As used herein, the term "similarity value" is a number that represents the degree of similarity between two things being compared. For example, a similarity value may be a number that indicates the overall similarity between a patient's expression profile using specific phenotype-related markers and a control specific to that phenotype (for instance, the similarity to a "good outcome" template, where the phenotype is a good prognosis). The similarity value may be expressed as a similarity metric, such as a correlation coefficient, or may simply be expressed as the expression level difference, or the aggregate of the expression level differences between a patient sample and a template.

A "patient subset" is a group of individuals, all of whom have a particular condition, or are subject to a particular condition, which is distinguished from other individuals having that condition by one or more phenotypic, genotypic, or clinical characteristics of the condition, or a response to the condition. For example, where the condition is colon cancer, individuals may belong to a subset having metastasis within 3 years of diagnosis, or may belong to a particular age group, or other patient subset.

A gene marker is "informative" for a condition, phenotype, genotype, or clinical characteristic if the expression of the gene marker is correlated or anti-correlated with the condition, phenotype, genotype, or clinical characteristic to a greater degree than would be expected by chance.

Gene Markers Useful in the Prognosis of Colon Cancer

In one aspect, the invention provides an isolated population of polynucleotide probes comprising a plurality of polynucleotides, each complementary and hybridizable to a sequence of at least five different markers selected from any one of TABLES 1-5.

In accordance with this aspect of the invention, a set of 100 genetic markers is provided that can be used to distinguish between colon cancer patients with a good prognosis (no colon cancer distant metastasis within three years after initial diagnosis of colon cancer) and a poor prognosis (distant metastasis within three years after initial diagnosis of colon cancer). These markers are listed in TABLE 1 (SEQ ID NOS: 1-100). Representative probes useful to measure these markers are also listed in TABLE 1 (SEQ ID NOS:101-200).

The invention also provides subsets of at least 5, 10, 15, 20, 25, 30, 35, 40, 45, 50, 55, 60, 65, 70, 75, 80, 85, 90, or 95 genetic markers, drawn from the set of 100 markers, which also may be used to distinguish between colon cancer patients with good and poor prognosis, as shown in TABLES 2-4. A preferred set of 23 markers is provided in TABLE 5.

In accordance with this aspect of the invention, as further described in EXAMPLES 1-2, genesets have been identified that enable the classification of individuals afflicted with colon cancer as those who will likely have no metastasis within three years of initial diagnosis of colon cancer (i.e., individuals with a good prognosis), or those who will likely have a metastasis within three years of initial diagnosis of colon cancer (i.e., individuals with a poor prognosis). Generally described, the pattern of expression within a subset of individuals having either a good outcome of colon cancer or a poor outcome of colon cancer led to the identification of genes within a subset that are predictive for prognosis of that subset. More specifically, the colon cancer prognostic genesets provided in TABLES 1-5 were identified by analyzing a population of 118 colon cancer patients who had undergone tumor removal in a retrospective study, as described in EXAMPLES 1-2. Within the population of 118 colon cancer patients, after a three-year follow-up period, a first subset of patients was identified as metastasis-free over the three-year follow-up period (good outcome), and a second subset of patients was identified as having a distant metastasis within the follow-up period (poor outcome). As described in EXAMPLE 1, approximately 4250 genes were first identified that were differentially expressed across the dataset. As described in EXAMPLE 2, a double loop of leave-one-out cross-validation was then carried out using a subset of the differentially expressed genes to establish a colon cancer classifier comprising the gene set provided in TABLES 1-5, or a subset thereof. The first loop of the cross-validation was carried out to select the training samples, and the second loop was carried out to evaluate the performance of the colon cancer prognostic classifier using all the patient samples. In the process of constructing the prognosis classifier, particular attention was paid to the homogenous patterns related to the tumor outcome, using the methods described by Dai, et al., *Cancer Res.* 65(10):4059-4066 (2005).

TABLE 1

100 COLON CANCER GENE MARKERS (SEQ ID NOS: 1-100) AND 100 REPRESENTATIVE PROBES: (SEQ ID NOS: 101-200)

| Genbank Accession Number | Gene Name | Full length cDNA Sequence (SEQ ID NO:) | Probe (SEQ ID NO:) |
|---|---|---|---|
| AL137734 | DKFZp586C0721 | 1 | 101 |
| AK002039 | MRVI1 | 2 | 102 |
| AF131817 | | 3 | 103 |
| AL050145 | | 4 | 104 |
| AL137342 | | 5 | 105 |
| AB002361 | KIAA0363 | 6 | 106 |
| NM_018492 | TOPK | 7 | 107 |
| NM_003360 | UGT8 | 8 | 108 |
| NM_007281 | SCRG1 | 9 | 109 |
| NM_015493 | FLJ20004 | 10 | 110 |
| NM_003199 | TCF4 | 11 | 111 |
| NM_001801 | CDO1 | 12 | 112 |
| NM_006006 | ZNF145 | 13 | 113 |
| NM_001864 | COX7A1 | 14 | 114 |
| NM_001885 | CRYAB | 15 | 115 |
| NM_004791 | ITGBL1 | 16 | 116 |
| NM_003793 | CTSF | 17 | 117 |
| NM_004663 | RAB11A | 18 | 118 |
| NM_004105 | EFEMP1 | 19 | 119 |
| NM_004462 | FDFT1 | 20 | 120 |
| NM_005100 | AKAP12 | 21 | 121 |
| NM_000189 | HK2 | 22 | 122 |
| NM_014710 | KIAA0443 | 23 | 123 |

TABLE 1-continued

100 COLON CANCER GENE MARKERS (SEQ ID NOS: 1-100) AND 100 REPRESENTATIVE PROBES: (SEQ ID NOS: 101-200)

| Genbank Accession Number | Gene Name | Full length cDNA Sequence (SEQ ID NO:) | Probe (SEQ ID NO:) |
|---|---|---|---|
| NM_014730 | KIAA0152 | 24 | 124 |
| NM_000627 | LTBP1 | 25 | 125 |
| NM_000637 | GSR | 26 | 126 |
| NM_000900 | MGP | 27 | 127 |
| NM_005545 | ISLR | 28 | 128 |
| NM_018964 | SLC37A1 | 29 | 129 |
| NM_002430 | MN1 | 30 | 130 |
| NM_012243 | SLC35A3 | 31 | 131 |
| NM_014942 | ANKRD6 | 32 | 132 |
| NM_004538 | NAP1L3 | 33 | 133 |
| NM_017993 | FLJ10094 | 34 | 134 |
| NM_018215 | FLJ10781 | 35 | 135 |
| NM_018302 | FLJ11017 | 36 | 136 |
| NM_002725 | PRELP | 37 | 137 |
| NM_000702 | ATP1A2 | 38 | 138 |
| NM_001189 | BAPX1 | 39 | 139 |
| NM_003014 | SFRP4 | 40 | 140 |
| NM_013401 | RAB3IL1 | 41 | 141 |
| NM_016839 | RBMS1 | 42 | 142 |
| NM_006384 | CIB1 | 43 | 143 |
| NM_014365 | H11 | 44 | 144 |
| NM_016836 | RBMS1 | 45 | 145 |
| Contig15693_RC | | 46 | 146 |
| Contig21679_RC | | 47 | 147 |
| Contig30092_RC | PRDM6 | 48 | 148 |
| Contig30994_RC | | 49 | 149 |
| Contig38980_RC | | 50 | 150 |
| Contig42882_RC | C20orf82 | 51 | 151 |
| Contig47308_RC | | 52 | 152 |
| Contig48249_RC | FLJ10849 | 53 | 153 |
| Contig50915_RC | MGC4618 | 54 | 154 |
| Contig51625_RC | | 55 | 155 |
| Contig52862_RC | | 56 | 156 |
| Contig53033_RC | | 57 | 157 |
| Contig53281_RC | | 58 | 158 |
| Contig53838_RC | | 59 | 159 |
| Contig53881_RC | | 60 | 160 |
| Contig53953_RC | AKAP12 | 61 | 161 |
| Contig57662_RC | STARD4 | 62 | 162 |
| Contig9310 | | 63 | 163 |
| AB033040 | KIAA1214 | 64 | 164 |
| NM_018274 | TNS | 65 | 165 |
| Contig1789_RC | LAGY | 66 | 166 |
| Contig5549_RC | | 67 | 167 |
| Contig7558_RC | SYNPO2 | 68 | 168 |
| Contig10455_RC | | 69 | 169 |
| Contig20304_RC | | 70 | 170 |
| Contig21891_RC | FLJ13231 | 71 | 171 |
| Contig23466_RC | | 72 | 172 |
| Contig26371_RC | FLJ20898 | 73 | 173 |
| Contig26642_RC | | 74 | 174 |
| Contig29223_RC | | 75 | 175 |
| Contig32377_RC | | 76 | 176 |
| Contig36409_RC | | 77 | 177 |
| Contig36951_RC | | 78 | 178 |
| Contig39655_RC | | 79 | 179 |
| Contig43102_RC | | 80 | 180 |
| Contig46089_RC | FLJ20967 | 81 | 181 |
| Contig46787_RC | | 82 | 182 |
| Contig47038_RC | MGC15476 | 83 | 183 |
| Contig49510_RC | GALGT | 84 | 184 |
| Contig50719_RC | RERG | 85 | 185 |
| Contig53959_RC | FLJ14054 | 86 | 186 |
| NM_016837 | RBMS1 | 87 | 187 |
| NM_002897 | RBMS1 | 88 | 188 |
| NM_018894 | EFEMP1 | 89 | 189 |
| Contig50367 | JAM3 | 90 | 190 |
| Contig59144 | SLC31A1 | 91 | 191 |
| AB006625 | PEG3 | 92 | 192 |
| AL050202 | MGC3047 | 93 | 193 |
| AL080059 | KIAA1750 | 94 | 194 |
| AL117617 | HCC-4 | 95 | 195 |
| AF228704 | GSR | 96 | 196 |
| AK000332 | MGC27034 | 97 | 197 |
| AK000500 | MRPL50 | 98 | 198 |
| AL137751 | RDX | 99 | 199 |
| NM_020372 | LOC57100 | 100 | 200 |

TABLE 2

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| Contig53953_RC | 0.79 | AKAP12 (AKAP250, DKFZp686M0430, DKFZp686O0331) | A kinase (PRKA) anchor protein (gravin) 12 | Hypothetical protein, Alternative splicing, Antigen, Repeat |
| NM_006384 | −0.79 | CIB1 (CIB, KIP, SIP2-28, CALMYRIN) | *Homo sapiens* calcium and integrin binding 1 (calmyrin) (CIB1), mRNA. | Calcium-binding, Repeat, 3D-structure |
| NM_014710 | 0.78 | KIAA0443 (GPRASP1, GASP, GASP1) | *Homo sapiens* G protein-coupled receptor associated sorting protein 1 (GPRASP1), mRNA. | Hypothetical protein |
| AL137342 | −0.78 | UGT8 (CGT) | UDP glycosyltransferase 8 (UDP-galactose ceramide galactosyltransferase). Endoplasmic reticulum, Glycoprotein, | |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| | | | Glycosyltransferase, Membrane, Microsome, Signal, Transferase, Transmembrane | |
| NM_000900 | 0.76 | MGP (NTI, MGLAP) | *Homo sapiens* matrix Gla protein (MGP), mRNA. | Gamma-carboxyglutamic acid, Vitamin K, Osteogenesis, Chondrogenesis, Signal, Phosphorylation, Polymorphism |
| Contig30092_RC | 0.74 | PRDM6 | PR domain containing 6 | Alternative splicing, DNA-binding, Metal-binding, Nuclear protein, Repeat, Transcription, Transcription regulation, Zinc, Zinc-finger |
| Contig23466_RC | 0.74 | oh99h06.s1 (NCI_CGAP_HN4) | *Homo sapiens* cDNA clone IMAGE: 1475195 3', mRNA sequence. | |
| NM_005100 | 0.73 | AKAP12 (AKAP250, DKFZp686M0430, DKFZp686O0331) | *Homo sapiens* A kinase (PRKA) anchor protein (gravin) 12 (AKAP12), transcript variant 1, mRNA. | Antigen, Repeat, Alternative splicing |
| Contig30994_RC | 0.73 | | Transcribed locus | |
| NM_003360 | −0.73 | UGT8 (CGT) | *Homo sapiens* UDP glycosyltransferase 8 (UDP-galactose ceramide galactosyltransferase) (UGT8), mRNA. Transferase, Glycosyltransferase, Glycoprotein, Transmembrane, Signal, Microsome | |
| Contig26371_RC | 0.72 | FLJ20898 (C16orf30, CLP24, MGC111564) | Chromosome 16 open reading frame 30 | Glycoprotein, Membrane, Transmembrane |
| NM_016839 | 0.72 | RBMS1 (YC1, MSSP, SCR2, MSSP-1, MSSP-2, MSSP-3, MGC3331, MGC15146) | *Homo sapiens* RNA binding motif, single stranded interacting protein 1 (RBMS1), transcript variant 2, mRNA. | DNA-binding, DNA replication, RNA-binding, Nuclear protein, Phosphorylation |
| AL050202 | 0.71 | MGC3047 (MXRA8) | Matrix-remodeling associated 8 | Nuclear protein, Polymorphism |
| NM_001885 | 0.71 | CRYAB (CRYA2, CTPP2, HSPB5) | *Homo sapiens* crystallin, alpha B (CRYAB), mRNA. | Eye lens protein, Acetylation, Phosphorylation, Glycoprotein, Disease mutation, Polymorphism |
| Contig53838_RC | 0.71 | LOC399959 (FLJ11490, FLJ34394, FLJ41953, DKFZp686J24156) | hypothetical gene supported by BX647608 | |
| Contig38980_RC | 0.71 | C21orf34 (C21orf35, FLJ38295) | Chromosome 21 open reading frame 34 | |
| NM_018215 | 0.71 | FLJ10781 | hypothetical protein FLJ10781 | Hypothetical protein |
| NM_003793 | 0.71 | CTSF (CATSF) | *Homo sapiens* cathepsin F (CTSF), mRNA. | Hydrolase, Thiol protease, Lysosome, Glycoprotein, Zymogen, Signal, 3D-structure |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| Contig32377_RC | 0.71 | USP51 | Ubiquitin specific peptidase 51 | Hydrolase, Metal-binding, Multigene family, Protease, Thiol protease, Ubl conjugation pathway, Zinc, Zinc-finger |
| Contig47308_RC | 0.71 | ZNF218 (ZABC2, OVC10-2, C20orf17, FLJ33887) | Chromosome 20 open reading frame 17 | Hypothetical protein |
| Contig36409_RC | 0.71 | RANBP9 (RANBPM) | RAN binding protein 9 | Alternative splicing, Nuclear protein, Phosphorylation, Ubl conjugation |
| Contig36951_RC | −0.71 | | Transcribed locus | |
| AF228704 | −0.71 | GSR (MGC78522) | Glutathione reductase | FAD, Flavoprotein, Oxidoreductase, 3D-structure, Acetylation, Alternative initiation, Direct protein sequencing, Mitochondrion, NADP, Polymorphism, Redox-active center, Transit peptide |
| NM_018274 | 0.70 | TNS (TNS1, MGC88584) | Tensin 1 | Hypothetical protein |
| AL137734 | 0.70 | DKFZp586C0721 | hypothetical protein DKFZp586C0721 | Hypothetical protein |
| NM_014365 | 0.70 | H11 (HSPB8, HMN2, DHMN2, E2IG1, HSP22) | *Homo sapiens* heat shock 22 kDa protein 8 (HSPB8), mRNA. | Heat shock, Transferase, Serine/threonine-protein kinase |
| Contig20304_RC | 0.70 | yb45b06.s1 | Stratagene fetal spleen (#937205) *Homo sapiens* cDNA clone IMAGE: 74099 3', mRNA sequence. | |
| NM_018302 | −0.70 | FLJ11017 | hypothetical protein FLJ11017 | Hypothetical protein |
| Contig50915_RC | −0.70 | MGC4618 (DGKQ, DAGK, DAGK4, DAGK7) | Diacylglycerol kinase, theta 110 kDa | Kinase, Metal-binding, Multigene family, Phorbol-ester binding, Repeat, Transferase, Zinc, Zinc-finger |
| NM_000637 | −0.70 | GSR (MGC78522) | *Homo sapiens* glutathione reductase (GSR), mRNA. | Redox-active center, Oxidoreductase, Flavoprotein, FAD, NADP, Acetylation, Alternative initiation, Mitochondrion, Transit peptide, 3D-structure, Polymorphism |
| Contig53281_RC | 0.69 | unknown | Tissue-type brain unknown mRNA | Hypothetical protein |
| Contig49510_RC | 0.69 | GALGT (GEFT, p63RhoGEF) | RAC/CDC42 exchange factor | Hypothetical protein, GTPase activation, Guanine-nucleotide releasing factor |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| Contig50367 | 0.69 | JAM3 (JAMC, JAM-C, FLJ14529) | Junctional adhesion molecule 3 | Direct protein sequencing, Glycoprotein, Immunoglobulin domain, Membrane, Signal, Transmembrane |
| AF131817 | 0.69 | RUNX1T1 (CDR, ETO, MTG8, MTG8b, AML1T1, ZMYND2, CBFA2T1, MGC2796) | Runt-related transcription factor 1; translocated to, 1 (cyclin D-related) | Alternative splicing, Chromosomal translocation, DNA-binding, Metal-binding, Nuclear protein, Proto-oncogene, Transcription, Transcription regulation, Zinc, Zinc-finger, Cyclin |
| NM_015493 | 0.69 | FLJ20004 (ANKRD25, SIP, MXRA3, KIAA1518, MGC119707, DKFZp434N161) | *Homo sapiens* ankyrin repeat domain 25 (ANKRD25), mRNA. | Hypothetical protein, ANK repeat, Repeat |
| AB033040 | 0.69 | KIAA1214 (RNF150, MGC125502) | Ring finger protein 150 | Metal-binding, Zinc, Zinc-finger |
| NM_002897 | 0.69 | RBMS1 (YC1, MSSP, SCR2, MSSP-1, MSSP-2, MSSP-3, MGC3331, MGC15146) | *Homo sapiens* RNA binding motif, single stranded interacting protein 1 (RBMS1), transcript variant 3, mRNA. | DNA-binding, DNA replication, RNA-binding, Nuclear protein, Phosphorylation |
| NM_016836 | 0.69 | RBMS1 (YC1, MSSP, SCR2, MSSP-1, MSSP-2, MSSP-3, MGC3331, MGC15146) | *Homo sapiens* RNA binding motif, single stranded interacting protein 1 (RBMS1), transcript variant 1, mRNA. | DNA-binding, DNA replication, RNA-binding, Nuclear protein, Phosphorylation |
| AL117617 | 0.69 | HCC-4 (C2orf12, DKFZp564H0764) | RNA binding motif, single stranded interacting protein 1 | Nuclear protein, RNA-binding, Alternative splicing, DNA replication, DNA-binding, Repeat |
| NM_006006 | 0.69 | ZNF145 (ZBTB16, PLZF) | *Homo sapiens* zinc finger and BTB domain containing 16 (ZBTB16), transcript variant 1, mRNA. | Transcription regulation, DNA-binding, Zinc-finger, Metal-binding, Nuclear protein, Repeat, Chromosomal translocation, Proto-oncogene, Phosphorylation, Alternative splicing, 3D-structure |
| NM_002725 | 0.69 | PRELP (MST161, SLRR2A, MSTP161, MGC45323) | *Homo sapiens* proline/arginine-rich end Leucine-rich repeat protein (PRELP), transcript variant 1, mRNA. | Glycoprotein, Extracellular matrix, Repeat, Leucine-rich repeat, Signal, Polymorphism |
| Contig10455_RC | 0.69 | CHD6 (CHD5, RIGB, KIAA1335) | Chromodomain helicase DNA binding protein 6 | Alternative splicing, ATP-binding, Chromatin regulator, DNA-binding, Helicase, Hydrolase, Nuclear protein, Nucleotide-binding, |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| | | | | Polymorphism, Repeat, Transcription, Transcription regulation |
| Contig29223_RC | 0.69 | CTNNBL1 (NAP, P14L, PP8304, C20orf33, FLJ21108, NYD-SP19, dJ633O20.1) | Catenin, beta like 1 | Alternative splicing, Apoptosis, Nuclear protein |
| Contig52862_RC | −0.69 | SGPP2 (SPP2, FLJ39004) | Sphingosine-1-phosphate phosphatase 2. | Endoplasmic reticulum, Hydrolase, Membrane, Transmembrane |
| NM_004663 | −0.69 | RAB11A (YL8, MGC1490) | *Homo sapiens* RAB11A, member RAS oncogene family (RAB11A), mRNA. | GTP-binding, Lipoprotein, Prenylation, Protein transport |
| NM_004538 | 0.68 | NAP1L3 (MB20, NPL3, MGC26312) | *Homo sapiens* nucleosome assembly protein 1-like 3 (NAP1L3), mRNA. | Nuclear protein |
| NM_018894 | 0.68 | EFEMP1 (DHRD, DRAD, FBNL, MLVT, S1-5, FBLN3, MGC111353) | Sim: U03877, Human extracellular protein (S1-5) mRNA, complete cds. (e = 0.0, score = 4980, 100% ID over 2512 nt [query = 2675 nt], plus strand, blastn, *Homo sapiens* | Repeat, EGF-like domain, Calcium-binding, Glycoprotein, Signal, Disease mutation, Polymorphism, Alternative splicing |
| NM_001864 | 0.68 | COX7A1 (COX7A, COX7AH, COX7AM) | *Homo sapiens* cytochrome c oxidase subunit VIIa polypeptide 1 (muscle) (COX7A1), mRNA. | Oxidoreductase, Inner membrane, Mitochondrion, Transit peptide |
| Contig42882_RC | 0.68 | C20orf82 (bA149I18.1, dJ1077I2.1) | Chromosome 20 open reading frame 82 | Hypothetical protein |
| Contig21679_RC | 0.68 | LMOD1 (1D, D1, 64kD, SM-LMOD) | Leiomodin 1 (smooth muscle) | Antigen, Cytoskeleton, Polymorphism, Repeat |
| Contig50719_RC | 0.68 | RERG (MGC15754) | RAS-like, estrogen-regulated, growth inhibitor | GTP-binding, Nucleotide-binding |
| NM_000627 | 0.68 | LTBP1 | *Homo sapiens* latent transforming growth factor beta binding protein 1 (LTBP1), transcript variant 2, mRNA. | Growth factor binding, Repeat, EGF-like domain, Hydroxylation, Signal, Glycoprotein, Alternative splicing |
| NM_013401 | 0.68 | RAB3IL1 | *Homo sapiens* RAB3A interacting protein (rabin3)-like 1 (RAB3IL1), mRNA. | Hypothetical protein |
| Contig43102_RC | 0.68 | REV3L (POLZ, REV3) | REV3-like, catalytic subunit of DNA polymerase zeta (yeast) | DNA damage, DNA repair, DNA replication, DNA-binding, DNA-directed DNA polymerase, Metal-binding, Nuclear protein, Nucleotidyl-transferase, Polymorphism, Transferase, Zinc, Zinc-finger, Hypothetical protein |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| Contig15693_RC | 0.68 | LOC441776 | similar to 40S ribosomal protein S3 | |
| NM_004462 | −0.68 | FDFT1 (SS, SQS, DGPT, ERG9) | *Homo sapiens* farnesyl-diphosphate farnesyltransferase 1 (FDFT1), mRNA. | Multifunctional enzyme, Transferase, Oxidoreductase, NADP, Magnesium, Isoprene biosynthesis, Cholesterol biosynthesis, Transmembrane, Endoplasmic reticulum, Polymorphism, 3D-structure |
| AK000332 | −0.68 | MGC27034 (RG9MTD2, TRM10, MGC27034) | RNA (guanine-9-) methyltransferase domain containing 2 | Methyltransferase, Transferase. Hypothetical protein |
| AB002361 | 0.67 | KIAA0363 | KIAA0363 protein | Hypothetical protein |
| NM_004105 | 0.67 | EFEMP1 (DHRD, DRAD, FBNL, MLVT,S1-5, FBLN3, MGC111353) | *Homo sapiens* EGF-containing fibulin-like extracellular matrix protein 1 (EFEMP1), transcript variant 1, mRNA. | Repeat, EGF-like domain, Calcium-binding, Glycoprotein, Signal, Disease mutation, Polymorphism, Alternative splicing |
| NM_001801 | 0.67 | CDO1 | *Homo sapiens* cysteine dioxygenase, type I (CDO1), mRNA. | Dioxygenase, Oxidoreductase, Iron |
| NM_001189 | 0.67 | BAPX1 (NKX3B, NKX3-2, NKX3.2) | *Homo sapiens* bagpipe homeobox homolog 1 (*Drosophila*) (BAPX1), mRNA. | Homeobox, DNA-binding, Nuclear protein |
| NM_003014 | 0.67 | SFRP4 (FRP-4, FRPHE, MGC26498) | *Homo sapiens* secreted frizzled-related protein 4 (SFRP4), mRNA. | |
| Contig5549_RC | 0.67 | | Transcribed locus | |
| NM_000702 | 0.67 | ATP1A2 (FHM2, MHP2, MGC59864) | *Homo sapiens* ATPase, Na+/K+ transporting, alpha 2 (+) polypeptide (ATP1A2), mRNA. | Hydrolase, Sodium/potassium transport, Transmembrane, Phosphorylation, Magnesium, Metal-binding, ATP-binding, Multigene family |
| Contig53033_RC | 0.67 | CPXM2 (UNQ676) | Carboxypeptidase X (M14 family), member 2 | Glycoprotein, Signal, Hypothetical protein |
| Contig51625_RC | 0.67 | LOC644538 | *Homo sapiens*, clone IMAGE: 3868989 | Hypothetical protein |
| Contig53959_RC | 0.67 | FLJ14054 | hypothetical protein FLJ14054 | Hypothetical protein |
| NM_018964 | −0.67 | SLC37A1 (G3PP) | *Homo sapiens* solute carrier family 37 (glycerol-3-phosphate transporter), member 1 (SLC37A1), mRNA. | Transmembrane, Transport, Sugar transport, Polymorphism |
| NM_017993 | 0.66 | FLJ10094 (bA64J21.1) | hypothetical protein FLJ10094 | Hypothetical protein |
| AB006625 | 0.66 | PEG3 (PW1, ZSCAN24, KIAA0287, DKFZp781A095) | Paternally expressed 3 | DNA-binding, Metal-binding, Nuclear protein, Polymorphism, Repeat, Transcription, Transcription regulation, Zinc, Zinc-finger, Hypothetical protein |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| NM_020372 | 0.66 | LOC57100 (SLC22A17, BOCT, BOIT, hBOIT) | *Homo sapiens* solute carrier family 22 (organic cation transporter), member 17 (SLC22A17), transcript variant 1, mRNA. | Transport, Transmembrane, Alternative splicing |
| Contig1789_RC | 0.66 | LAGY (HOP, OB1, Toto, Cameo, NECC1, SMAP31, MGC20820) | homeodomain-only protein | Alternative splicing, Developmental protein, Homeobox, Nuclear protein, Proto-oncogene, Repressor, Transcription, Transcription regulation |
| NM_005545 | 0.66 | ISLR (HsT17563) | *Homo sapiens* immunoglobulin superfamily containing leucine-rich repeat (ISLR), transcript variant 1, mRNA. | Signal |
| AK002039 | 0.66 | MRVI1 (IRAG, JAW1L) | Murine retrovirus integration site 1 homolog | Hypothetical protein |
| Contig47038_RC | 0.66 | MGC15476 | thymus expressed gene 3-like | |
| NM_002430 | 0.66 | MN1 (MGCR, MGCR1, MGCR1-PEN, dJ353E16.2) | *Homo sapiens* meningioma (disrupted in balanced translocation) 1 (MN1), mRNA. | Anti-oncogene, Chromosomal translocation, Alternative splicing |
| NM_016837 | 0.66 | RBMS1 (YC1, MSSP, SCR2, MSSP-1, MSSP-2, MSSP-3, MGC3331, MGC15146) | *Homo sapiens* RNA binding motif, single stranded interacting protein 1 (RBMS1), transcript variant 2, mRNA. | DNA-binding, DNA replication, RNA-binding, Nuclear protein, Phosphorylation |
| NM_014942 | 0.66 | ANKRD6 | *Homo sapiens* ankyrin repeat domain 6 (ANKRD6), mRNA. | Hypothetical protein, Repeat, ANK repeat, Alternative splicing |
| Contig46787_RC | 0.66 | ZCCHC7 (HSPC086, FLJ22611, RP11-397D12.1) | Zinc finger, CCHC domain containing 7 | Alternative splicing, Metal-binding, Repeat, Zinc, Zinc-finger |
| Contig39655_RC | 0.66 | WDSUB1 (UBOX6, WDSAM1, FLJ36175) | WD repeat, SAM and U-box domain containing 1 | Kinase |
| Contig9310 | 0.66 | YAP1 (YAP, YAP2, YAP65) | Yes-associated protein 1, 65 kDa | Hypothetical protein |
| AL050145 | 0.66 | LOC441776 | similar to 40S ribosomal protein S3 | |
| Contig59144 | 0.66 | SLC31A1 (AS3MT, CYT19) | Arsenic (+3 oxidation state) methyltransferase | Methyltransferase, Transferase |
| Contig21891_RC | 0.66 | FLJ13231 (FLJ21126) | hypothetical protein FLJ13231 | Hypothetical protein |
| NM_000189 | −0.66 | HK2 (HKII, HXK2, DKFZp686M1669) | *Homo sapiens* hexokinase 2 (HK2), mRNA. | Transferase, Kinase, Glycolysis, Allosteric enzyme, Repeat, ATP-binding, Membrane, Polymorphism |

TABLE 2-continued

DESCRIPTION OF THE 100 COLON CANCER MARKERS FROM TABLE 1 LISTED IN ORDER OF CORRELATION VALUE (CORRELATION WITH POOR OUTCOME)

| Identifier | Correlation (with Poor Prognosis) | Sequence name | Description | Keywords |
|---|---|---|---|---|
| NM_014730 | −0.66 | KIAA0152 | *Homo sapiens* KIAA0152 (KIAA0152), mRNA. | Hypothetical protein, Transmembrane |
| NM_012243 | −0.66 | SLC35A3 (DKFZp781P1297) | *Homo sapiens* solute carrier family 35 (UDP-N-acetylglucosamine (UDP-GlcNAc) transporter), member A3 (SLC35A3), mRNA. | Transport, Sugar transport, Transmembrane, Golgi stack |
| Contig57662_RC | −0.66 | STARD4 | START domain containing 4, sterol regulated | Lipid transport, Lipid-binding, Transport, Hypothetical protein |
| NM_018492 | −0.66 | TOPK (PBK, SPK, Nori-3, FLJ14385) | *Homo sapiens* PDZ binding kinase (PBK), mRNA. | Hypothetical protein, ATP-binding, Kinase, Transferase |
| Contig48249_RC | 0.65 | FLJ10849 (SEPT11) | Septin 11 | Acetylation, Cell cycle, Cell division, Chromosomal translocation, Coiled coil, Direct protein sequencing, GTP-binding, Nucleotide-binding, Proto-oncogene, Hypothetical protein |
| AL080059 | 0.65 | KIAA1750 (TSPYL5) | TSPY-like 5 | Hypothetical protein |
| Contig53881_RC | 0.65 | MSRB3 (FLJ36866) | Methionine sulfoxide reductase B3 | Hypothetical protein |
| NM_003199 | 0.65 | TCF4 (E2-2, ITF2, SEF2, SEF2-1, SEF2-1A, SEF2-1B) | *Homo sapiens* transcription factor 4 (TCF4), mRNA. | Transcription regulation, DNA-binding, Activator, Nuclear protein, Alternative splicing |
| NM_004791 | 0.65 | ITGBL1 (OSCP, TIED) | *Homo sapiens* integrin, beta-like 1 (with EGF-like repeat domains) (ITGBL1), mRNA. | Cell adhesion, Glycoprotein, Integrin, Repeat, Signal, Transmembrane |
| NM_007281 | 0.65 | SCRG1 (SCRG-1, MGC26468) | scrapie responsive protein 1 | Signal |
| Contig7558_RC | 0.65 | SYNPO2 | Synaptopodin 2 | Actin-binding, Nuclear protein, Polymorphism |
| AL137751 | 0.65 | RDX | *Homo sapiens* mRNA; cDNA DKFZp434I0812 (from clone DKFZp434I0812); partial cds. | Structural protein, Cytoskeleton, Actin-binding, Phosphorylation, Actin capping, Hypothetical protein |
| Contig26642_RC | 0.65 | SORBS1 (CAP, FLAF2, R85FL, SH3D5, SORB1, SH3P12, FLJ12406, KIAA1296, DKFZp451C066, DKFZp586P1422) | Sorbin and SH3 domain containing 1 | Alternative splicing, Membrane, Nuclear protein, Polymorphism, Repeat, SH3 domain, Transport, Hypothetical protein |
| AK000500 | −0.65 | MRPL50 (MRP-L50, FLJ20493, FLJ21990) | Mitochondrial ribosomal protein L50 | Mitochondrion, Ribosomal protein |
| Contig46089_RC | −0.65 | FLJ20967 (SH2D4A, SH2A) | SH2 domain containing 4A | Hypothetical protein |

TABLE 3

100 GENE MARKERS USED FOR A GOOD OUTCOME TEMPLATE AND/OR A POOR OUTCOME TEMPLATE FOR DETERMINING COLON CANCER PROGNOSIS

Figures 2A, 2B:
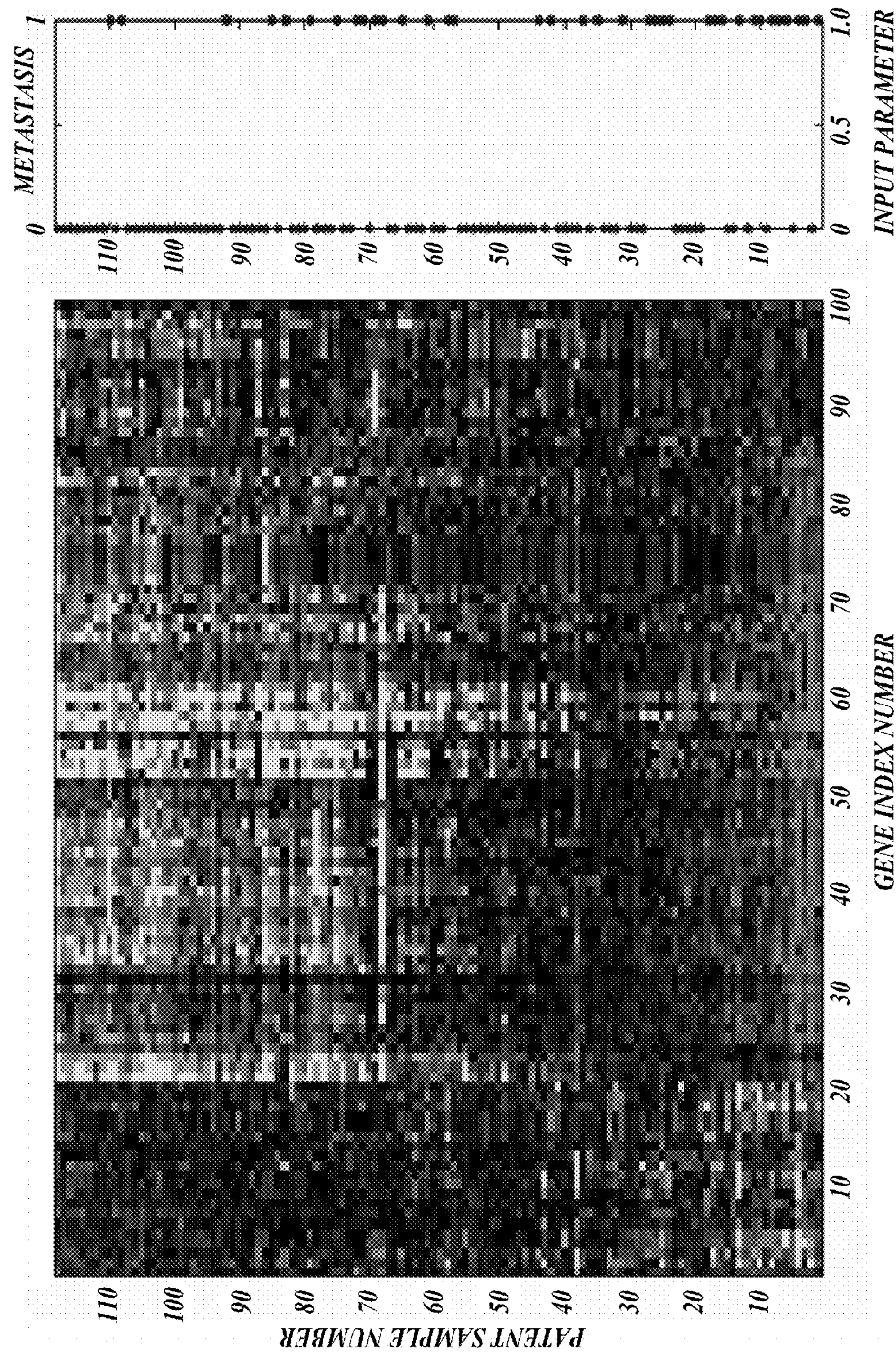
FIG. 2A is a heatmap showing 118 samples (rows) over 100 prognosis genes (columns). The prognosis genes are ordered with respect to the gene index number (as shown in TABLE 3) and were selected by a "coherent pattern" method as described in EXAMPLE 2. Samples were ranked by the correlation coefficient (cor1-cor2) to the good and poor templates in the leave-one-out cross-validation (LOOCV)
FIG. 2B graphically illustrates the status of metastasis for each of the 118 clinical samples (row) shown in FIG. 2A, with "0" representing a patient that was metastasis-free within the whole follow-up period and with "1" representing a patient that developed metastasis within the whole follow-up period, as described in EXAMPLE 1 and EXAMPLE 2.
Figure 4:
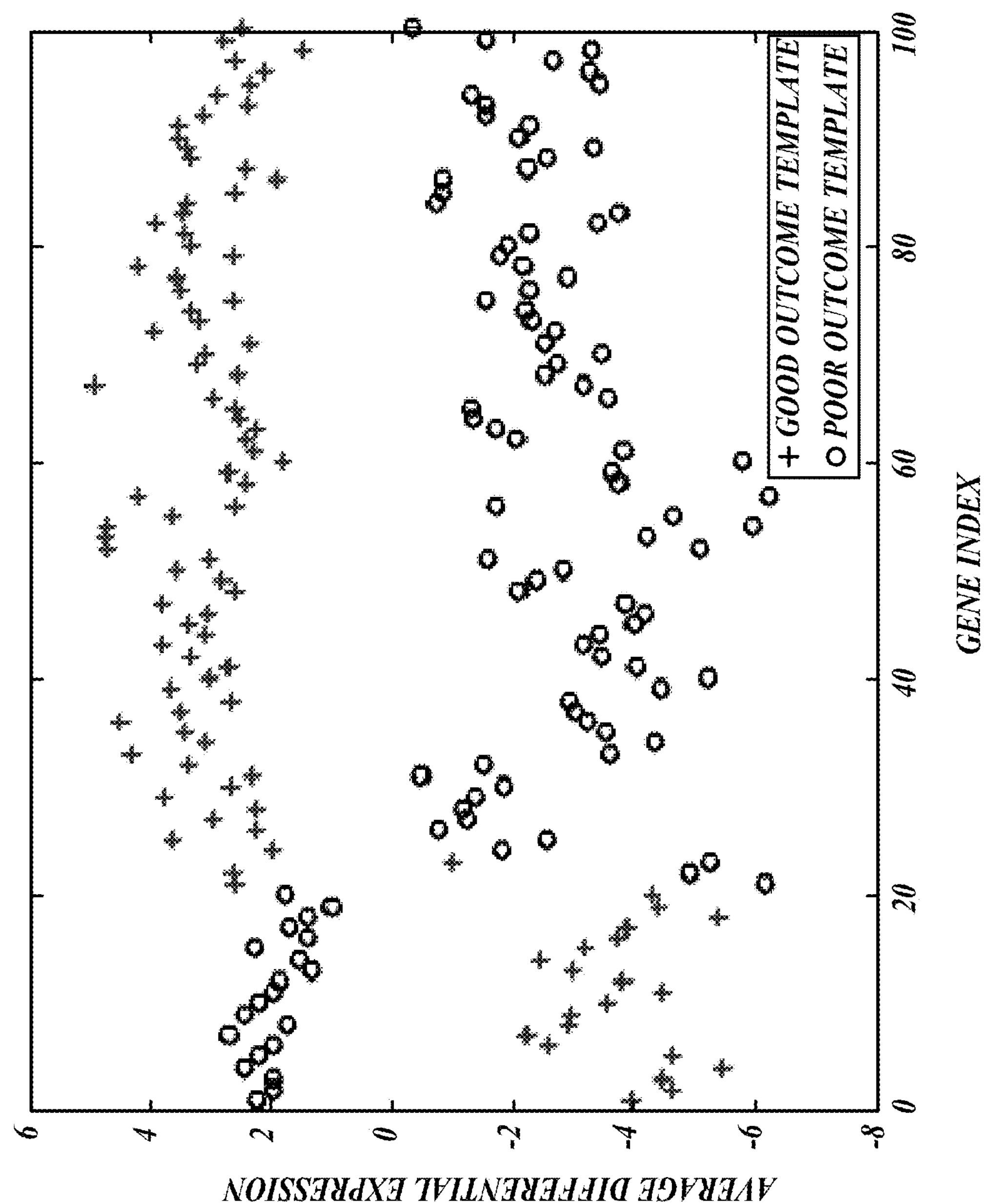
FIG. 4 graphically illustrates the expression patterns of the 100 genes (X-axis), listed in the same order as FIG. 2A (with reference to the corresponding gene index for each gene as shown in TABLE 3), in a good outcome template (shown as "o" symbols) and a poor outcome template (shown as "+" symbols); positive values in average differential expression represent overexpression; negative values represent underexpression as compared to the reference pool, with the reference pool defined as the pool of all 118 samples in the study, as described in EXAMPLE 2.

| Gene Index (as shown in FIGS. 2A and 4) | Identifier | Gene Name | average good xdev | average poor xdev |
|---|---|---|---|---|
| 1 | NM_006384 | CIB 1 | 2.23 | −3.95 |
| 2 | Contig52862_RC | Contig52862_RC | 1.97 | −4.63 |
| 3 | NM_000189 | HK2 | 1.98 | −4.46 |
| 4 | AL137342 | AL137342 | 2.44 | −5.43 |
| 5 | NM_003360 | UGT8 | 2.2 | −4.61 |
| 6 | NM_014730 | KIAA0152 | 1.98 | −2.57 |
| 7 | AK000332 | MGC27034 | 2.7 | −2.22 |
| 8 | AK000500 | MRPL50 | 1.74 | −2.92 |
| 9 | NM_012243 | SLC35A3 | 2.46 | −2.95 |
| 10 | Contig36951_RC | Contig36951_RC | 2.22 | −3.54 |
| 11 | NM_018302 | FLJ11017 | 1.96 | −4.46 |
| 12 | NM_018964 | SLC37A1 | 1.86 | −3.8 |
| 13 | Contig50915_RC | MGC4618 | 1.3 | −2.96 |
| 14 | NM_004663 | RAB11A | 1.53 | −2.41 |
| 15 | Contig57662_RC | STARD4 | 2.27 | −3.19 |
| 16 | AF228704 | GSR | 1.39 | −3.73 |
| 17 | NM_000637 | GSR | 1.7 | −3.86 |
| 18 | NM_018492 | TOPK | 1.4 | −5.36 |
| 19 | NM_004462 | FDFT1 | 1.01 | −4.37 |
| 20 | Contig46089_RC | FLJ20967 | 1.77 | −4.29 |
| 21 | Contig53953_RC | AKAP12 | −6.14 | 2.59 |
| 22 | NM_005100 | AKAP12 | −4.88 | 2.61 |
| 23 | NM_017993 | FLJ10094 | −5.24 | −0.99 |
| 24 | AB002361 | KIAA0363 | −1.8 | 1.97 |
| 25 | NM_014710 | KIAA0443 | −2.54 | 3.63 |
| 26 | Contig30994_RC | Contig30994_RC | −0.74 | 2.24 |
| 27 | NM_004538 | NAP1L3 | −1.24 | 2.93 |
| 28 | AB006625 | PEG3 | −1.17 | 2.24 |
| 29 | Contig48249_RC | FLJ10849 | −1.37 | 3.75 |
| 30 | NM_018894 | EFEMP1 | −1.83 | 2.67 |
| 31 | NM_004105 | EFEMP1 | −0.46 | 2.32 |
| 32 | NM_001801 | CDO1 | −1.5 | 3.33 |
| 33 | Contig30092_RC | PRDM6 | −3.58 | 4.31 |
| 34 | NM_001189 | BAPX1 | −4.3 | 3.05 |
| 35 | Contig53281_RC | Contig53281_RC | −3.52 | 3.42 |
| 36 | AL050202 | MGC3047 | −3.21 | 4.46 |
| 37 | NM_020372 | LOC57100 | −3 | 3.47 |
| 38 | AL080059 | KIAA1750 | −2.91 | 2.65 |
| 39 | NM_001885 | CRYAB | −4.41 | 3.66 |
| 40 | NM_018274 | TNS | −5.2 | 3.01 |
| 41 | Contig49510_RC | GALGT | −4.01 | 2.7 |
| 42 | Contig53838_RC | Contig53838_RC | −3.44 | 3.32 |
| 43 | Contig50367 | JAM3 | −3.16 | 3.79 |
| 44 | Contig53881_RC | Contig53881_RC | −3.41 | 3.08 |
| 45 | AL137734 | DKFZp586C0721 | −3.96 | 3.34 |
| 46 | AK002039 | MRVI1 | −4.13 | 3.02 |
| 47 | AF131817 | AF131817 | −3.83 | 3.8 |
| 48 | NM_003199 | TCF4 | −2.07 | 2.58 |
| 49 | NM_015493 | FLJ20004 | −2.37 | 2.78 |
| 50 | Contig26371_RC | FLJ20898 | −2.8 | 3.53 |
| 51 | NM_001864 | COX7A1 | −1.58 | 3.01 |
| 52 | Contig42882_RC | C20orf82 | −5.05 | 4.68 |
| 53 | NM_004791 | ITGBL1 | −4.18 | 4.7 |
| 54 | NM_003014 | SFRP4 | −5.94 | 4.69 |
| 55 | Contig1789_RC | LAGY | −4.62 | 3.63 |
| 56 | NM_005545 | ISLR | −1.72 | 2.59 |
| 57 | NM_000900 | MGP | −6.21 | 4.2 |
| 58 | NM_007281 | SCRG1 | −3.73 | 2.42 |
| 59 | Contig5549_RC | Contig5549_RC | −3.62 | 2.69 |
| 60 | NM_000702 | ATP1A2 | −5.75 | 1.79 |
| 61 | Contig7558_RC | SYNPO2 | −3.78 | 2.26 |
| 62 | NM_014365 | H11 | −2.05 | 2.43 |
| 63 | Contig47038_RC | MGC15476 | −1.7 | 2.24 |
| 64 | AB033040 | KIAA1214 | −1.33 | 2.51 |
| 65 | Contig21679_RC | Contig21679_RC | −1.29 | 2.59 |
| 66 | Contig50719_RC | RERG | −3.54 | 2.94 |
| 67 | Contig53033_RC | Contig53033_RC | −3.13 | 4.88 |
| 68 | Contig38980_RC | Contig38980_RC | −2.48 | 2.55 |
| 69 | NM_000627 | LTBP1 | −2.7 | 3.19 |
| 70 | NM_018215 | FLJ10781 | −3.46 | 3.08 |
| 71 | NM_002430 | MN1 | −2.49 | 2.35 |
| 72 | NM_016839 | RBMS1 | −2.66 | 3.93 |
| 73 | NM_002897 | RBMS1 | −2.3 | 3.18 |
| 74 | NM_016836 | RBMS1 | −2.18 | 3.32 |
| 75 | NM_016837 | RBMS1 | −1.52 | 2.62 |
| 76 | AL117617 | HCC-4 | −2.26 | 3.48 |
| 77 | NM_003793 | CTSF | −2.86 | 3.54 |
| 78 | NM_013401 | RAB3IL1 | −2.16 | 4.2 |
| 79 | Contig51625_RC | Contig51625_RC | −1.76 | 2.63 |
| 80 | Contig32377_RC | Contig32377_RC | −1.92 | 3.29 |
| 81 | NM_006006 | ZNF145 | −2.25 | 3.4 |
| 82 | Contig47308_RC | Contig47308_RC | −3.39 | 3.89 |
| 83 | AL137751 | RDX | −3.72 | 3.46 |
| 84 | NM_002725 | PRELP | −0.71 | 3.36 |
| 85 | NM_014942 | ANKRD6 | −0.82 | 2.57 |
| 86 | Contig53959_RC | FLJ14054 | −0.81 | 1.89 |
| 87 | Contig23466_RC | Contig23466_RC | −2.22 | 2.43 |
| 88 | Contig36409_RC | Contig36409_RC | −2.53 | 3.29 |
| 89 | Contig46787_RC | Contig46787_RC | −3.3 | 3.38 |
| 90 | Contig10455_RC | Contig10455_RC | −2.07 | 3.5 |
| 91 | Contig29223_RC | Contig29223_RC | −2.26 | 3.5 |
| 92 | Contig39655_RC | Contig39655_RC | −1.53 | 3.11 |
| 93 | Contig43102_RC | Contig43102_RC | −1.54 | 2.38 |
| 94 | Contig9310 | Contig9310 | −1.3 | 2.85 |
| 95 | Contig20304_RC | Contig20304_RC | −3.41 | 2.36 |
| 96 | Contig15693_RC | Contig15693_RC | −3.26 | 2.09 |
| 97 | AL050145 | AL050145 | −2.62 | 2.6 |
| 98 | Contig59144 | SLC31A1 | −3.29 | 1.44 |
| 99 | Contig21891_RC | FLJ13231 | −1.53 | 2.75 |
| 100 | Contig26642_RC | Contig26642_RC | −0.32 | 2.49 |

TABLE 4

GOOD AND POOR OUTCOME TEMPLATES: Mean log10 (ratio) values for each of the 100 GENE MARKERS listed in TABLE 4 for 82 colon cancer patients having a good outcome or 36 colon cancer patients having a poor outcome see EXAMPLES). Ratio is defined as the intensity ratio of each individual sample to the pool of all colon tumor samples in this study.

| Gene Index (as shown in FIGS. 2A and 4) | Identifier | Gene Name | mean log10 (ratio) Good Template | mean log10 (ratio) Poor Template |
|---|---|---|---|---|
| 1 | NM_006384 | CIB 1 | 0.11709917 | −0.191082362 |
| 2 | Contig52862_RC | Contig52862_RC | 0.127175178 | −0.353028073 |
| 3 | NM_000189 | HK2 | 0.126832645 | −0.28252639 |
| 4 | AL137342 | AL137342 | 0.136819769 | −0.402656725 |
| 5 | NM_003360 | UGT8 | 0.121621777 | −0.352177827 |

TABLE 4-continued

GOOD AND POOR OUTCOME TEMPLATES:
Mean log10 (ratio) values for each of the 100 GENE MARKERS listed in TABLE 4 for 82 colon cancer patients having a good outcome or 36 colon cancer patients having a poor outcome see EXAMPLES). Ratio is defined as the intensity ratio of each individual sample to the pool of all colon tumor samples in this study.

| Gene Index (as shown in FIGS. 2A and 4) | Identifier | Gene Name | mean log10 (ratio) Good Template | mean log10 (ratio) Poor Template |
|---|---|---|---|---|
| 6 | NM_014730 | KIAA0152 | 0.105705947 | −0.136399565 |
| 7 | AK000332 | MGC27034 | 0.161337167 | −0.145285469 |
| 8 | AK000500 | MRPL50 | 0.091091073 | −0.149833918 |
| 9 | NM_012243 | SLC35A3 | 0.126538307 | −0.169025186 |
| 10 | Contig36951_RC | Contig36951_RC | 0.120612708 | −0.291137711 |
| 11 | NM_018302 | FLJ11017 | 0.103472072 | −0.315232599 |
| 12 | NM_018964 | SLC37A1 | 0.114945695 | −0.234607063 |
| 13 | Contig50915_RC | MGC4618 | 0.072308796 | −0.174952979 |
| 14 | NM_004663 | RAB11A | 0.086242769 | −0.137512886 |
| 15 | Contig57662_RC | STARD4 | 0.13793885 | −0.258609132 |
| 16 | AF228704 | GSR | 0.081272255 | −0.224029374 |
| 17 | NM_000637 | GSR | 0.091682931 | −0.231044182 |
| 18 | NM_018492 | TOPK | 0.075274632 | −0.358366383 |
| 19 | NM_004462 | FDFT1 | 0.080007359 | −0.276307423 |
| 20 | Contig46089_RC | FLJ20967 | 0.083423243 | −0.257748461 |
| 21 | Contig53953_RC | AKAP12 | −0.426613106 | 0.146356115 |
| 22 | NM_005100 | AKAP12 | −0.354196474 | 0.166363785 |
| 23 | NM_017993 | FLJ10094 | −0.347567936 | −0.065909315 |
| 24 | AB002361 | KIAA0363 | −0.14709153 | 0.141850902 |
| 25 | NM_014710 | KIAA0443 | −0.20149784 | 0.231169531 |
| 26 | Contig30994_RC | Contig30994_RC | −0.114284189 | 0.226835162 |
| 27 | NM_004538 | NAP1L3 | −0.134821672 | 0.24244194 |
| 28 | AB006625 | PEG3 | −0.132161872 | 0.188136865 |
| 29 | Contig48249_RC | FLJ10849 | −0.076033897 | 0.203630726 |
| 30 | NM_018894 | EFEMP1 | −0.150505443 | 0.216420461 |
| 31 | NM_004105 | EFEMP1 | −0.031292944 | 0.157735801 |
| 32 | NM_001801 | CDO1 | −0.1661645 | 0.268598092 |
| 33 | Contig30092_RC | PRDM6 | −0.252471353 | 0.261968262 |
| 34 | NM_001189 | BAPX1 | −0.308314488 | 0.198635029 |
| 35 | Contig53281_RC | Contig53281_RC | −0.236285353 | 0.197816243 |
| 36 | AL050202 | MGC3047 | −0.225567017 | 0.271214835 |
| 37 | NM_020372 | LOC57100 | −0.178044418 | 0.21472357 |
| 38 | AL080059 | KIAA1750 | −0.174225573 | 0.152521988 |
| 39 | NM_001885 | CRYAB | −0.268816792 | 0.249656025 |
| 40 | NM_018274 | TNS | −0.309831542 | 0.191675194 |
| 41 | Contig49510_RC | GALGT | −0.236442948 | 0.162801526 |
| 42 | Contig53838_RC | Contig53838_RC | −0.231867683 | 0.188637776 |
| 43 | Contig50367 | JAM3 | −0.165604318 | 0.213107333 |
| 44 | Contig53881_RC | Contig53881_RC | −0.229286958 | 0.186551277 |
| 45 | AL137734 | DKFZp586C0721 | −0.263020339 | 0.245740807 |
| 46 | AK002039 | MRVI1 | −0.237371907 | 0.16662089 |
| 47 | AF131817 | AF131817 | −0.225667687 | 0.21704431 |
| 48 | NM_003199 | TCF4 | −0.152653889 | 0.189020252 |
| 49 | NM_015493 | FLJ20004 | −0.136024931 | 0.167955667 |
| 50 | Contig26371_RC | FLJ20898 | −0.158847481 | 0.189484088 |
| 51 | NM_001864 | COX7A1 | −0.0907652 | 0.183026627 |
| 52 | Contig42882_RC | C20orf82 | −0.389956916 | 0.279419289 |
| 53 | NM_004791 | ITGBL1 | −0.283432204 | 0.302740816 |
| 54 | NM_003014 | SFRP4 | −0.482589785 | 0.323284083 |
| 55 | Contig1789_RC | LAGY | −0.283089089 | 0.208078942 |
| 56 | NM_005545 | ISLR | −0.108212426 | 0.156364356 |
| 57 | NM_000900 | MGP | −0.425553236 | 0.315680282 |
| 58 | NM_007281 | SCRG1 | −0.509119477 | 0.086409244 |
| 59 | Contig5549_RC | Contig5549_RC | −0.276783742 | 0.15742284 |
| 60 | NM_000702 | ATP1A2 | −0.544155687 | 0.101393446 |
| 61 | Contig7558_RC | SYNPO2 | −0.323657717 | 0.139589151 |
| 62 | NM_014365 | H11 | −0.189656876 | 0.176053063 |
| 63 | Contig47038_RC | MGC15476 | −0.134601061 | 0.157809797 |
| 64 | AB033040 | KIAA1214 | −0.157059017 | 0.200648844 |
| 65 | Contig21679_RC | Contig21679_RC | −0.151423699 | 0.23607205 |
| 66 | Contig50719_RC | RERG | −0.259634234 | 0.169297031 |
| 67 | Contig53033_RC | Contig53033_RC | −0.216425394 | 0.33097204 |
| 68 | Contig38980_RC | Contig38980_RC | −0.295615669 | 0.191397911 |
| 69 | NM_000627 | LTBP1 | −0.171045569 | 0.205477445 |
| 70 | NM_018215 | FLJ10781 | −0.251114811 | 0.21223574 |
| 71 | NM_002430 | MN1 | −0.199483189 | 0.19903004 |
| 72 | NM_016839 | RBMS1 | −0.161072721 | 0.229044481 |
| 73 | NM_002897 | RBMS1 | −0.133585166 | 0.184352728 |
| 74 | NM_016836 | RBMS1 | −0.123998148 | 0.183409809 |
| 75 | NM_016837 | RBMS1 | −0.102333078 | 0.174730789 |

TABLE 4-continued

GOOD AND POOR OUTCOME TEMPLATES: Mean log10 (ratio) values for each of the 100 GENE MARKERS listed in TABLE 4 for 82 colon cancer patients having a good outcome or 36 colon cancer patients having a poor outcome see EXAMPLES). Ratio is defined as the intensity ratio of each individual sample to the pool of all colon tumor samples in this study.

| Gene Index (as shown in FIGS. 2A and 4) | Identifier | Gene Name | mean log10 (ratio) Good Template | mean log10 (ratio) Poor Template |
|---|---|---|---|---|
| 76 | AL117617 | HCC-4 | −0.133125056 | 0.211941352 |
| 77 | NM_003793 | CTSF | −0.172214489 | 0.226077094 |
| 78 | NM_013401 | RAB3IL1 | −0.124047733 | 0.25852116 |
| 79 | Contig51625_RC | Contig51625_RC | −0.136851104 | 0.198284942 |
| 80 | Contig32377_RC | Contig32377_RC | −0.132362674 | 0.205959464 |
| 81 | NM_006006 | ZNF145 | −0.139798979 | 0.227594494 |
| 82 | Contig47308_RC | Contig47308_RC | −0.217309022 | 0.211930628 |
| 83 | AL137751 | RDX | −0.216853189 | 0.186647296 |
| 84 | NM_002725 | PRELP | −0.092881634 | 0.279617906 |
| 85 | NM_014942 | ANKRD6 | −0.078391058 | 0.212637641 |
| 86 | Contig53959_RC | FLJ14054 | −0.142658366 | 0.246032428 |
| 87 | Contig23466_RC | Contig23466_RC | −0.204368567 | 0.180163153 |
| 88 | Contig36409_RC | Contig36409_RC | −0.139896631 | 0.181063698 |
| 89 | Contig46787_RC | Contig46787_RC | −0.20607855 | 0.177708545 |
| 90 | Contig10455_RC | Contig10455_RC | −0.139747181 | 0.196160426 |
| 91 | Contig29223_RC | Contig29223_RC | −0.13739829 | 0.207280426 |
| 92 | Contig39655_RC | Contig39655_RC | −0.121994093 | 0.18717025 |
| 93 | Contig43102_RC | Contig43102_RC | −0.098911307 | 0.134861761 |
| 94 | Contig9310 | Contig9310 | −0.086699712 | 0.17948786 |
| 95 | Contig20304_RC | Contig20304_RC | −0.239501835 | 0.14520797 |
| 96 | Contig15693_RC | Contig15693_RC | −0.236600831 | 0.138034507 |
| 97 | AL050145 | AL050145 | −0.179667273 | 0.197050063 |
| 98 | Contig59144 | SLC31A1 | −0.294037879 | 0.083612743 |
| 99 | Contig21891_RC | FLJ13231 | −0.129053729 | 0.178301248 |
| 100 | Contig26642_RC | Contig26642_RC | −0.052811745 | 0.230607992 |

TABLE 5

23 PREFERRED GENE MARKERS FROM TABLES 1-3 FOR CLASSIFYING COLON CANCER PATIENTS WITH REGARD TO PROGNOSIS

| GenBank Accession Number | Gene Name | Full length cDNA Sequence SEQ ID NO: | Exemplary Probe Sequence: SEQ ID NO: | Correlation Value (with poor prognosis) |
|---|---|---|---|---|
| Contig53953_RC | AKAP12 (AKAP250, DKFZp686M0430, DKFZp686O0331) | 61 | 161 | 0.79 |
| NM_006384 | CIB 1 (CIB, KIP, SIP2-28, CALMYRIN) | 43 | 143 | −0.79 |
| NM_014710 | KIAA0443 (GPRASP1, GASP, GASP1) | 23 | 123 | 0.78 |
| AL137342 | UGT8 (CGT) | 5 | 105 | −0.78 |
| NM_000900 | MGP (NTI, MGLAP) | 27 | 127 | 0.76 |
| Contig30092_RC | PRDM6 | 48 | 148 | 0.74 |
| Contig23466_RC | oh99h06.s1 (NCI_CGAP_HN4) | 72 | 172 | 0.74 |
| NM_005100 | AKAP12 (AKAP250, DKFZp686M0430, DKFZp686O0331) | 21 | 121 | 0.73 |
| Contig30994_RC | | 49 | 149 | 0.73 |
| NM_003360 | UGT8 (CGT) | 8 | 108 | −0.73 |
| Contig26371_RC | FLJ20898 (C16orf30, CLP24, MGC111564) | 73 | 173 | 0.72 |

TABLE 5-continued

23 PREFERRED GENE MARKERS FROM TABLES 1-3 FOR CLASSIFYING COLON CANCER PATIENTS WITH REGARD TO PROGNOSIS

| GenBank Accession Number | Gene Name | Full length cDNA Sequence SEQ ID NO: | Exemplary Probe Sequence: SEQ ID NO: | Correlation Value (with poor prognosis) |
|---|---|---|---|---|
| NM_016839 | RBMS 1 (YC1, MSSP, SCR2, MSSP-1, MSSP-2, MSSP-3, MGC3331, MGC15146) | 42 | 142 | 0.72 |
| AL050202 | MGC3047 (MXRA8) | 93 | 193 | 0.71 |
| NM_001885 | CRYAB (CRYA2, CTPP2, HSPB5) | 15 | 115 | 0.71 |
| Contig53838_RC | LOC399959 (FLJ11490, FLJ34394, FLJ41953, DKFZp686J24156) | 59 | 159 | 0.71 |
| Contig38980_RC | C21orf34 (C21orf35, FLJ38295) | 50 | 150 | 0.71 |
| NM_018215 | FLJ10781 | 35 | 135 | 0.71 |
| NM_003793 | CTSF (CATSF) | 17 | 117 | 0.71 |
| Contig32377_RC | USP51 | 76 | 176 | 0.71 |
| Contig47308_RC | ZNF218 (ZABC2, OVC10-2, C20orf17, FLJ33887) | 52 | 152 | 0.71 |

TABLE 5-continued

23 PREFERRED GENE MARKERS FROM TABLES 1-3 FOR CLASSIFYING COLON CANCER PATIENTS WITH REGARD TO PROGNOSIS

| GenBank Accession Number | Gene Name | Full length cDNA Sequence SEQ ID NO: | Exemplary Probe Sequence: SEQ ID NO: | Correlation Value (with poor prognosis) |
|---|---|---|---|---|
| Contig36409_RC | RANBP9 (RANBPM) | 77 | 177 | 0.71 |
| Contig36951_RC | | 78 | 178 | −0.71 |
| AF228704 | GSR (MGC78522) | 96 | 196 | −0.71 |

The sets of markers listed in TABLES 1-5 overlap. The markers in TABLE 5 are a subset of the markers listed in TABLES 1-4.

The set of markers listed in TABLES 1-5 may be used in the methods described herein for classifying an individual afflicted with colon cancer as having a good prognosis or a poor prognosis. Any of the marker sets provided above may also be used in combination with other markers for classifying an individual afflicted with colon cancer, or for any other clinical or physiological condition.

In one embodiment, the isolated population of polynucleotide probes comprising a plurality of polynucleotides, each complementary and hybridizable to a sequence of at least five different markers selected from any one of TABLES 1-5, are attached to a diagnostic tool, such as, for example, a microarray, as described in more detail herein.

In another embodiment, the isolated population of polynucleotide probes comprise PCR primers for amplifying a portion of at least five different markers selected from any one of TABLES 1-5. PCR primers are preferably chosen based on the sequence of the marker that will result in amplification of specific fragments of the marker gene. Computer programs that are well known in the art are useful in the design of primers with the required specificity and optimal amplification properties, such as Oligo version 5.0 (National Biosciences). PCR methods are well known in the art, and are described, for example, in Innis, et al., eds., *PCR Protocols: A Guide to Methods and Applications*, Academic Press Inc., San Diego, Calif. (1990).

The use of marker sets described herein is not restricted to the prognosis of colon cancer-related conditions, and may be applied in a variety of phenotypes or conditions, clinical or experimental, in which gene expression plays a role. Where a set of markers has been identified that corresponds to two or more phenotypes, the marker set can be used to distinguish these phenotypes. For example, the phenotypes may be the diagnosis and/or prognosis of clinical states or phenotypes associated with other cancers, other disease conditions, or other physiological conditions, wherein the expression level data is derived from a set of genes correlated with the particular physiological or disease condition. Further, the expression of markers specific to other types of cancer may be used to differentiate patients or patient populations for those cancers for which different therapeutic regimens are indicated.

Use of the Colon Cancer Markers to Generate Prognostic Profiles

In another aspect, the invention provides a method for classifying a human individual afflicted with colon cancer as having a good prognosis or a poor prognosis, where said good prognosis indicates that said individual is expected to have no distant metastasis within three years of initial diagnosis of colon cancer, and wherein said poor prognosis indicates that said individual is expected to have distant metastasis within three years of initial diagnosis of colon cancer, comprising: (i) calculating a first measure of similarity between a first expression profile comprising the expression levels of a plurality of genes comprising at least five of the genes for which markers are listed in any of TABLES 1-5 in a cell sample taken from the individual and a poor outcome template, wherein said poor outcome template comprises expression levels of said plurality of genes that are average expression levels of the respective genes of a plurality of colon cancer patients having distant metastasis within three years of initial diagnosis of colon cancer; (ii) classifying said individual as having said poor prognosis if said first expression profile has a similarity to said poor outcome template that is above a predetermined threshold, or classifying said patient as having said good prognosis if said first expression profile has a similarity to said poor outcome template that is below a predetermined threshold; and (iii) displaying or outputting to a user interface device a computer-readable storage medium, or a local or remote computer system, the classification produced by said classifying step (ii).

In accordance with this aspect of the invention, the poor outcome template comprises the expression levels of a plurality of genes comprising at least five of the genes for which markers are listed in any of TABLES 1-5 that are the average expression levels of the respective genes in a plurality of patients having distant metastasis within three years of initial diagnosis of colon cancer. The poor outcome template for use in this aspect of the invention may be generated by hybridization of nucleic acids derived from a plurality of colon cancer patients having distant metastasis within three years of initial diagnosis of colon cancer against nucleic acids derived from a pool of samples from tumors obtained from a plurality of patients having colon cancer.

In another embodiment, the method further comprises calculating a second measure of similarity between said first expression profile and a good outcome template, said good outcome template comprising expression levels of said plurality of genes that are average expression levels of the respective genes of a plurality of colon cancer patients having no distant metastasis within three years of initial diagnosis of colon cancer; and classifying said individual as having said good prognosis if said first expression profile has a first expression profile has a similarity to said poor outcome template that is below a predetermined threshold and said first expression profile has a similarity to said good outcome template that is above a predetermined threshold.

In accordance with this embodiment of the method, the good outcome template comprises the expression levels of a plurality of genes comprising at least five of the genes for which markers are listed in any of TABLES 1-5 that are the average expression levels of the respective genes in a plurality of patients having no distant metastasis within three years of initial diagnosis of colon cancer. The good outcome template for use in this embodiment of the method of the invention may be generated by hybridization of nucleic acids derived from a plurality of colon cancer patients having no distant metastasis within three years of initial diagnosis of colon cancer against nucleic acids derived from a pool of samples from tumors obtained from a plurality of patients having colon cancer.

Selection of at least five markers from the markers provided in TABLE 1 for use in the methods of the invention (e.g., for generating a poor outcome template or a good outcome template) may be made based upon a correlation of expression of either significant up- or down-regulation of the marker in the patient sample as compared to disease outcome (i.e., presence or absence of distant metastasis). Marker selection may also be made by calculation of the statistical significance (i.e., the p-value) of the correlation between the expression of the marker and disease outcome. Preferably, both selection criteria are used.

As described herein, the present invention provides sets of markers for the prognosis of colon cancer that were identified based upon a significant difference of expression in cell samples from tumors obtained from individuals afflicted with colon cancer, as compared to a standard or control condition. The set of 100 markers, or a subset of at least 5 or more markers selected from the 100 markers, may be used in the methods of the invention.

Thus, in one embodiment of the present invention, markers associated with the outcome of colon cancer are selected for use in the methods of the invention based on a correlation coefficient value. For example, using a number of colon cancer tumor samples, the markers listed in TABLE 1 were identified by calculation of correlation coefficients ρ between the clinical category (e.g., good or poor outcome) c, and the linear, logarithmic or any transform of the expression ratio r across all samples for each individual gene.

Specifically, the at least five gene markers may be selected based on a correlation coefficient calculated as the correlation coefficients ρ between the clinical category c and logarithmic expression ratio $\vec{r}$ across all the samples for each individual gene:

$$\rho=(\vec{c}\cdot\vec{r})/(\|\vec{c}\|\cdot\|\vec{r}\|) \qquad \text{(Eq. 3)}$$

Gene markers whose expression ratios either correlate or anti-correlate well with the patient outcome of colon cancer are shown in TABLES 1-5, with the correlation coefficients provided in TABLE 2. For example, as described in EXAMPLE 2, in one embodiment of the method, genes having a correlation coefficient larger than 0.65 ("correlated genes") or less than −0.65 ("anti-correlated genes") with patient outcome of colon cancer may be selected as reporter genes.

A threshold value, such as 0.65, may be selected based on the correlation distribution for cases where there was no real correlation. Statistically, this distribution width depends upon the number of samples used in the correlation calculation. The distribution width for control cases (no real correlation) is approximately $1/\sqrt{n-3}$, where n=the number of samples. In our case, n=118. Therefore, a threshold of 0.65 corresponds to greater than 3-σ in the distribution $3\times 1/\sqrt{n-3}$. Genes with high correlation values are likely to be better predictors of outcome.

In another embodiment, marker selection may also be made by calculation of the statistical significance (i.e., the p-value) of the correlation between the expression of the marker and disease outcome. The significance of the correlation may be calculated by any suitable method. For example, a set of correlation data may be generated using a Monte-Carlo technique to randomize the association between the expression of a particular marker and the prognosis. The frequency distribution of markers satisfying the criteria in the Monte-Carlo runs may be used to determine whether the number of markers selected by correlation with clinical data was significant.

In another embodiment, the at least five markers provided in TABLE 1 may be selected for use in the methods of the invention based on the rank-order in order of significance of discrimination by the amplitude of correlation between the change in gene expression of the marker and the specific condition being discriminated, or by using a metric similar to a Fisher statistic:

$$t=\frac{(<x_1>-<x_2>)}{\sqrt{[\sigma_1^2(n_1-1)+\sigma_2^2(n_2-1)]/(n_1+n_2-1)/(1/n_1+1/n_2)}} \qquad \text{(Eq. 4)}$$

In Equation (4), $<x_1>$ is the error-weighted average of log ratio within the poor outcome group, and $<x_2>$ is the error-weighted average of log ratio within the good outcome group. $\sigma_1$ is the variance of log ratio within the poor outcome group, and $n_1$ is the number of samples that had valid measurements of log ratios. $\sigma_2$ is the variance of log ratio within the good outcome group, and $n_2$ is the number of samples that had valid measurements of log ratios. The t-value in Equation (4) represents the variance-compensated difference between two means. The confidence level of each gene in the candidate list was estimated with respect to a null hypothesis derived from the actual data set using a bootstrap technique; that is, many artificial data sets were generated by randomizing the association between the clinical data and the gene expression data.

The rank-ordered marker set may be used to optimize the number of markers in the set used for discrimination (e.g., a good outcome template or a poor outcome template). This is accomplished generally in a "leave-one-out" method as described in Dai, et al., *Cancer Res.* 65(10):4059-4066 (2005) and Van't Veer, et al., *Nature* 415:530-536 (2002), and as further described in Example 2 herein.

In various embodiments, the methods of the invention comprise generating a template profile for a good outcome and/or a poor outcome of colon cancer, comprising measurements of levels of a plurality of at least five markers from the set of markers provided in TABLE 1. A good outcome template comprises measurements of a plurality of transcripts representative of levels of said markers in a plurality of good outcome colon cancer patients, while a poor outcome template comprises measurements of a plurality of transcripts representative of said plurality of markers in a plurality of poor outcome colon cancer patients.

In one embodiment, the measurement of each said transcript in said good outcome template is an average of expression levels of said transcript in said plurality of good outcome colon cancer patients. In one embodiment, the measurement of each said transcript in said poor outcome template is an average of expression levels of said transcript in said plurality of poor outcome colon cancer patients.

For example, a template for a good outcome group ($\vec{z}_1$) may be generated using the error-weighted log ratio average of the selected group of genes. Similarly, a template for a poor outcome group (called $\vec{z}_2$) may be generated using the error-weighted log ratio average of the selected group of genes. Two classifier parameters ($P_1$ and $P_2$) may be defined based on either correlation or distance. $P_1$ measures the similarity between one sample $\vec{y}$ and the good outcome template $\vec{z}_1$ over this selected group of genes. $P_2$ measures the similarity between one sample $\vec{y}$ and the poor outcome template $\vec{z}_2$ over this selected group of genes. The correlation $P_i$ is defined as:

$$P_i=(\vec{z}_i\cdot\vec{y})/(\|\vec{z}_i\|\cdot\|\vec{y}\|) \qquad \text{Eq. (5)}$$

where i=1 and 2.

Thus, in one embodiment, y is classified as a good prognosis profile if $P_1$ is greater than a selected correlation threshold (for example, the threshold can be a value between 0 and 1), or if $P_2$ is equal to or less than a selected correlation threshold (for example, the threshold can be a value between −1 and 0).

In another embodiment, y is classified as a poor prognosis profile if $P_1$ is less than a selected correlation threshold (for example, the threshold can be a value between −1 and 0), or if $P_2$ is above a selected correlation threshold (for example, the threshold can be a value between 0 and 1).

In still another embodiment, y is classified as a good prognosis profile if $P_1$ is greater than a first selected correlation threshold and y is classified as a poor prognosis profile if $P_2$ is greater than a second selected correlation threshold.

In one embodiment, a good outcome template comprises 100 markers with the expression pattern as shown in FIG. 4 and TABLE 3, with a correlation threshold of $\geqq 0$ (correlation to the good outcome template). In another embodiment, a poor outcome template comprises the same 100 markers with the expression pattern as shown in FIG. 4 and TABLE 3 with a correlation threshold of $\geqq 0$ (correlation to the poor outcome template).

Sample Collection:

In accordance with the practice of various embodiments of the invention, target polynucleotide molecules are extracted from a cell sample taken from an individual afflicted with colon cancer. The sample may be collected in any clinically acceptable manner, but must be collected such that marker-derived polynucleotides (i.e., RNA) are preserved. mRNA or nucleic acids derived therefrom (i.e., cDNA or amplified DNA) are preferably labeled distinguishably from standard or control polynucleotide molecules, and both are simultaneously or independently hybridized to a nucleic acid array, such as a microarray comprising some or all of the markers or marker sets or subsets described above. Alternatively, mRNA or nucleic acids derived therefrom may be labeled with the same label as the standard or control polynucleotide molecules, wherein the intensity of hybridization of each at a particular probe is compared. A cell sample may comprise any clinically relevant tissue sample from a colon cancer patient, such as a colon tumor biopsy, a fine needle aspirate, or a colorectal polyp.

The cell sample may be taken from a mammalian subject suffering from colon cancer, preferably a human, or, in a veterinary context, from non-human animals such as ruminants, horses, swine or sheep, or from domestic companion animals such as felines and canines.

Methods for preparing total and poly(A)+RNA are well known and are described generally in Sambrook, et al., *Molecular Cloning: A Laboratory Manual* (2nd ed.), Vols. 1-3, Cold Spring Harbor Laboratory, Cold Spring Harbor, N.Y. (1989) and Ausubel, et al., *Current Protocols in Molecular Biology*, Vol. 2, Current Protocols Publishing, New York (1994).

RNA may be isolated from eukaryotic cells by procedures that involve lysis of the cells and denaturation of the proteins contained therein. Cells of interest include wild-type cells (i.e., non-cancerous), drug-exposed wild-type cells, tumor- or tumor-derived cells, modified cells, normal or tumor cell line cells, and drug-exposed modified cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin, et al., *Biochemistry* 18:5294 5299 (1979)). Poly(A)+RNA is selected by selection with oligo-dT cellulose (see Sambrook, et al., *Molecular Cloning: A Laboratory Manual* (2nd ed.), Vols. 1-3, Cold Spring Harbor Laboratory, Cold Spring Harbor, N.Y. (1989)). Alternatively, separation of RNA from DNA can be accomplished by organic extraction, for example, with hot phenol or phenol/chloroform/isoamyl alcohol.

If desired, RNAse inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX® medium (see Ausubel, et al., *Current Protocols in Molecular Biology*, Vol. 2, Current Protocols Publishing, New York (1994)). Once bound, poly(A)+ mRNA is eluted from the affinity column using 2 mM EDTA/0.1% SDS.

The sample of RNA can comprise a plurality of different mRNA molecules, each different mRNA molecule having a different nucleotide sequence. In a specific embodiment, the mRNA molecules in the RNA sample comprise at least 100 different nucleotide sequences. More preferably, the mRNA molecules of the RNA sample comprise mRNA molecules corresponding to each of the marker genes. In another specific embodiment, the RNA sample is a mammalian RNA sample, such as a human RNA sample.

In a specific embodiment, total RNA or mRNA from cells are used in the methods of the invention. The source of the RNA can be cells of a plant or animal, human, mammal, primate, non-human animal, dog, cat, mouse, rat, bird, yeast, eukaryote, prokaryote, etc. In specific embodiments, the method of the invention is used with a sample containing total mRNA or total RNA from $1\times10^6$ cells or less. In another embodiment, proteins can be isolated from the foregoing sources, by methods known in the art, for use in expression analysis at the protein level.

Probes to the homologs of the marker sequences disclosed herein can be employed preferably wherein non-human nucleic acid is being assayed.

In one embodiment, the prognostic methods can use at least 5, 10, 15, 20, 25, 30, 35, 40, 45, 50, 55, 60, 65, 70, 75, 80, 85, 90, 95 or the complete set of 100 markers listed in TABLES 1-5. In a preferred embodiment, the subset of 23 markers listed in TABLE 5 is used.

Comparison Methods:

Generally described, in the practice of the prognostic methods described herein, the expression of specific marker genes in a cell sample taken from an individual afflicted with colon cancer is determined and compared to a standard or control to determine a degree of similarity. In one embodiment, the expression of specific marker genes in a cell sample is a differential expression profile comprising differential measurements of the plurality of transcripts in a sample derived from the patient versus measurements of the plurality of transcripts in a control sample. The differential measurements can be xdev, log(ratio), error-weighted log(ratio), or a mean subtracted log(intensity) (see, e.g., Stoughton, et al., PCT publication WO 00/39339, published on Jul. 6, 2000; U.S. patent application Ser. No. 10/848,755, filed May 18, 2004, by Mao et al., each of which is incorporated herein by reference in its entirety). The term "xdev" refers to the log (ratio)/[error of log(ratio)], which provides a measure of the significance of the differential expression of the gene marker between the sample types (e.g., patient and control samples), as it is normalized by the error.

The similarity between the marker expression profile of an individual and that of a control can be assessed by a number of methods. In the simplest case, the profiles can be compared visually in a printout of expression difference data. Alternatively, the similarity can be calculated mathematically.

For example, assume two colon cancer-related conditions, X (poor outcome) and Y (good outcome). One can compare the level of expression of colon cancer prognostic markers for condition X in an individual to the level of the marker-derived polynucleotides in a control, wherein the level represents the level of expression exhibited by samples having condition X. In this instance, if the expression of the markers in the individual's sample is substantially (i.e., statistically) different from that of the control, then the individual does not have condition X. Where, as here, the choice is bimodal (i.e., a sample is either X or Y), the individual can additionally be said to have condition Y. Of course, the comparison to a control representing condition Y can also be performed. Preferably both are performed simultaneously, such that each control acts as both a positive and a negative control. The distinguishing result may thus either be a demonstrable difference from the expression levels (i.e., the amount of marker-derived RNA, or polynucleotides derived therefrom) represented by the control, or no significant difference.

In one embodiment, classification of a cell sample taken from an individual afflicted with colon cancer as "good prognosis" or "poor prognosis" is accomplished by generating one or more expression profile template(s) to which the marker expression levels in the cell sample are compared. Thus, in one embodiment of the above method, the level of polynucleotides (i.e., mRNA or polynucleotides derived therefrom) in a sample from an individual colon cancer patient, expressed from at least five of the markers provided in any of TABLES 1-5, is compared to the level of expression of the same markers from a control, wherein the control comprises marker-related polynucleotides derived from colon cancer tumor samples taken from colon cancer patients clinically determined to have a good outcome ("good outcome" control), colon cancer patients clinically determined to have a poor outcome ("poor outcome" control), or both. The comparison may be to both good outcome and poor outcome controls, and preferably the comparison is to polynucleotide pools from a number of good prognosis and poor prognosis samples, respectively. Where the individual's marker expression most closely resembles or correlates with the good outcome control, and does not resemble or correlate with the poor outcome control, the individual is classified as having a good prognosis. Where the pool is not pure 'good outcome' or 'poor outcome', a set of additional experiments may be performed in which nucleic acids from samples from individuals with known outcomes are hybridized against the pool to define the expression templates for the good outcome and poor outcome groups. Nucleic acids from each individual with unknown outcome are hybridized against the same pool and the resulting expression profile is compared to the templates to predict its outcome.

In one embodiment, the methods of the invention comprise determining the similarity of a first expression profile comprising marker expression levels in a cell sample obtained from an individual to a good outcome template and to a poor outcome template, wherein if said first expression profile is more similar to the good outcome template, the individual is classified as having a good prognosis, and if said first expression profile is more similar to the poor outcome template, the individual is classified as having a poor prognosis. The similarity between profiles can be represented by a similarity measure, such as a correlation coefficient, wherein the expression profile that has the highest similarity to the template is determined by maximizing the correlation coefficient, as described herein and in U.S. Pat. No. 6,203,987, hereby incorporated by reference. A similarity measure may also be calculated by measuring using a distance, wherein the expression profile that has the highest similarity to the template is determined by minimizing the distance, e.g., by a least squares method, as described in U.S. Pat. No. 6,218,122, hereby incorporated by reference.

The Standard or Control

The control or standard for use in the methods of the invention may be presented in a number of different formats. In one embodiment, the standard or control molecules comprise marker-derived polynucleotides from a pool of samples from normal individuals, or a pool of tumor samples from individuals having colon cancer tumors. In another embodiment, the standard or control is an artificially generated pool of marker-derived polynucleotides, which pool is designed to mimic the level of marker expression exhibited by clinical samples of normal or colon cancer tumor tissue having a particular clinical indication (i.e., obtained from good outcome or poor outcome patients). In another specific embodiment, the control molecules comprise a pool derived from normal or colon cancer cell lines.

For example, the control, or template, to which the expression of marker genes in a cell sample derived from an individual afflicted with colon cancer is compared may be the average absolute level of expression of each of the genes in a pool of marker-derived nucleic acids pooled from colon cancer tumor samples obtained from a plurality of colon cancer patients. In this case, the difference between the absolute level of expression of these genes in the control and in a sample from a colon cancer patient provides the degree of similarity or dissimilarity of the level of expression in the patient sample and the control. The absolute level of expression may be measured by the intensity of the hybridization of the nucleic acids to an array.

In other embodiments, the values for the expression levels of the markers in both the patient sample and control are transformed (see section on *Improving Sensitivity to Expression Level Differences*). For example, the expression level value for the patient and the average expression level value for the pool, for each of the marker genes selected, may be transformed by taking the logarithm of the value. Moreover, the expression level values may be normalized by, for example, dividing by the median hybridization intensity of all of the samples that make up the pool. The control may be derived from hybridization data obtained simultaneously with the patient sample expression data, or may constitute a set of numerical values stores on a computer, or on a computer-readable medium In one embodiment, the invention provides a method of determining whether an individual afflicted with colon cancer will likely experience a relapse within three years of initial diagnosis (i.e., whether an individual has a poor prognosis) comprising (1) comparing the level of expression of at least five of the markers listed in any of TABLES 1-5 in a sample taken from the individual to the level of the same markers in a standard or control, where the standard or control levels represent those found in individuals with a poor outcome; and (2) determining whether the level of the marker-related polynucleotides in the sample from the individual is significantly different than that of the control, wherein if no substantial difference is found, the patient has a poor prognosis, and if a substantial difference is found, the patient has a good prognosis. Persons of skill in the art will readily see that the markers associated with good outcome can also be used as controls. In a more specific embodiment, both controls are run.

Poor prognosis of colon cancer may indicate that a tumor is relatively aggressive, while good prognosis may indicate that a tumor is relatively non-aggressive. Therefore, in another embodiment, the invention provides for a method of determining a course of treatment of a colon cancer patient, comprising determining whether the level of expression of at least five of the 100 markers of TABLE 1 correlates with the level of these markers in a sample representing a good outcome expression pattern or a poor outcome pattern; and determining a course of treatment, wherein if the expression correlates with the poor outcome expression pattern, the tumor is treated as an aggressive tumor.

As described in EXAMPLES 1-2, colon cancer tumor samples were taken from each patient, and marker-related polynucleotides were generated. The expression levels of each of the marker genes listed in TABLE 1, or a subset thereof, preferably at least five of the marker genes listed in TABLE 5, was determined for each tumor sample (i.e., for each patient) to generate a patient expression profile. Marker-derived polynucleotides from patients within the group clinically determined to have a good outcome (i.e., no distant metastases within three years of initial diagnosis) were pooled and mean expression levels for each of the prognosis-related marker genes were determined to obtain a control expression profile. Patients were then rank ordered in descending order of similarity of patient expression profiles to the control expression profile to produce a rank-ordered list of patients, where the similarity is a value expressed by a single similarity metric such as a correlation coefficient. A first threshold similarity value was then selected, which divided the group of patients into those predicted to have a good prognosis and those predicted to have a poor prognosis.

This first threshold similarity value may be the similarity value that most accurately predicts clinical outcomes (i.e., results in an expression profile classification that results in the fewest misclassifications when compared to actual clinical outcomes), or a similarity value that results in a particular number or percentage of false negatives in the group, where a false negative is an expression-based good prognosis prediction for a colon cancer patient that actually develops a distant metastasis within the three-year period after initial diagnosis. Patients whose similarity values are less than the first threshold similarity value are classified as having a "poor prognosis." Subsequent patients may be similarly classified by calculating a similarity value for the patient, where the control is the "good outcome" template or expression profile, and comparison of this similarity metric to the similarity metrics obtained above.

Methods of Classifying a Colon Cancer Patient with Regard to Prognosis

Thus, in one embodiment, the invention provides a method for classifying a colon cancer patient according to prognosis comprising comparing the levels of expression of at least five of the genes for at least five of the markers listed in any of TABLES 1-5 in a cell sample taken from said colon cancer patient to control levels of expression of said at least five markers; and classifying said colon cancer patient according to prognosis of his or her colon cancer based on the similarity between said levels of expression in said cell sample and said control levels. In one embodiment, the method comprises: (i) calculating a first measure of similarity between a first expression profile comprising the expression levels of a plurality of genes comprising at least five of the genes for which markers are listed in any of TABLES 1-5 in a cell sample taken from the individual and a poor outcome template, wherein said poor outcome template comprises expression levels of said plurality of genes that are average expression levels of the respective genes of a plurality of colon cancer patients having distant metastasis within three years of initial diagnosis of colon cancer; (ii) classifying said individual as having said poor prognosis if said first expression profile has a similarity to said poor outcome template that is above a predetermined threshold, or classifying said patient as having said good prognosis if said first expression profile has a similarity to said poor outcome template that is below a predetermined threshold; and (iii) displaying or outputting to a user interface device a computer-readable storage medium, or a local or remote computer system, the classification produced by said classifying step (ii).

In one embodiment, the second step of this method comprises determining whether said similarity exceeds one or more predetermined threshold values of similarity. In another embodiment of this method, said control levels are the mean levels of expression of each of said at least five genes in a pool of tumor samples obtained from a plurality of colon cancer patients who have no distant metastases within three years of initial diagnosis. In another embodiment of this method, said control levels comprise the expression levels of said genes in colon cancer patients who have had distant metastases within three years of initial diagnosis.

In yet another embodiment of this method, said control levels comprise, for each of said at least five of the genes for which markers are listed in TABLE 1, mean log ratio values stored on a computer. In another embodiment of this method, said control levels comprise, for each of said at least five genes listed in TABLE 1, the mean log ratio values that are listed in TABLE 4. The set of mean log ratio values listed in TABLE 4 may be used as a "good outcome" template for any of the prognostic methods described herein. The above method may also compare the level of expression of at least 5, at least 10, 15, 20, 25, 30, 35, 40, 45, 50, 55, 60, 65, 70, 75, 80, 85, 90, 95, or 100 of the genes for which markers are listed in TABLE 1, or may use the 23 preferred genes for which markers are listed in TABLE 5.

In one embodiment of the above method, said threshold similarity value is selected by a method comprising (a) rank ordering in descending order said tumor samples that compose said pool of tumor samples by the degree of similarity between the level of expression of said genes in each of said tumor samples to the mean level of expression of the same genes of the good outcome and/or poor outcome templates to obtain a rank-ordered list, said degree of similarity being expressed as a similarity value; (b) determining an acceptable number of false negatives in said classifying, wherein said false negatives are colon cancer patients for whom the expression levels of said at least five of the genes for which markers are listed in TABLE 1 in said cell sample predicts that said patient will have no distant metastases within the first three years after initial diagnosis, but who has had a distant metastasis within the first three years after initial diagnosis; (c) determining a similarity value above which in said rank-ordered list fewer than said acceptable number of tumor samples are false negatives; and (d) selecting said similarity value determined in step (c) as said first threshold similarity value.

In even more specific embodiments, said first threshold similarity value is a correlation coefficient, and said first threshold similarity value is greater that 0.50. In accordance with one embodiment of the method, new colon cancer patients whose expression profile correlates with (i.e., have a correlation coefficient greater than 0.50) the average "good outcome" expression profile are classified as having a "good prognosis."

In another embodiment, said first similarity value is a similarity value above which at most 10% false negatives are predicted in a training set of tumors. In the above and other embodiments, "false negatives" are patients classified by the expression of the marker genes as having a good prognosis, or who are predicted by such expression to have a good prognosis, but who actually do develop distant metastases within three years.

In another embodiment, the similarity value is the degree of difference between the absolute (i.e., untransformed) level of expression of each of the genes in a tumor sample taken from a colon cancer patient and the mean absolute level of expression of the same genes in a control. In another, more specific, embodiment, the similarity value is calculated using expression level data that is transformed (as described in the section entitled *Improving Sensitivity to Expression Level Differences*). In another embodiment, the similarity value is expressed as a similarity metric, such as a correlation coefficient, representing the similarity between the level of expression of the marker genes in the tumor sample and the mean level of expression of the same genes in a plurality of colon cancer tumor samples taken from colon cancer patients with poor outcomes (or good outcomes).

In another specific embodiment, said first similarity value is derived from control expression data obtained in the same hybridization experiment as that in which the patient expression level data is obtained. In another specific embodiment, said first similarity value is derived from an existing set of expression data. In a more specific embodiment, said first correlation coefficients are derived from a mathematical sample pool. For example, comparison of the expression of marker genes in new tumor samples may be compared to the pre-existing template determined for these genes for the 118 patients in the initial study; the template, or average expression levels of each of the 5 to 100 genes, can be used as a reference or control for any tumor sample. Preferably, the comparison is made to a template comprising the average expression level of at least 5 of the 100 genes listed in TABLE 1 for the 49 out of 118 patients clinically determined to have a good outcome in a retrospective study, and for which their outcome was correctly predicted using the classifier. The coefficient of correlation of the level of expression of these genes in the tumor sample to the "good outcome" template (generated with the 49 patients with a good clinical outcome) is then determined to produce a tumor correlation coefficient. For this control patient set, a similarity value has been derived using the 100 marker gene set listed in TABLE 1 as having a first correlation coefficient of −1.0 to 1.0. New colon cancer patients whose coefficients of correlation of the expression of these marker genes with the 49 patient "good outcome" template that exceed 0 are classified as having a "good prognosis"; those having a coefficient of correlation of less than 0 are classified as having a "poor prognosis."

The correlation coefficient of the 100 marker genes in a tumor sample can also be compared to the average expression ratio values in the "good template" and the correlation coefficient can be compared to the average expression ratio values in "poor template," as provided in TABLE 4. If C1 (correlation to the good template) is greater than C2 (correlation to the poor template), the patient is predicted to have a good prognosis, and if C2 is greater than C1, the patient is predicted to have a poor prognosis.

In one embodiment, the above methods utilize arrays to which fluorescently labeled, marker-derived target nucleic acids are hybridized. In such embodiments, the invention also provides a method of classifying a colon cancer patient according to prognosis comprising the steps of (a) contacting first nucleic acids derived from a tumor sample taken from said colon cancer patient, and second nucleic acids derived from two or more tumor samples from colon cancer patients who have had no distant metastases within three years of initial diagnosis, with an array under conditions such that hybridization can occur, detecting at each of a plurality of discrete loci on said array a first fluorescent emission signal from said first nucleic acids and a second fluorescent emission signal from said second nucleic acids that are bound to said array under said conditions, wherein said array comprises at least five of the genes for which markers are listed in TABLE 1 and wherein at least 50% of the probes on said array are listed in TABLE 1; (b) calculating the similarity between said first fluorescent emission signals and said second fluorescent emission signals across said at least five genes; and (c) classifying said colon cancer patient according to prognosis of his or her colon cancer based on the similarity between said first fluorescent emission signals and said second fluorescent emission signals across said at least five genes.

Thus, in one embodiment, the method for classifying a patient afflicted with colon cancer as having a good prognosis or a poor prognosis comprises the steps of (1) hybridizing labeled target polynucleotides from a patient afflicted with colon cancer to a microarray containing one of the above colon cancer marker sets; (2) hybridizing standard or control polynucleotides molecules to the microarray, wherein the standard or control molecules are differentially labeled from the target molecules; and (3) determining the difference in transcript levels, or lack thereof, between the target and standard or control, wherein the difference, or lack thereof, determines the patient's prognosis.

As described herein, the invention provides sets of markers useful for distinguishing colon cancer patients with a good prognosis from colon cancer patients with a poor prognosis. Thus, in one embodiment of the above method, the level of polynucleotides (i.e., mRNA or polynucleotides derived therefrom) in a sample from an individual, expressed from the markers provided in TABLE 1, are compared to the level of expression of the same markers from a control, wherein the control comprises marker-related polynucleotides derived from good outcome patients, poor outcome patients, or both. Preferably, the comparison is to both good outcome and poor outcome controls, and preferably the comparison is to polynucleotide pools from a number of good outcome and poor outcome samples, respectively. Where the individual's marker expression most closely resembles or correlates with the good outcome control (or "template"), and does not resemble or correlate with the poor outcome control (or "template"), the individual is classified as having a good prognosis.

As described in EXAMPLES 1-2, a set of experiments was performed in which nucleic acids from individuals with known good outcome or poor outcome status were hybridized against the pool, in order to define the expression templates for the good outcome and poor outcome groups. In accordance with the methods for classifying a human patient afflicted with colon cancer, nucleic acids from each patient afflicted with colon cancer with unknown prognosis are hybridized against the same pool and the expression profile is compared to the templates(s) to determine each patient's prognosis.

For the above embodiments of the method, the full set of markers may be used (i.e., the complete set of markers for TABLES 1-4). In other embodiments, subsets of the markers may be used. In a preferred embodiment, the preferred markers listed in TABLE 5 are used.

The degree of similarity between a patient's cellular constituent profile and a template profile can be determined using any method known in the art. In the simplest case, the profiles can be compared visually in a printout of expression difference data. Alternatively, the similarity can be calculated mathematically.

In one embodiment, the similarity between two patients x and y, or patient x and a template y, expressed as a similarity value, can be calculated using the following equation:

$$S = 1 - \left[ \sum_{i=1}^{N_v} \frac{(x_i - \overline{x})}{\sigma_{x_i}} \frac{(y_i - \overline{y})}{\sigma_{y_i}} \Big/ \sqrt{\sum_{i=1}^{N_v} \left( \frac{x_i - \overline{x}}{\sigma_{x_i}} \right)^2 \sum_{i=1}^{N_v} \left( \frac{y_i - \overline{y}}{\sigma_{y_i}} \right)^2} \right] \quad \text{(Eq. 1)}$$

In Equation (1), X and Y are two patients with components of log ratio $x_i$ and $y_i$, i=1, . . . , N=4250. Associated with every value $x_i$ is error $\sigma_{x_i}$. The smaller the value $\sigma_{x_i}$, the more reliable the measurement.

$$x_i \cdot \overline{x} = \sum_{i=1}^{N_v} \frac{x_i}{\sigma_{x_i}^2} \Big/ \sum_{i=1}^{N_v} \frac{1}{\sigma_{x_i}^2} \quad \text{(Eq. 2)}$$

is the error-weighted arithmetic mean.

In another embodiment, the similarity is represented by a correlation coefficient between the patient's profile $\vec{y}$ and the template. For example, the comparison of the similarity between the transcript levels of the patient; and a predefined template may be accomplished by means of the statistic of a correlation $P_i$ defined as:

$$P_i = (\vec{z}_i \cdot \vec{y}) / (\|\vec{z}_i\| \cdot \|\vec{y}\|) \quad \text{Eq. (5)}$$

where i=1 and 2.

Wherein a template for the good outcome group defined as $(\vec{z}_1)$ (e.g., a profile consisting of the xdev's (the log(ratio/[error of log(ratio)]) listed in the good template column of TABLE 4 is generated using the error-weighted log ratio average of the selected group of genes. Similarly, a template for poor outcome group defined as $(\vec{z}_2)$ (e.g., a profile consisting of the xdev's (the log(ratio/[error of log(ratio)]) listed in the poor template column of TABLE 4 is generated using the error-weighted log ratio average of the selected group of genes. Either one or both of the two classifier parameters ($P_1$ and $P_2$) can then be used to measure degrees of similarities between a patient's profile $\vec{y}$ and the respective templates: $P_1$ measures the similarity between the patient's profile $\vec{y}$ and the good outcome template $\vec{z}_1$ over this selected group of genes. $P_2$ measures the similarity between $\vec{y}$ and the poor outcome template $\vec{z}_2$ over this selected group of genes.

Thus, in one embodiment, patient profile $\vec{y}$ is classified as a good prognosis profile if $P_1$ is greater than a selected correlation threshold or if $P_2$ is equal to or less than a selected correlation threshold. In another embodiment, patient profile $\vec{y}$ is classified as a poor prognosis profile if $P_1$ is less than a selected correlation threshold or if $P_2$ is above a selected correlation threshold. In still another embodiment, patient profile $\vec{y}$ is classified as a good prognosis profile if $P_1$ is greater than a first selected correlation threshold and patient profile $\vec{y}$ is classified as a poor prognosis profile if $P_2$ is greater than a second selected correlation threshold.

In one embodiment, a correlation coefficient above a correlation threshold indicates high similarity, whereas a correlation coefficient below the threshold indicates low similarity. In preferred embodiments, the correlation threshold is set as 0.3, 0.4, 0.5 or 0.6.

In another embodiment, similarity between a patient's profile and a template is represented by a distance between the patient's profile and the template. In one embodiment, a distance below a given value indicates high similarity, whereas a distance equal to or greater than the given value indicates low similarity.

Thus, in a more specific embodiment, the above method of classifying a human patient afflicted with colon cancer as having a good prognosis or a poor prognosis comprises the steps of (1) hybridizing labeled target polynucleotides from a patient afflicted with colon cancer to a microarray containing one of the above marker sets; (2) hybridizing standard or control polynucleotides molecules to the microarray, wherein the standard or control molecules are differentially labeled from the target molecules; and (3) determining the ratio (or difference) of transcript levels between two channels (individual and control), or simply the transcript levels of the patient; and (4) comparing the results from (3) to the predefined templates, wherein said determining is accomplished by means of the statistic of Equation 1 or Equation 5, and wherein the difference, or lack thereof, determines the patient's colon cancer prognosis.

Improving Sensitivity to Expression Level Differences

In using the markers disclosed herein, and, indeed, using any sets of markers to differentiate an individual having one phenotype from another individual having a second phenotype, one can compare the absolute expression of each of the markers in a sample to a control; for example, the control can be the average level of expression of each of the markers, respectively, in a pool of individuals. To increase the sensitivity of the comparison, however, the expression level values are preferably transformed in a number of ways.

For example, the expression level of each of the markers can be normalized by the average expression level of all markers, the expression level of which has been determined, or by the average expression level of a set of control genes. Thus, in one embodiment, the markers are represented by probes on a microarray, and the expression level of each of the markers is normalized by the mean or median expression level across all of the genes represented on the microarray, including any non-marker genes. In a specific embodiment, the normalization is carried out by dividing the median or mean level of expression of all of the genes on the microarray. In another embodiment, the expression levels of the markers is normalized by the mean or median level of expression of a set of control markers. In a specific embodiment, the control markers comprise a set of housekeeping genes. In another specific embodiment, the normalization is accomplished by dividing by the median or mean expression level of the control genes.

The sensitivity of a marker-based assay will also be increased if the expression levels of individual markers are compared to the expression of the same markers in a pool of samples. Preferably, the comparison is to the mean or median expression level of each of the marker genes in the pool of samples. Such a comparison may be accomplished, for example, by dividing by the mean or median expression level of the pool for each of the markers from the expression level of each of the markers in the sample. This has the effect of accentuating the relative differences in expression between markers in the sample and markers in the pool as a whole, making comparisons more sensitive and more likely to produce meaningful results than the use of absolute expression levels alone. The expression level data may be transformed in any convenient way; preferably, the expression level data for all is log transformed before means or medians are taken.

In performing comparisons to a pool, two approaches may be used. First, the expression levels of the markers in the sample may be compared to the expression level of those markers in the pool, where nucleic acid derived from the sample and nucleic acid derived from the pool are hybridized during the course of a single experiment. Such an approach requires that a new pool of nucleic acid be generated for each comparison or limited numbers of comparisons, and is therefore limited by the amount of nucleic acid available. Alternatively, and preferably, the expression levels in a pool, whether normalized and/or transformed or not, are stored on a computer, or on computer-readable media, to be used in comparisons to the individual expression level data from the sample (i.e., single-channel data).

Thus, the current invention provides the following method of classifying a first cell or organism as having one of at least two different phenotypes, where the different phenotypes comprise a first phenotype and a second phenotype. The level of expression of each of a plurality of genes in a first sample from the first cell or organism is compared to the level of expression of each of said genes, respectively, in a pooled sample from a plurality of cells or organisms, the plurality of cells or organisms comprising different cells or organisms exhibiting said at least two different phenotypes, respectively, to produce a first compared value.

The first compared value is then compared to a second compared value, wherein said second compared value is the product of a method comprising comparing the level of expression of each of said genes in a sample from a cell or organism characterized as having said first phenotype to the level of expression of each of said genes, respectively, in the pooled sample. The first compared value is then compared to a third compared value, wherein said third compared value is the product of a method comprising comparing the level of expression of each of the genes in a sample from a cell or organism characterized as having the second phenotype to the level of expression of each of the genes, respectively, in the pooled sample.

Optionally, the first compared value can be compared to additional compared values, respectively, where each additional compared value is the product of a method comprising comparing the level of expression of each of said genes in a sample from a cell or organism characterized as having a phenotype different from said first and second phenotypes but included among the at least two different phenotypes, to the level of expression of each of said genes, respectively, in said pooled sample. Finally, a determination is made as to which of said second, third, and, if present, one or more additional compared values, said first compared value is most similar, wherein the first cell or organism is determined to have the phenotype of the cell or organism used to produce said compared value most similar to said first compared value.

In a specific embodiment of this method, the compared values are each ratios of the levels of expression of each of said genes. In another specific embodiment, each of the levels of expression of each of the genes in the pooled sample are normalized prior to any of the comparing steps. In a more specific embodiment, the normalization of the levels of expression is carried out by dividing by the median or mean level of the expression of each of the genes or dividing by the mean or median level of expression of one or more housekeeping genes in the pooled sample from said cell or organism. In another specific embodiment, the normalized levels of expression are subjected to a log transform, and the comparing steps comprise subtracting the log transform from the log of the levels of expression of each of the genes in the sample. In another specific embodiment, the two or more different phenotypes are good prognosis and poor prognosis of colon cancer. In yet another specific embodiment, the levels of expression of each of the genes, respectively, in the pooled sample or said levels of expression of each of said genes in a sample from the cell or organism characterized as having the first phenotype, second phenotype, or said phenotype different from said first and second phenotypes, respectively, are stored on a computer or on a computer-readable medium In another specific embodiment, the comparison is made between the expression of each of the genes in the sample and the expression of the same genes in a pool representing only one of two or more phenotypes. In the context of prognosis-correlated genes, for example, one can compare the expression levels of prognosis-related genes in a sample to the average level of expression of the same genes in a "good outcome" pool of samples (as opposed to a pool of samples that include samples from patients having poor prognoses and good prognoses). Thus, in this method, a sample is classified as having a good prognosis if the level of expression of prognosis-correlated genes exceeds a chosen coefficient of correlation to the average "good outcome" expression profile (i.e., the level of expression of prognosis-correlated genes in a pool of samples from patients having a "good outcome." Patients whose expression levels correlate more poorly with the "good outcome" expression profile (i.e., whose correlation coefficient fails to exceed the chosen coefficient) are classified as having a poor prognosis.

The method can be applied to subdivisions of these prognostic classes. For example, in a specific embodiment, the phenotype is good prognosis and said determination comprises (1) determining the coefficient of correlation between the expression of said plurality of genes in the sample and of the same genes in said pooled sample; (2) selecting a first correlation coefficient value between 0.4 and +1; and (3) classifying said sample as having a "good prognosis" if said coefficient of correlation equals or is greater than said first correlation coefficient value, or "poor prognosis" if said coefficient of correlation is less than said first correlation coefficient value.

Of course, single-channel data may also be used without specific comparison to a mathematical sample pool. For example, a sample may be classified as having a first or a second phenotype, wherein the first and second phenotypes are related, by calculating the similarity between the expression of at least five markers in the sample, where the markers are correlated with the first or second phenotype, to the expression of the same markers in a first phenotype template and a second phenotype template, by (a) labeling nucleic acids derived from a sample with a fluorophore to obtain a pool of fluorophore-labeled nucleic acids; (b) contacting said fluorophore-labeled nucleic acid with a microarray under conditions such that hybridization can occur, detecting at each of a plurality of discrete loci on the microarray a fluorescent emission signal from said fluorophore-labeled nucleic acid that is bound to said microarray under said conditions; and (c) determining the similarity of marker gene expression in the individual sample to the first and second templates, wherein if said expression is more similar to the first template, the sample is classified as having the first phenotype, and if said expression is more similar to the second template, the sample is classified as having the second phenotype.

Determination of Marker Gene Expression Levels

The expression levels of the marker genes in a sample may be determined by any means known in the art. The expression level may be determined by isolating and determining the level (i.e., amount) of nucleic acid transcribed from each marker gene. Alternatively, or additionally, the level of specific proteins translated from mRNA transcribed from a marker gene may be determined.

The level of expression of specific marker genes can be accomplished by determining the amount of mRNA, or polynucleotides derived therefrom, present in a sample. Any method for determining RNA levels can be used. For example, RNA is isolated from a sample and separated on an agarose gel. The separated RNA is then transferred to a solid support, such as a filter. Nucleic acid probes representing one or more markers are then hybridized to the filter by northern hybridization, and the amount of marker-derived RNA is determined. Such determination can be visual, or machine-aided, for example, by use of a densitometer.

Another method of determining RNA levels is by use of a dot-blot or a slot-blot. In this method, RNA, or nucleic acid derived therefrom, from a sample is labeled. The RNA, or nucleic acid derived therefrom, is then hybridized to a filter containing oligonucleotides derived from one or more marker genes, wherein the oligonucleotides are placed upon the filter at discrete, easily identifiable locations. Hybridization, or lack thereof, of the labeled RNA to the filter-bound oligonucleotides is determined visually or by densitometer. Polynucleotides can be labeled using a radiolabel or a fluorescent (i.e., visible) label.

These examples are not intended to be limiting; other methods of determining RNA abundance are known in the art.

The level of expression of particular marker genes may also be assessed by determining the level of the specific protein expressed from the marker genes. This can be accomplished, for example, by separation of proteins from a sample on a polyacrylamide gel, followed by identification of specific marker-derived proteins using antibodies in a western blot. Alternatively, proteins can be separated by two-dimensional gel electrophoresis systems. Two-dimensional gel electrophoresis is well known in the art and typically involves isoelectric focusing along a first dimension followed by SDS-PAGE electrophoresis along a second dimension. See, e.g., Hames, et al., 1990, *Gel Electrophoresis of Proteins: A Practical Approach*, IRL Press, New York; Shevchenko, et al., *Proc. Nat'l Acad. Sci. USA* 93:1440-1445 (1996); Sagliocco et al., *Yeast* 12:1519-1533 (1996); Lander, *Science* 274:536-539 (1996). The resulting electropherograms can be analyzed by numerous techniques, including mass spectrometric techniques, western blotting and immunoblot analysis using polyclonal and monoclonal antibodies.

Alternatively, marker-derived protein levels can be determined by constructing an antibody microarray in which binding sites comprise immobilized, preferably monoclonal, antibodies specific to a plurality of protein species encoded by the cell genome. Preferably, antibodies are present for a substantial fraction of the marker-derived proteins of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art. Generally, the expression, and the level of expression, of proteins of diagnostic or prognostic interest can be detected through immunohistochemical staining of tissue slices or sections.

Finally, expression of marker genes in a number of tissue specimens may be characterized using a "tissue array" (Kononen, et al., *Nat. Med.* 4(7):844-7 (1998)). In a tissue array, multiple tissue samples are assessed on the same microarray. The arrays allow in situ detection of RNA and protein levels; consecutive sections allow the analysis of multiple samples simultaneously.

Microarrays

In preferred embodiments, polynucleotide microarrays are used to measure expression so that the expression status of each of the markers above is assessed simultaneously. In a specific embodiment, the invention provides for oligonucleotide or cDNA arrays comprising probes hybridizable to the genes corresponding to each of the marker sets described above (i.e., markers to distinguish patients with good versus poor prognosis of colon cancer).

The microarrays provided by the present invention comprise probes hybridizable to the genes corresponding to at least five markers provided in TABLE 1 that are able to distinguish patients with good versus poor prognosis of colon cancer. In particular, the invention provides polynucleotide arrays comprising probes to a subset or subsets of at least 5, 10, 15, 20, 25, 30, 35, 40, 45, 50, 55, 60, 65, 70, 75, 80, 85, 90, 95, up to the full set of 100 markers (SEQ ID NOS:1-100), which distinguish good prognosis and poor prognosis colon cancer patients or tumors. The invention also provides probes to subsets of at least 5, 10, 15, 20, 25, 30, 35, 40, 45, 50, 55, 60, 65, 70, 75, 80, 85, 90, 95, up to the full set of 100 markers (e.g., probes comprising or consisting of SEQ ID NOS:101-200), which distinguish good prognosis and poor prognosis colon cancer patients or tumors.

In specific embodiments, the invention provides polynucleotide arrays in which the colon cancer-related markers described herein comprise at least 50%, 60%, 70%, 80%, 85%, 90%, 95%, or 98% of the probes on said array. In another specific embodiment, the invention provides polynucleotide arrays in which the colon cancer status-related markers selected from TABLE 1 comprise at least 50%, 60%, 70%, 80%, 85%, 90%, 95%, or 98% of the probes on said array. In another specific embodiment, the invention provides polynucleotide arrays in which colon cancer markers selected from TABLE 5 comprise at least 50%, 60%, 70%, 80%, 85%, 90%, 95%, or 98% of the probes on said array.

In yet another specific embodiment, microarrays that are used in the methods disclosed herein optionally comprise markers in addition to at least some of the markers listed in TABLES 1-5. For example, in a specific embodiment, the microarray is a screening or scanning array as described in Altschuler, et al., International Publication No. WO 02/18646, published Mar. 7, 2002, and Scherer, et al., International Publication No. WO 02/16650, published Feb. 28, 2002. The scanning and screening arrays comprise regularly spaced, positionally addressable probes derived from genomic nucleic acid sequence, both expressed and unexpressed. Such arrays may comprise probes corresponding to a subset of, or all of, the markers listed in TABLES 1-5, or a subset thereof as described above, and can be used to monitor marker expression in the same way as a microarray containing only markers listed in TABLES 1-5.

In yet another specific embodiment, the microarray is a commercially available cDNA microarray that comprises at least five of the markers listed in TABLES 1-5. Preferably, a commercially available cDNA microarray comprises all of the markers listed in TABLES 1-5. However, such a microarray may comprise at least 5, 10, 15, 20, 25, 30, 35, 40, 45, 50, 55, 60, 65, 70, 75, 80, 85, 90, 95, up to the full set of 100 markers in TABLE 1. In a specific embodiment of the microarrays used in the methods disclosed herein, the markers that are all or a portion of TABLES 1-5 make up at least 50%, 60%, 70%, 80%, 90%, 95%, or 98% of the probes on the microarray.

General methods pertaining to the construction of microarrays comprising the marker sets and/or subsets above are described in the following sections.

Construction of Microarrays

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter covalently at either the 3' or the 5' end of the polynucleotide. Such hybridization probes are well known in the art (see, e.g., Sambrook, et al., *Molecular Cloning: A Laboratory Manual* (2nd ed.), Vols. 1-3, Cold Spring Harbor Laboratory, Cold Spring Harbor, N.Y. (1989)). Alternatively, the solid support or surface may be a glass or plastic surface. In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In preferred embodiments, a microarray comprises a support or surface with an ordered array of binding (e.g., hybridization) sites or "probes" each representing one of the markers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 1 $cm^2$ and 25 $cm^2$, between 12 $cm^2$ and 13 $cm^2$, or 3 $cm^2$. However, larger arrays are also contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross-hybridize to a given binding site.

The microarrays of the present invention include one or more test probes, each of which has a polynucleotide sequence that is complementary to a subsequence of RNA or DNA to be detected. Preferably, the position of each probe on the solid surface is known. Indeed, the microarrays are preferably positionally addressable arrays. Specifically, each probe of the array is preferably located at a known, predetermined position on the solid support such that the identity (i.e., the sequence) of each probe can be determined from its position on the array (i.e., on the support or surface).

According to the invention, the microarray is an array (i.e., a matrix) in which each position represents one of the markers described herein. For example, each position can contain a DNA or DNA analogue based on genomic DNA to which a particular RNA or cDNA transcribed from that genetic marker can specifically hybridize. The DNA or DNA analogue can be, e.g., a synthetic oligomer or a gene fragment. In one embodiment, probes representing each of the markers is present on the array. In a preferred embodiment, the array comprises probes corresponding to at least 5 markers listed in TABLE 1, such as at least 10, 15, 20, 25, 30, 35, 40, 45, 50, 55, 60, 65, 60, 75, 80, 85, 90, 95, or all 100 of the markers in TABLE 1.

Preparing Probes for Microarrays

As noted above, the "probe" to which a particular polynucleotide molecule specifically hybridizes according to the invention contains a complementary genomic polynucleotide sequence. The probes of the microarray preferably consist of nucleotide sequences of no more than 1,000 nucleotides. In some embodiments, the probes of the array consist of nucleotide sequences of 10 to 1,000 nucleotides. In a preferred embodiment, the nucleotide sequences of the probes are in the range of 10 to 200 nucleotides in length and are genomic sequences of a species of organism, such that a plurality of different probes is present, with sequences complementary and thus capable of hybridizing to the genome of such a species of organism, sequentially tiled across all or a portion of such genome. In other specific embodiments, the probes are in the range of 10 to 30 nucleotides in length, in the range of 10 to 40 nucleotides in length, in the range of 20 to 50 nucleotides in length, in the range of 40 to 80 nucleotides in length, in the range of 50 to 150 nucleotides in length, in the range of 80 to 120 nucleotides in length, and most preferably are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically, each probe on the microarray will be between 10 bases and 50,000 bases in length, usually between 300 bases and 1,000 bases in length. PCR methods are well known in the art, and are described, for example, in Innis, et al., eds., *PCR Protocols: A Guide to Methods and Applications*, Academic Press Inc., San Diego, Calif. (1990). It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler, et al., *Nucleic Acid Res.* 14:5399-5407 (1986); McBride, et al., *Tetrahedron Lett.* 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm, et al., *Nature* 363:566-568 (1993); U.S. Pat. No. 5,539,083). Probes are preferably selected using an algorithm that takes into account binding energies, base composition, sequence complexity, cross-hybridization binding energies, and secondary structure (see Friend, et al., International Publication No. WO 01/05935, published Jan. 25, 2001; Hughes, et al., *Nat. Biotech.* 19:342-7 (2001)).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

Attaching Probes to the Solid Surface

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena, et al., *Science* 270:467-470 (1995). This method is especially useful for preparing microarrays of cDNA (see also, DeRisi, et al., *Nature Genetics* 14:457-460 (1996); Shalon, et al., *Genome Res.* 6:639-645 (1996); and Schena, et al., *Proc. Natl. Acad. Sci. USA* 93:10539-11286 (1995)).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor, et al., *Science* 251:767-773 (1991); Pease et al., *Proc. Natl. Acad. Sci. USA* 91:5022-5026 (1994); Lockhart, et al., *Nature Biotechnology* 14:1675, 1996; U.S. Pat. Nos. 5,578,832; 5,556,752; and 5,510,270) or other methods for rapid synthesis and deposition of defined oligonucleotides (Blanchard, et al., *Biosensors & Bioelectronics* 11:687-690). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, *Nuc. Acids. Res.* 20:1679-1684 (1992)), may also be used. In principle, and as noted, supra, any type of array, for example, dot blots on a nylon hybridization membrane (see Sambrook, et al., *Molecular Cloning: A Laboratory Manual* (2nd ed.), Vols. 1-3, Cold Spring Harbor Laboratory, Cold Spring Harbor, N.Y. (1989)) could be used. However, as will be recognized by those skilled in the art, very small arrays will frequently be preferred because hybridization volumes will be smaller.

In one embodiment, the arrays of the present invention are prepared by synthesizing polynucleotide probes on a support. In such an embodiment, polynucleotide probes are attached to the support covalently at either the 3' or the 5' end of the polynucleotide.

In a particularly preferred embodiment, microarrays of the invention are manufactured by means of an ink jet printing device for oligonucleotide synthesis, e.g., using the methods and systems described by Blanchard in U.S. Pat. No. 6,028,189; Blanchard, et al., *Biosensors and Bioelectronics* 11:687-690 (1996); Blanchard, *Synthetic DNA Arrays in Genetic Engineering*, Vol. 20 (1998), J. K. Setlow, ed., Plenum Press, New York, pp. 111-123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 $cm^2$. The polynucleotide probes are attached to the support covalently at either the 3' or the 5' end of the polynucleotide.

Target Polynucleotide Molecules

The polynucleotide molecules which may be analyzed by the present invention (the "target polynucleotide molecules") may be from any clinically relevant source, but are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly$(A)^+$ messenger RNA (mRNA) or fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. Nos. 5,545,522, 5,891,636, or 5,716,785). Methods for preparing total and poly$(A)^+$ RNA are well known in the art, and are described generally, e.g., in Sambrook, et al., *Molecular Cloning: A Laboratory Manual* (2nd ed.), Vols. 1-3, Cold Spring Harbor Laboratory, Cold Spring Harbor, N.Y. (1989). In one embodiment, RNA is extracted from cells of the various types of interest in this invention using guanidinium thiocyanate lysis followed by CsCl centrifugation (Chirgwin, et al., *Biochemistry* 18:5294-5299 (1979)). In another embodiment, total RNA is extracted using a silica gel-based column, commercially available examples of which include RNeasy (Qiagen, Valencia, Calif.) and StrataPrep (Stratagene, La Jolla, Calif.). In an alternative embodiment, which is preferred for *S. cerevisiae*, RNA is extracted from cells using phenol and chloroform, as described in *Current Protocols in Molecular Biology*, Ausubel, et al., eds., Vol III, Green Publishing Associates, Inc., John Wiley & Sons, Inc., New York, 1989, pp. 13.12.1-13.12.5. Poly(A)±RNA can be selected, e.g., by selection with oligo-dT cellulose or, alternatively, by oligo-dT primed reverse transcription of total cellular RNA. In one embodiment, RNA can be fragmented by methods known in the art, e.g., by incubation with $ZnCl_2$, to generate fragments of RNA. In another embodiment, the polynucleotide molecules analyzed by the invention comprise cDNA, or PCR products of amplified RNA or cDNA.

In one embodiment, total RNA, mRNA, or nucleic acids derived therefrom, is isolated from a sample taken from a person afflicted with colon cancer. Target polynucleotide molecules that are poorly expressed in particular cells may be enriched using normalization techniques (Bonaldo, et al., *Genome Res.* 6:791-806 (1996)).

As described above, the target polynucleotides are detectably labeled at one or more nucleotides. Any method known in the art may be used to detectably label the target polynucleotides. Preferably, this labeling incorporates the label uniformly along the length of the RNA, and more preferably, the labeling is carried out at a high degree of efficiency. One embodiment for this labeling uses oligo-dT primed reverse transcription to incorporate the label; however, conventional methods of this method are biased toward generating 3' end fragments. Thus, in a preferred embodiment, random primers (e.g., 9-mers) are used in reverse transcription to uniformly incorporate labeled nucleotides over the full length of the target polynucleotides. Alternatively, random primers may be used in conjunction with PCR methods or T7 promoter-based in vitro transcription methods in order to amplify the target polynucleotides.

In a preferred embodiment, the detectable label is a luminescent label. For example, fluorescent labels, bioluminescent labels, chemiluminescent labels, and colorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.). In another embodiment, the detectable label is a radiolabeled nucleotide.

In a further preferred embodiment, target polynucleotide molecules from a patient sample are labeled differentially from target polynucleotide molecules of a standard. The standard can comprise target polynucleotide molecules from normal individuals (i.e., those not afflicted with colon cancer). In a highly preferred embodiment, the standard comprises target polynucleotide molecules pooled from samples from normal individuals or tumor samples from individuals having colon cancer tumors. In another embodiment, the target polynucleotide molecules are derived from the same individual, but are taken at different time points, and thus indicate the efficacy of a treatment by a change in expression of the markers, or lack thereof, during and after the course of treatment (i.e., chemotherapy, radiation therapy, or cryotherapy), wherein a change in the expression of the markers from a poor prognosis pattern to a good prognosis pattern indicates that the treatment is efficacious. In this embodiment, different time points are differentially labeled.

Hybridization to Microarrays

Nucleic acid hybridization and wash conditions are chosen so that the target polynucleotide molecules specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self-complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook, et al., *Molecular Cloning: A Laboratory Manual* (2nd ed.), Vols. 1-3, Cold Spring Harbor Laboratory, Cold Spring Harbor, N.Y. (1989), and in Ausubel, et al., *Current Protocols in Molecular Biology*, Vol. 2, Current Protocols Publishing, New York (1994). Typical hybridization conditions for the cDNA microarrays of Schena, et al. are hybridization in 5×SSC plus 0.2% SDS at 65'C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena, et al., *Proc. Natl. Acad. Sci. USA* 93:10614 (1993)). Useful hybridization conditions are also provided in, e.g., Tijessen, *Hybridization With Nucleic Acid Probes*, Elsevier Science Publishers B. V., 1993; and Kricka, *Nonisotopic DNA Probe Techniques*, Academic Press, San Diego, Calif., 1992.

Particularly preferred hybridization conditions include hybridization at a temperature at or near the mean melting temperature of the probes (e.g., within 5° C., more preferably within 2° C.) in 1 M NaCl, 50 mM MES buffer (pH 6.5), 0.5% sodium sarcosine and 30% formamide.

Signal Detection and Data Analysis

When fluorescently labeled probes are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon, et al., "A DNA Microarray System for Analyzing Complex DNA Samples Using Two-Color Fluorescent Probe hybridization," *Genome Research* 6:639-645 (1996), which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena, et al., *Genome Res.* 6:639-645 (1996), and in other references cited herein. Alternatively, the fiber-optic bundle described by Ferguson, et al., *Nature Biotech.* 14:1681-1684 (1996), may be used to monitor mRNA abundance levels at a large number of sites simultaneously.

Signals are recorded and, in a preferred embodiment, analyzed by computer, e.g., using a 12 or 16 bit analot-to-digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated in association with the different colon cancer-related condition.

Diagnostic Tool

In one embodiment, the invention provides a diagnostic tool for predicting colon cancer prognosis in a human patient, the diagnostic tool comprising reagents for detecting at least five markers derived from any one of TABLES 1-5. The diagnostic tool may assume a variety of formats, such as, for example, libraries of soluble molecules, libraries of compounds tethered to resin beads, silica chips, or other solid supports. In one embodiment, the diagnostic tool of the invention is a nucleic acid array. In another embodiment, the diagnostic tool of the invention is a microarray, as described herein. For example, all or a subset of the genes on the marker gene list provided in TABLES 1-5 can be synthesized on a small-scale microarray using ink-jet technology. Each gene in TABLES 1-5 may be represented by single or multiple oligonucleotide probes, depending on its sequence uniqueness across the genome. This custom designed mini-array, in combination with the sample preparation protocol described herein, can be used as a diagnostic/prognostic kit, for example, in clinics Kits The present invention further provides for kits comprising the marker sets above. In a preferred embodiment, the kit contains a diagnostic tool for predicting colon cancer prognosis in a human patient, the diagnostic tool comprising reagents for detecting at least five markers derived from any one of TABLES 1-5.

In one embodiment, the kit contains at least one microarray comprising a plurality of polynucleotide probes each complementary and hybridizable to a sequence of at least five different genes listed in any one of TABLES 1-5. In one embodiment, the kit further comprises software for the data analyses described herein.

Method of Assigning a Therapeutic Regimen Based on Prognosis

Once colon cancer patients have been classified as having a "good prognosis" or "poor prognosis," this information can be combined with the patient's clinical data to determine an appropriate treatment regimen. For example, the patient clinical data may include the presence or absence of additional risk factors for colon cancer including colorectal polyps, family history of colon cancer, ulcerative colitis, Crohn's disease, and dietary factors. The patient's clinical data may include the presence or absence of symptoms associated with colon cancer such as diarrhea, constipation, (or other changes in bowel habits), blood in the stool, unexplained anemia, abdominal pain in the lower abdomen, intestinal obstruction, unexplained weight loss, and narrow stools.

For example, patients who are classified as having a "good prognosis" profile are typically treated with surgery to remove the cancer cells, without chemotherapy or radiation. Patients who are classified as having a "poor prognosis" are assigned a therapeutic regimen that typically includes surgery and further comprises chemotherapy and/or radiation treatment.

For example, patients who are classified as having a "poor prognosis" may be treated with one or more of the following chemotherapeutic agents: 5-fluorouracil, Capecitabine, Leucovorin, Oxaliplatin, Irinotecan, Bevacizumab, Cetuximab, Panitumumab, Bortezomib, Oblimersen, Gefitinib or Erlotinib.

In some embodiments of the invention, a method of assigning treatment to a colon cancer patient is provided comprising classifying the colon cancer patient as having a good prognosis or a poor prognosis as determined by comparison to a good outcome and/or poor outcome template, determining the stage of disease in the colon cancer patient, and assigning a course of treatment for the patient.

The patient clinical data may also include the staging of the colon cancer, as shown in TABLE 6.

TABLE 6

COLORECTAL CANCER: STAGING, TREATMENT AND 5 YEAR SURVIVAL

| Stage | TNM | Group | Group | Duke's | 5 Year Survival after Surgery | Adjvant Chemotherapy Recommendation: |
|---|---|---|---|---|---|---|
| Stage I | T1 | N0 | M0 | Duke's A | 97% | No |
| | T2 | N0 | M0 | | 90% | No |
| Stage II | T3 | N0 | M0 | Duke's B | 78% | Debatable |
| | T4 | N0 | M0 | | 63% | Debatable |
| Stage III | any T | N1-3 | M0 | Duke's C | 66% | Recommended |
| | any T | N > 4 | M0 | | 37% | Recommended |
| Stage IV | any T | any N | M1 (distant) | Duke's D | <10% | NA |

As shown in TABLE 6 above, there are at least two different methods of classifying the stage of colon cancer. The Duke's system uses four stages lettered A, B, C, D. Another method is called the TNM staging system, also shown in TABLE 6. This system uses four stages, I, II, III, and IV, which correspond to the Duke system as shown, but each stage is further broken down to reflect more detailed information. "T" is used to describe the size and extent of the main tumor (T1-T4). The higher the number, the more invasive the tumor. "N" is used to describe whether lymph nodes are involved, and how many "M" is used to describe the degree of metastases to other parts of the body. MO means there is no metastases.

As can be seen in TABLE 6, prognosis is highly dependent on the stage of colorectal cancer. Duke's Stage A indicates that the cancer has only penetrated the mucosa (most superficial layer) of the bowel wall. Duke's Stage B indicates that the cancer has penetrated into the muscular layer of the bowel wall. Duke's Stage C indicates that the cancer has spread to nearby lymph nodes. Duke's stage D indicates that the cancer has spread to other sites (distant metastasis), such as the liver and the lung.

Standard treatment for colon cancer involves surgery to remove the affected section of the colon. As shown in TABLE 6, surgical treatment of Stage I and Stage II disease appears to be quite effective, with a 5 year survival rate of at least 90%, and 63%, respectively. Stage III indicates lymph node involvement, and patients with 1 to 3 lymph nodes involved have a higher 5 year survival rate after surgery (66%) than those with 4 or more lymph nodes involved (37%). As shown in TABLE 6, under a standard treatment protocol based on staging information, adjuvant chemotherapy is not recommended for Stage I disease, may be used for Stage II, and is recommended for Stage III colon cancer. The present invention provides improved prognostic methods that can be combined with the staging information to choose the most appropriate course of therapy for colorectal cancer patients.

Thus, in one embodiment, the invention provides for a method of assigning a therapeutic regimen to a colon cancer patient, comprising (a) classifying said patient as having a "poor prognosis" or a "good prognosis" on the basis of the levels of expression of at least five of the genes for which markers are listed in TABLE 1, (b) classifying the patient with respect to colon cancer staging, and (c) assigning said patient a therapeutic regimen, said therapeutic regimen comprising no adjuvant chemotherapy if the patient is classified as having a good prognosis or comprising adjuvant chemotherapy if said patient is classified as having a poor prognosis.

For example, as described above, patients may be classified according to the Dukes Staging method. In one embodiment, a patient determined to have a Dukes B stage colon cancer and classified as having a poor prognosis profile in accordance with the methods of the invention would be assigned to treatment with chemotherapy. In another embodiment, a patient determined to have a Dukes C stage colon cancer and classified as having a good prognosis profile in accordance with the methods of the invention would not be given chemotherapy.

Computer-Facilitated Analysis

The present invention also provides a computer system for predicting disease outcome in a patient, the computer system comprising: a computer having a processor and a memory, the memory having executable code stored thereon for execution by the processor for performing the steps of: obtaining gene expression profiles from a plurality of genes from cell samples, wherein the cell samples are derived from one or more individuals afflicted with colon cancer, comparing said gene expression profiles to a control to predict disease outcome in the patient. The computer system further comprises a display device for displaying to a user the results (i.e., classification of a sample with regard to prognosis) of the methods of the invention.

The analytical methods described in the previous sections can be implemented by use of the following computer systems according to the following programs and methods. A computer system comprises internal components linked to external components. The internal components of a typical computer system include a processor element interconnected with a main memory. For example, the computer system can be an Intel 8086-, 80386-, 80486-, Pentium™, or Pentium™-based processor with preferably 32 MB or more of main memory. The computer system may also be a Macintosh or a Macintosh-based system, but may also be a minicomputer or mainframe.

The external components may include mass storage. This mass storage can be one or more hard disks (which are typically packaged together with the processor and memory). Such hard disks are preferably of 1 GB or greater storage capacity. Other external components include a user interface device, which can be a monitor, together with an inputting device, which can be a "mouse", or other graphic input devices, and/or a keyboard. A printing device can also be attached to the computer.

Typically, a computer system is also linked to a network, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant invention. These software components collectively cause the computer system to function according to the methods of this invention. These software components are typically stored on the mass storage device. A software component comprises the operating system, which is responsible for managing the computer system and its network interconnections. This operating system can be, for example, of the Microsoft Windows® family, such as Windows 3.1, Windows 95, Windows 98, Windows 2000, or Windows NT, or may be of the Macintosh OS family, or may be UNIX, or an operating system specific to a minicomputer or mainframe.

The software component represents common languages and functions conveniently present on the system to assist programs in implementing the methods specific to this invention. Many high- or low-level computer languages can be used to program the analytic methods of this invention. Instructions can be interpreted during runtime or compiled. Preferred languages include C/C++, FORTRAN and JAVA. Most preferably, the methods of this invention are programmed in mathematical software packages that allow symbolic entry of equations and high-level specification of processing, including some or all of the algorithms to be used, thereby freeing a user of the need to procedurally program individual equations or algorithms. Such packages include Mathlab from Mathworks (Natick, Mass.), MATHEMATICA® software package from Wolfram Research (Champaign, Ill.), or S-PLUS® software package from Math Soft (Cambridge, Mass.). Specifically, the software component includes the analytic methods of the invention as programmed in a procedural language or symbolic package.

The software to be included with the kit comprises the data analysis methods of the invention as disclosed herein. In particular, the software may include mathematical routines for marker discovery, including the calculation of similarity values between clinical categories (e.g., good prognosis or poor prognosis) and marker expression. The software may also include mathematical routines for calculating the similarity between sample marker expression and control marker expression, and/or using array-generated fluorescence data to determine the clinical classification of a sample.

Additionally, the software may also include mathematical routines for determining the prognostic outcome and recommended therapeutic regimen for a particular colon cancer patient. Such software would include instructions for the computer system's processor to receive data structures that include the level of expression of five or more of the marker genes listed in TABLE 1 in a colon cancer tumor sample obtained from the colon cancer patient; the mean level of expression of the same genes in a control or template; and, optionally, additional information regarding the colon cancer patient's clinical information. The software may additionally include mathematical routines for transforming the hybridization data and for calculating the similarity between the expression levels for the marker genes in the patient's colon cancer tumor sample and the control or template. In a specific embodiment, the software includes mathematical routines for calculating a similarity metric, such as a coefficient of correlation, representing the similarity between the expression levels for the marker genes in the patient's colon cancer tumor sample and the control or template, and expressing the similarity as that similarity metric.

The software would include decisional routines that integrate the patient's clinical and marker gene expression data, and recommend a course of therapy. In one embodiment, for example, the software causes the processor unit to receive expression data for the patient's tumor sample, calculate a metric of similarity of these expression values to the values for the same genes in a template or control, compare this similarity metric to a pre-selected similarity metric threshold or thresholds that differentiate prognostic groups, assign the patient to the prognostic group, and, on the basis of the prognostic group, assign a recommended therapeutic regimen. In a specific example, the software additionally causes the processor unit to receive data structures comprising clinical information about the colon cancer patient. In a more specific example, such clinical information includes the patient's age and stage of colon cancer.

Where the control is an expression template comprising expression values for marker genes within a group of colon cancer patients, the control can comprise either hybridization data obtained at the same time (i.e., in the same hybridization experiment) as the patient's individual hybridization data, or can be a set of hybridization or marker expression values stored on a computer, or on computer-readable media. If the latter is used, new patient hybridization data for the selected marker genes, obtained from initial or follow-up tumor samples, or suspected tumor samples, can be compared to the stored values for the same genes without the need for additional control hybridizations. However, the software may additionally comprise routines for updating the control data set, i.e., to add information from additional colon cancer patients or to remove existing members of the control data set, and, consequently, for recalculating the average expression level values that comprise the template. In another specific embodiment, said control comprises a set of single-channel mean hybridization intensity values for each of said at least five or more of the marker genes from TABLE 1 stored on a computer-readable medium Clinical data relating to a colon cancer patient, and used by the computer program products of the invention, can be contained in a database of clinical data in which information on each patient is maintained in a separate record, which record may contain any information relevant to the patient, the patient's medical history, treatment, prognosis, or participation in a clinical trial or study, including expression profile data generated as part of an initial diagnosis or for tracking the progress of the colon cancer during treatment.

Thus, one embodiment of the invention provides a computer program product for classifying a colon cancer patient according to prognosis, the computer program product for use in conjunction with a computer having a memory and a processor, the computer program product comprising a computer-readable storage medium having a computer program mechanism encoded thereon, wherein said computer program product can be loaded into the one or more memory units of a computer and causes the one or more processor units of the computer to execute the steps of (a) receiving a first data structure comprising the level of expression of at least five of the genes for which markers are listed in TABLE 1 in a cell sample taken from said colon cancer patient; (b) determining the similarity of the level of expression of said at least five genes to control levels of expression of said at least five genes to obtain a patient similarity value; (c) comparing said patient similarity value to a selected first threshold value of similarity of said level of expression of said genes to said control levels of expression to obtain first similarity threshold values; and (d) classifying said colon cancer patient as having a first prognosis if said patient similarity value exceeds said first threshold similarity values, and a second prognosis if said patient similarity value does not exceed said first threshold similarity value.

In a specific embodiment of said computer program product, said first threshold value of similarity is stored in said computer. In another more specific embodiment, said first prognosis is a "good prognosis," said second prognosis is a "poor prognosis," and wherein said computer program mechanism may be loaded into the memory and further cause said one or more processor units of said computer to execute the step of assigning said colon cancer patient a therapeutic regimen comprising no adjuvant chemotherapy if the patient is classified as having a good prognosis, or comprising chemotherapy if said patient has any other expression profile. In another specific embodiment, said computer program mechanism may be loaded into the memory and further cause said one or more processor units of the computer to execute the steps of receiving a data structure comprising clinical data specific to said colon cancer patient.

In a more specific embodiment, said single-channel hybridization intensity values are log transformed. The computer implementation of the method, however, may use any desired transformation method.

In another specific embodiment, the computer program product causes said processing unit to perform said comparing step (c) by calculating the difference between the level of expression of each of said genes in said cell sample taken from said colon cancer patient and the level of expression of the same genes in said control. In another specific embodiment, the computer program product causes said processing unit to perform said comparing step (c) by calculating the mean log level of expression of each of said genes in said control to obtain a control mean log expression level for each gene, calculating the log expression level for each of said genes in a colon cancer sample from said colon cancer patient to obtain a patient log expression level, and calculating the difference between the patient log expression level and the control mean log expression for each of said genes. In another specific embodiment, the computer program product causes said processing unit to perform said comparing step (c) by calculating similarity between the level of expression of each of said genes in said cell sample taken from said colon cancer patient and the level of expression of the same genes in said control, wherein said similarity is expressed as a similarity value. In a more specific embodiment, said similarity value is a correlation coefficient. The similarity value may, however, be expressed as any art-known similarity metric.

In an exemplary implementation, to practice the methods of the present invention, a user first loads experimental data into the computer system. Data can be directly entered by the user from a keyboard, or remotely from other computer systems linked by a network connection, or on removable storage media such as a CD-ROM, floppy disk (not illustrated), tape drive (not illustrated), ZIP® drive (not illustrated), or through the network. Next, the user causes execution of expression profile analysis software which performs the methods of the present invention.

In another exemplary implementation, a user first loads experimental data and/or databases into the computer system. This data is loaded into the memory from the storage media or from a remote computer, preferably from a dynamic geneset database system, through the network. Next, the user causes execution of software that performs the steps of the present invention.

Alternative computer systems and software for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

EXAMPLES

The following examples merely illustrate the best mode now contemplated for practicing the invention, but should not be construed to limit the invention. All literature citations herein are expressly incorporated by reference.

Example 1

This Example describes a gene expression profiling study that was done in a plurality of primary colon tumor samples obtained from colon cancer patients during surgical resection.

Sample Collection

This study was approved by the Medical Ethics Committee of the Netherlands Cancer Institute. 118 colorectal cancer patients that were treated at the Netherlands Cancer Institute or the Leiden University Medical Center, of whom primary colon tumor specimens, including rectumsigmoid localization of the tumor, were selected for this study.

Patient Characteristics:

Characteristics of the patients included in this study are listed below in TABLE 7. All patients had previously undergone resection of a primary colorectal tumor.

In this retrospective study, the samples were designated based on the patient outcome after at least three years of follow up after the samples were obtained. A "poor outcome" patient designation was based on patients who developed a metastasis after excision of the primary tumor (36 patients, of which 30 developed a metastasis (tumor outside the colon) within three years, of which 80% of the metastasis positive patients died). A "good outcome" patient designation was based on patients who had not developed a metastasis after tumor excision (82 patients, of which 70 had a follow-up time of greater than three years).

TABLE 7

INFORMATION ABOUT PATIENTS FROM WHICH TUMOR SAMPLES WERE COLLECTED:

| Sample ID (N = 118) | Metastasis | Time (yrs) to Metastasis | Total Follow-up Time (yrs) |
|---|---|---|---|
| US-963802 | 0 | NA | 8.82 |
| US-963803 | 0 | NA | 12.35 |
| US-963804 | 0 | NA | 22.51 |
| US-963805 | 1 | 0 | 0.416 |
| US-963806 | 0 | NA | 11.26 |
| US-963807 | 1 | 2.51 | 5.25 |
| US-963810 | 0 | NA | 13.26 |
| US-963812 | 0 | NA | 16.7 |
| US-963813 | 0 | NA | 8.35 |
| US-963814 | 0 | NA | 5.83 |
| US-963815 | 1 | 0 | 2.18 |
| US-963816 | 0 | NA | 9.89 |
| US-963818 | 0 | NA | 7.19 |
| US-963819 | 0 | NA | 2.75 |
| US-963820 | 0 | NA | 14.8 |
| US-963821 | 1 | 1.06 | 2.41 |
| US-963823 | 0 | NA | 14.26 |
| US-963824 | 0 | NA | 6.61 |
| US-963828 | 0 | NA | 8.48 |
| US-963829 | 1 | 0 | 4.29 |
| US-963832 | 0 | NA | 10.08 |
| US-963833 | 0 | NA | 7.35 |
| US-963834 | 0 | NA | 10.91 |
| US-963835 | 0 | NaN | 4.85 |
| US-963836 | 0 | NA | 10.64 |
| US-963837 | 0 | NA | 5.42 |
| US-963838 | 0 | NA | 0.67 |
| US-963839 | 0 | NA | 4.72 |
| US-963840 | 0 | NA | 7.86 |
| US-963844 | 0 | NA | 8.34 |
| US-963846 | 0 | NA | 6.09 |
| US-963847 | 0 | NA | 0.22 |
| US-963851 | 1 | 0 | 0.97 |
| US-963853 | 0 | NA | 5.49 |
| US-963854 | 1 | 0.99 | 1.07 |

TABLE 7-continued

INFORMATION ABOUT PATIENTS FROM WHICH TUMOR SAMPLES WERE COLLECTED:

| Sample ID (N = 118) | Metastasis | Time (yrs) to Metastasis | Total Follow-up Time (yrs) |
|---|---|---|---|
| US-963855 | 0 | NA | 5.35 |
| US-963856 | 1 | 2.19 | 3.37 |
| US-963857 | 0 | NA | 4.64 |
| US-963862 | 0 | NA | 2.86 |
| US-963863 | 1 | 3.92 | 2.41 |
| US-963864 | 1 | 0 | 3.91 |
| US-963881 | 0 | NA | 13.05 |
| US-963887 | 0 | NA | 7.20 |
| US-963888 | 0 | NA | 7.87 |
| US-963891 | 0 | NA | 13.64 |
| US-963897 | 1 | 2.70 | 4.25 |
| US-963905 | 0 | NA | 0.95 |
| US-963906 | 0 | NA | 2.6 |
| US-963907 | 0 | NA | 6.48 |
| US-963908 | 0 | NA | 5.90 |
| US-963910 | 0 | NA | 10.10 |
| US-963911 | 0 | NA | 9.64 |
| US-963912 | 0 | NA | 9.65 |
| US-963913 | 0 | NA | 10.43 |
| US-963914 | 0 | NA | 5.73 |
| US-963915 | 0 | NA | 1.30 |
| US-963916 | 0 | NA | 10.02 |
| US-963917 | 0 | NA | 9.56 |
| US-963918 | 0 | NA | 9.60 |
| US-963919 | 0 | NA | 9.34 |
| US-963920 | 0 | NA | 8.64 |
| US-963922 | 1 | 5.60 | 5.93 |
| US-963923 | 0 | NA | 5.88 |
| US-963924 | 0 | NA | 8.64 |
| US-963925 | 1 | 1.92 | 2.75 |
| US-963926 | 1 | 1.97 | 3.41 |
| US-963928 | 0 | NA | 5.50 |
| US-963929 | 0 | NA | 8.57 |
| US-963931 | 0 | NA | 7.55 |
| US-963935 | 0 | NA | 0.15 |
| US-963936 | 0 | NA | 6.11 |
| US-963937 | 0 | NA | 6.36 |
| US-963941 | 0 | NA | 6.02 |
| US-963945 | 1 | 0.38 | 2.56 |
| US-963946 | 0 | NA | 12.60 |
| US-963948 | 0 | NA | 11.55 |
| US-963949 | 0 | NA | 3.15 |
| US-963952 | 0 | NA | 7.65 |
| US-963953 | 0 | NA | 4.84 |
| US-963954 | 1 | 0.80 | 3.02 |
| US-963956 | 1 | 3.41 | 5.43 |
| US-963957 | 0 | NA | 14.70 |
| US-963960 | 0 | NA | 4.44 |
| US-963961 | 0 | NA | 11.0 |
| US-963977 | 1 | 0.97 | 1.60 |
| US-963978 | 1 | 0.45 | 2.30 |
| US-963822 | 1 | 1.56 | 4.67 |
| US-963830 | 0 | NA | 11.69 |
| US-963843 | 1 | 0 | 1.05 |
| US-963852 | 1 | 0 | 0.43 |
| US-963858 | 1 | 1.82 | 3.54 |
| US-963866 | 0 | NA | 3.41 |
| US-963867 | 1 | 2.62 | 6.88 |
| US-963871 | 0 | NA | 2.63 |
| US-963873 | 0 | NA | 14.34 |
| US-963874 | 0 | NA | 12.55 |
| US-963875 | 1 | 3.59 | 3.65 |
| US-963878 | 1 | 2.36 | 2.46 |
| US-963883 | 0 | NA | 9.06 |
| US-963885 | 0 | NA | 11.30 |
| US-963886 | 0 | NA | 0.34 |
| US-963889 | 0 | NaN | 6.925 |
| US-963893 | 1 | 4.13 | 4.20 |
| US-963894 | 1 | 1.20 | 1.50 |
| US-963898 | 1 | 0.83 | 1.0 |
| US-963899 | 1 | 0 | 3.75 |
| US-963900 | 1 | 1.58 | 3.53 |
| US-963901 | 1 | 0.70 | 1.53 |
| US-963902 | 1 | 0.93 | 3.15 |

TABLE 7-continued

| INFORMATION ABOUT PATIENTS FROM WHICH TUMOR SAMPLES WERE COLLECTED: | | | |
|---|---|---|---|
| Sample ID (N = 118) | Metastasis | Time (yrs) to Metastasis | Total Follow-up Time (yrs) |
| US-963904 | 0 | NA | 10.17 |
| US-963927 | 1 | 1.25 | 4.89 |
| US-963930 | 0 | NA | 1.60 |
| US-963939 | 0 | NA | 6.42 |
| US-963940 | 0 | NA | 1.066 |
| US-963942 | 1 | 4.24 | 6.11 |
| US-963950 | 0 | NA | 9.76 |
| US-963951 | 1 | 1.04 | 3.04 |
| US-963955 | 0 | NA | 4.63 |

NA = not applicable
"1" = metastasis
"0" = no metastasis

Sample Preparation and Analysis

FIG. 1 is a flow diagram illustrating the experimental procedures for measuring differential changes in mRNA transcript abundance in colorectal tumor samples isolated from the 118 colon cancer patients used in this study. In each experiment, Cy5-labeled cRNA from one tumor X is hybridized on a 25K human microarray together with a Cy3-labeled cRNA pool made of cRNA samples from tumors 1, 2, . . . N. The digital expression data were obtained by scanning and image processing. The error modeling allowed for the assignment of a p-value to each transcript ratio measurement.

RNA isolation, Amplification and Labeling

The tumor samples were frozen after excision. Samples were processed essentially as described in van't Veer, L. J., et al., *Nature* 415:530-536 (2002), hereby incorporated by reference. Briefly described, 30 frozen sections of 30 μM thickness were used for total RNA isolation of each snap frozen tumor specimen. Total RNA was isolated with RNAzol™ B (Campro Scientific, Veenendaal, The Netherlands) according to the manufacturer's protocol, including homogenization of the tissue using a Polytron PT-MR2100 (Merck, Amsterdam, The Netherlands) and finally dissolved in RNAse-free $H_2O$. The quality of the total RNA was assessed by A260/A280 ratio and had to be between 1.7 and 2.1 as well as visual inspection of the RNA on an agarose gel which should indicate a stronger 28S ribosomal RNA band compared to the 18S ribosomal RNA band, subsequently, 25 μg of total RNA was DNase treated using the Qiagen RNASE-free DNase kit and RNeasy spin columns (Qiagen Inc, GmbH, Germany) according to the manufacturer's protocol. DNase treated total RNA was dissolved in RNASE-free $H_2O$ to a final concentration of 0.2 μg/μl.

cRNA was generated by in vitro transcription using T7 RNA polymerase on 5 μg total RNA as follows. An oligo-dT primer containing a T7 RNA polymerase promoter sequence was used to prime first strand cDNA synthesis, and random primers (pdN6) were used to prime second strand cDNA synthesis by MMLV reverse transcriptase. This reaction yielded a double-stranded cDNA that contained the T7 RNA polymerase (T7RNAP) promoter. The double-stranded cDNA was then transcribed into cRNA by T7RNAP.

Pooling of Samples: A reference cRNA pool was formed by pooling equal amounts of cRNA from each of the 118 individual tumor specimens.

Labeling:

The cRNA from each specimen was labeled with Cy3 or Cy5 dyes using a two-step process. First, allylamine-derivatized nucleotides were enzymatically incorporated into cRNA products. For cRNA labeling, a 3:1 mixture of 5-(3-Aminoallyl)uridine 5'-triphosphate (Sigma) and UTP was substituted for UTP in the in vitro transcription (IVT) reaction. Allylamine-derivatized cRNA products were then reacted with N-hydroxy succinimide esters of Cy3 or Cy5 (CyDye, Amersham Pharmacia Biotech). 5 μg Cy5-labeled cRNA from each specimen was then mixed with the same amount of Cy3-labeled product from a reference pool which consisted of an equal amount of cRNA from each of the individual clinical specimens.

Expression Profiling Using Microarray

Microarray hybridizations were done in duplicate with fluor reversals. Before hybridization, labeled cRNAs were fragmented to an average size of 50 to 100 nt by heating at 60° C. in the presence of 10 mM $ZnCl_2$. Fragmented cRNAs were added to hybridization buffer containing 1 M NaCl, 0.5% sodium sarcosine and 50 mM MES, pH 6.5, which stringency was regulated by the addition of formamide to a final concentration of 30%.

Microarray:

The cRNA mixture was then hybridized to ink-jet synthesized 25K Human microarrays containing approximately 25,000 spots of 60-mer oligonucleotides representing approximately 23,551 human genes, and various control spots as described below.

Surface-bound oligonucleotides were synthesized essentially as proposed by Blanchard, et al., *Biosens. Bioelectron.* 6(7):687-690 (1996); see also, Hughes, et al., *Nature Biotech.* 19(4):342-347 (2000). Hydrophobic glass surfaces (3 inches by 3 inches) containing exposed hydroxyl groups were used as substrates for nucleotide synthesis. Phosphoramidite monomers were delivered to computer-defined positions on the glass surfaces using ink-jet printer heads. Unreacted monomers were then washed away and the ends of the extended oligonucleotides were deprotected. This cycle of monomer coupling, washing and deprotection was repeated for each desired layer of nucleotide synthesis. Oligonucleotide sequences to be printed were specified by computer files.

Microarrays containing approximately 25,000 human gene sequences (Hu25K microarrays) were used for this study. Sequences for microarrays were selected from RefSeq (a collection of non-redundant mRNA sequences, located on the Internet and Phil Green EST contigs, which is a collection of EST contigs assembled by Dr. Phil Green, et al. at the University of Washington (Ewing and Green, *Nat. Genet.* 25(2): 232-4 (2000)), available on the Internet. Each mRNA or EST contig was represented on Hu25K microarray by a single 60-mer oligonucleotide essentially as described in Hughes, et al., *Nature Biotech.* 19(4):342-347 and in International Publication WO 01/06013, published Jan. 25, 2001, and in International Publication WO 01/05935, published Jan. 25, 2001, except that the rules for oligo screening were modified to remove oligonucleotides with more than 30% C or with six or more contiguous C residues.

Hybridizations were carried out in a final volume of 3 ml at 40'C on a rotating platform in a hybridization oven (Robbins Scientific) for 48 h.

After hybridization, slides were washed and scanned using a confocal laser scanner (Agilent Technologies). Fluorescence intensities on scanned images were quantified, normalized and corrected for background noise.

Data Analysis:

Genes with informative variation in expression were first identified by selecting those genes that had greater than a two-fold difference in expression as compared to the reference pool, and if the p-value for differential regulation (Hughes, et al., *Cell* 102:109-126 (2000)) was less than 0.01 either upwards or downwards in at least 10 out of 118 tumor samples. Specifically, only genes with log 10(ratio)>log 10(2) and P-value (for log(ratio)=0)<0.01 in more than 15 samples were kept. This step removed all the genes that never had any significant change across all samples. A total of approximately 4250 genes were identified that had meaningful variation across the dataset (data not shown). Subsequent analysis was restricted to genes that met these criteria.

Unsupervised Clustering of 4250 Differentially Expressed Genes:

To obtain a broad overview of the diversity in gene expression patterns in the tumor samples, an unsupervised clustering algorithm was used to group the samples based on the similarity in expression measured over this set of 4250 significant genes. Similarly, genes were grouped based on the similarity in expression across the clinical samples.

Unsupervised analysis of the data was performed using two-dimensional agglomerative hierarchical clustering, as described in J. A. Hartigan, "Clustering Algorithms" (Wiley, New York, 1975), hereby incorporated by reference.

An unsupervised clustering algorithm was used to cluster patients based on their similarities measured over this set of about 4,250 significant genes. The similarity between two patients x and y is defined as $$S = 1 - \left[ \sum_{i=1}^{N_v} \frac{(x_i - \overline{x})}{\sigma_{x_i}} \frac{(y_i - \overline{y})}{\sigma_{y_i}} \Big/ \sqrt{\sum_{i=1}^{N_v} \left(\frac{x_i - \overline{x}}{\sigma_{x_i}}\right)^2 \sum_{i=1}^{N_v} \left(\frac{y_i - \overline{y}}{\sigma_{y_i}}\right)^2} \right] \quad \text{(Eq. 1)}$$

In Equation (1), X and Y are two patients with components of log ratio $x_i$ and $y_i$, $i=1, \ldots, N=4250$. Associated with every value $x_i$ is error $\sigma_{x_i}$. The smaller the value $\sigma_{x_i}$, the more reliable the measurement.

$$x_i \cdot \overline{x} = \sum_{i=1}^{N_v} \frac{x_i}{\sigma_{x_i}^2} \Big/ \sum_{i=1}^{N_v} \frac{1}{\sigma_{x_i}^2} \quad \text{(Eq. 2)}$$

is the error-weighted arithmetic mean.

The use of correlation as similarity metric emphasizes the importance of co-regulation in clustering rather than the amplitude of regulations.

Results of Unsupervised Clustering Analysis:

The 2D clustering analysis based on the differentially expressed genes was able to separate the patient samples into two branches, with an enrichment of poor outcome patients in the bottom branch (data not shown). The overall odds ratio was 5.5 (95% confidence interval: 2.2-13.8) with Fisher's Exact Test P value of 0.03%. The metastasis-free probability and survival probability as a function of time was also significantly different between these two branches, with the log-rank-test P values less than 0.1% in both cases.

Conclusion: Therefore, the fact that the 2D clustering approach based on the 4250 differentially expressed genes was able to separate poor outcome patients from good outcome patients shows that prognosis information is contained within the gene expression patterns of the 4250 differentially expressed genes.

Example 2

This Example describes the generation and validation of a prognosis classifier with the differentially expressed genes identified in EXAMPLE 1 using a double loop of leave-one-out cross-validation, with the first loop to select the "training samples" and the second loop to evaluate the performance of the prognosis classifier using all the samples.

Rationale: A double loop of leave-one-out cross-validation (LOOCV) procedure was carried out using the methods described in Dai, et al., *Cancer Res.* 65(10):4059-4066 (2005). Briefly described, the first loop of LOOCV was used to select the "training samples" and the second loop of LOOCV was used to evaluate the performance of the classifier. Prognostic features for colon cancer were selected based on the "training samples" by their correlation to outcome and were re-selected during each step of LOOCV, as described in more detail below.

Selection of Training Samples:

In order to identify homogenous patterns and reveal the dominant mechanisms, a homogenous method was used to generate the classifier, as described in Dai, et al., *Cancer Res.* 65(10):4059-4066 (2005).

In the first step, only the samples from colon cancer patients who had metastasis within 3 years of initial diagnosis (i.e., the "poor outcome" group), or were metastasis-free with more than 3 years of follow-up time (i.e., the "good outcome" group) were used as the training set. Based on these training samples, a complete LOOCV (including reselecting features) process was performed. During this step, the number of features was fixed at 50 genes. The training samples that could not be correctly predicted (poor outcome samples correlating more to the average good outcome, or vice versa) by this LOOCV process were further removed from the training set in the second round of LOOCV. This is the opposite of the "boost" algorithm (described by Freund, Y., *Information and Computation* 121: 256-285 (1995)). The "boost" algorithm increases the weight of the misclassified samples in the training set for the accuracy of the classifier. In contrast, the current algorithm focuses on the most common prediction rule (mechanism) within the data set by excluding the "unpredictable" samples from the training set for robust feature selection.

Of the samples obtained from 36 patients that developed metastasis during the follow-up period, 20 were included in the second round of the LOOCV as a training set. 49 (out of 82) samples from metastasis-free patients were also included in the second round of the LOOCV as the contrast training group.

The justification for such an iteration operation is threefold. First, biologically, there are always a few individuals with specific reasons (different from the vast majority) to stay metastasis-free or to develop metastasis. Second, statistically, most groups of patients include outliers that do not follow the distribution of the majority of samples. Third, methodologically, the iteration operation is similar to the idea of "boosting," but instead of increasing the weights of the samples predicted incorrectly, emphasis is placed on the well-behaved samples for selecting features and training the classifier. Since this process was used to select "training samples" and the performance was evaluated using the LOOCV (including the feature selection) after the training sample was fixed, there was no issue of overfitting involved in our procedures. This method of iteration is therefore more likely to reveal the dominant mode to metastasis within each group.

Feature Selection and Performance Evaluation

We started with filtering out non-informative genes in the dataset. Specifically, only genes with |log 10(ratio)|>log 10(2) and P-value (for log(ratio)≠0)<0.01 in more than three samples were kept. This step removed all genes that never had any significant change across all samples. The second step involved a double loop of leave-one-out cross-validation (LOOCV) procedure to select the training samples classifier features and evaluate the performance. Even though all samples were used to evaluate the classifier, only those "training samples" (see the description of "training sample" selection), had a chance to be involved in developing the classifier. In the leave-one-out process, if the left-out sample is one of the training samples, it is removed from the feature selection and classifier construction from that leave-one-out step. As discussed below, the classifier features were selected according to their correlation with disease outcome. Because of the "iterative training sample selection" the features selected from each step of the second loop of leave-one-out process are highly overlapping. As stated in the previous section, the first LOOCV loop is for selecting the "training samples" and the second LOOCV loop is for evaluating the performance of the classifier. The number of reporter genes was fixed at 100 in the second LOOCV. For use in future classification of colon cancer patient samples, the final "optimal" reporter genes shown in TABLES 1-4 were selected using all the training samples.

The prognostic features (i.e., gene markers) were selected by the features relation with patient outcome. Specifically, the gene markers were identified by calculation of the correlation coefficient ρ between the clinical category c and logarithmic expression ratio across all the samples for each individual gene:

$$\rho=(\vec{c}\cdot\vec{r})/(\|\vec{c}\|\cdot\|\vec{r}\|) \quad \text{(Eq. 3)}$$

Gene markers whose expression ratios either correlated or anti-correlated well with the diagnostic category of interest were used as reporter genes for the category. The resultant correlation coefficients with regard to poor outcome are shown in TABLE 2.

The top 100 genes with the highest value of correlation to outcome were selected. Within the training set, the value of correlation coefficient of these 100 genes is 0.65 and above, as shown in TABLE 2.

Next, the significance of the correlation was calculated. The frequency distribution of markers satisfying the criteria in the Monte-Carlo runs was used to determine whether the number of markers selected by correlation with clinical data was significant.

Once the gene marker set is identified, the markers may be rank-ordered in order of significance of discrimination by the amplitude of correlation between the change in gene expression of the marker and the specific condition being discriminated.

The markers may be rank-ordered either by amplitude of correlation, or by using a metric similar to a Fisher statistic:

$$t=\frac{(\langle x_1\rangle-\langle x_2\rangle)}{\sqrt{[\sigma_1^2(n_1-1)+\sigma_2^2(n_2-1)]/(n_1+n_2-1)/(1/n_1+1/n_2)}} \quad \text{(Eq. 4)}$$

In Equation (4), $\langle x_1\rangle$ is the error-weighted average of log ratio within the poor outcome group, and $\langle x_2\rangle$ is the error-weighted average of log ratio within the good outcome group. $\sigma_1$ is the variance of log ratio within the poor outcome group, and $n_1$ is the number of samples that had valid measurements of log ratios. $\sigma_2$ is the variance of log ratio within the good outcome group, and $n_2$ is the number of samples that had valid measurements of log ratios. The t-value in Equation (4) represents the variance-compensated difference between two means. The confidence level of each gene in the candidate list may be estimated with respect to a null hypothesis derived from the actual data set using a bootstrap technique; that is, many artificial data sets were generated by randomizing the association between the clinical data and the gene expression data.

Classification Based on Marker Genes

In the next step, a set of classifier parameters was calculated for each type of training data set based on the above ranking methods. A template for the good outcome group ($\vec{z}_1$) was generated using the error-weighted log ratio average of the selected group of genes. Similarly, a template for the poor outcome group (called $\vec{z}_2$) was generated using the error-weighted log ratio average of the selected group of genes. Two classifier parameters ($P_1$ and $P_2$) were defined based on either correlation or distance. $P_1$ measures the similarity between one sample $\vec{y}$ and the good outcome template $\vec{z}_1$ over this selected group of genes. $P_2$ measures the similarity between one sample $\vec{y}$ and the poor outcome template $\vec{z}_2$ over this selected group of genes. The correlation $P_i$ is defined as:

$$P_i=(\vec{z}_i\cdot\vec{y})/(\|\vec{z}_i\|\cdot\|\vec{y}\|) \quad \text{Eq. (5)}$$

where i=1 and 2.

In this round of analysis, a patient was predicted to have a favorable outcome (a good prognosis), that is, no metastasis within three years of initial diagnosis, if the expression of the marker genes in a tumor sample from the individual was more similar to the "average good profile" than the "average poor profile," and a poor outcome (a poor prognosis), that is, a metastasis within three years, if the expression of the reporter genes in the sample was more similar to the "average poor profile" than the "average good profile."

Error Rate and Odds Ratio:

Unless otherwise stated, the error rate was the average error rate from two populations: (1) the number of poor outcome samples misclassified as good outcome samples, divided by the total number of poor outcome samples, and (2) the total number of good outcome samples misclassified as poor outcome samples, divided by the total number of good samples. Two odds ratios were reported for a given threshold: (1) the overall odds ratio and (2) the three-year odds ratio. The three-year odds ratio was calculated from samples from individuals that were metastasis-free for more than three years, and those who experienced metastasis within three years. The threshold was applied to cor1−cor2 where "cor1" stands for the correlation to the "average good profile" in the training set, and "cor2" stands for the correlation to the "average poor profile" in the training set.

The odds ratio is the ratio of the odds in favor of developing distant metastases within three years for a patient in this study. If a patient sample has a cor1−cor2>0, the profile is similar to good outcome. If a patient sample has a cor1−cor2<0, the profile is similar to poor outcome.

Threshold in the Final Round of LOOCV

The threshold in the final round of LOOCV was defined using the following steps: (1) for each of the N samples i left out for training, features based on the training set were selected, (2) given a feature set, an incomplete LOOCV with N−1 samples was performed (only the "average poor profile" and "average good profile" is varied depending on whether the left out sample is in the training set or not), (3) the threshold based on the minimum error rate from N−1 samples was determined, and that threshold was assigned to sample i in step (1), (4) the median threshold from all N samples was taken, and designated the final threshold.

Classification Method: All classifiers described herein, feature selection and optimization were included inside the LOOCV loop. Classifier performance was based on the LOOCV results. The profile based on the selected features from each patient was compared to the "average good profile" and "average poor profile" (by correlation), and the predicted outcome is determined based on whether the profile is more similar to the average good profile (predicted as good outcome or good prognosis) or more similar to the average poor profile (predicted as poor outcome or poor prognosis).

Correlation calculation: The correlation between each gene's expression log(ratio) and the endpoint data (final outcome) was calculated using the Pearson's correlation coefficient. The correlation between each patient's gene expression profile and the "average good profile" and "average poor profile" was the cosine product (no mean subtraction).

2. Performance of the Colon Cancer Classifier(s):

Results:

The comprehensive prognosis strategy described herein was employed on microarray expression profiles of 118 patients diagnosed with colorectal cancer to establish and validate a 100-gene prognosis profile. A double loop of leave-one-out cross-validation was used to establish a colon cancer classifier with an optimal set of 100 marker genes (shown in TABLES 1-4), with the first loop to select the "training samples" and the second loop to evaluate the performance of the colon cancer prognosis classifier using all the samples. There are two templates in the classifier, a poor outcome template and a good outcome template. An individual colon cancer patient from which a tumor sample is derived is classified with regard to outcome prediction, based whether the gene marker profile in the sample is more similar to the good outcome template or to the poor outcome template. FIG. 2A is a heatmap showing 118 clinical samples (rows) over 100 prognosis genes (columns) selected as described herein (with genes clustered by their differential expression and samples ranked by cor1−cor2 in LOOCV), and set forth according to gene index number (shown in TABLE 3). FIG. 2B graphically illustrates the status of metastasis for each of the 118 clinical samples (rows) shown in FIG. 2A, with "0" representing a patient that was metastasis-free within the whole follow-up period, and with "1" representing a patient that developed metastasis within the whole follow-up period.

Figure 3A:
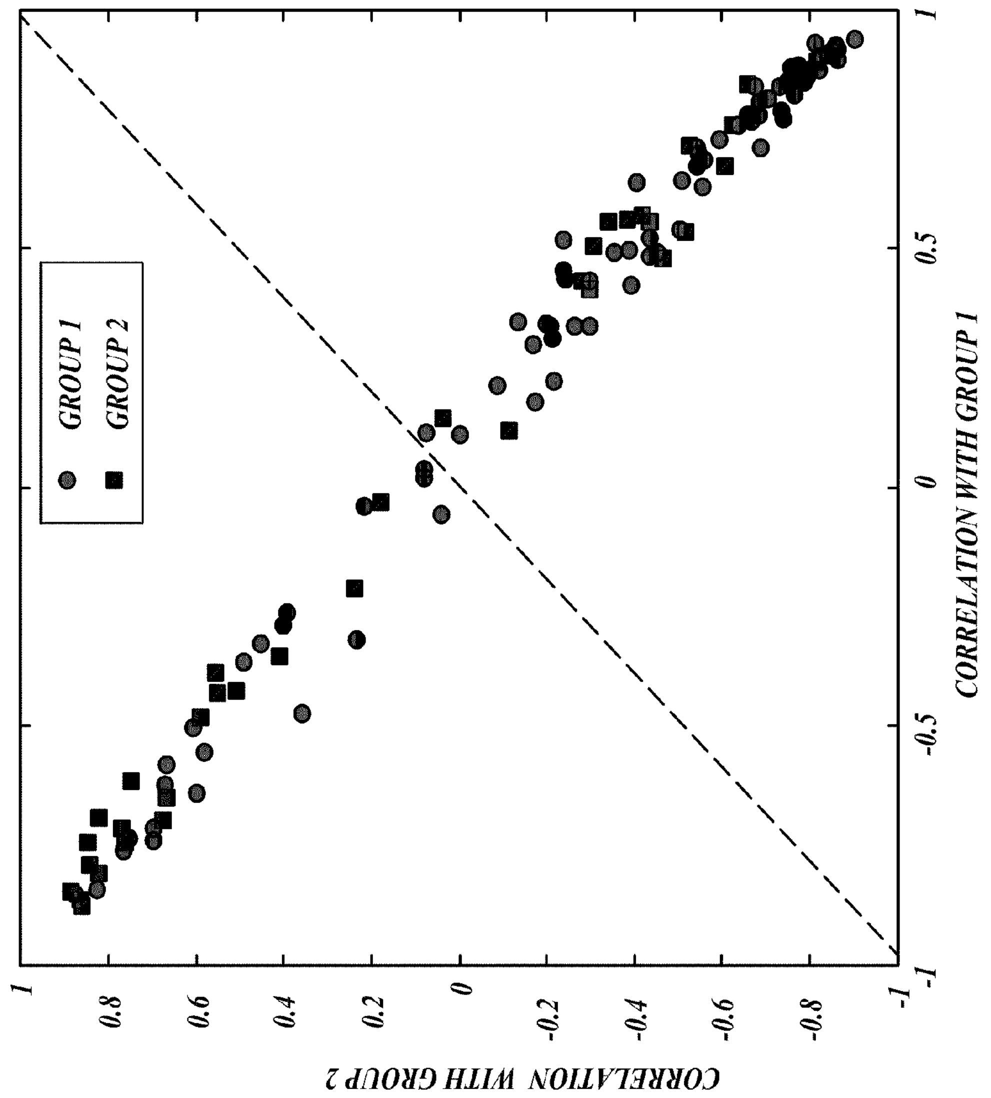
FIG. 3A is a scatter plot illustrating the performance of the colon cancer prognosis classifier. Circles indicate samples from clinically metastasis-free patients (Group 1); squares indicate samples from clinically metastasis-positive patients (Group 2). The scatter plot shows the correlation of samples to a good outcome expression template (X-axis) and to a poor outcome expression template (Y-axis). The dashed line indicates an exemplary threshold for separating poor from good, as described in EXAMPLE 2.
Figure 3B:
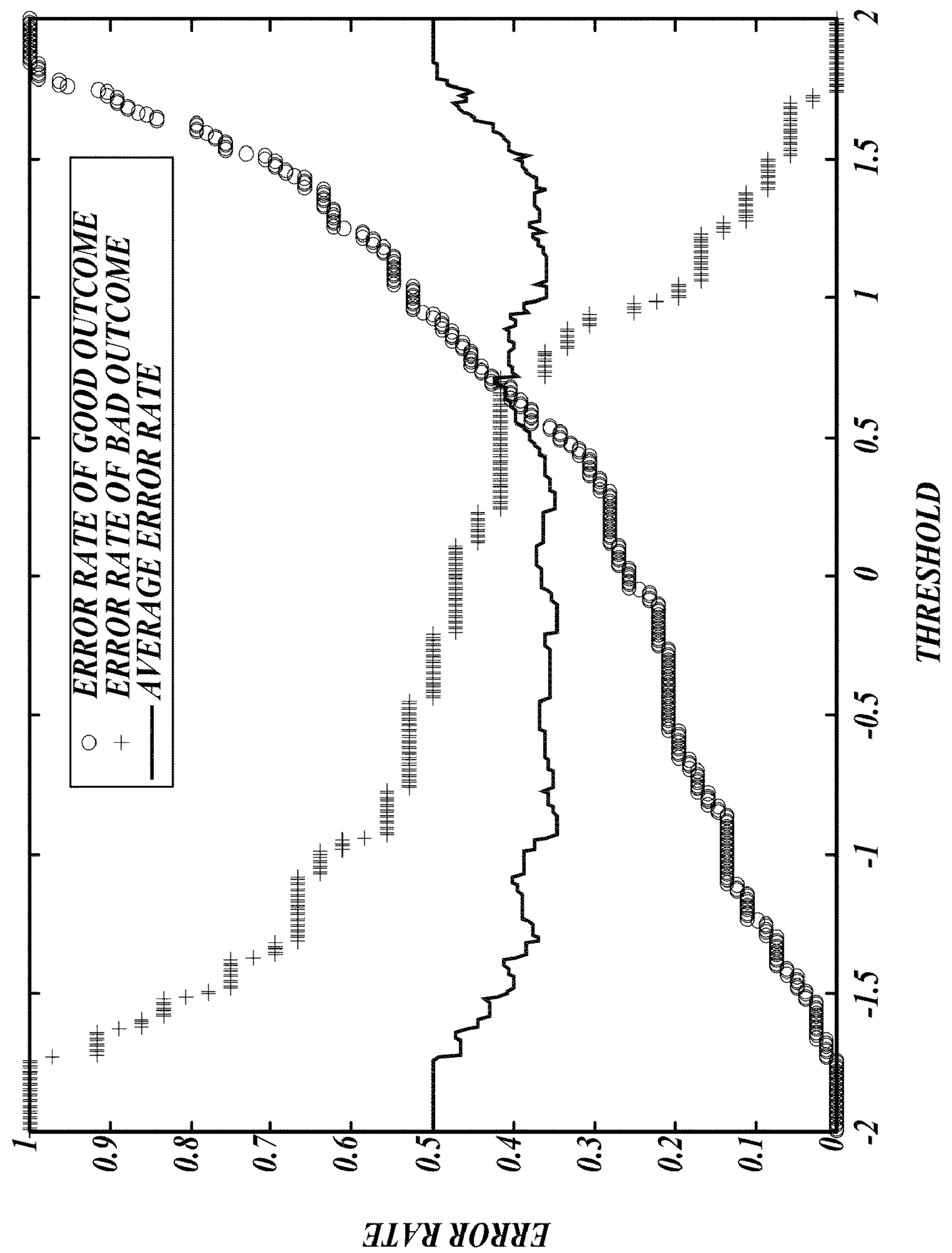
FIG. 3B graphically illustrates the error rate for the colon cancer classifier calculated with respect to the good outcome group, shown as circles (good outcome misclassified as poor divided by total number of good), or the poor outcome group, shown as asterisks (poor outcome misclassified as good divided by total number of poor), or the average of the two rates, shown as a solid line, as described in Example 2.

FIG. 3A is a scatter plot illustrating the performance of the colon cancer prognosis classifier. Circles indicate samples from clinically metastasis-free patients (Group 1); squares indicate samples from clinically metastasis-positive patients (Group 2). The scatter plot shows the correlation samples to a good outcome expression template (X-axis) and to a poor outcome expression template (Y-axis). The dashed line indicates a threshold for separating poor from good. FIG. 3B shows the error rate (false positive, false negative, and average error rate) as a function of threshold on cor1−cor2.

FIG. 4 graphically illustrates the expression patterns of the 100 genes (X-axis), identified by their gene index (as described in TABLE 3) in a good outcome template (shown as o symbols) and a poor outcome template (shown as + symbols); positive values in average differential expression represent overexpression; negative values represent underexpression as compared to the reference pool, with the reference pool defined as the pool of all 118 samples in this study.

Validation of the Colon Cancer Classifier

The colon cancer prognosis classifier was used to analyze patient samples to determine whether the patient has a good or poor prognosis. The patient was classified as having a poor prognosis profile if the patient's cellular constituent profile had a low similarity to a good outcome template and/or had a high similarity to a poor outcome template.

Methods:

To evaluate the prognostic classification of samples obtained from colon cancer patients, the outcome of each patient was predicted by the classifier trained by the training set as described above.

Figure 5:
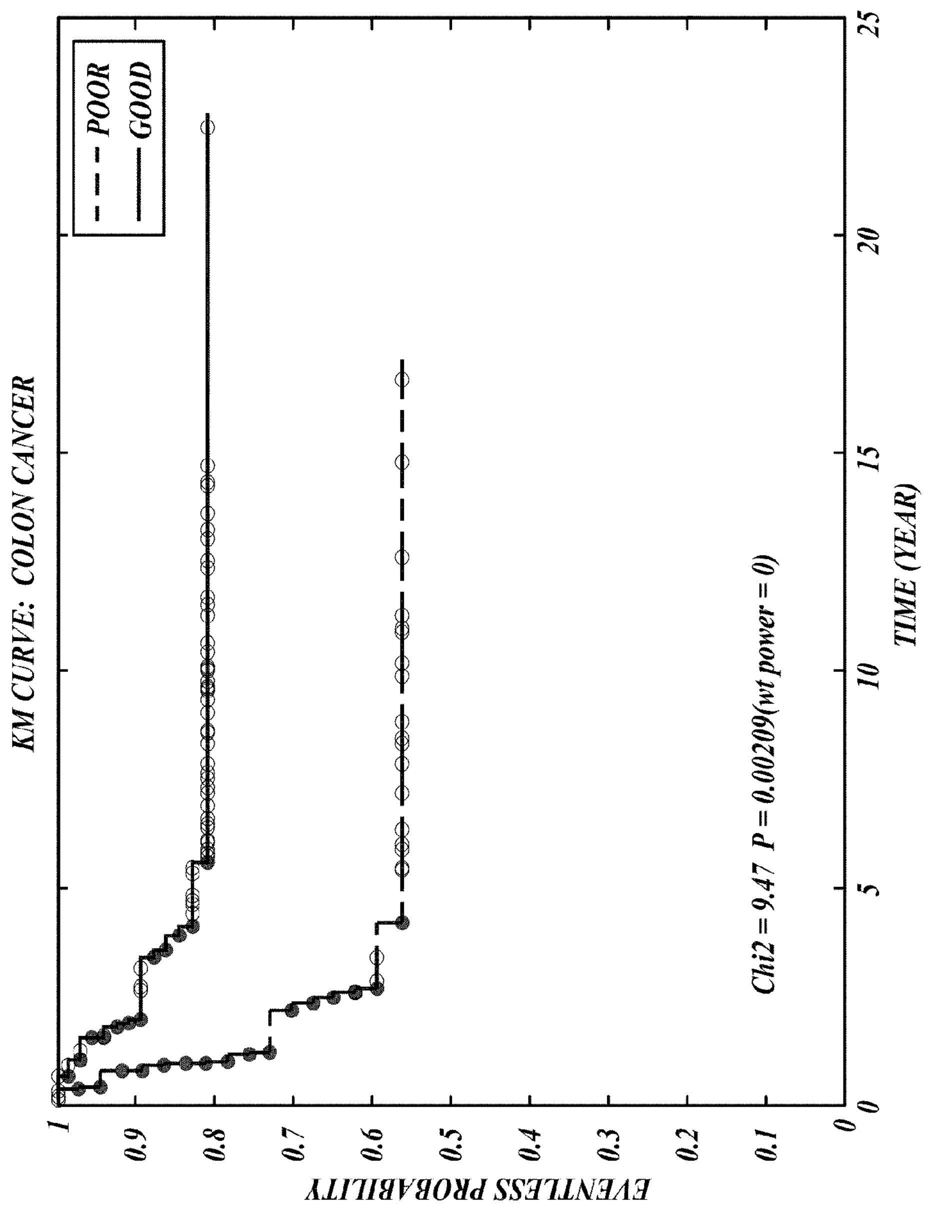
FIG. 5 graphically illustrates a Kaplan-Meier plot showing the metastasis-free probability and disease-specific survival probability as a function of time from initial diagnosis for the two predicted groups (good prognosis or poor prognosis). Patients were divided into two groups according to the colon cancer prognosis classifier demonstrated in FIG. 2A. The upper line is the predicted good outcome group, and the lower line is the predicted poor outcome group. The prediction was based on a leave-one-out cross-validation as described in EXAMPLE 2.

FIG. 5 graphically illustrates a Kaplan-Meier plot that plots the metastasis-free probability and disease-specific survival probability as a function of time from initial diagnosis for the two predicted groups (good prognosis or poor prognosis). Patients were divided into two groups according to the colon cancer prognosis classifier demonstrated in FIG. 2A. The lower line is the poor prognosis group, and the upper line is the good prognosis group. The good group and poor group were predicted by using a leave-one-out method based on the set of prognosis genes. As shown in FIG. 5, the metastasis-free probabilities are significantly different between the two groups. By fixing the number of reporter genes at 100, the LOOCV (including reselecting reporters) yielded an overall odds ratio of 3.9 (95% confidence interval: 1.6-9.5) and a three-year odds ratio of 5.8 (95% confidence interval 2.0-16.3). As shown in FIG. 5, the classifier can separate the poor outcome from the good outcome samples (log-rank-test P<0.1% in both cases).

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for classifying a human individual afflicted with colon cancer as having a good prognosis or a poor prognosis, where said good prognosis indicates that said individual is expected to have no distant metastasis within three years of initial diagnosis of colon cancer, and wherein said poor prognosis indicates that said individual is expected to have distant metastasis within three years of initial diagnosis of colon cancer, comprising:

(i) calculating a first measure of similarity between a first expression profile, the first expression profile comprising the mRNA expression levels of a plurality of genes comprising at least five of the genes for which markers are listed in any of TABLES 1-5 in a colon cancer cell sample taken from the individual and a poor outcome template, wherein said poor outcome template comprises expression levels of said plurality of genes that are average mRNA expression levels of the respective genes in colon cancer cells of a plurality of colon cancer patients having distant metastasis within three years of initial diagnosis of colon cancer; and (ii) classifying said individual as having said poor prognosis if said first expression profile has a similarity to said poor outcome template that is above a predetermined threshold, or classifying said patient as having said good prognosis if said first expression profile has a similarity to said poor outcome template that is below a predetermined threshold; and (iii) displaying; or outputting to a user interface device, a computer-readable storage medium, or a local or remote computer system, the classification produced by said classifying step (ii).

2. The method of claim 1 further comprising determining a first expression profile, the first expression profile comprising the expression levels of a plurality of genes comprising at least ten of the genes for which markers are listed in any of TABLES 1-5 in a cell sample taken from a human individual afflicted with colon cancer.

3. The method of claim 1, wherein step (i) further comprises:

calculating a second measure of similarity between said first expression profile and a good outcome template, said good outcome template comprising expression levels of said plurality of genes that are average mRNA expression levels of the respective genes in colon cancer cells of a plurality of colon cancer patients having no distant metastasis within three years of initial diagnosis of colon cancer; and classifying said individual as having said good prognosis if said first expression profile has a similarity to said poor outcome template that is below a predetermined threshold and said first expression profile has a similarity to said good outcome template that is above a predetermined threshold.

4. The method of claim 1, wherein step (i) further comprises:

calculating a second measure of similarity between said first expression profile and a good outcome template, said good outcome template comprising expression levels of said plurality of genes that are average mRNA expression levels of the respective genes in colon cancer cells of a plurality of colon cancer patients having no distant metastasis within three years of initial diagnosis of colon cancer; and classifying said individual as having said good prognosis if said first expression profile has a higher similarity to said good outcome template than to said poor outcome template, or classifying said individual as having said poor prognosis if said first expression profile has a higher similarity to said poor outcome template than to said good outcome template.

5. The method of claim 1, wherein said plurality of genes comprises at least 20 of the genes for which markers are listed in any of TABLES 1-5.

6. The method of claim 1, wherein said plurality of genes comprises at least 50 of the genes for which markers are listed in any of TABLES 1-4.

7. The method of claim 1, wherein said plurality of genes comprises each of the genes for which markers are listed in TABLE 5.

8. The method of claim 1, wherein said plurality of genes comprises each of the 100 genes for which markers are listed in TABLE 1.

9. The method of claim 1, wherein said expression level of each gene in said first expression profile is a relative expression level of said gene in said cell sample versus expression level of said gene in a reference pool.

10. The method of claim 9, wherein said reference pool is derived from a pool of colon cancer tumors derived from a plurality of individual colon cancer patients.

11. The method of claim 9, wherein said relative expression level is represented as a log ratio.

12. The method of claim 1, wherein said poor outcome template comprising expression levels of the plurality of genes is an error-weighted average.

13. The method of claim 1, wherein said predetermined threshold is based on a correlation coefficient between said first expression profile and said poor outcome template.

14. The method of claim 3, wherein said first measure of similarity is represented by a correlation coefficient between said first expression profile and said poor outcome template, and wherein said second measure of similarity is represented by a correlation between said first expression profile and said good outcome template, wherein said correlation coefficient greater than a correlation threshold indicates a high similarity and said correlation coefficient equal to or less than said correlation threshold indicates a low similarity.

15. The method of claim 1 comprising classifying the individual as having a poor prognosis if the level of expression of the at least five marker genes correlates with the average level of expression of each of said markers in said poor outcome template with a correlation coefficient greater than 0.5.

16. The method of claim 13, wherein the correlation threshold is in the range from −1 to 1.0.

17. A method of classifying a human individual afflicted with colon cancer according to prognosis comprising the steps of:

(a) contacting first nucleic acids derived from mRNA of a colon tumor sample taken from a human individual afflicted with colon cancer, and second nucleic acids derived from mRNA of two or more colon tumor samples from colon cancer patients who have had no distant metastases within three years of initial diagnosis, with an array under conditions such that hybridization can occur, wherein the first nucleic acids are labeled with a first fluorescent label, and the second nucleic acids are labeled with e second fluorescent label, detecting at each of a plurality of discrete loci on said array a first fluorescent emission signal from said first nucleic acids and a second fluorescent emission signal from said second nucleic acids that are bound to said array under said conditions, wherein said array comprises at least five of the genes for which markers are listed in TABLE 1 and wherein at least 50% of the probes on said array are listed in TABLE 1;

(b) calculating the similarity between said first fluorescent emission signals and said second fluorescent emission signals across said at least five genes;

(c) classifying said individual afflicted with colon cancer according to prognosis of his or her colon cancer based on the similarity between said first fluorescent emission signals and said second fluorescent emission signals across said at least five genes wherein said individual is classified as having a good prognosis if said similarity is above a predetermined threshold, or is classified as having a poor prognosis if said similarity is below a predetermined threshold; and (d) displaying; or outputting to a user interface device, a computer readable storage medium, or a local or remote computer system; the classification produced by said classifying step (c).

* * * * *

```
                         SEQUENCE LISTING

<160> NUMBER OF SEQ ID NOS: 200

<210> SEQ ID NO 1
<211> LENGTH: 5785
<212> TYPE: DNA
<213> ORGANISM: Homo sapiens

<400> SEQUENCE: 1

cccagacccg cccccacttc ccccctcacc ctcccctccg gcagcctctc ccatggccac      60

tgctgcgggc tgtgagcaga gccccgtcct tgagcagatt gacctcatct ttcagtcctg     120

cagctgggct gagcggggag tcagctcaga agacactggc ctggggatga gactcgggtc     180

atgcttcaga gggaagaaag agcttctgaa cagacaatgc tgtcttaaag gtggcatctt     240
```

```
ggtgctttct catgccttgt tttctttcat cctcagaatg tgtctggggg tgagaggacg    300
ggtgtgactg ctgaaacttc ctttcttggt gattccacat cactcctttc tgatccctga    360
gcctgtgcca cgccctgtgt gatgtgccgg ggacaccagg gtgaatactt acaggccctg    420
ttccccttcc ttcatgaaac agcctccttc gggctgggtc actgggcact ggggcctccc    480
tggtcttcca ggattgcaac ttcacagaat cccttttcca taaggcacat gaaagtgact    540
gtgacccgca acgggagcct tgacaaccag ccaattcaga acacagacct tgacatcgga    600
aggccccgag ttcaaatcct gccttgctcc ctttcagctg gaaagctgtg gtcaaattac    660
ttagcctctc caagccagtt ttcccttctg caaaatgagg ttacacaagc tgccacctca    720
cagaatgagt gtgagaatta attcttattt tccacaccct catttgacag gggagaaac    780
agaagcccag agagggaaag ggcttggtta ggatcacacc atgagttggg ggttaagtca    840
ggatggggta ggtcccctct ttctctgggt gttcctctcc cccatccctt atctcaacat    900
aaatcctccc cagttgccca ggttgtccag gcgattcctg gcacacgtcc tggggcctgc    960
cctccacctt tagccctgct ctggcttctg cagcagcaga gtcctgggtg accagcagtg   1020
gcccctggcc ctctgagtgg tggtggaggg tgggggtgca ctgcagcaag ctcccagccc   1080
agagcagcct ggccatataa gggaaggagc tcagggaggc ctcctggctc aggcctggcg   1140
agaaaaccca gacagccact gtttattttc tcctccccag ctcacccacg cctctccaag   1200
cctcccaaca gaagacagag gtcccccaca gccagagaca tttcctgaag acatggggaa   1260
cacagaggca gaaacagccc atccacccag gagctgtccc ccacactgcc gggagccggc   1320
acccagagcc gccaggtaaa actgaggcca cctggttcaa catcaccttt cacagaaggg   1380
gaagcagcca cagaaagaag ggcctcgtta agaagtggaa cctgggaccc ccaagcggtg   1440
tctctcatcc tgactgggga tccagagtag gagggagcct ttggtggggt aagtggaatg   1500
gggtgggggg ggggcggggt ggccatagac ccctcttctc agtaaggccc tcatgtgaag   1560
gaggcagggg ttgggacaag tgctaagtat gcaagactca agggaagagc tgctggagcc   1620
aggagaagca cctccctccc ggcccctctg cccctcctca tagcccagct gcactgactc   1680
ctcctccagg aagccttctc agcttcccca ggggtgggaa ccttttttgtc ctccaggtgt   1740
gcttggctgt cctttcttgg gctctctctc tctctctctc ctcatcccac ttgagtctgc   1800
cccctattca ccttgtgagg ggaattttcc ttctactcaa tctgaccgag gtcctccagg   1860
tcaaggacag cgaggctctc agtcccactt ccccttggca catagaagag gcagtgcgct   1920
gaagggacag gtgaaatgat tagaccctgc ccccaaacca aggcctggcc aattggacag   1980
ggcatgagac attcagcgta gaggttaaaa cgagggccct gggttaggaa ccccagctca   2040
gttctcagct ctgtaccctt ggaaaattcc cttcccatgg agctttgtgg atgcacaagg   2100
acttgcacaa agaaaacatt caatatccag gactataaaa ttccacaaat gattgtgctt   2160
attacattca ttatcacgat gattattcca gacacaaagg aacagaacga ggcaccaaca   2220
gcaaggggca agcagattca agggccacag aggagatgga ggcaaacacc ttcccctggt   2280
cagaggctgt gcctcagccc ttctccctgc atcagtttct ccttcagaag catgggacta   2340
cctcccatct agttctcgtt tctaaaccta ggggagatgc tatctttgct gcaataatct   2400
tagcctacat cttggaatgg aaatggcctt ggtggaaatg gtcttcaact cctctggtcc   2460
aagctcaggc cctgtgaccc tggaacaatc cccttcctgg tcctccatgt aggagcaata   2520
acattcccct gccagcagca ccagccattc tgatgattaa atggtatcgg actctgtttt   2580
ccaaactcag tcattcagat gccccctatt ttatttcttc catgtctgca aatgattata   2640
```

```
atatttttaa atgtaggatg agtccttttt attacacata gaaatagcta ctgtaaatag   2700
caaactctaa cactgtgcct aattaggaaa taaaggtaac cataaataca gtaaaaatga   2760
aacaatgtta ttatggttta acctgatagt gtggcttgca aggccctggg cctgaagcct   2820
gggcaataag tgagagttag aaaggtgtca aagacatgat agcagcaaac tgaggctttg   2880
taccccacgg taaataggac tgaaagcaaa ttcacaggga gcaactgatc cattccacaa   2940
cagaatgctc cctgtcaatt cgctttccat tctgttgtgt cctgtctccc agcagagact   3000
acaaactccc caaaaccact tacccaccag ctgcacgtga gaagccaaag gtagtttatg   3060
tgaaagggct ttggaaataa tcacgcacca agtgaaggca gaggacacac cttgtcagct   3120
tagttctcag cagcaaatca tctcttttcc aggataaccc tccctgattc ttattgaaat   3180
ctctttgctg accacactaa gctcttctct ctcaggggca gtgggagccg tggagagtgg   3240
aatagaccag ctgtctgtga cctgcgaggg agtccaatgt cggaatcact ccccagccaa   3300
atgcacggtt ttaaaaaatc tatttattta tttatgtaga gaccaggcta tgagactggc   3360
taatttttcg tatttttgga tagagacagg atttcatcgt gttgcccagg ctggtcttga   3420
actcctgggc tcaagcgatc cacctgcctc ggcttcccaa agtgctcagg attacaggcg   3480
tgagccactg tgcccagcca ccaaatgcag ttgaaaagag tttctgcaag ataattccac   3540
agaagaggaa agcagttatc tggctgggaa taccttagac agaggctgtc ctctacacag   3600
gctgtcagaa ctgacctact gacctgcctg ctggcatgat agaccagagg gaaacactct   3660
ttccactctt cccagactga gtgtaagaga cagacttttt tttttttttt tgagacggag   3720
tctcactctg tcacccaggc tggagtgcaa tggcaagatc tcggctcact gcaacctcca   3780
cctccccggg ttcaaaccat tctcctgcct cagcctccca ggtagctggg attacaggct   3840
cccgccacca cgcctggcta atttttgtat ttttagtaga gacagggttt caccatgttg   3900
gccgggctgg tctcgaactc ccaacctcag gtgatccgcc taccttggcc tcccaaaggg   3960
ttgggattac aggtgtaagc cactgctccc agcctttttt ttttttttat tagagacaag   4020
ggctccccat gttgcccagg ctgatcttga actctaggct caagcgatcc tcctgcctga   4080
gcctcccaaa gtgctaggat tacaggcatg agcactgctc ccagctctgt ttttgttttt   4140
ttaaggaggt atatttttc tgttctctct cagccctgaa gaaaggctac ccatcccctt   4200
cagacattcc tgaaaatata tgtcatccaa catcaaggcc accacagtga ccactaagca   4260
atgcaagaag gtcctctggg gtgccctgag atcttggcag ggcaggaaga gtgagaaggg   4320
gctttgcctg ctcacctgaa agttcccacc caagccgggc ccagaaaaca aaatgaatta   4380
tctacatggt catccaatca gccaccaaat ggcattacct aggtccatca tcatgtacca   4440
agccacaggt cagacccagg gccccccaaa ttaacaagac acaggcactg tcctcaggaa   4500
gtggagatct agccaggtca gacccacaca caaataacac tgatactaga gataatgaga   4560
ttgggaatta tgattcagcc attcaacctg ggcttatgtg gcatctacac cacctggccc   4620
tgatttcagt agtgagcaca gttgacaggg tcccttccct tcacaggtga gccatgtagt   4680
ccacaagtgg aggtggtcgt aagtgaaaac cacattacca gcatggtaaa gggttagaaa   4740
gagggcaccg ggtgggcgag aacatgaagc agggggtgct gatggctaaa gaagtaaagg   4800
aggggctggg cactgtggtt catgcctata atcccagcac tttgggagac caaggcgggt   4860
ggatcacctg aggtcaggag ttctagacca gcctgggcaa cgtggtgaaa ccctgtctct   4920
actaaaaata caaaaattag ccaggcatgg tggtgcacgc ctgtagtccc agctacttgg   4980
gaggctgggg catgagaatt gctttaaccc ggaaggtgga gtttgcagtg agccgagatc   5040
```

```
gtgtcactgc actccagcct gggcgacaga gggagactct gtctcaaaaa aaaaaaaaag   5100
tcaaggaggg tttcccagag tggccacttg attagagacc tagcacagga ggaagagatg   5160
ggcagggaga gtgacgggga gcagcacagt ccctgggagc ccgaagtggg tgggcacagg   5220
gctccctagg agaatggaag gacatctatg agctgtagcc caagaggaag aggtcactgg   5280
ggctagatgc ggcagaccct cgcaggcttt gggaagggct tcagaattca gcctgagggc   5340
aatggggagc ccttttggga tattaaactt gagtaagata tgagcatatt tgcatcttga   5400
aaaatcatta tgggaagatg gctgggaaga gaggaggagt ggcagaagaa agataggttg   5460
gagacaattg attgctcgat gatataaaat gttaagtacc atgaatgatg ctgttaggct   5520
ggaatgcgcc aagcataaag gtggggcatg gcatcaaaag gtaggtcaac atattaaata   5580
attccatgta ttgaaatatc cagaaaatat atagacagat ctatagagat agaaactggt   5640
ctgcccagga ctaggggttg tctaaggata aggagcttct tttttggatg gtgaaataac   5700
ctaaaatata ttgtgccatt gtttgcacaa ctttgtgaat atattaaaaa cctgttaatt   5760
gtactcacaa aaaaaaaaaa aaaaa                                         5785
```

<210> SEQ ID NO 2
<211> LENGTH: 1891
<212> TYPE: DNA
<213> ORGANISM: Homo sapiens

<400> SEQUENCE: 2

```
ataggtatga attcatttaa gtcctgaaga aaaagaaaaa aaatacgaag tggatattac     60
ccttcccatt ttcaaataag gaaactgaag cacaaaaaga acaagtaact tgacaaggac    120
accccggtag taaatcatgg ggctggagct caaccccagg gtaggctggc tccagagctg    180
tgctctcctt gactcttctg atggtctcct agctggaagc ctcacatttc agtctcattc    240
ccccaagtgg cccatcagct actccatctc tggctcccca actaaacagt ttctctcata    300
gtgctggacc tccactcact agtttttttt ccagctgttc ttctcttttc ttcaggtcac    360
tcttctcgac cgagtgcaaa aattatcccc tccataccag ctttgatgac cttccttcca    420
tactcctcac cagacacaac ataataggtc acacactcct ctgtgctttc tggcacgttt    480
taaacattat tattattgac ctttacctat agtataccat ggcctattta tgtatccatc    540
tcccctagca tttttcctca aagacaagaa ccatgtctta cccatctctt gggtaagtgc    600
ctagcatggt ggctgacgct tgggagggtg tcattaaatg ttgctcaaaa gaacaagcaa    660
acatttaagg tggtggagag cagcctgggg acagctgaca tgctgcatgc ttctcagtac    720
cagcaccatc acaatgcaaa aagcaacatc tttcttaacc tcagcttatt ctgtttttca    780
gtctactctg tgagagagca ggaatgagac cagactagca acaccattgc caagctcaag    840
gactgggctc aatgcagtca ctccttcaga gagacccccc accccaagca tgccccactt    900
taaaatagca tgtttattga agggggcatc ctttacagta gctagaaaat gactgaggcc    960
caagccaggg ttgatcaagg atgtgccatt aaggtaaaga gttacagagc agggcagagg   1020
gactctgggg gcagaagtgg atgatttgcc cggcctcttc cagggggtct ggatacaact   1080
gaaggagctt tagctacatg aggccctcag agccaaagac aggatgcaaa tagagttcta   1140
gagagtggcc gtggaagcag aactccaggt ggggaatgtt caatctctgc ctcccttaaa   1200
gcagggccag gctcagctgg ccccattgtt cacttggtca caagtttcct acctttgttt   1260
ctggatgagt caaaggccag gaaggcagtt atggagagct cctgcacctc cagctgcccc   1320
acagaaaagc ctgcaagagt acttccaggc acaggccctc tcccacccta ttccatttgt   1380
```

```
aagcaaggga ggtcgaggaa aaggacatct ccaaaaggga gcataagaat agccatatat   1440

acaggggctg aaaaagtgct catgagtcca tcttttctgg aaagcaaaga ccagcctgaa   1500

gcagtgggag ctgctgccca agcggtagtg aactggagag aaacaggccc tggattttca   1560

gtgaggatgt ggatctgaag agtcccccaa atgcctctga agtctgacat ctctgcttag   1620

ccctaggagt ctggttccct gccttcagtt gcagagtgat gtgtttgtgt cattgttgat   1680

gtcacctcct aaaaagacct tcactttctg gctgccacaa agccatatgt gttgctcccc   1740

atatacagcc tgacagagta aatggagagg aagtgctgga tttgtgtatc actggctatc   1800

agttcctcat gttgttaagc ctcacacagg tgtgctagca ttgaactgta gagtgtcaca   1860

tacctgagtt tgaaaataaa agcacatttc c                                   1891
```

<210> SEQ ID NO 3
<211> LENGTH: 1466
<212> TYPE: DNA
<213> ORGANISM: Homo sapiens

<400> SEQUENCE: 3

```
cctcgtgcca tgttattttt tttaaatgac tttttagttt agaaagttct gatgagcaaa     60

taaatacatc tatctacatg ttggaagtcc atctgccagc acacctgctt aaagtgaaat    120

gaaagcacat aaccaggctc tgaatgggtt atattttatc atggtgctcc cagaatcctt    180

tgacctcact ctgctttcta gtctgcttgt gacactggac agtcctttct tacagagcta    240

ttatatgttc taggctacga agggttaaat aatcccaaaa atgaggtatg tcatacccac    300

acgtctttat ctctagaagc tgtgatgtat gtgaaacagc actgttattc ttaacactag    360

tgtgtaaaat aaggattagt acagtacgtc tcattacttt ttaattcagg gcaccctgag    420

tgaaaacaaa tacaaaaaaa aatccctaac tctgagctct atctctgatt cctcttcctc    480

cttcccctct tcctcctctt cctctcctcc tgttttgcta cattctcctc agtggcaaaa    540

agtttcactc tacctctgac agcatgtata ttgcaccagt agctaacaaa aactggtcta    600

gtcaaaccaa atgggcacaa aagaaccagg ataccaaaag ttaagctcat acagctgcaa    660

accatatcac ttcttggtaa caatgcagac ctcataaacc taaagaagag aaagaaaaga    720

aaacttttgt tactttcctt ttttgcttgt cacttatata caggctatgt gagaatataa    780

tttgtaggta taacacatta agaaaaagtt atcttcattg gatagaattg aatggtggtc    840

gctgatagga atagggcgtc ctctagctct tatctctgtc tcttactctt ttctctttct    900

ctttttctct gtcatgagac tgtgtgtgac agggccacct gtcttttttt ttttcttaaa    960

tttttttttt ttttttatgt gtaggtgcat gtcttgggga tttaaaaatt tcaaggctgg   1020

tttacttatg caaagcatgc ctacgtctgg aatacttagg gaaagaaagc gactccatgt   1080

tgtccgaatt cctcaaggga cagaaaaaaa attggagact gttgaaatgc agatttgaag   1140

taattttttt aaaatattat tttgggttct gcgacattgt gaaaaattaa agttgttgtg   1200

caatacttaa ttcagacatg taccacaagt taatggtaga ctaacactgg ggggtggggt   1260

ctaggcatca tgcttttgtc agcatactct tgagctttta agtctactat gtctgaactg   1320

tggtttcttg tttatccttt tttccttagt tggactgtaa tgtatggtct gtcaacctgt   1380

gaatctttaa agtatgattc aggtattgtt gtattcttta ctgtgtaata aaaaagttga   1440

aaaaaaaaaa aaaaaaaaaa aaaaaa                                         1466
```

<210> SEQ ID NO 4
<211> LENGTH: 2006
<212> TYPE: DNA

<213> ORGANISM: Homo sapiens

<400> SEQUENCE: 4

```
gggtatgtga atttcacatt aataaagtca taaaaaatga attccaggac cattaaatca     60
ggtgactgag ccaatagtta caggaacata gaaagatttt cacccattct gtataattag    120
acaaattctg ttactatctg tccaacagtt tagcaagagt cactctgaga ttgaagagag    180
gaagggaacg ttggaaccaa tgctgatgag ccattcatag gctctggctc actatatatg    240
tctaaaattc acatgcccct aaccctcaga taatgaccat taataatctg gcaggagagg    300
aaagacctgc agctcttcta gtccttatgc tatctcattg tctcatggat ttttaatatg    360
tctttgcatc ccttagaaat ttgcactttt ccccccttt tccattaaaa cacacctgcg     420
tgcaaacgtc catacacacc catgtacaca cagacacaca cacacatgca tgcgatctgt    480
aaaaagtcac aaaggccaaa gttttaaagg aagaaaataa aaatcacctg tagtcctatc    540
attcagagat aaccactgta tgtttattta cattagtttt gattacatta gtttagaatg    600
aaattttaaa tacactagta tatgtaatta aaattgtata tacgttttag tcaaccatca    660
gctgacttat tcatgttctg tggactctgt ggtgggtggg gtccaagcct ccctgaagca    720
gatctctatc ctgtcaccct gctggaaatg aaacacttag gggttagaag gggatcaagg    780
aaagtccgag agttggttct gattatcttc agtcagaaag tgcctacttt tccaagcatc    840
cagactgcaa cctgtttttc ctactcaaaa tggtttttat ggattctatt cttatttggc    900
aattgcctgg actacagtca ccaacacaag tttatacgca agaagtgcac acagccctcc    960
ctcccagctc atccggtaac aatttagatg aaggatgtaa aataggattc atttcatgac   1020
ccaagtctgg tcaattgaaa cagccgattg aagtgctgtg ttgaaaagga ttttgacact   1080
gcgcatgggc tcgttgggaa agggtgtcat gatgggttac tgattctgcg gtatttttgt   1140
ggacgtgggg agtggtggcc tacttacagt gcatcgccca ctctgattta gatgagcaag   1200
agctgctgag ttgtagattt ctagtttcta aacaacaata agtcttgctc gcagatagcc   1260
tcttagcaga gccaaaagcc agcagagaga agactcagca tttgctttgg agtaagtttg   1320
tgtgtgtatg tttatctccc ttttactcat gggctctttt ttcccaaata actgaggggc   1380
cagcacattt ggagaacatg ggatttatca ttgacgtcag tgccttggga gtctatgttt   1440
atgtgagctt aaaggttttg gaagctgaat gacacagatc aaagtctctc cactgatctg   1500
tcttccagtc ctccagggga cttcttccat caactacaaa tcattgatca aagtattggt   1560
ctgtcacctg tccatgtgta aggccaggcc taagtgctct gacagggcat gactcaatcc   1620
tcaaacagga agggggaaat tgctttccgt ctcctaaccc taagatcctg gatggcaggt   1680
aatctgcttc ctcaagattc tgttgataca cattcaggac tctggtttct gttttgcttg   1740
atgacaatga cccagtttct ttgactaaat aaatgtatag acacacatta cttcttttca   1800
ttctaagaat cataagtttt tcaaacttta gaatcacaag gtccattaaa ggacatctcc   1860
cctgaccttc ccattttgta gatgggaaga ctaaggtcca agcttgaatg acctgccatc   1920
atggggataa ccggaattga tacaatgtct tgattcaaga ttcagagctc atttttctg    1980
tgtcagatta aaaaaaaaaa aaaaaa                                        2006
```

<210> SEQ ID NO 5
<211> LENGTH: 1642
<212> TYPE: DNA
<213> ORGANISM: Homo sapiens

<400> SEQUENCE: 5

```
tcttaataat gtgtgtgtgt gtatgtgtgt gtgtgtgtgt gtgtgtttgt gtgtgtgtgt     60

gtgtgtccta attaagagaa tttttactgg ctgcttgtta catttgttga gggtacaaca    120

cactcaagaa taaagtaaaa ggatagtcag gatccagatg tttcttttct agcatttaat    180

gtgtgtgaac tcagaacact accatgaaag aacacttccc cccaaaactg gatgcagagg    240

aagaaaaaaa aaaaaagaaa tggcacagtt ttttgtattt tttttttag ttattttttg    300

ttgttgttgt ttgtattgtt tctcttttct gatagagtat ggccacttct gggggaaaaa    360

catgtaatta agtaaatgta tacattggtt ttcacgtttt acttttgttt tcccactacc    420

aataattttc ctctggaaga attttatagt tttttctatt tcattttaat gagtaacaat    480

atgttaaatg cataattaag acaaagcaat gaaattctga ctttattcaa agtactgaag    540

attattgctt ctagggcatt tttaaacagc accattgtat tgttgaatgt ttatgtaact    600

gatggctttt ctataatgta atttttgaat gttcaggtgt tacatttcca aagtttaact    660

tttaaaaaac catcttctga tccctttat tgtctgggcc atacaatcta tattacatag    720

gtgccaacat ttaattcttt taaatggaac atttgcagtt ttccatattg gtacctgctt    780

tttctggaga ggtttgagat cttgttaaca aatcagactt tacactatat acagatgtga    840

cagataaatt gaaccacttg tttgtgaaaa tgagttcctg tcatcttcct cattcactca    900

gccctcaccc cagcagcctt ttccggtcat tgtagctgac atggagcagt gacagtattc    960

atttgagaac agggatgcaa gtcacagaca tcataaaatc agggtctccc tgctgaagca   1020

ttcactagtt ggcaactatg aatttattcc atgtcattct gtttacttag cacttgcact   1080

acccttgttg gttgagtgta tgctttattt gtttctagtt tgaaatccca catctgatag   1140

ctgagagtag gcaaatacaa catttaccta atgtcattca ctaacatgga agagttgtga   1200

aaattctaga gtgctgtaaa tccttggcat acactatgac aaacaacttc attactctcc   1260

caccaggagc tgctctcctg cacttagaaa taatgtcaca agtagttttc taatgtacaa   1320

tgcagacaaa tgtactgctc tctgaatact tgaagaaatg gtattataca tacatagaaa   1380

cttattagtt ataccttttc acaatcttat tacgatgttg ccgttaaaag ggaaaaaaga   1440

cacaggcaat gaatggtggg atagtaagag gacttagagt gtatgaatga gttgatttta   1500

ctttttgga atttgattaa gttgacagta ggcactgatt ggatgattaa acataagtta   1560

atctccactg tgataaaaac ttaaataata aacatgattt aaaatagaaa aaaaaaaaaa   1620

aaaaaaaaaa aaaaaaaaaa aa                                            1642
```

<210> SEQ ID NO 6
<211> LENGTH: 4642
<212> TYPE: DNA
<213> ORGANISM: Homo sapiens

<400> SEQUENCE: 6

```
gggagccctg tgctctgacc ccagggccca gccacctggc cctcacgttc ctgcccagca     60

agccgggtgc ccggccccag cccgagggag ccagctggga tgcagggcct ggtggggcac    120

cctcggcctg ggcggaccca ggggagggcg gcccaagccc catgctcctc cctgagggcc    180

tgtcttccca ggctctgtcc acggaggctc ctctcccggc caccctggag ccccggattg    240

tgatgggaga ggagacgtgc caggccctcc tgtcacccag agctgcccgg acagcgctca    300

gggaccagga gggtgggcac gcaagcccag acccaccccc cgagctgtgt tctcagggtg    360

atctttctgt gccttcccct cccccagacc ctgattcctt cttcacgcct ccctccaccc    420

ccaccaagac cacctatgcc ctgcttcctg cctgtgggcc ccacggggac gccagggact    480
```

```
cagaggctga gctgcgggat gagctgctgg actcgccccc cgcctcaccc tcgggctcct    540

acattacggc cgatggggac agctgggcct cttcaccctc ctgttccctc agcctgctgg    600

ctccggctga agggctggac ttcccctcag gctggggcct gtccccgcag ggtccatgg     660

tggatgaacg agagctgcac ccagcaggga ccccagagcc cccgtcctct gagtccagcc    720

tctctgcaga cagcagctcc tcctggggcc aggagggcca cttcttcgac ctggacttcc    780

tggccaatga cccaatgatc cccgcagccc tcctaccctt ccagggcagc ctcatctttc    840

aggtggaggc agtggaggtg acaccgctat ccccagagga agaagaagag gaggctgtgg    900

cggatcccga cccaggtggg gacctggctg gggagggtga ggaggacagc acgtctgcct    960

ccttcctgca gtcactgtct gacctgtcca tcacggaggg catggacgag gcttttgcct   1020

tccgggacga cacctctgca gcctcctctg attcagactc agcctcctac gcagaggcag   1080

atgatgagag gctgtacagc ggggagcccc atgcccaggc cactttgctc caggacagtg   1140

tccagaagac agaggaggag agcggaggtg gggccaaggg gctgcaggct caggatggga   1200

ctgtgtcctg ggccgtggag gctgctcctc agacctcaga cagaggggcc tatctgtccc   1260

agagacagga attgatctca gaagtaacag aagagggcct tgctttaggc caggagtcca   1320

ctgccactgt gacccctcac actctgcagg tagccccagg cctccaggtg gaggtggcta   1380

ccagagtgac cccacaggct ggggaggaag aaacagactc caccgctgga caagaatctg   1440

ctgccatggc aatgcctcag ccctcccagg agggcatcag cgagatctta ggccaagagt   1500

ctgtcactgc agaaaaactt ccaactccac aggaagaaac aagcctcaca ttgtgtccag   1560

actctcctca gaacttgaag gaagaaggag ggctggacct cccctctggc agaaagcctg   1620

tagctgcagc cacgattgtc cccaggcagg ctaaagagga cctcacctta ccccaggact   1680

ccgctatgac accgcctctg cccctacaag acacagatct ctcatcagcc ccaaagcctg   1740

tggctgcagc cacgattgtg tcccagcagg ctgaagaggg cctcacctta ccccaggact   1800

ccgttatgac accgcctctg cccctacaag acacagaact ctcgtcagcc ccaaagcctg   1860

tggctgcagc cacgcttgtg tcccagcagg ctgaagaggg cctcacctta ccccaggact   1920

ccgctatgac accgcctctg cccctacaag acacagatct ctcgtcagcc ccaaagcctg   1980

tggctgcagc cacgcttgtg tcccagcagg ctgaagaggg cctcacctta ccccaggact   2040

ccgctatgac accgcctctg cccctacaag acacagatct ctcgtcagcc ccaaagcctg   2100

tggctgcagc cacgcttgtg tcccagcagg ctgaagaggg cctcacctta ccccaggact   2160

ccgctatgac accgcctctg cccctacaag acacagatct ctcgtcagcc ccaaagcctg   2220

tggctgcagc cacgattgtg tcccagcagg ctgaagaggg cctcacctta ccccaggact   2280

ccgctatgac accgcctctg cccctacaag acacagatct ctcgtcagcc ccaaagcctg   2340

tggctgcagc cacgattgtg tcccagcagg ctgaagaggg cctcacctta ccccaggact   2400

ccgctatgac accgcctctg cccctacaag acacagatct ctcgtcagcc ccaaagcctg   2460

tggctgcagc cacgcctgtg tcccagcagg ctgaagaggg cctcacctta ccccaggact   2520

ccgctatgac accgcctctg cccctacaag acacagatct ctcgtcagcc ccaaagcctg   2580

tggctgcagc cacgcctgtg tcccagcagg ctgaagaggg cctcacctta ccccaggact   2640

ccgctatgac agcacctctg cctctgcaag acacaggccc cacctcaggt ccagagcctc   2700

tggctgtggc caccccctcaa accttgcagg cagaagcagg ctgtgcccca gggacagagc   2760

ctgtggccac catggctcag caggaagtag gtgaggcctt aggccccagg ccagcacctg   2820

aggagaagaa tgcagccctc cctacagtcc cggagcctgc agccttggac caggtccaac   2880
```

```
aggatgaccc acagccagct gcagaagctg ggacaccttg ggccgcacag gaagatgcgg   2940
attccacttt gggcatggag gccctcagtc tccctgagcc ggcctctggt gctggggagg   3000
aaatagcaga agccctttct aggcctggac gggaagcatg tctggaagcg cgagcgcaca   3060
caggtgatgg ggctaagcct gactcacccc aaaaggagac cctggaggtt gagaaccagc   3120
aggaaggagg cctgaagcta ctggcacagg aacatggacc caggtcagca cttggaggtg   3180
caagggaggt ccccgatgcg cctcctgctg cctgccctga ggtcagccag gcccggctcc   3240
tgagcccagc cagggaggaa agaggcctga gtggcaagtc caccccggag cccacgcttc   3300
cctcagctgt ggccacagag gccagtctgg actcctgccc agagtcttca gtaggggctg   3360
tgtccagtct ggacagaggc tgccctgacg cgcctgcccc cacgtctgca ccaacctccc   3420
agcagccgga gcctgtactg ggtctgggca gtgttgagca accccacgaa gtacccagtg   3480
tccttggcac cccctgctg cagcccccag aaaaccttgc caagggtcag cccagcacgc   3540
ccgtggacag gcccctgggc cctgaccctt ctgctcctgg taccttgct ggggcagccc   3600
tacccccact ggagccccca gcccctgcc tgtgccagga cccccaggaa gactctgtgg   3660
aagacgagga gcccccaggc tctctgggcc tcccaccgcc ccaggcagga gtccagcctg   3720
ccgctgctgc tgtctcagga accacacagc ctctggggac tgggccgcga gtcagcctct   3780
cgcctcactc ccactcctc agccccaagg tggcctccat ggatgccaaa gacctggcct   3840
tgcagatctt gccgccttgc caagtgcctc ctccctctgg gccccagagc ccagctggcc   3900
ctcaagggct ctcagccccc gagcagcaag aggatgagga cagcctggag gaagactcgc   3960
ctcgggccct gggctcgggc cagcattcgg atagccacgg ggagtcatca gccgagctgg   4020
acgagcagga catcttggct cctcagaccg tgcagtgtcc agcccaggcc ccagcaggcg   4080
gcagtgagga gaccatcgcc aaagccaagc agagtcgcag tgagaagaag gcccgaaagg   4140
caatgtcaaa gctgggcttg cggcagattc agggagtcac caggatcacc atccagaagt   4200
ccaagaacat cctctttgtc atcgccaagc ctgatgtctt caagagccca gcctcagaca   4260
cttatgtggt ctttggcgag gccaagattg aggacctgtc ccagcaagtg cacaaagccg   4320
cagctgagaa gtttaaggtg ccctcagagc cctcagcctt ggtccctgag tcagcaccca   4380
ggccccgggt gaggctggag tgcaaggaag aggaagagga ggaggaggaa gaggtggacg   4440
aggcggggct ggaactgcgt gacattgagc tggtgatggc gcaggccaat gtgtccaggg   4500
ccaaggccgt gcgggctctg agagacaacc acagtgacat cgtcaacgcc atcatggaac   4560
tgaccatgta gccactgacc ggaagctgga gccatcctac gccttccctc agctctgcta   4620
ctcaataaat cggtgtccct tc                                            4642
```

<210> SEQ ID NO 7
<211> LENGTH: 1899
<212> TYPE: DNA
<213> ORGANISM: Homo sapiens

<400> SEQUENCE: 7

```
agcgcgcgac tttttgaaag ccaggagggt tcgaattgca acggcagctg ccgggcgtat     60
gtgttggtgc tagaggcagc tgcagggtct cgctgggggc cgctcgggac caattttgaa    120
gaggtacttg gccacgactt attttcacct ccgacctttc cttccaggcg gtgagactct    180
ggactgagag tggctttcac aatggaaggg atcagtaatt tcaagacacc aagcaaatta    240
tcagaaaaaa agaaatctgt attatgttca actccaacta taaatatccc ggcctctccg    300
tttatgcaga agcttggctt tggtactggg gtaaatgtgt acctaatgaa aagatctcca    360
```

```
agaggtttgt ctcattctcc ttgggctgta aaaaagatta atcctatatg taatgatcat    420
tatcgaagtg tgtatcaaaa gagactaatg gatgaagcta agattttgaa aagccttcat    480
catccaaaca ttgttggtta tcgtgctttt actgaagcca atgatggcag tctgtgtctt    540
gctatggaat atggaggtga aaagtctcta aatgacttaa tagaagaacg atataaagcc    600
agccaagatc cttttccagc agccataatt ttaaaagttg ctttgaatat ggcaagaggg    660
ttaaagtatc tgcaccaaga aaagaaactg cttcatggag acataaagtc ttcaaatgtt    720
gtaattaaag gcgatttga aacaattaaa atctgtgatg taggagtctc tctaccactg    780
gatgaaaata tgactgtgac tgaccctgag gcttgttaca ttggcacaga gccatggaaa    840
cccaaagaag ctgtggagga gaatggtgtt attactgaca aggcagacat atttgccttt    900
ggccttactt tgtgggaaat gatgacttta tcgattccac acattaatct ttcaaatgat    960
gatgatgatg aagataaaac ttttgatgaa agtgattttg atgatgaagc atactatgca   1020
gcgttgggaa ctaggccacc tattaatatg gaagaactgg atgaatcata ccagaaagta   1080
attgaactct tctctgtatg cactaatgaa gaccctaaag atcgtccttc tgctgcacac   1140
attgttgaag ctctggaaac agatgtctag tgatcatctc agctgaagtg tggcttgcgt   1200
aaataactgt ttattccaaa atatttacat agttactatc agtagttatt agactctaaa   1260
attggcatat ttgaggacca tagtttcttg ttaacatatg gataactatt tctaatatga   1320
aatatgctta tattggctat aagcacttgg aattgtactg ggttttctgt aaagttttag   1380
aaactagcta cataagtact ttgatactgc tcatgctgac ttaaaacact agcagtaaaa   1440
cgctgtaaac tgtaacatta aattgaatga ccattacttt tattaatgat ctttcttaaa   1500
tattctatat tttaatggat ctactgacat tagcactttg tacagtacaa aataaagtct   1560
acatttgttt aaaacactga accttttgct gatgtgttta tcaaatgata actggaagct   1620
gaggagaata tgcctcaaaa agagtagctc cttggatact tcagactctg gttacagatt   1680
gtcttgatct cttggatctc ctcagatctt tggtttttgc tttaatttat taaatgtatt   1740
ttccatactg agtttaaaat ttattaattt gtaccttaag catttcccag ctgtgtaaaa   1800
acaataaaac tcaaatagga tgataaagaa taaaggacac tttgggtacc agaaaaaaaa   1860
aaaaaaaaaa aaaaaaaaaa aaaaaaaaaa aaaaaaaaa                          1899
```

```
<210> SEQ ID NO 8
<211> LENGTH: 1894
<212> TYPE: DNA
<213> ORGANISM: Homo sapiens

<400> SEQUENCE: 8
```

```
ggctgaggac ccgagggagg acacggttaa agcatcgcta tcaactgcgt aacccagaga     60
gccctcctta gccaacacgc taactccgaa gcctcccctt acgcccccga accaccgaag    120
gcggcgacac ctgattcagc gcacaaacac aggtcccttc tgtcccggat acaattacgc    180
ggcagacaca cactcagact cgcgcggggc agccaagaga cgagctatga agtcttacac    240
tccatatttc attctcctgt ggagtgctgt tgggatagcg aaggctgcta aaatcatcat    300
cgtgccgcca attatgtttg aaagccatat gtacattttc aagacgctag cctcagcctt    360
gcacgagaga ggccaccata cagtgttcct cctctctgaa ggcagagaca tcgccccatc    420
taatcattac agcctccagc gctacccagg aatctttaac agtaccacct cagatgcttt    480
cctacagtcc aagatgcgga atattttctc tgggagattg ccagcaatcg aactgtttga    540
catactggat cactatacta agaactgtga catgatggtt ggcaaccatg ccctgatcca    600
```

```
gggtctgaag aaagaaaaat ttgacctgct gctggtggac cctaatgata tgtgtggatt    660

tgtgatagct catcttttag gggttaaata tgctgtattt tcaactggcc tttggtatcc    720

tgctgaagtg ggtgctcctg ctccattagc atacgtccca gagtttaact cactcctcac    780

agaccgcatg aacttgctgc aaaggatgaa aaataccggt gtttacctca tttccagatt    840

aggggtcagc tttctggttc ttcccaaata tgaaaggata atgcagaagt acaacctgct    900

gccggagaag tccatgtatg atttggttca tgggtccagc ctgtggatgc tgtgtactga    960

cgtagcactg gaattcccaa gacccactct gcctaatgtt gtttatgtag gaggaatcct   1020

aaccaaacca gccagcccac taccagaaga tctccaaaga tgggtaaatg gtgctaatga   1080

acatggcttt gtcttggtgt cttttggagc tggtgtcaag tatctgtcag aagacattgc   1140

taacaaactg gcaggagctc tggggagatt gcctcaaaaa gtgatttgga ggttttctgg   1200

acccaaacca aagaatctag gaaacaacac taaactcata gaatggttac cacaaaatga   1260

cctgcttggg cattcaaaga ttaaagcctt cgtgagccat ggtggtttga acagtatttt   1320

tgaaactatg tatcatggtg tgcctgtagt gggaattcca gtctttggag accattatga   1380

tactatgacc agagtacagg caaaaggcat ggggatattg ctagaatgga agacagttac   1440

tgaaaaagag ctctatgaag cactagtgaa ggttatcaat aatcccagct accgtcagag   1500

ggctcagaag ctttcggaaa ttcacaagga tcaacctggt caccctgtca atcgaactat   1560

ctattggata gattatatta ttcgtcacaa tggagcccat cacctacgtg ccgctgtcca   1620

tcagatctcc ttttgtcagt atttttact ggatattgcc tttgtgcttt tgcttggtgc    1680

tgccttgtta tactttctct tgtcttgggt gacaaaattt atctacagaa aatcaaaag    1740

tctgtggtct agaaataagc atagcacagt taatggacat taccacaatg gaatcctcaa   1800

tggcaagtac aaaagaaatg gccatattaa acatgaaaag aaagtgaaat gagccgacag   1860

cccaggtgat agaaataaat tggttcactc attg                               1894
```

```
<210> SEQ ID NO 9
<211> LENGTH: 907
<212> TYPE: DNA
<213> ORGANISM: Homo sapiens

<400> SEQUENCE: 9

cttttcttaa gggaaaaatc acgctgtgtt cttttaaaat ccctcaggtt ttatgtttta     60

ttgctaccag agtctgcctc cctgaggttc ttgtatagac tagttatttc cctctgtaaa    120

gaagctgttc tattcgttct cgcctggttt ggaacaaact gaacacttcc aaaggaggca    180

gtccttgcag ccttgtctcc ttccactccc ctcctcccca cagtcctggc tggagcagcg    240

agtctgtcga tcccaggcca gagacaaggc agacaaaggt tcatttgtaa agaagctcct    300

tccagcacct cctctcttct ccttttgccc aaactcaccc agtgagtgtg agcatttaag    360

aagcatcctc tgccaagacc aaaaggaaag aagaaaaagg gccaaaagcc aaaatgaaac    420

tgatggtact tgttttcacc attgggctaa ctttgctgct aggagttcaa gccatgcctg    480

caaatcgcct ctcttgctac agaaagatac taaaagatca caactgtcac aaccttccgg    540

aaggagtagc tgacctgaca cagattgatg tcaatgtcca ggatcatttc tgggatggga    600

agggatgtga gatgatctgt tactgcaact tcagcgaatt gctctgctgc ccaaaagacg    660

ttttctttgg accaaagatc tctttcgtga ttccttgcaa caatcaatga gaatcttcat    720

gtattctgga gaacaccatt cctgatttcc cacaaactgc actacatcag tataactgca    780

tttctagttt ctatatagtg caatagagca tagattctat aaattcttac ttgtctaaga    840
```

caagtaaatc tgtgttaaac aagtagtaat aaaagttaat tcaatctaat ttttctctgt 900
ggaaaaa 907

<210> SEQ ID NO 10
<211> LENGTH: 5370
<212> TYPE: DNA
<213> ORGANISM: Homo sapiens

<400> SEQUENCE: 10
agacgctcgg gcggcgggac ccagggaagg cagcggccgg agcgcgcaag aattagctag 60
gcgtggtggc aggtgcctgt aatcccagct actcaggagg ctgaggcagg agaatcgctt 120
gaacctggga ggcagaggtt gccgtgagct gagatcgcgc cattgcactc cagcctgggc 180
gacaagagca aaactccgtc tcagaaaaaa aaaaaaaaaa aaaagagttg atgtgttgaa 240
agacagagaa gcgaagacag agacgtggaa agacagggag agagacacgg agagagacgc 300
agaaggacag agacgtggag agagacgcag agagacagag acgtggagag acacagagag 360
acttggagag agacaaagca agacaggacg ggagaacaag gacaagctca ggtgcccctg 420
gagccccagc cctgccttca tgctcagcag gtgccctacc tggcccatcc tcccaaggta 480
agcctcagcc ggtgctgcag gcagtctgac tcgcagtccc tcaagtgact tccaaggagc 540
atctgtagaa aagaagatgg cccaggtcct gcacgtgcct gctcccttcc cagggacccc 600
tggcccagcc tccccacctg ccttccctgc caaggacccc gatccaccct actccgtgga 660 gacccccctat ggctaccgcc tggacctgga cttcctcaag tacgtggatg acatcgagaa 720
gggccacacg ctgcgacgcg tggcagtgca gcgccgcccc cgcctgagct cgctgccccg 780
tggccctggc tcctggtgga cgtccactga gtcgctgtgc tccaatgcca gtggggacag 840
ccgccactca gcctattcct actgcggccg tggcttctac cctcagtatg gtgctctgga 900
gacccgcggt ggcttcaatc cgcgggtgga gcgcacgctg ctggatgccc gtcgccgtct 960
cgaggaccag gcggccacac ccaccggcct gggctccctg acccccagtg cggccggctc 1020
gacagcctcc ctggtgggcg tggggttgcc acccccgaca ccacggagtt caggactgtc 1080
cacaccggtg cctcccagtg ccgggcacct ggcccacgtg cgggagcaga tggcgggtgc 1140
cctgcggaag ctgcggcagc tggaggagca ggtgaagctg atccctgtgc tccaggtgaa 1200
gctctcggtg ctccaggagg aaaagcggca gctcacagta caacttaaga gccagaagtt 1260
cctgggccac cccacagcgg gccggggtcg cagcgagctc tgcctggacc tccccgatcc 1320
cccagaggac ccagtggcac tggagacccg gagtgtgggc acctgggtcc gagaacggga 1380
cttgggcatg cctgatgggg aggctgccct cgccgccaag gtcgctgtgc tggagaccca 1440
gctcaagaag gcgctgcagg agctgcaggc agctcaggcc cggcaggctg acccccagcc 1500
ccaggcctgg ccaccgccgg acagcccggt ccgcgtggat acagtccggg tggtagaagg 1560
gccacgggag gtggaggtgg tggccagcac agccgctggc gcccccgcac agcgggccca 1620
gagcctggag ccttacggca cagggctgag ggccctggca atgcctggta ggcctgagag 1680
cccacctgtg ttccgcagcc aggaggtggt ggagacaatg tgcccagtgc ccgctgcagc 1740
taccagcaac gtccatatgg tgaagaagat tagcatcaca gagcgaagct gcgatggagc 1800
agcaggcctc ccagaagttc ctgccgaatc gtcttcgtca cccccggggt ccgaggtagc 1860
ctcccttaca cagcctgaga agagcacagg ccgagtgccc acccaggagc ccacccacag 1920
ggagcccacc aggcaagcag cctcccaaga gtccgaggag gccgggggca ccggcgggcc 1980
cccggcaggc gtgcgatcta tcatgaaacg gaaagaggag gttgcagacc ccacggccca 2040

-continued

```
ccggaggagc ctccagttcg tgggggtcaa cggcgggtat gagtcgtcat ccgaggactc   2100

cagcacagca gagaacatct cagacaacga cagcacagag aacgaggccc cagagccgag   2160

ggagagggtt ccgagtgtgg ccgaagcccc ccagctcagg cctgcaggga cggcagcggc   2220

caagaccagc cggcaggagt gtcagctgtc tcgagaatct cagcacatac ccactgctga   2280

gggggcatca ggatcaaaca cggaggagga gatcaggatg gagctaagcc ctgacctcat   2340

ctcagcctgc ttggccctgg aaaagtacct ggacaatccc aacgccctca cagagcggga   2400

gctgaaagtg gcctacacca cagtgctgca ggagtggctg cgcctggcct gccgcagcga   2460

cgcacacccc gagctggtgc ggcggcacct ggtcacgttc cgggccatgt ctgcgcggct   2520

gctggactac gtggtcaaca tcgccgacag caacggcaac acagccctgc actactccgt   2580

gtctcatgcc aacttccccg tggtgcagca gctgctcgac agcggtgtct gcaaggtgga   2640

caaacagaac cgtgctggct acagccctat tatgctcacc gccctggcca ccctgaagac   2700

ccaggacgac atcgagactg tccttcagct cttccggctt ggcaacatca atgccaaagc   2760

cagccaggca ggacagacgg ccctgatgct ggccgtcagc cacgggcggg tggacgttgt   2820

caaagccctg ctggcctgtg aggcagatgt caacgtgcaa gatgatgacg gctccacggc   2880

cctcatgtgc gcctgtgagc acggccacaa ggagatcgcg ggctgctgc tggccgtgcc   2940

cagctgtgac atctcactca cagatcgcga tgggagcaca gctctgatgg tggccttgga   3000

cgcagggcag agtgagattg cgtccatgct gtattcccgc atgaacatca agtgctcgtt   3060

tgccccaatg tcagatgacg agagccctac atcatcctcg gcagaagagt agccgtgagg   3120

gaggcgggga ccagccagac cgggagcaaa ccgtcccttg tccccgtctc ctccctgttc   3180

ccgttcctcc ctggcccacc ccactcacac tccccaaggc ccacggctca aaggcaagcg   3240

agctctccct ctgcttccct gggggagccc caacggccac aggactccag ctccaagtgg   3300

gttttcttgg ctcccctgtt caaagtggcc acagcgcaga ccgaagcaaa attcttgtat   3360

acattggcgc cagggctgat gctggggtgt gggttttatg aagaacattg agaacaatca   3420

gctggtaatt atggatggag gaagagggag aggaaaaaaa tattgtattt ttgaatcatt   3480

gttgcaggag ggggtgggaa tcttaggatt tgttgccaga tttgaaagtc actggaactt   3540

gcatattttc attttaatcc taagtgttat tacgcaccag ttggggttca cccttcatcc   3600

ctcacattta attgtctgat atagaatagt gttgtgtcca ctgccccgct agacggcttt   3660

cttaggggaa ttttcttctg gttgtttcac aagacagatt ctgtccttgt cacccgggac   3720

agaaaactca gtcttttcac cctcattcag atgaagggac tcaggacagg ctctgtgact   3780

tacagggacc caatcaattc acaatgagaa attaccggcc aggcgtggtg actcacgtct   3840

gtaatcccag cactttggga gggcaaggca agagcttgag cttgagccta gacgttaaag   3900

accagcctgg gcaacacagc aagacccatc tctacaagaa atttaaaaac tagccaggcg   3960

tggtggtgcg cgcctgtagt cccagctact tgggaggctg agccctggag gtcgaggcta   4020

cagtgagcta tgatcacacc attgcacttc agcctgggcg acacagcgag accctgtctc   4080

aagaaagaaa aaaaaaagag acaaattacc cagaaacccc tcccttcccc acatggaggc   4140

cttggcaaat gttaattttc ctagaaaatc cttcagacct gaagacgcag gaaaagaatc   4200

tggctctcag ggtggcttct gcgtccccgc cgccaggccc cagactatgg tcacagggcc   4260

gtcctgttcc tccccgggac tccagaattt ctctcctcaa aggaaagaaa acagggcatg   4320

cgcttgttgg caaaacgcag ggccggctcc caaaaacccc atgtgtgtac gattaaaagt   4380

tggccgtccc caggcctccc agcgcaaact taaagagaca gggctttgct gaaaaccaaa   4440
```

-continued

```
catgggccag ctgggctttt taacaaccta gagactttcc ggagctgcct ggaacagagc   4500

ctgtgggaaa cggggcttgc cagagacact cacagtttcc ttcatggcct gttttggtcc   4560

cctaagaatc tccacatcat tgtctttctt gtgccttttc cttggtgagc aacagaaagg   4620

gaagggttcc aagcctctaa aaatgtgctt tgtgatcagg agtgcgctcc aaaccaaata   4680

cgcgcgctgc cctttcgagg ccagtgagct cagcctccaa ggctttaaag ccacatttca   4740

gcaagagaaa gcgctgagag ctcgcaggtt cattaaagaa ggcaaagcac tggtttctct   4800

ccttagaaaa gtaggtttct tggcttgatg tagactggct tgctttgatt tttagtgaag   4860

ggaatgtacg taaaacaaaa tagggcttgg ctggtcaaag gagacaagca ggatggatgg   4920

atggatggat gaatagatag atggtgtttg catgtaaatt gcagagaaaa caaaaccaaa   4980

gctgattgga aacaattaat tgtgggtgtc tgagggggaa ggtcgcagct ttgggcagct   5040

ttgagaagcg gtacaagagc tctgtgcctg tgtgtccagc cctggagcca gccagtgcat   5100

ttattttaag ctcttagaag caactccttg gcccaggaat gcgtgacccc tgagatgggt   5160

ccacgcatct ctctacacgt ccttctctcc gtgggatact ggactcgtgc ctctgcgccc   5220

attctcttct cacgcatatc catgagcttt aatttcactt tctgatcacg gtacgtccat   5280

aaagccagta ttacacttaa atgaagtatt ctttttttgta atcgtttttt ttagaaggta   5340

aacaaattta ataaagctac caataatgtt                                    5370
```

<210> SEQ ID NO 11
<211> LENGTH: 2500
<212> TYPE: DNA
<213> ORGANISM: Homo sapiens

<400> SEQUENCE: 11

```
cggggggatc ttggctgtgt gtctgcggat ctgtagtggc ggcggcggcg gcggcggcgg     60

ggaggcagca ggcgcgggag cgggcgcagg agcaggcggc ggcggtggcg gcggcggtta    120

gacatgaacg ccgcctcggc gccggcggtg cacggagagc cccttctcgc gcgcgggcgg    180

tttgtgtgat tttgctaaaa tgcatcacca acagcgaatg gctgccttag ggacggacaa    240

agagctgagt gatttactgg atttcagtgc gatgttttca cctcctgtga gcagtgggaa    300

aaatggacca acttctttgg caagtggaca ttttactggc tcaaatgtag aagacagaag    360

tagctcaggg tcctggggga atggaggaca tccaagcccg tccaggaact atggagatgg    420

gactccctat gaccacatga ccagcaggga ccttgggtca catgacaatc tctctccacc    480

ttttgtcaat tccagaatac aaagtaaaac agaaaggggc tcatactcat cttatgggag    540

agaatcaaac ttacagggtt gccaccagca gagtctcctt ggaggtgaca tggatatggg    600

caacccagga accctttcgc ccaccaaacc tggttcccag tactatcagt attctagcaa    660

taatccccga aggaggcctc ttcacagtag tgccatggag gtacagacaa agaaagttcg    720

aaaagttcct ccaggtttgc catcttcagt ctatgctcca tcagcaagca ctgccgacta    780

caatagggac tcgccaggct atccttcctc caaaccagca accagcactt tccctagctc    840

cttcttcatg caagatggcc atcacagcag tgacccttgg agctcctcca gtgggatgaa    900

tcagcctggc tatgcaggaa tgttgggcaa ctcttctcat attccacagt ccagcagcta    960

ctgtagcctg catccacatg aacgtttgag ctatccatca cactcctcag cagacatcaa   1020

ttccagtctt cctccgatgt ccactttcca tcgtagtggt acaaaccatt acagcacctc   1080

ttcctgtacg cctcctgcca acgggacaga cagtataatg gcaaatagag gaagcggggc   1140

agccggcagc tcccagactg gagatgctct ggggaaagca cttgcttcga tctattctcc   1200
```

```
agatcacact aacaacagct tttcatcaaa cccttcaact cctgttggct ctcctccatc   1260

tctctcagca ggcacagctg tttggtctag aaatggagga caggcctcat cgtctcctaa   1320

ttatgaagga cccttacact ctttgcaaag ccgaattgaa gatcgtttag aaagactgga   1380

tgatgctatt catgttctcc ggaaccatgc agtgggccca tccacagcta tgcctggtgg   1440

tcatggggac atgcatggaa tcattggacc ttctcataat ggagccatgg gtggtctggg   1500

ctcagggtat ggaaccggcc ttctttcagc caacagacat tcactcatgg tggggaccca   1560

tcgtgaagat ggcgtggccc tgagaggcag ccattctctt ctgccaaacc aggttccggt   1620

tccacagctt cctgtccagt ctgcgacttc ccctgacctg aacccacccc aggaccctta   1680

cagaggcatg ccaccaggac tacaggggca gagtgtctcc tctggcagct ctgagatcaa   1740

atccgatgac gagggtgatg agaacctgca agacacgaaa tcttcggagg acaagaaatt   1800

agatgacgac aagaaggata tcaaatcaat tactagcaat aatgacgatg aggacctgac   1860

accagagcag aaggcagagc gtgagaagga gcggaggatg gccaacaatg cccgagagcg   1920

tctgcgggtc cgtgacatca acgaggcttt caaagagctc ggccgcatgg tgcagctcca   1980

cctcaagagt gacaagcccc agaccaagct cctgatcctc caccaggcgg tggccgtcat   2040

cctcagtctg gagcagcaag tccgagaaag gaatctgaat ccgaaagctg cgtgtctgaa   2100

aagaagggag gaagagaagg tgtcctcgga gcctccccct ctctccttgg ccggcccaca   2160

ccctggaatg ggagacgcat cgaatcacat gggacagatg taaaagggtc caagttgcca   2220

cattgcttca ttaaaacaag agaccacttc cttaacagct gtattatctt aaacccacat   2280

aaacacttct ccttaacccc catttttgta atataagaca agtctgagta gttatgaatc   2340

gcagacgcaa gaggtttcag cattcccaat tatcaaaaaa cagaaaaaca aaaaaaagaa   2400

agaaaaaagt gcaacttgag ggacgacttt ctttaacata tcattcagaa tgtgcaaagc   2460

agtatgtaca ggctgagaca cagcccagag actgaacggc                         2500
```

<210> SEQ ID NO 12
<211> LENGTH: 1556
<212> TYPE: DNA
<213> ORGANISM: Homo sapiens

<400> SEQUENCE: 12

```
cggtcagatt tgtgtgtgca ccgcgtctcc agcgatcccg gatccactgc gctgccaggg     60

gcctgggggt gggtctcttg ctgtctctgc gacgacatcc ttacgtttcg gcactctaat    120

gctgggtttg tgcgtgtgtg tctgcttagc ggtctagcgg gctgttaggc tccctcgccc    180

ccagctcctt ggctcgctca gctcctccac cgcagcccag cagtgagacg cgcgcgcagc    240

cagctcccca cgagatggaa cagaccgaag tgctgaagcc acggaccctg gctgatctga    300

tccgcatcct gcaccagctc tttgccggcg atgaggtcaa tgtagaggag gtgcaggcca    360

tcatggaagc ctacgagagc gaccccatcg agtgggcaat gtacgccaag ttcgaccagt    420

acaggtatac ccgaaatctt gtggatcaag gaaatggaaa atttaatctg atgattctct    480

gttggggtga aggacatggc agcagtattc atgatcatac caactcccac tgctttctga    540

agatgctaca gggaaatcta aaggagacat tatttgcctg gcctgacaaa aaatccaatg    600

agatggtcaa gaagtctgaa agagtcttga gggaaaacca gtgtgcctac atcaatgatt    660

ccattggctt acatcgagta gagaacatca gccatacgga acctgctgtg agccttcact    720

tgtacagtcc accttttgat acatgccatg cctttgatca aagaacagga cataaaaaca    780

aagtcacaat gacattccat agtaaatttg gaatcagaac tccaaatgca acttcgggct    840
```

```
cgctggagaa caactaaggg gcaccaaacc ctctgaggtt ttactttaag gttcgctgta    900

tgtttgcctt ggacaaaaag gctacctacc acgtgctatc cagtaatata cttaaataag    960

ccaatactta gatctactgt aaggcagatg ctaattataa ggcattaagt aagcaaatag   1020

tgccctcagc tactgcagaa gaaaagtccc actgaggaaa agaaagtctt gtgattttta   1080

aaggcaagtt ttcaagtgct ctcatagttc tatcctctaa ttccattaaa tccatactag   1140

gagcgtcagt gagggttttc atagcttttg gaaatacttt ggtctctgaa ctgtaattag   1200

caagaagtaa aaacagaaac gtcaaacgtc aaatgtttgc tttgttacct ggaggactaa   1260

atgtagatgt ctttagtata ctttgtatgt tcttaaatat tggaagataa ttttgtgaat   1320

ctgtagattt tattttttca gtcttacctt acaaatttct tttctatgaa taatagagga   1380

actcacggca ctctgccact tgttaatgaa aggaagtgca gaggatttag aaaagtacat   1440

gatccccaga ccacaacaaa ccaaaacata aactcatgtc tgtgtcccat ggtcatagtc   1500

aaagattttg tactgctaaa attaccaaat aatttaaata aagtggattt gaacac         1556
```

<210> SEQ ID NO 13
<211> LENGTH: 2374
<212> TYPE: DNA
<213> ORGANISM: Homo sapiens

<400> SEQUENCE: 13

```
gggcgatgag agcgggtact gcgaactgcc gggcgatgct gtcgctgccg ccgtgatacg     60

gagagcaaca gttccccagc aacacccctc cccgacacag gcacacaccc cccgacaggc    120

acgcacaccc accccacagt gcccggctcg gctgcgcctc ctctattggc ccaggaagcc    180

cacccagccc cgccacgcag agcccagaag gaaagaaagc ctcatgcctg agccgagggg    240

agcaccatgg atctgacaaa aatgggcatg atccagctgc agaaccctag ccaccccacg    300

gggctactgt gcaaggccaa ccagatgcgg ctggccggga ctttgtgcga tgtggtcatc    360

atggtggaca gccaggagtt ccacgcccac cggacggtgc tggcctgcac cagcaagatg    420

tttgagatcc tcttccaccg caatagtcaa cactatactt tggacttcct ctcgccaaag    480

accttccagc agattctgga gtatgcatat acagccacgc tgcaagccaa ggcggaggac    540

ctggatgacc tgctgtatgc ggccgagatc ctggagatcg agtacctgga ggaacagtgc    600

ctgaagatgc tggagaccat ccaggcctca gacgacaatg acacggaggc caccatggcc    660

gatggcgggg ccgaggaaga agaggaccgc aaggctcggt acctcaagaa catcttcatc    720

tcgaagcatt ccagcgagga gagtgggtat gccagtgtgg ctggacagag cctccctggg    780

cccatggtgg accagagccc ttcagtctcc acttcatttg gtctttcagc catgagtccc    840

accaaggctg cagtggacag tttgatgacc ataggacagt ctctcctgca gggaactctt    900

cagccacctg cagggcccga ggagccaact ctggctgggg gtgggcggca ccctggggtg    960

gctgaggtga agacggagat gatgcaggtg gatgaggtgc ccagccagga cagccctggg   1020

gcagccgagt ccagcatctc aggagggatg ggggacaagg ttgaggaaag aggcaaagag   1080

gggcctggga ccccgactcg aagcagcgtc atcaccagtg ctagggagct acactatggg   1140

cgagaggaga gtgccgagca ggtgccaccc ccagctgagg ctggccaggc ccccactggc   1200

cgacctgagc acccagcacc cccgcctgag aagcatctgg gcatctactc cgtgttgccc   1260

aaccacaagg ctgacgctgt attgagcatg ccgtcttccg tgacctctgg cctccacgtg   1320

cagcctgccc tggctgtctc catggacttc agcacctatg gggggctgct gccccagggc   1380

ttcatccaga gggagctgtt cagcaagctg gggggagctgg ctgtgggcat gaagtcagag   1440
```

```
agccggacca tcggagagca gtgcagcgtg tgtggggtcg agcttcctga taacgaggct   1500

gtggagcagc acaggaagct gcacagtggg atgaagacgt acgggtgcga gctctgcggg   1560

aagcggttcc tggatagttt gcggctgaga atgcacttac tggctcattc agcgggtgcc   1620

aaagcctttg tctgtgatca gtgcggtgca cagttttcga aggaggatgc cctggagaca   1680

cacaggcaga cccatactgg cactgacatg gccgtcttct gtctgctgtg tgggaagcgc   1740

ttccaggcgc agagcgcact gcagcagcac atggaggtcc acgcgggcgt gcgcagctac   1800

atctgcagtg agtgcaaccg caccttcccc agccacacgg ctctcaaacg ccacctgcgc   1860

tcacatacag gcgaccaccc ctacgagtgt gagttctgtg gcagctgctt ccgggatgag   1920

agcacactca agagccacaa acgcatccac acgggtgaga aaccctacga gtgcaatggc   1980

tgtggcaaga agttcagcct caagcatcag ctggagacgc actatagggt gcacacaggt   2040

gagaagccct ttgagtgtaa gctctgccac cagcgctccc gggactactc ggccatgatc   2100

aagcacctga gaacgcacaa cggcgcctcg ccctaccagt gcaccatctg cacagagtac   2160

tgccccagcc tctcctccat gcagaagcac atgaagggcc acaagcccga ggagatcccg   2220

cccgactgga ggatagagaa gacgtacctc tacctgtgct atgtgtgaag ggaggcccgc   2280

ggcggtggag ccgagcgggg agccaggaaa gaagagttgg agtgagatga aggaaggact   2340

atgacaaata aaaaaaaaaa aaaaaaaaaa aaaa                                2374
```

<210> SEQ ID NO 14
<211> LENGTH: 783
<212> TYPE: DNA
<213> ORGANISM: Homo sapiens

<400> SEQUENCE: 14

```
gttacagata cggaaacagg ctcggaggtg caatctctgg ctgtgtagac agaacaggga     60

gttggaacac ggccttctgc gtttcctcac tctcacatac cagcgggcag ggagagatcc    120

ggggaggagt tgcacttgcc cccggcggaa atctccaaaa atctgcaaaa atgtattccc    180

tggtaccgct ttgggctccg gtgggaccaa gcgaaattcc gagaccgaaa cggatgcgcg    240

ctgcggccca gggtgcgggt ctggaccgcc tcctccgtgg tggacgaatc cgaggagcag    300

gactccccgc aacccagccc cagccccagc cccagccccg ccgcgtcccc agctgtcacg    360

ctgcgcgcag cgggtggggc ctggggttcc tggacagagg aggactacgc gtgtccttgg    420

gcggagaagg gaggtgactc cggcggaaga ggacaaggca gaatgcaggc ccttcgggtg    480

tcccaggcgc tgatccgctc cttcagctcc accgcccgga accgctttca gaaccgagtg    540

cgcgagaaac agaagctctt ccaggaggac aatgacatcc cgttgtacct gaagggcggc    600

atcgttgaca acatcctgta ccgagtgaca atgacgctgt gtctgggcgg cactgtctac    660

agcttgtact ccccttggctg ggcctccttc cccaggaatt aagaccaaga agcctggggg    720

gcctgagaga cttgaacaag tgtcaataaa cgctggcctc tgaaaaaaaa aaaaaaaaaa    780

aaa                                                                  783
```

<210> SEQ ID NO 15
<211> LENGTH: 691
<212> TYPE: DNA
<213> ORGANISM: Homo sapiens

<400> SEQUENCE: 15

```
gacccctcac actcacctag ccaccatgga catcgccatc caccacccct ggatccgccg     60

cccccttcttt cctttccact cccccagccg cctctttgac cagttcttcg gagagcacct    120
```

```
gttggagtct gatcttttcc cgacgtctac ttccctgagt cccttctacc ttcggccacc    180

ctccttcctg cgggcaccca gctggtttga cactggactc tcagagatgc gcctggagaa    240

ggacaggttc tctgtcaacc tggatgtgaa gcacttctcc ccagaggaac tcaaagttaa    300

ggtgttggga gatgtgattg aggtgcatgg aaaacatgaa gagcgccagg atgaacatgg    360

tttcatctcc agggagttcc acaggaaata ccggatccca gctgatgtag accctctcac    420

cattacttca tccctgtcat ctgatggggt cctcactgtg aatggaccaa ggaaacaggt    480

ctctggccct gagcgcacca ttcccatcac ccgtgaagag aagcctgctg tcaccgcagc    540

ccccaagaaa tagatgccct ttcttgaatt gcattttta aaacaagaaa gtttccccac    600

cagtgaatga aagtcttgtg actagtgctg aagcttatta atgctaaggg caggcccaaa    660

ttatcaagct aataaaatat cattcagcaa c                                   691
```

<210> SEQ ID NO 16
<211> LENGTH: 2498
<212> TYPE: DNA
<213> ORGANISM: Homo sapiens

<400> SEQUENCE: 16

```
accagcaccc cgcccagagc agtgccgctg cccaaatcct cgcaggcagc tcatcaacgc     60

aattgcaact ccggctggag ccccggacct gcaagcctgg gtgtccgtgg gtccgtctgc    120

ccagccatct gctggtggca cctctccctc ctgccgcctc cctcggtgaa ccccaccttg    180

cagaagtgca gctcgcccgg agcagcccag gagctcagca tgcgtccccc aggcttcagg    240

aacttcttgc tgctggcgtc ctcccttctc tttgctgggt tgtcagctgt tcctcaaagc    300

ttctcgccat ctctgaggag ctggccgggc gccgcctgca ggctgtcccg ggccgagtcg    360

gagcgacgct gccgcgcacc tggcagcccc ccgggggccg cgctgtgcca cggccggggc    420

cgctgcgact gcggcgtctg catctgccac gtgactgagc cgggcatgtt cttcgggccc    480

ctgtgtgagt gccatgagtg ggtgtgcgag acctacgacg ggagcacctg tgcaggccat    540

ggtaagtgtg actgtggcaa gtgcaagtgt gaccagggat ggtatgggga tgcttgccag    600

tacccaacta actgtgactt gacaaagaag aaaagtaacc aaatgtgcaa gaattcacaa    660

gacatcatct gctctaatgc aggtacatgt cactgtggca ggtgtaagtg tgataattca    720

gatggaagtg gacttgtgta tggtaaattt tgtgagtgtg acgatagaga atgcatagac    780

gatgaaacag aagaaatatg tggaggccat gggaagtgtt actgtggaaa ctgctactgc    840

aaggctggtt ggcatggaga taaatgtgaa ttccagtgcg atatcacccc ctgggaaagc    900

aagcgaagat gcacgtctcc agatggcaaa atctgcagta acagagggac ttgtgtatgt    960

ggtgaatgta cctgtcacga tgttgatccg actggggact ggggagatat tcatggggac   1020

acctgtgaat gtgatgagag ggactgtaga gctgtctatg accgatattc tgatgacttc   1080

tgttcaggtc atggacagtg taattgcgga agatgtgact gcaaagcagg ctggtatggg   1140

aagaagtgtg agcacccaca gtcctgcacg ctgtcagctg aggagagcat caggaagtgc   1200

cagggaagct cggatctgcc ttgctctggg aggggtaaat gtgaatgtgg caaatgcacc   1260

tgctatcctc caggagatcg ccgggtgtat ggcaagactt gtgagtgtga tgatcgccgc   1320

tgtgaagacc tcgatggtgt ggtctgtgga ggccacggca catgttcctg tggtcgctgt   1380

gtttgtgaga gaggatggtt tggaaagctc tgccaacatc cgcggaagtg taacatgacg   1440

gaagaacaaa gcaagaatct gtgtgaatca gcagatggca tattgtgctc ggggaagggt   1500

tcttgtcatt gtgggaagtg catttgttct gctgaagagt ggtatatttc tggggagttc   1560
```

```
tgtgactgtg atgacagaga ctgcgacaaa catgatggtc tcatttgtac agggaatgga   1620

atatgtagct gtggaaactg tgaatgctgg gatggatgga atggaaatgc atgtgaaatc   1680

tggcttggct cagaatatcc ttaacaatta catgagagag gtctggattc ttattttttc   1740

tgggccatta gaacatataa atgcgaagga aaccatgtat attcaccact aggacaggtt   1800

aaaaagacca ttgtatgttt ttctatttct gaattacgaa tgaaatccga gtacctatta   1860

gaaatgagtt atgcaaattt agatgcaaat aacattagaa aaaaaagatt cttccataat   1920

taacataagt ggttcctaac gagagcaatt tttccaccca aaagtcattt ggcaacatct   1980

acagacaatt ttgattgtca cactgggtcg ggtaggaagg tatgctgcag acatttggtg   2040

ggtagaggcc agggatgctg ctgagcatcc cgcagtgtac aggacagccc ccaaacaagg   2100

aattatccag ccccaaatgc caatagggct cagactgaga aacattgagt tatatggcta   2160

ttagaaatcc acattcttac acaagaaaga ccatattaga atctaaggaa aacatgcata   2220

ttcacattaa ttaatcgatc agatttttcc agaattccgt atcagtcacc attttaatat   2280

ggggacaatg aagacaagca cacaggaggt agaatatcag agtggggctg gatcaagggc   2340

aaaaactggt cattaagtca tctgacatta aatcatttag ccactaagtt atttgtgtac   2400

tctcacttta aactcaccaa agaagattct cttaaagaaa ttatgaaaaa tgtacaattt   2460

aacattttaa ataaatagtg acagaagttg tttaaaaa                           2498
```

<210> SEQ ID NO 17
<211> LENGTH: 2039
<212> TYPE: DNA
<213> ORGANISM: Homo sapiens

<400> SEQUENCE: 17

```
ggaggactca ggccccgctg gccgcgggct cggtacccgg tgggtcggtg gagcgtctgt     60

tgggtccggg ccgccggctt cgccctcgcc atggcgccct ggctgcagct cctgtcgctg    120

ctggggctgc tcccgggcgc agtggccgcc cccgcccagc cccgagccgc cagctttcag    180

gcctgggggc cgccgtcccc ggagctgctg gcgcctaccc gcttcgcgct ggagatgttc    240

aaccgcggcc gggctgcggg gacgcgggcc gtgctgggcc ttgtgcgcgg ccgcgtccgc    300

cgggcgggcc aagggtcgct gtactccctg gaggccaccc tggaggagcc accctgcaac    360

gaccccatgg tgtgccggct ccccgtgtcc aagaaaaccc tgctctgcag cttccaagtc    420

ctggatgagc tcggaagaca cgtgctgctg cggaaggact gtggcccagt ggacaccaag    480

gttccaggtg ctggggagcc caagtcagcc ttcactcagg gctcagccat gatttcttct    540

ctgtcccaaa accatccaga caacagaaac gagactttca gctcagtcat ttccctgttg    600

aatgaggatc ccctgtccca ggacttgcct gtgaagatgg cttcaatctt caagaacttt    660

gtcattacct ataaccggac atatgagtca aaggaagaag cccggtggcg cctgtccgtc    720

tttgtcaata acatggtgcg agcacagaag atccaggccc tggaccgtgg cacagctcag    780

tatggagtca ccaagttcag tgatctcaca gaggaggagt tccgcactat ctacctgaat    840

actctcctga gaaaagagcc tggcaacaag atgaagcaag ccaagtctgt gggtgacctc    900

gccccacctg aatgggactg gaggagtaag ggggctgtca caaaagtcaa agaccagggc    960

atgtgtggct cctgctgggc cttctcagtc acaggcaatg tggagggcca gtggtttctc   1020

aaccagggga ccctgctctc cctctctgaa caggagctct tggactgtga caagatggac   1080

aaggcctgca tgggcggctt gccctccaat gcctactcgg ccataaagaa tttgggaggg   1140

ctggagacag aggatgacta cagctaccag ggtcacatgc agtcctgcaa cttctcagca   1200
```

```
gagaaggcca aggtctacat caatgactcc gtggagctga gccagaacga gcagaagctg   1260
gcagcctggc tggccaagag aggcccaatc tccgtggcca tcaatgcctt tggcatgcag   1320
ttttaccgcc acgggatctc ccgccctctc cggcccctct gcagcccttg gctcattgac   1380
catgcggtgt tgcttgtggg ctacggcaac cgctctgacg ttcccttttg ggccatcaag   1440
aacagctggg gcactgactg ggtgagaag ggttactact acttgcatcg cgggtccggg   1500
gcctgtggcg tgaacaccat ggccagctcg gcggtggtgg actgaagagg ggcccccagc   1560
tcgggacctg gtgctgatca gagtggctgc tgccccagcc tgacatgtgt ccaggcccct   1620
ccccgggagg tacagctggc agagggaaag gcactgggta cctcagggtg agcagagggc   1680
actgggctgg ggcacagccc ctgcttccct gcaccccatt cccaccctga agttctgcac   1740
ctgcaccttt gttgaattgt ggtagcttag gaggatgtcg ggtgaaggg tggtatcttg   1800
gcagttgaag ctggggcaag aactctgggc ttgggtaatg agcaggaaga aaattttctg   1860
atcttaagcc cagctctgtt ctgccccgc tttcctctgt ttgatactat aaattttctg   1920
gttcccttgg atttagggat agtgtccctc tccatgtcca ggaaacttgt aaccaccctt   1980
ttctaacagc aataaagagg tgtccttgta aaaaaaaaaa aaaaaaaaaa aaaaaaaaa    2039
```

<210> SEQ ID NO 18
<211> LENGTH: 2474
<212> TYPE: DNA
<213> ORGANISM: Homo sapiens

<400> SEQUENCE: 18

```
ggcacgaggg ttgaagctcg gcgctcgggt taccccctgca gcgacgcccc ctggtcccac     60
agataccact gctgctcccg ccctttcgct cctcggccgc gcaatgggca cccgcgacga    120
cgagtacgac tacctcttta aagttgtcct tattggagat tctggtgttg gaaagagtaa    180
tctcctgtct cgatttactc gaaatgagtt taatctggaa agcaagagca ccattggagt    240
agagtttgca acaagaagca tccaggttga tggaaaaaca ataaaggcac agatatggga    300
cacagcaggg caagagcgat atcgagctat aacatcagca tattatcgtg gagctgtagg    360
tgccttattg gtttatgaca ttgctaaaca tctcacatat gaaaatgtag agcgatggct    420
gaaagaactg agagatcatg ctgatagtaa cattgttatc atgcttgtgg gcaataagag    480
tgatctacgt catctcaggg cagttcctac agatgaagca agagcttttg cagaaaagaa    540
tggtttgtca ttcattgaaa cttcggccct agactctaca aatgtagaag ctgcttttca    600
gacaatttta acagagattt accgcattgt ttctcagaag caaatgtcag acagacgcga    660
aaatgacatg tctccaagca acaatgtggt tcctattcat gttccaccaa ccactgaaaa    720
caagccaaag gtgcagtgct gtcagaacat ctaaggcatt tctcttctcc cctagaaggc    780
tgtgtatagt ccatttccca ggtctgagat ttaaatatat ttgtaattct tgtgtcactt    840
ttgtgtttta ttacttcata cttatgaatt tttccatgtc ctaagtcttt tgattttagc    900
tttataaaat catccacttg tcccgaatga ctgcagcttt ttttcatgct atggcttcac    960
tagccttagt ttaataaact gaatgtttgg attcctcagt tattgtttac ttttcatcat   1020
ggaagcctgt cactgtatgt aggacataat agaacttgat cacttgaagc tcagacctat   1080
tggtcttgat caaatcaaac taagaagacc ttagaaataa gctaccattt tgccacagag   1140
cagcttatag gtaatacact cttctctcag tgcagtgtac atttccacaa atctaagaat   1200
tgccctataa acatagcagg attttgagag cttgaaaatt ttccattatt ctggacatga   1260
atttctaaaa tgccttaata ggtttatgta gttgagtaaa ttttgttttt taatttttgt   1320
```

```
aagcatcaaa gttgattaga gagggggca ctttttctgg agaattctct tagtaaacac   1380

aaaagattgt tacggtttca ttagtagtat ggttgtgggg ccataagtta aacagtgctg   1440

cctggtaggc tgggaactga agagacttgt ggtattccat ctcgggtgcc tctgttggca   1500

atgatcaggc agcccaaaag atttaaatga tctataataa tttccaagcg gtagattatg   1560

tggcatttta ttgctcaggc aataattggt ttaatgctgg tagtgtcaaa ttttgtctta   1620

gaaccttcca gtaagtgaaa tacaacctag ttttatcacc atatccacca gcaggcatgg   1680

ataattattt taacaatgct aatatttgag ttttgcagta tattatagaa tatagtccag   1740

ttaaatcttt ggtttcagta tgtctgaaga gtacagtgag aggttaattt ctgctcaagt   1800

ggtaccactt aaaggcatgt attcttttag tatgtaaaat gaaatagtac cttgagttta   1860

aatagaatgc atttaggcat tgtagagatc tgaaatagtt ttcttccact acattgttga   1920

aatcaatgaa gcaattagtt tctcattcag aaatgtgcac actaatattt agttttgctt   1980

tctcgtggat aatattaagc acttactctg cagtttcctg gaagttgtgt caactgcagt   2040

gatactattc aggatggtgg gaaatcccca aaaatatgta tgtgtgggct tgcttagatt   2100

actatatttc atagttaatc ttttgtctct tgcggtgctc atgatgtgtg gggcacacgg   2160

aaggcattgc tgtagtcagt cattttggtt ttcttctata gccattttat tattttagtg   2220

tattagttat gaagataata ttatctattt gtaaattgct actttgtatt ttatgcatgc   2280

tctgtaattt gatttttttt tagttattga tttggattat attcacattc taataaacag   2340

ttataggggg aaaaaaaaaa aaaaaaaaaa aaaaaaaaaa aaaaaaaaaa aaaaaaaaaa   2400

aaaaaaaaaa aaaaaaaaaa aaaaaaaaaa aaaaaaaaaa aaaaaaaaaa aaaaaaaaaa   2460

aaaaaaaaaa aaaa                                                     2474


<210> SEQ ID NO 19
<211> LENGTH: 2742
<212> TYPE: DNA
<213> ORGANISM: Homo sapiens

<400> SEQUENCE: 19

ctagtattct actagaactg gaagattgct ctccgagttt tttttttgtt attttgttaa     60

aaaataaaaa gcttgagcag caattcatat tactgtcaca ggtatttttg ctgtgctgtg    120

caaggtaact ctgctagcta agattcacaa tgttgaaagc ccttttccta actatgctga    180

ctctggcgct ggtcaagtca caggacaccg aagaaaccat cacgtacacg caatgcactg    240

acggatatga gtgggatcct gtgagacagc aatgcaaaga tattgatgaa tgtgacattg    300

tcccagacgc ttgtaaaggt ggaatgaagt gtgtcaacca ctatggagga tacctctgcc    360

ttccgaaaac agcccagatt attgtcaata atgaacagcc tcagcaggaa acacaaccag    420

cagaaggaac ctcaggggca accaccgggg ttgtagctgc cagcagcatg gcaaccagtg    480

gagtgttgcc cgggggtggt tttgtggcca gtgctgctgc agtcgcaggc cctgaaatgc    540

agactggccg aaataacttt gtcatccggc ggaacccagc tgaccctcag cgcattccct    600

ccaacccttc ccaccgtatc cagtgtgcag caggctacga gcaaagtgaa cacaacgtgt    660

gccaagacat agacgagtgc actgcaggga cgcacaactg tagagcagac caagtgtgca    720

tcaatttacg ggatcctttt gcatgtcagt gccctcctgg atatcagaag cgaggggagc    780

agtgcgtaga catagatgaa tgtaccatcc ctccatattg ccaccaaaga tgcgtgaata    840

caccaggctc attttattgc cagtgcagtc ctgggtttca attggcagca aacaactata    900

cctgcgtaga tataaatgaa tgtgatgcca gcaatcaatg tgctcagcag tgctacaaca    960
```

```
ttcttggttc attcatctgt cagtgcaatc aaggatatga gctaagcagt gacaggctca   1020

actgtgaaga cattgatgaa tgcagaacct caagctacct gtgtcaatat caatgtgtca   1080

atgaacctgg gaaattctca tgtatgtgcc cccagggata ccaagtggtg agaagtagaa   1140

catgtcaaga tataaatgag tgtgagacca caaatgaatg ccgggaggat gaaatgtgtt   1200

ggaattatca tggcggcttc cgttgttatc cacgaaatcc ttgtcaagat ccctacattc   1260

taacaccaga gaaccgatgt gtttgcccag tctcaaatgc catgtgccga gaactgcccc   1320

agtcaatagt ctacaaatac atgagcatcc gatctgatag gtctgtgcca tcagacatct   1380

tccagataca ggccacaact atttatgcca acaccatcaa tacttttcgg attaaatctg   1440

gaaatgaaaa tggagagttc tacctacgac aaacaagtcc tgtaagtgca atgcttgtgc   1500

tcgtgaagtc attatcagga ccaagagaac atatcgtgga cctggagatg ctgacagtca   1560

gcagtatagg gaccttccgc acaagctctg tgttaagatt gacaataata gtggggccat   1620

tttcatttta gtcttttcta agagtcaacc acaggcattt aagtcagcca aagaatattg   1680

ttaccttaaa gcactatttt atttatagat atatctagtg catctacatc tctatactgt   1740

acactcaccc ataacaaaca attacaccat ggtataaagt gggcatttaa tatgtaaaga   1800

ttcaaagttt gtctttatta ctatatgtaa attagacatt aatccactaa actggtcttc   1860

ttcaagagag ctaagtatac actatctggt gaaacttgga ttctttccta taaaagtggg   1920

accaagcaat gatgatcttc tgtggtgctt aaggaaactt actagagctc cactaacagt   1980

ctcataagga ggcagccatc ataaccattg aatagcatgc aagggtaaga atgagttttt   2040

aactgctttg taagaaaatg gaaaaggtca ataaagatat atttctttag aaaatgggga   2100

tctgccatat ttgtgttggt ttttattttc atatccagcc taaaggtggt tgtttattat   2160

atagtaataa atcattgctg tacaacatgc tggtttctgt agggtatttt taattttgtc   2220

agaaatttta gattgtgaat attttgtaaa aaacagtaag caaaattttc cagaattccc   2280

aaaatgaacc agataccccc tagaaaatta tactattgag aaatctatgg ggaggatatg   2340

agaaaataaa ttccttctaa accacattgg aactgacctg aagaagcaaa ctcggaaaat   2400

ataataacat ccctgaattc aggcattcac aagatgcaga acaaaatgga taaaaggtat   2460

ttcactggag aagttttaat ttctaagtaa aatttaaatc ctaacacttc actaatttat   2520

aactaaaatt tctcatcttc gtacttgatg ctcacagagg aagaaaatga tgatggtttt   2580

tattcctggc atccagagtg acagtgaact taagcaaatt accctcctac ccaattctat   2640

ggaatatttt atacgtctcc ttgtttaaaa tctgactgct ttactttgat gtatcatatt   2700

tttaaataaa aataaatatt cctttagaag atcactctaa aa                       2742
```

<210> SEQ ID NO 20
<211> LENGTH: 2051
<212> TYPE: DNA
<213> ORGANISM: Homo sapiens

<400> SEQUENCE: 20

```
cgagacctac tccacaggtc cagccggccg gtgagcgcct ggggaccgca gaggtgagag     60

tcgcgcccgg gagtccgccg cctgcgccag gatggagttc gtgaaatgcc ttggccaccc    120

cgaagagttc tacaacctgg tgcgcttccg gatcgggggc aagcggaagg tgatgcccaa    180

gatggaccag gactcgctca gcagcagcct gaaaacttgc tacaagtatc tcaatcagac    240

cagtcgcagt ttcgcagctg ttatccaggc gctggatggg gaaatgcgca acgcagtgtg    300

catattttat ctggttctcc gagctctgga cacactggaa gatgacatga ccatcagtgt    360
```

```
ggaaaagaag gtcccgctgt tacacaactt tcactctttc ctttaccaac cagactggcg    420

gttcatggag agcaaggaga aggatcgcca ggtgctggag gacttcccaa cgatctccct    480

tgagtttaga aatctggctg agaaatacca aacagtgatt gccgacattt gccggagaat    540

gggcattggg atggcagagt tttggataa gcatgtgacc tctgaacagg agtgggacaa    600

gtactgccac tatgttgctg ggctggtcgg aattggcctt tcccgtcttt tctcagcctc    660

agagtttgaa gacccccttag ttggtgaaga tacagaacgt gccaactcta tgggcctgtt    720

tctgcagaaa acaaacatca tccgtgacta tctggaagac cagcaaggag gaagagagtt    780

ctggcctcaa gaggtttgga gcaggtatgt taagaagtta ggggattttg ctaagccgga    840

gaatattgac ttggccgtgc agtgcctgaa tgaacttata accaatgcac tgcaccacat    900

cccagatgtc atcacctacc tttcgagact cagaaaccag agtgtgttta acttctgtgc    960

tattccacag gtgatggcca ttgccacttt ggctgcctgt tataataacc agcaggtgtt   1020

caaaggggca gtgaagattc ggaaagggca agcagtgacc ctgatgatgg atgccaccaa   1080

tatgccagct gtcaaagcca tcatatatca gtatatggaa gagatttatc atagaatccc   1140

cgactcagac ccatcttcta gcaaaacaag gcagatcatc tccaccatcc ggacgcagaa   1200

tcttcccaac tgtcagctga tttcccgaag ccactactcc cccatctacc tgtcgtttgt   1260

catgcttttg gctgccctga gctggcagta cctggccact ctctcccagg taacagaaga   1320

ctatgttcag actggagaac actgatccca aatttgtcca tagctgaagt ccaccataaa   1380

gtggatttac tttttttctt taaggatgga tgttgtgttc tctttatttt tttcctacta   1440

ctttaatccc taaaagaacg ctgtgtggct gggaccttta ggaaagtgaa atgcaggtga   1500

gaagaaccta aacatgaaag gaaagggtgc ctcatcccag caacctgtcc ttgtgggtga   1560

tgatcactgt gctgcttgtg gctcatggca gagcattcag tgccacggtt taggtgaagt   1620

cgctgcatat gtgactgtca tgagatccta cttagtatga tcctggctag aatgataatt   1680

aaaagtattt aatttgaagc accatttgaa tgttcgtaat agtagaaaat gatgtgaatt   1740

ttctttctgt tcggctccta tttttctcat cattttgttt tctttaattg ggttgaatgg   1800

agtagataga aatatttatg gtttaggtaa cagttagatg tttcctaaga atgcaaactg   1860

ccttttccac acaaaggctg ggaataaaat tctgggtatt ctcgtattct catttaaagg   1920

agtttagctt tcagagagaa acagcaggat tgcttttgac cttttagaag attggtctcc   1980

agtaaaggtg gacatttttg agatttttat aataaagaat ttaattgctc tgcaaaaaaa   2040

aaaaaaaaaa a                                                        2051
```

<210> SEQ ID NO 21
<211> LENGTH: 6609
<212> TYPE: DNA
<213> ORGANISM: Homo sapiens

<400> SEQUENCE: 21

```
ttcttttaag gagtttgccg cgagcgcgtc tccttcattc gcaggctggg cgcgttcgca     60

gtcggctggc ggcgaaggaa ggcgctctcg ggacctcgcg ggcgcgcgtc ttttggctct    120

tgcccctgtc cctgcggctt ggggaaggcg taacccggcg gctaggcgcg ggagaagtgc    180

ggaggagcca tgggcgccgg gagctccacc gagcagcgca gcccggagca gccgcccgag    240

gggagctcca cgccggctga gcccgagccc agcggcggcg gcccctcggc cgaggcggcg    300

ccagacacca ccgcggaccc cgccatcgct gcctcggacc ccgccaccaa gctcctacag    360

aagaatggtc agctgtccac catcaatggc gtagctgagc aagatgagct cagcctccag    420
```

-continued

```
gagggtgacc taaatggcca gaaaggagcc ctgaacggtc aaggagccct aaacagccag    480

gaggaagaag aagtcattgt cacagaggtt ggacagagag actctgaaga tgtgagcaaa    540

agagactccg ataaagagat ggctactaag tcagcggttg ttcacgacat cacagatgat    600

gggcaggagg agacacccga aataatcgaa cagattcctt cttcagaaag caatttagaa    660

gagctaacac aacccactga gtcccaggct aatgatattg gatttaagaa ggtgtttaag    720

tttgttggct ttaaattcac tgtgaaaaag gataagacag agaagcctga cactgtccag    780

ctactcactg tgaagaaaga tgaaggggag ggagcagcag gggctggcga ccacaaggac    840

cccagccttg gggctggaga agcagcatcc aaagaaagcg aacccaaaca atctacagag    900

aaacccgaag agaccctgaa gcgtgagcaa agccacgcag aaatttctcc cccagccgaa    960

tctggccaag cagtggagga atgcaaagag gaaggagaag agaaacaaga aaaagaacct   1020

agcaagtctg cagaatctcc gactagtccc gtgaccagtg aaacaggatc aaccttcaaa   1080

aaattcttca ctcaaggttg ggccggctgg cgcaaaaaga ccagtttcag gaagccgaag   1140

gaggatgaag tggaagcttc agagaagaaa aaggaacaag agccagaaaa agtagacaca   1200

gaagaagacg gaaaggcaga ggttgcctcc gagaaactga ccgcctccga gcaagcccac   1260

ccacaggagc cggcagaaag tgcccacgag ccccggttat cagctgaata tgagaaagtt   1320

gagctgccct cagaggagca agtcagtggc tcgcagggac cttctgaaga gaaacctgct   1380

ccgttggcga cagaagtgtt tgatgagaaa atagaagtcc accaagaaga ggttgtggcc   1440

gaagtccacg tcagcaccgt ggaggagaga accgaagagc agaaaacgga ggtggaagaa   1500

acagcagggt ctgtgccagc tgaagaattg gttgaaatgg atgcagaacc tcaggaagct   1560

gaacctgcca aggagctggt gaagctcaaa gaaacgtgtg tttccggaga ggaccctaca   1620

cagggagctg acctcagtcc tgatgagaag gtgctgtcca aaccccccga aggcgttgtg   1680

agtgaggtgg aaatgctgtc atcacaggag agaatgaagg tgcagggaag tccactaaag   1740

aagcttttta ccagcactgg cttaaaaaag ctttctggaa agaaacagaa agggaaaaga   1800

ggaggaggag acgaggaatc aggggagcac actcaggttc cagccgattc tccggacagc   1860

caggaggagc aaaagggcga gagctctgcc tcatcccctg aggagcccga ggagatcacg   1920

tgtctggaaa agggcttagc cgaggtgcag caggatgggg aagctgaaga aggagctact   1980

tccgatggag agaaaaaaag agaaggtgtc actccctggg catcattcaa aaagatggtg   2040

acgcccaaga agcgtgttag acggccttcg gaaagtgata aagaagatga gctggacaag   2100

gtcaagagcg ctaccttgtc ttccaccgag agcacagcct ctgaaatgca agaagaaatg   2160

aaagggagcg tggaagagcc aaagccggaa gaaccaaagc gcaaggtgga tacctcagta   2220

tcttgggaag ctttaatttg tgtgggatca tccaagaaaa gagcaaggag agggtcctct   2280

tctgatgagg aagggggacc aaaagcaatg ggaggagacc accagaaagc tgatgaggcc   2340

ggaaaagaca aagagacggg gacagacggg atccttgctg gttcccaaga acatgatcca   2400

gggcagggaa gttcctcccc ggagcaagct ggaagcccta ccgaagggga gggcgtttcc   2460

acctgggagt catttaaaag gttagtcacg ccaagaaaaa aatcaaagtc caagctggaa   2520

gagaaaagcg aagactccat agctgggtct ggtgtagaac attccactcc agacactgaa   2580

cccggtaaag aagaatcctg ggtctcaatc aagaagttta ttcctggacg aaggaagaaa   2640

aggccagatg ggaaacaaga acaagcccct gttgaagacg cagggccaac aggggccaac   2700

gaagatgact ctgatgtccc ggccgtggtc cctctgtctg agtatgatgc tgtagaaagg   2760

gagaaaatgg aggcacagca agcccaaaaa agcgcagagc agcccgagca gaaggcagcc   2820
```

```
actgaggtgt ccaaggagct cagcgagagt caggttcata tgatggcagc agctgtcgct   2880
gacgggacga gggcagctac cattattgaa gaaaggtctc cttcttggat atctgcttca   2940
gtgacagaac ctcttgaaca agtagaagct gaagccgcac tgttaactga ggaggtattg   3000
gaaagagaag taattgcaga agaagaaccc cccacggtta ctgaacctct gccagagaac   3060
agagaggccc ggggcgacac ggtcgttagt gaggcggaat tgaccccccga agctgtgaca   3120
gctgcagaaa ctgcagggcc attgggtgcc gaagaaggaa ccgaagcatc tgctgctgaa   3180
gagaccacag aaatggtgtc agcagtctcc cagttaaccg actccccaga caccacagag   3240
gaggccactc cggtgcagga ggtggaaggt ggcgtacctg acatagaaga gcaagagagg   3300
cggactcaag aggtcctcca ggcagtggca gaaaaagtga aagaggaatc ccagctgcct   3360
ggcaccggtg ggccagaaga tgtgcttcag cctgtgcaga gagcagaggc agaaagacca   3420
gaagagcagg ctgaagcgtc gggtctgaag aaagagacgg atgtagtgtt gaaagtagat   3480
gctcaggagg caaaaactga gccttttaca caagggaagg tggtggggca gaccacccca   3540
gaaagctttg aaaaagctcc tcaagtcaca gagagcatag agtccagtga gcttgtaacc   3600
acttgtcaag ccgaaacctt agctggggta aaatcacagg agatggtgat ggaacaggct   3660
atccccccctg actcggtgga aacccctaca gacagtgaga ctgatggaag cacccccgta   3720
gccgactttg acgcaccagg cacaacccag aaagacgaga ttgtggaaat ccatgaggag   3780
aatgaggtcg catctggtac ccagtcaggg ggcacagaag cagaggcagt tcctgcacag   3840
aaagagaggc ctccagcacc ttccagtttt gtgttccagg aagaaactaa agaacaatca   3900
aagatggaag acactctaga gcatacagat aaagaggtgt cagtggaaac tgtatccatt   3960
ctgtcaaaga ctgaggggac tcaagaggct gaccagtatg ctgatgagaa aaccaaagac   4020
gtaccatttt tcgaaggact tgaggggtct atagacacag gcataacagt cagtcgggaa   4080
aaggtcactg aagttgccct taaaggtgaa gggacagaag aagctgaatg taaaaaggat   4140
gatgctcttg aactgcagag tcacgctaag tctcctccat cccccgtgga gagagagatg   4200
gtagttcaag tcgaaaggga gaaaacagaa gcagagccaa cccatgtgaa tgaagagaag   4260
cttgagcacg aaacagctgt taccgtatct gaagaggtca gtaagcagct cctccagaca   4320
gtgaatgtgc ccatcataga tggggcaaag gaagtcagca gtttggaagg aagccctcct   4380
ccctgcctag gtcaagagga ggcagtatgc accaaaattc aagttcagag ctctgaggca   4440
tcattcactc taacagcggc tgcagaggag gaaaaggtct taggagaaac tgccaacatt   4500
ttagaaacag gtgaaacgtt ggagcctgca ggtgcacatt tagttctgga agagaaatcc   4560
tctgaaaaaa atgaagactt tgccgctcat ccaggggaag atgctgtgcc cacagggccc   4620
gactgtcagg caaaatcgac accagtgata gtatctgcta ctaccaagaa aggcttaagt   4680
tccgacctgg aaggagagaa aaccacatca ctgaagtgga agtcagatga agtcgatgag   4740
caggttgctt gccaggaggt caaagtgagt gtagcaattg aggatttaga gcctgaaaat   4800
gggattttgg aacttgagac caaaagcagt aaacttgtcc aaaacatcat ccagacagcc   4860
gttgaccagt ttgtacgtac agaagaaaca gccaccgaaa tgttgacgtc tgagttacag   4920
acacaagctc acgtgataaa agctgacagc caggacgctg gacaggaaac ggagaaagaa   4980
ggagaggaac ctcaggcctc tgcacaggat gaaacaccaa ttacttcagc caaagaggag   5040
tcagagtcaa ccgcagtggg acaagcacat tctgatattt ccaaagacat gagtgaagcc   5100
tcagaaaaga ccatgactgt tgaggtagaa ggttccactg taaatgatca gcagctggaa   5160
gaggtcgtcc tcccatctga ggaagaggga ggtggagctg gaacaaagtc tgtgccagaa   5220
```

gatgatggtc atgccttgtt agcagaaaga atagagaagt cactagttga accgaaagaa 5280
gatgaaaaag gtgatgatgt tgatgaccct gaaaaccaga actcagccct ggctgatact 5340
gatgcctcag gaggcttaac caaagagtcc ccagatacaa atggaccaaa acaaaaagag 5400
aaggaggatg cccaggaagt agaattgcag gaaggaaaag tgcacagtga atcagataaa 5460
gcgatcacac cccaagcaca ggaggagtta cagaaacaag agagagaatc tgcaaagtca 5520
gaacttacag aatcttaaaa catcatgcag ttaaactcat tgtctgtttg gaagaccaga 5580
atgtgaagac aagtagtaga agaaaatgaa tgctgctgct gagactgaag accagtattt 5640
cagaactttg agaattggag agcaggcaca tcaactgatc tcatttctag agagcccctg 5700
acaatcctga ggcttcatca ggagctagag ccatttaaca tttcctcttt ccaagaccaa 5760
cctacaattt tcccttgata accatataaa ttctgattta aggtcctaaa ttcttaacct 5820
ggaactggag ttggcaatac ctagttctgc ttctgaaact ggagtatcat tctttacata 5880
tttatatgta tgttttaagt agtcctcctg tatctattgt atattttttt cttaatgttt 5940
aaggaaatgt gcaggatact acatgctttt tgtatcacac agtatatgat ggggcatgtg 6000
ccatagtgca ggcttgggga gctttaagcc tcagttatat aacccacgaa aaacagagcc 6060
tcctagatgt aacattcctg atcaaggtac aattctttaa aattcactaa tgattgaggt 6120
ccatatttag tggtactctg aaattggtca ctttcctatt acacggagtg tgctaaaact 6180
aaaaagcatt ttgaaacata cagaatgttc tattgtcatt gggaaatttt tctttctaac 6240
ccagtggagg ttagaaagaa gttatattct ggtagcaaat taactttaca tccttttttcc 6300 tacttgttat ggttgtttgg accgataagt gtgcttaatc ctgaggcaaa gtagtgaata 6360
tgttttatat gttatgaaga aaagaattgt tgtaagtttt tgattctact cttatatgct 6420
ggactgcatt cacacatggc atgaaataag tcaggttctt tacaaatggt attttgatag 6480
atactggatt gtgtttgtgc catatttgtg ccattctttt aagaacaatg ttgcaacaca 6540
ttcatttgga taagttgtga tttgacgact gatttaaata aaatatttgc ttcacttaaa 6600
aaaaaaaaa 6609

<210> SEQ ID NO 22
<211> LENGTH: 4251
<212> TYPE: DNA
<213> ORGANISM: Homo sapiens

<400> SEQUENCE: 22
gttgcatgaa actccggcgc aggagtcccg ggctgccgct ggcaacatcg tgtcacccag 60
ctaagaaaat ccgcgggccc gagccacgcg cctgtgaatc ggagaggtcc cactgcccga 120
gtggagccgg gctgagattc ttctcaagtt gagcctcagt gatcctgtgg ccgaagttag 180
cgccttgacg tgggacaacc ggacacgtcg ccaggagaga actgaggcgc cttctagcag 240
ttgtgacgcc aaaatcacgt ctccggagac ccgcgccctc cgccagccgg gcgcaccctc 300
gccggtagcc ttctttgtgc gccgtccgga ctcccagctc ccggcccggc agccgagccc 360
cagcacaaag cagtcggacc gcgccgcccg cctcccctct cgcgtctccg cctcggtttc 420
ccaactctgc gccgtcgggc cgcggcagga tgattgcctc gcatctgctt gcctacttct 480
tcacggagct caaccatgac caagtgcaga aggttgacca gtatctctac cacatgcgcc 540
tctctgatga gaccctcttg gagatctcta agcggttccg caaggagatg gagaaagggc 600
ttggagccac cactcaccct actgcagcag tgaagatgct gcccaccttt gtgaggtcca 660
ctccagatgg gacagaacac ggagagttcc tggctctgga tcttggaggg accaacttcc 720

```
gtgtgctttg ggtgaaagta acggacaatg ggctccagaa ggtggagatg gagaatcaga    780
tctatgccat ccctgaggac atcatgcgag gcagtggcac ccagctgttt gaccacattg    840
ccgaatgcct ggctaacttc atggataagc tacaaatcaa agacaagaag ctcccactgg    900
gttttacctt ctcgttcccc tgccaccaga ctaaactaga cgagagtttc ctggtctcat    960
ggaccaaggg attcaagtcc agtggagtgg aaggcagaga cgttgtggct ctgatccgga   1020
aggccatcca gaggagaggg gactttgata tcgacattgt ggctgtggtg aatgacacag   1080
ttgggaccat gatgacctgt ggttatgatg accacaactg tgagattggt ctcattgtgg   1140
gcacgggcag caacgcctgc tacatggaag agatgcgcca catcgacatg gtggaaggcg   1200
atgaggggcg gatgtgtatc aatatggagt gggggccttc ggggacgat ggctcgctca    1260
acgacattcg cactgagttt gaccaggaga ttgacatggg ctcactgaac ccgggaaagc   1320
aactgtttga gaagatgatc agtgggatgt acatggggga gctggtgagg cttatcctgg   1380
tgaagatggc caaggaggag ctgctctttg gggggaagct cagcccagag cttctcaaca   1440
ccggtcgctt tgagaccaaa gacatctcag acattgaagg ggagaaggat ggcatccgga   1500
aggcccgtga ggtcctgatg cggttgggcc tggacccgac tcaggaggac tgcgtggcca   1560
ctcaccggat ctgccagatc gtgtccacac gctccgccag cctgtgcgca gccaccctgg   1620
ccgccgtgct gcagcgcatc aaggagaaca aaggcgagga gcggctgcgc tctactattg   1680
gggtcgacgg ttccgtctac aagaaacacc cccattttgc caagcgtcta cataagaccg   1740
tgcggcggct ggtgcccggc tgcgatgtcc gcttcctccg ctccgaggat ggcagtggca   1800
aaggtgcagc catggtgaca gcagtggctt accggctggc cgatcaacac cgtgcccgcc   1860
agaagacatt agagcatctg cagctgagcc atgaccagct gctggaggtc aagaggagga   1920
tgaaggtaga aatggagcga ggtctgagca aggagactca tgccagtgcc cccgtcaaga   1980
tgctgcccac ctacgtgtgt gctaccccgg acggcacaga gaaaggggac ttcttggcct   2040
tggaccttgg aggaacaaat ttccgggtcc tgctggtccg tgttcggaat gggaagtggg   2100
gtggagtgga gatgcacaac aagatctacg ccatcccgca ggaggtcatg cacggcaccg   2160
gggacgagct ctttgaccac attgtccagt gcatcgcgga cttcctcgag tacatgggca   2220
tgaagggcgt gtccctgcct ctgggtttta ccttctcctt cccctgccag cagaacagcc   2280
tggacgagag catcctcctc aagtggacaa aaggcttcaa ggcatctggc tgcgagggcg   2340
aggacgtggt gaccctgctg aaggaagcga tccaccggcg agaggagttt gacctggatg   2400
tggttgctgt ggtgaacgac acagtcggaa ctatgatgac ctgtggcttt gaagaccctc   2460
actgtgaagt tggcctcatt gttggcacgg gcagcaatgc ctgctacatg gaggagatgc   2520
gcaacgtgga actggtggaa ggagaagagg ggcggatgtg tgtgaacatg gaatgggggg   2580
cattcgggga caatggatgc ctagatgact tccgcacaga atttgatgtg gctgtggatg   2640
agctttcact caaccccggc aagcagaggt tcgagaaaat gatcagtgga atgtacctgg   2700
gtgagattgt ccgtaacatt ctcatcgatt tcaccaagcg tggactgctc ttccgaggcc   2760
gcatctcaga gcggctcaag acaaggggca tctttgaaac caagttcttg tctcagattg   2820
agagtgactg cctggccctg ctgcaagtcc gagccatcct gcaacactta gggcttgaga   2880
gcacctgtga cgacagcatc attgttaagg aggtgtgcac tgtggtggcc cggcgggcag   2940
cccagctctg tggcgcaggc atggccgctg tggtggacag gatacgagaa aaccgtgggc   3000
tggacgctct caaagtgaca gtgggtgtgg atgggaccct ctacaagcta catcctcact   3060
ttgccaaagt catgcatgag acagtgaagg acctggctcc gaaatgtgat gtgtctttcc   3120
```

```
tgcagtcaga ggatggcagc gggaaggggg cggcgctcat cactgctgtg gcctgccgca   3180

tccgtgaggc tggacagcga tagaacccct gaaatcggaa gggacttcct ctttctctcc   3240

ttcttccctg ttttaaatta taagatgtca tccccttgtg tcagagacag acccccttggc   3300

ttttgcttgg cagagaggac ccccactggac tgggttttgt ctctgcatct cattgtagag   3360

cttggtggct gagcttggcc ctattaagat aaatagagtt ccaaataagg atttgttcac   3420

atgcatcata accattccca ttggttctcc taaaacatga aaattatctc ccttagtaat   3480

ccccccttgcc aaattccatg tccctgtata attctacagg atggggacac taatgaagat   3540

acggttgctt caccttggag cctgaacatg acatttctaa gtggggtgca tcccccagca   3600

ctgatgttgt tactgattct cctgtcagag atctgggagg tctccactga ggatgtgagc   3660

ctgattatcc tataggcaga cgtggggagg gtggaggggt gacagtggag gaaaatccat   3720

ggatatccac gcagcagccc ctctttaacc tcatctacaa gcatttgccc tgtggattcc   3780

agcatttgcc attcctggaa tcaaggaatc ctgagtctgg gcaatgaaac caaagccagg   3840

agttgacgca tcctgcagtt gggccagctg tcgcatctca gcggggcgca catgttatcc   3900

acaagcaatg gacctttggg gaaggggggag tttttagttt gttttacaaa tttttcctgc   3960

aaaagtggaa tcactgtatt ttcattttaa tttatattg aaattttatt tagttcttga   4020

gtagatctgc ttcttcatct tgacatgtaa tgaatggtca gttgtacgta atgtatttat   4080

atgttaattt gttatgtata tagatgtgca agtcttgtca gaattggcct cagtgtagtt   4140

aaagggcaga aggggaagat actgactagt catagaaata cctcattcgc ctgtgggaag   4200

agaagggaag cctcttcagg gtgagtgaat ggcaaagcgg ttgcttctcc g            4251
```

<210> SEQ ID NO 23
<211> LENGTH: 5190
<212> TYPE: DNA
<213> ORGANISM: Homo sapiens

<400> SEQUENCE: 23

```
tgggaatcca actgaagagc agccagagga gagctgaaga gaggaggggg aggccgatga     60

cctgggctct gggcctctga aggtctggcg tattctgaca ggacacagtg agcatctgta    120

gaggagaggc ttgaaataaa ggaggagcac gaatattccc tggatttctg gaggcctgct    180

ttaaggctgg ccagttctgc aagaaaggca aggaggagga gactggctca cacctctgga    240

ggaccccctt ctgtcagctg tggggcttga cactacttga acaagaaaag gagggggaaa    300

ctgcaccaca taagtgaaga tccacctcca gtggctgctc tgctggtggt ggggttgctg    360

ctgacaacca ccctcaacgg gtctgcaccc atccaggaaa tctctgtctt cctcaagctt    420

ggttgtgcct gttctacact ctatctgtat tattgaatta ctgactgaga ctgtgtttgg    480

gaaggaggct gagtgactac tggactggat attgactcta actcttgttt ccaagcttat    540

atcctcaatc acctaaagat cagagtgtga agaaacaaac ctgtgacaga tctgtggttg    600

aggtttagac tgggggagga gtatagtact ggactttctt tgtaacttgt accatgactg    660

gggcagagat tgagtctggt gcccaggtca agcctgaaaa gaagcctggg gaagaggttg    720

taggtggggc tgagatagag aatgatgtcc ctctggtggt cagacccaag gttaggaccc    780

aggcccagat aatgcctggg gcaaggccca agaataagtc caaggttatg cctggagcaa    840

gcaccaaagt tgagacaagt gcagtgggtg gggcacgccc taagagtaag gccaaggcaa    900

tacctgtttc acgatttaag gaagaagccc agatgtgggc tcagcccagg tttggtgctg    960

aaagattgtc taagacagag agaaactccc agaccaatat catagcctct ccacttgtca   1020
```

```
gtactgattc tgtcttggtt gctaaaacaa agtacctgtc tgaggataga gaactggtta   1080

atacagacac tgagagcttt cctagaagga aggcccatta ccaagcagga ttccagcctt   1140

cttttaggtc aaaggaggag accaatatgg ggtcctggtg ctgtcctagg cctacatcca   1200

aacaagaagc ctctcctaat tctgatttca aatgggtaga caaatctgtg agttccttgt   1260

tctggagtgg agatgaggtc actgcaaaat ttcatcctgg gaataggta aaagacagta    1320

acagatccat gcacatggcc aatcaagagg ctaataccat gtctaggtcc caaactaacc   1380

aggagctcta tattgcatct agttctggtt ctgaggatga gtctgttaag acaccctggt   1440

tctgggccag agataaaacc aatacctggt ctgggcccag ggaagatccc aatagcaggt   1500

ccaggtttag gtctaagaaa gaagtctatg ttgaatcaag ttctggatct gagcatgaag   1560

accatttgga gtcctggttt ggggctggaa aggagggcaa attcaggtcc aaaatgagag   1620

ctgggaagga ggccaataac agggccaggc acagggccaa gcgagaagct tgcattgatt   1680

tcatgcctgg gtctatagat gtaattaaaa aagagtcctg tttctggcct gaagaaaatg   1740

ctaatacctt ttcaaggccc atgatcaaga aagaggccag ggccagagca atgacaaagg   1800

aagaggccaa aaccaaggcc cgagccaggg ccaagcaaga agccaggtca gaggaggaag   1860

ccctcattgg gacctggttc tgggctacag acgagtccag catggcagat gaagccagca   1920

tagagtccag tctacaagtg gaggatgagt ccataattgg gagttggttc tggactgaag   1980

aagaggccag tatggggact ggggctagca gtaaatccag accaaggact gatggggagc   2040

gtattggtga ttccttattt ggggctaggg aaaagaccag tatgaaaact ggggctgagg   2100

ccacctctga atctatacta gcagctgatg atgaacaggt cattattggt tcctggttct   2160

gggctggtga agaggtcaac caagaggctg aggaagagac catttttggg tcgtggttct   2220

gggtcattga tgcggccagt gtggaatctg gtgttggggt cagctgtgag tccaggacaa   2280

ggtctgagga agaagaggtc attggtccct ggttttggtc tggagaacaa gttgatatag   2340

aggctggaat cggagaagag gccaggccag gagctgaaga agagacaata ttcgggtcct   2400

ggttttgggc tgaaaaccag acctatatgg attgtagggc tgaaactagc tgtgacacca   2460

tgcaaggggc tgaggaggag gagcccatta ttgggtcctg gttttggacc agagtagaag   2520

cttgtgtgga gggtgatgtc aacagcaagt ctagcctgga ggacaaggaa gaggccatga   2580

taccatgttt tggagccaaa gaagaggtca gtatgaagca tgggactggt gtcagatgca   2640

gatttatggc aggggctgag gagaccaata ataagtcttg cttctgggca gaaaaagaac   2700

cctgtatgta tcctgccggt ggaggaagtt ggaagtctag gccagaggag gaagaggaca   2760

ttgtcaattc gtggttctgg tccagaaaat acacaaagcc agaggccatt atagggtcct   2820

ggttatgggc tacagaagag agtaatatag atgggactgg agaaaaggcc aagttactga   2880

ctgaagagga gaccataatc aattcctggt tctggaaaga agatgaagcc atttcagagg   2940

ctactgacag agaagagtcc aggccagaag ctgaggaggg ggacattgtt ggttcttggt   3000

tctgggctgg agaagaggac agactagagc cagctgctga gactagagaa gaagacaggc   3060

tagcagctga gaaagaaggt attgttgggt cctggtttgg ggccagagaa gagaccatta   3120

gaagagaggc tgggtcttgc agcaaatcca gtcctaaagc tgaagaggaa gaagtcatta   3180

ttgggtcctg gttctgggaa gaagaggcca gtccggaggc agtggcagga gtcggctttg   3240

agtcaaagcc tgggactgag gaggaagaaa tcactgttgg gtcctggttc tggcctgaag   3300

aagaagccag tatacaggct ggatctcagg cagtagagga aatggagtca gagactgaag   3360

aggaaaccat ttttgggtcc tggttctggg atggaaaaga agtcagtgaa gaagcaggac   3420
```

```
catgctgtgt atccaagcca gaggatgatg aagagatgat tgttgagtcc tggttctggt   3480

ctagagacaa agccattaag gaaactggaa ctgtggccac ctgtgagtcc aagccagaaa   3540

atgaggaagg ggccattgtt gggtcttggt ttgaggctga agatgaggta gataacagga   3600

ctgacaatgg aagcaactgt gggtccagga cattagctga tgaagatgag gccatagtgg   3660

ggtcctggtt ctgggcagga gatgaggccc attttgaatc aaatcctagc cccgtgttca   3720

gggccatttg caggtccacg tgttcagttg aacaggagcc tgatccttca cgcaggcctc   3780

agagttggga ggaggtcact gttcagttca agcctggtcc atggggtagg gtcggcttcc   3840

catctataag cccctttaga tttccgaaag aggcagcatc tttattctgt gaaatgtttg   3900

ggggcaaacc caggaacatg gtacttagcc cagaagggga agatcaggaa tctttgcttc   3960

agcctgatca gcctagtcct gagttcccat ttcagtatga tccttcctac aggtcagtcc   4020

aggaaattcg agagcatctt agggccaagg agagtacaga gcctgagagt tcatcctgta   4080

actgcataca atgtgagctg aaaattggtt ctgaagagtt tgaagaactc cttttattaa   4140

tggaaaaaat tcgggatcct tttattcatg aaatatctaa aatcgcaatg ggtatgagaa   4200

gtgcttctca atttacccga gatttcattc gagattcagg tgttgtctca cttattgaaa   4260

ccttgcttaa ttatccgtcc tcccgagtta gaacaagttt tttggaaaat atgattcgca   4320

tggccccacc ttatccgaat ctaaacataa ttcagacata catatgtaaa gtgtgtgagg   4380

aaacccttgc ttatagcgtg gattccccgg aacagctgtc tggaataagg atgattagac   4440

atctcactac tactactgac tatcacacac tggttgccaa ttatatgtct gggtttctct   4500

ccttattagc tacaggcaat gccaaaacaa ggtttcatgt tttgaaaatg ctactgaatt   4560

tgtctgaaaa tcttttcatg acaaaagaac tactcagtgc tgaagcagtg tcagaattta   4620

taggcctctt taacagggaa gagacaaatg acaatattca aattgttctt gcaatatttg   4680

agaatattgg caacaatatc aaaaaagaaa cagtgttctc tgatgatgat ttcaatattg   4740

agccgcttat ttctgcattc cacaaagttg agaaatttgc taaggaactg caaggcaaaa   4800

cagacaatca aaatgaccct gaaggggacc aagaaaatta gtaatggtta attgctggcc   4860

tcagattgtc cttatgttcc tgagttatga tccttgagta atgctttgat tttaatagtt   4920

ggttctgtgt tgcaacatat atctttagtg ctgacactaa ctttgtccaa ctctgtctgt   4980

aagctggagc atttttctga tgccagctga atattagagc tgaaaacaca tttgttgata   5040

tttgtcttgt ccacattgtg atgttcagta tttgagctta tagtgaactg agcaatcata   5100

aataagccac ccttctgatt gtcgttctac tgtatatata tatatatttg agtgttgttt   5160

gtgtttcaat aaagtcctat gttaaagttg                                   5190
```

<210> SEQ ID NO 24
<211> LENGTH: 6322
<212> TYPE: DNA
<213> ORGANISM: Homo sapiens

<400> SEQUENCE: 24

```
ctgagagcga catgtccccg gcggctcagg cggagcggcc cgtggcgctg tttttctgag     60

tccggggtgg cctggcagcc ggccgaggac gagggtcggc gggggctgcc cccgtggtgg    120

tggccgccat gctgggagcc tgggcggttg agggaaccgc tgtggcgctc ctgcgactgc    180

tgctgctgct gctgccgccg gcgatccggg gacccgggct cggcgtggcc ggcgtggccg    240

gcgcggcggg ggccgggctg cccgagagcg tcatttgggc ggtcaacgcg ggtggagagg    300

cgcatgtgga cgtgcacggg atccacttcc gcaaggaccc tttggaaggc cgggtgggcc    360
```

-continued

```
gagcctcaga ctatggcatg aaactgccaa tcctgcgttc caaccctgag gaccagatcc    420
tgtatcaaac tgagcggtac aatgaggaga cctttggcta cgaagtgccc atcaaagagg    480
agggggacta cgtgctggtc ttgaaatttg cagaggtcta ctttgcacag tcccagcaaa    540
aggtatttga tgtacgattg aatggccacg tcgtggtgaa ggacttggat atctttgatc    600
gtgttgggca tagcacagct cacgatgaaa ttatacctat gagcatcaga aaggggaagc    660
tgagtgtcca gggggaggtg tccaccttca cagggaaact ctacattgag tttgtcaagg    720
ggtactatga caatcccaag gtctgtgcac tctacatcat ggctgggaca gtggatgatg    780
taccaaagct tcagcctcat ccgggattgg agaagaaaga agaggaagaa gaagaagaag    840
aatatgatga agggtctaat ctcaaaaaac agaccaataa gaaccgggtg cagtcaggcc    900
cccgcacacc caacccctat gcctcggaca acagcagcct catgtttccc atcctggtgg    960
ccttcggagt cttcattcca accctcttct gcctctgccg gttgtgagaa caaatgacta   1020
tcctgaacag ggtggagggg tgtgggaaag aaaccagcca tattggtttt ggtttctgta   1080
tttttcacaa tgattaatga acaaaaacaa agagaaaaaa aacacacatc aattaaagga   1140
gacaaaaaga ggcagagcga gtagagagca gccctcattc accacctggt cccagacgtg   1200
cttcagtcct cgtcctctct ttgtggctgg ctcccagcct tctctttcct cttgaggata   1260
cttagggtaa actggatcct tcctgctcaa ggatcctcat ttgtatacct agtggaaagg   1320
actctgaact cagaggagtc actgttcctt tttttaggtt agaaattaac agcagggaaa   1380
tgccatctta ttacctgaga cgaccagcac tgggagttag gtacggtctg aagttatgtc   1440
tagataagac ttcagacgtc ctgggattga aagaatgtgt gtgaaggggt agaatttgtg   1500
cggtaaagac ttaaaaaaaa aagtagggag attaaaaaaa aagaaagaaa atgcttcctt   1560
atctggaagc ctttctggat taatccagtg atggtcccac ctttagtgtt tgagctttgt   1620
cattgcttgt ctccctggca tgtgccagtt atagactgtc cagcatccaa gacgtttcgg   1680
ttatgtcggg tcctcagatc gcctctgact tgttaccaca acaaatcatt ttgatttcag   1740
tgcctgttgg ggacttgatt tcttctcagg ttttgtttgt ttgtttgttt ccttaatctg   1800
gctcatttga aatttcttct ccctctcaac catcccacta agttatagcc aagaagggaa   1860
ggagacacgg ggatttgggg ttctctgctt gaatgtcttc tcctttacca cctcaccttg   1920
ttggtacctc cctccctgga tctctgagcc agcagccagg aggacctgac ccagcagttc   1980
tttactggcc cctttgtagg gccttgctgc cagggggcag ggatgctttc cagcctgcag   2040
caacagaaca cttgacctta aaagtctctt ctggtctttg gattagaaaa ggcttatgtt   2100
agcatagctt aagagcaacc tcagagactt gagccctact aagtgactga ccactgttta   2160
gagtgtctgg tatctgatgt tcatttattc ccatgttctt gtgtgtcaca gttcagccag   2220
ttttggttta tgcctagagc tacttcaagg aactagacta attagctata taggcccagc   2280
gatgcttctt attgatctta atagtatgcc cttccttccc ctgtcctttc atttctctat   2340
ccaagtagca gtcaggttct tggtgtgatg ggactgaaag aattccagtc agccagagcc   2400
ttggcagctc tgaagctaac cttagcatct aagtgtcgat cttgaattcc ctgaaaaaat   2460
ttctatagga aatgaagctt ccctggtccc ctcctttctg gccattgtca tccatttccc   2520
agttagggca acaatgaagg aggacccagc caagctagaa ggaattttgt ggatgggaga   2580
cagcaggatt agcttcagct tgggctggag cagtcaatat aggatctcag gccaggcccg   2640
cttttctaga atgtgtttaa ttttgagttt gctttattag atatgttttt taagagctct   2700
gtatatttga actgctcctt atgtgacaaa ataggtagct cttgggctca tgtcctgggt   2760
```

```
tttggctctt taatgattac tccaggccag catttagtcg tttgagaatt gtagcctgtt   2820

gttttcgctg tgacttgggt ctcagtgcta gggtattgag tcaggcagct ggagggttgt   2880

ggcccgaggc tgcagtcaga ggtatacttc ccatagtgct tcacacagct cccctgcttc   2940

taaaggataa ggtactgtag ccttggtcct ggggaccacc tgcctggggc agtggacatc   3000

ctaactaaac aggcttctgg cagtagcttt ggttcctatc ccatcgaaat tccccaaagc   3060

cctgggccac tgccattggg ttagtcaaga tgaaggagga ggactggctg cctccatttt   3120

gccttgtttg ttagtttgcc tgggtctgtc tgaggaagga gggggtcccg ccttccacct   3180

caacacatcc cttcagtgac tcagagtctc agaaggaaac cctgactcct ggggccattt   3240

cctaatggta ctgtaagcca agcagctttg cttctgcctc tgtttccaag cccacccttt   3300

tcccctgagc tcagggttag ggatgggcgc tttcctctct ggttgtgaac gaaaggaagg   3360

aacatctttc tatggctaac aaaaactaaa ggggaagtga ggaaacagga agaagtatgg   3420

tgggggctgg ggtagactcc cctggagcca agcctatcca gctaacaaga gctccctggg   3480

gctggtcaca gctggctcat gatgctgaac ttgaaagttt ttttgttttt gtttttgttt   3540

tgtggctcct ccaagatata ggtacatgaa gtttaggtta aaggggtggg attctttatt   3600

tttatttttg tattgtatgt gtcaagaatt actctgttgt tcaccttttg ctttttgcac   3660

tgtttgttct cttatctgta ttttgagctt agtgctagga ctgagaggct gcaccatagg   3720

gaatgtatgg gagatggtga ggggtgccag tgaggggtgc gtggaggaga ggcctgggct   3780

cctctactgg atctacactc tgtcccaggt ttttagatcc cactgagccc agctgactga   3840

aaacaaggac agtcagggtg aaacttcttt tgccagaagt gtggcctgag ttgaatttct   3900

gggaggatga cgcagatgtc tgctgcagag ctgggctgag agttctgcag tctagctctg   3960

acttaggtca ggggcctgtt ggtctctcat tggacgtttt tgggtctcac tcatgcttac   4020

tgaaacattg tgccaagaaa ctctgtggga tttgtgtccc ttaaaccaga ctcacttttc   4080

tgaaaaatct ccattgttga ggagaggctg ctcaatcgac accccgagtt ctcatgactg   4140

ggaagatagt tttcttcagg tgtcaatggc gttagactcc caggaagact agccctgccc   4200

acagggccac ctgttggttt gagagcgtgt tcgtgttctc ttgccctccc tgcctaagag   4260

ctactgggat cacgttagcg ggcatttagg ctttgatgag agggcacagt ttgagttagg   4320

tttacctccc cctttctgtg cctgggaact gtttggtcca gctttagaac tgtggttttg   4380

acttccttat ctcttgggag aagcttctgt tttaaggaat ttctcttcct tcttctcctg   4440

cctctagcct ctcctggaaa ggcctggata tggtttctaa aatctcagct gagaacttca   4500

gaaaacagca gcagtatttt ccttttccta gtgctaaaat ccctttccct agaaattggc   4560

tcaccttggg aaacccaggg aaagaatcag caggttctct gccctcccta ggggttgggg   4620

aaggacccac cccggtcagc acagtgcctt ttcctctcct gctctgagcc agggtggggc   4680

attccctcta gattcaggtt tgggcagggg tcctatagtc cctgccatgg ggctgcttcc   4740

ctgtcccttc cctccccttt gctggcctac tctggcataa ttcaagtgtc ttcttgcctt   4800

ggggatcctt agtggcatca aatggcaaca tggaatattg tcctccatgc ccctccagaa   4860

ggacctagga gagtaggtga gctttccaaa gtgagagacg aatctttctt tcttttttttt   4920

tttaaagggc aggatgggta tgctttgggc tttctccttc tgtggccccg gaggaaggag   4980

agactgaggc aaggcaaagt gatagtacac tgaagcagaa ccggaaacac ccaggaactg   5040

ttcagaaatc tcagaagaaa tctgcttctc ttcgatggaa agatataatt aacgatcaaa   5100

gagctctaag aaaattgcaa agaagcctta atgttcaagc tttagaaaga tcagagcaat   5160
```

```
ttttctcttt cagtccaaac taagactctc tgtatttaaa tctctctggg gcaagagggc   5220

tagatttcct cattttgtta tgagactaga ttggtaccag tagatcagct gcctagcgag   5280

ggcaggtttc ttctttgcat ctgtgtggct tgcttccagt ctggcctgtc ctttccagct   5340

gccttttgtc tagcctgcta tggggggcca gattatcttg ataagagcag gtgatttggg   5400

gactagctgg gttggtagga aaagagcagg atggatctct tgggacaggt tcccccagga   5460

gtataaacac aaggagccag gattgtcctg gcagccaagg aaacagtagt gcctgtttga   5520

gttggcagag agggccttgg cacctcttgc atccaggcag tcttgtgaga tgggggcaca   5580

tagcactggg gaaagcagaa ctccattctc acctctattt tgagcttcag tgctttattt   5640

cagtatgagg aaaaacaaca acaaactgaa gtgcgctttc cgtcctttca aaggacaact   5700

gtcgggaagg gagagccgag ttgcgaggta ggaggggagc actggcaggg agagacattc   5760

ttgactcctc tcttccctgg tgtgttgtga tccagggaat gaaaagaaat ttgaccctgg   5820

attggttctc tccttggact taaggaatct taccttttcc ttccacaaag ttctcccagg   5880

caaggaccag ctgcccattc tgagcccagg gcagcctctt caaccattat tggtctaacc   5940

tggcttgtca ggaaaccaag cccacccttc cacattgggc ctggctgctc tattctgtac   6000

caagtactgg agaaaaagca tcaagttctt agcccttgta gcttctaccc tagtttccca   6060

tcctctctct gtggaggcca aaccaactct ttgccagcag ccacaacatg cattgacagc   6120

ggcacagtga gatataactg atgggctttg aacctggttg gccggggaag ctgtaggggt   6180

ggatagagct ggctttcctt ctgggctgtc tccatctgac cctacccctt ccatgtccca   6240

ccccactccc accaaaaagt acaaaatcag gatgtttttc actgtccatt gctttgtgtt   6300

ttaataaaca atttgcagtg ac                                            6322
```

<210> SEQ ID NO 25
<211> LENGTH: 5075
<212> TYPE: DNA
<213> ORGANISM: Homo sapiens

<400> SEQUENCE: 25

```
tgaattcggc acgaggtggg ctctctcttt tcccctcttg ctcctttctt ttcttttttt     60

ctgttttttt aaaccttcca aggcaagttc atggatacta agctgatgtg tttgttgttc    120

tttttctccc tgcctccgct cctagtgagt aaccacactg gccgcatcaa ggtggtcttt    180

actccgagca tctgtaaagt gacctgcacc aagggcagct gtcagaacag ctgtgagaag    240

gggaacacca ccactctcat tagtgagaat ggtcatgctg ccgacaccct gacggccacg    300

aacttccgag tggtaatttg ccatcttcca tgtatgaatg gtggccagtg cagttcaagg    360

gacaaatgtc agtgccctcc aaatttcaca ggaaaacttt gtcagatccc agtccatggt    420

gccagcgtgc ctaaacttta tcagcattcc cagcagccag gcaaggcgtt ggggacgcat    480

gtcatccatt caacacatac cttgcctctg accgtgacta gccagcaagg agtcaaagtg    540

aaatttcctc ctaacatagt caatatccat gtgaaacatc ctcctgaagc ttccgtccag    600

atacatcagg tttcaagaat tgatggccca acaggccaga agacaaaaga agctcaacca    660

ggccaatccc aagtctcgta ccaagggctt cctgtccaga agacccagac catacattcc    720

acatactccc accagcaggt cattcctcac gtctaccccg tggctgctaa gacacagctt    780

ggccggtgct tccaggaaac cattgggtca cagtgtggca aagcgctccc tggcctttca    840

aagcaagagg actgctgtgg aactgtgggt acctcctggg gctttaacaa atgccagaaa    900

tgccccaaga aaccatctta tcatggatac aaccaaatga tggaatgcct accgggttat    960
```

```
aagcgggtta acaacacctt ttgccaagat attaatgaat gtcagctaca aggtgtatgc   1020
cctaatggtg agtgtttgaa taccatgggc agctatcgat gtacctgcaa aataggattt   1080
gggccggatc ctaccttttc aagttgtgtt cctgatcccc ctgtgatctc ggaagagaaa   1140
gggccctgtt accgacttgt cagttctgga agacagtgta tgtaccctct gtctgttcac   1200
ctcaccaagc agctctgctg ttgtagtgtg ggcaaggctg ggccacactg tgagaaatgt   1260
ccccttccag gcacagctgc ttttaaggaa atctgtcctg gtggaatggg ttatacggtt   1320
tctggcgttc atagacgcag gccaatccat caccatgtag gtaaaggacc tgtatttgtc   1380
aagccaaaga acactcaacc tgttgctaaa agtactcatc ctccacctct cccagccaag   1440
gaagagccag tggaggccct gaccttctcc cgggaacacg gggccaggag tgcggagcca   1500
gaagtggcaa ctgcaccccc tgaaaaggaa ataccttcat tggatcaaga gaaaaccaaa   1560
cttgagcctg gtcaacccca gctgtctcca ggcatttccg ctattcatct gcatccacag   1620
tttccagtag tgattgaaaa aacatcacct cctgtgcctg ttgaagtagc tcctgaagct   1680
tctacgtcta gtgccagcca agtgattgct cctactcaag tgacagaaat caatgaatgt   1740
actgtgaacc ctgatatctg tggagcagga cactgcatta acctaccagt gagatatacc   1800
tgtatatgct acgagggcta caggttcagt gaacaacaga ggaaatgtgt ggatattgat   1860
gagtgtactc aggtccaaca cctctgctcc cagggccgct gtgaaaacac cgagggaagt   1920
ttcttgtgca tttgcccagc aggatttatg gccagtgagg agggtactaa ctgcatagat   1980
gttgacgaat gcctgaggcc ggacgtctgt ggggaggggc actgtgtcaa tactgtgggg   2040
gccttccggt gtgaatactg tgacagcggg taccgcatga ctcagagagg ccgttgtgag   2100
gatattgatg aatgtttgaa tccaagcact tgtccagatg agcagtgtgt gaattctcct   2160
ggatcttacc agtgcgttcc ctgcacagaa ggattccgag gctggaatgg acagtgcctt   2220
gatgtggacg agtgcctgga accaaacgtc tgcgcaaatg gtgattgttc caaccttgaa   2280
ggctcctaca tgtgttcatg ccacaaaggc tatacccgga ctccggacca caagcactgt   2340
agagatattg atgaatgtca gcaagggaat ctatgtgtaa acgggcagtg caaaaatacc   2400
gagggctcct tcaggtgcac ctgtggacag ggtaccagc tgtcggcagc taaagaccag   2460
tgtgaagaca ttgatgaatg ccagcaccgt catctctgtg ctcatgggca gtgcaggaac   2520
actgagggct cttttcaatg tgtgtgtgac cagggttaca gagcatctgg gcttggagac   2580
cactgtgaag atatcaatga atgcttggag gacaagagtg tttgccagag aggagactgc   2640
attaatactg cagggtccta tgattgtact tgtccggatg gatttcagct agatgacaat   2700
aaaacatgtc aagatattaa tgaatgtgaa catccagggc tctgtggtcc gcaaggggag   2760
tgcctaaaca cagagggttc tttccattgt gtctgccagc agggtttctc aatctctgca   2820
gatggccgta cgtgtgaaga tattgatgaa tgtgtaaaca acactgtttg tgacagtcac   2880
gggttttgtg acaatacagc tggctccttc cgctgcctct gttatcaggg ctttcaagcc   2940
ccacaggatg ggcaagggtg tgtggatgtg aatgaatgtg aactgctcag tggggtgtgt   3000
ggtgaagcct tctgtgaaaa cgtggaaggg tccttcctgt gcgtgtgtgc tgatgaaaac   3060
caagagtaca gccccatgac tgggcagtgc cgctcccgga cctccacaga tttagatgta   3120
gatgtagatc aacccaaaga agaaaagaaa gaatgctact ataatctcaa tgacgccagt   3180
ctctgtgata atgtgttggc ccccaatgtc acgaaacaag aatgctgctg tacatcaggc   3240
gcgggatggg gagataactg cgaaatcttc ccctgcccgg tcttgggaac tgctgagttc   3300
actgaaatgt gtcccaaagg gaaaggtttt gtgcctgctg gagaatcatc ttctgaagct   3360
```

```
ggtggtgaga actataaaga tgcagatgaa tgcctacttt ttggacaaga aatctgcaaa   3420
aatggtttct gtttgaacac tcggcctggg tatgaatgct actgtaagca agggacgtac   3480
tatgatcctg tgaaactgca gtgctttgat atggatgaat gtcaagaccc cagtagttgt   3540
attgatggcc agtgtgttaa tacagagggc tcttacaact gcttctgtac tcaccccatg   3600
gtcctggatg cgtcagaaaa aagatgtata cgaccggctg agtcaaacga acaaatagaa   3660
gaaactgatg tctaccaaga tttgtgctgg gaacatctga gtgatgaata cgtgtgtagc   3720
cggcctcttg tgggcaagca gacaacgtac actgagtgct gctgtctgta tggagaggcc   3780
tggggcatgc agtgtgccct ctgccccctg aaggattcag atgactatgc tcagctgtgt   3840
aacatccccg tgacgggacg ccggcagcca tatggacggg acgccttggt tgacttcagt   3900
gaacagtata ctccagaagc cgatccctac ttcatccaag accgttttct aaatagcttt   3960
gaggagttac aggctgagga atgcggcatc ctcaatggat gtgaaaatgg tcgctgtgtg   4020
agggtccagg aaggttacac ctgcgattgc ttggatgggt atcacttgga tactgccaag   4080
atgacctgtt tcgatgtaaa tgaatgcgat gagttgaaca accggatgtc tctctgcaag   4140
aatgccaagt gcattaacac cgatggttcc tacaagtgtt tgtgtctgcc aggctacgtg   4200
ccttctgaca agccaaacta ctgcactccg ttgaataccg ccttgaattt agagaaagac   4260
agtgacctgg agtgaaacag aatctacata acctaagccc atatactctg cactgtgtaa   4320
aggaaaaggg agaaatgtat tatacttgag acattgcacc taccccggaa ggctggaaat   4380
acagaaacag catggagttg caagtcctct gaagacaatg agaggattta ggatgagccc   4440
gataggtgtg gcagaccaaa tggacatttc tctaaaaaac cagtatatat agtctgttca   4500
tatgtaaaat tcaatggaag agaggtggaa cagtgctgtt attttaaaca gaaggttgta   4560
ttattatgtt gttttgtttt ttttactatt gcttgattaa atttggcatt taaatagtgg   4620
tggaaatatt tttatataat tttcattttt tggttgtgca gttccttggc tactgttttt   4680
cttttacttc agtttttttaa aaatctcaaa tgaaaaagtc ttcgatacaa tattgttaag   4740
ctgtattata agtattgtta cacagggtta tgcaattccc ggcctggagc atttttgaaa   4800
ttcaaattgt ctgtcctgtg gagcaggcag tgattttgtt ccaaaacttt gtatacacat   4860
ttggagaaaa gtactttata ttttcagtgt tttgtctgat tttaatgtcc gttcttagcc   4920
aagctgctag caggtgttaa ttggatccct ttccttcact gaaatggaag agtttataag   4980
cttacgttag tattgtaata tgtaaagtaa gcccaacaaa aatttttaaa aatttgatga   5040
tccccaatat atctaccatt gtatgttaaa taaat                              5075
```

<210> SEQ ID NO 26
<211> LENGTH: 1618
<212> TYPE: DNA
<213> ORGANISM: Homo sapiens

<400> SEQUENCE: 26

```
gagcgccggc gcgggaccga gctggcggcg ggcggcgcgc gcttccgagg cttcctgctg     60
cttctgcccg agcccgcggc ctcacgcgcg ccctctcccg tgccatggcc tgcaggcagg    120
agccgcagcc gcagggcccg ccgcccgctg ctggcgccgt ggcctcctat gactacctgg    180
tgatcggggg cggctcgggc gggctggcca gcgcgcgcag ggcggccgag ctgggtgcca    240
gggccgccgt ggtggagagc cacaagctgg gtggcacttg cgtgaatgtt ggatgtgtac    300
ccaaaaaggt aatgtggaac acagctgtcc actctgaatt catgcatgat catgctgatt    360
atggctttcc aagttgtgag ggtaaattca attggcgtgt tattaaggaa aagcgggatg    420
```

```
cctatgtgag ccgcctgaat gccatctatc aaaacaatct caccaagtcc catatagaaa    480

tcatccgtgg ccatgcagcc ttcacgagtg atcccaagcc cacaatagag gtcagtggga    540

aaaagtacac cgccccacac atcctgatcg ccacaggtgg tatgccctcc acccctcatg    600

agagccagat ccccggtgcc agcttaggaa taaccagcga tggatttttt cagctggaag    660

aattgcccgg ccgcagcgtc attgttggtg caggttacat tgctgtggag atggcaggga    720

tcctgtcagc cctgggttct aagacatcac tgatgatacg gcatgataag gtacttagaa    780

gttttgattc aatgatcagc accaactgca cggaggagct ggagaacgct ggcgtggagg    840

tgctgaagtt ctcccaggtc aaggaggtta aaaagacttt gtcgggcttg gaagtcagca    900

tggttactgc agttcccggt aggctaccag tcatgaccat gattccagat gttgactgcc    960

tgctctgggc cattgggcgg gtcccgaata ccaaggacct gagtttaaac aaactgggga   1020

ttcaaaccga tgacaagggt catatcatcg tagacgaatt ccagaatacc aacgtcaaag   1080

gcatctatgc agttggggat gtatgtggaa aagctcttct tactccagtt gcaatagctg   1140

ctggccgaaa acttgcccat cgactttttg aatataagga agattccaaa ttagattata   1200

acaacatccc aactgtggtc ttcagccacc cccctattgg gacagtggga ctcacggaag   1260

atgaagccat tcataaatat ggaatagaaa atgtgaagac ctattcaacg agctttaccc   1320

cgatgtatca cgcagttacc aaaaggaaaa caaaatgtgt gatgaaaatg gtctgtgcta   1380

acaaggaaga aaaggtggtt gggatccata tgcagggact tgggtgtgat gaaatgctgc   1440

agggttttgc tgttgcagtg aagatgggag caacgaaggc agactttgac aacacagtcg   1500

ccattcaccc tacctcttca gaagagctgg tcacacttcg ttgagaacca ggagacacgt   1560

gtggcgggca gtgggaccca tagatcttct gaaatgaaac aaataatcac attgactt     1618
```

<210> SEQ ID NO 27
<211> LENGTH: 603
<212> TYPE: DNA
<213> ORGANISM: Homo sapiens

<400> SEQUENCE: 27

```
cgtgctgcta cacaagaacc ctgagactga cctgcaggac gaaaccatga agagcctgat     60

ccttcttgcc atcctggccg ccttagcggt agtaactttg tgttatgaat cacatgaaag    120

catggaatct tatgaactta atcccttcat taacaggaga aatgcaaata ccttcatatc    180

ccctcagcag agatggagag ctaaagtcca agagaggatc cgagaacgct ctaagcctgt    240

ccacgagctc aatagggaag cctgtgatga ctacagactt tgcgaacgct acgccatggt    300

ttatggatac aatgctgcct ataatcgcta cttcaggaag cgccgagggg ccaaatgaga    360

ctgagggaag aaaaaaaatc tcttttttc tggaggctgg cacctgattt tgtatccccc     420

tgtagcagca ttactgaaat acataggctt atatacaatg cttctttcct gtatattctc    480

ttgtctggct gcacccccttt ttcccgcccc cagattgata agtaatgaaa gtgcactgca   540

gtgagggtca aaggagagtc aacatatgtg attgttccat aataaacttc tggtgtgata    600

ctt                                                                  603
```

<210> SEQ ID NO 28
<211> LENGTH: 2294
<212> TYPE: DNA
<213> ORGANISM: Homo sapiens

<400> SEQUENCE: 28

```
aagcagttgt tttgctggaa ggagggagtg cgcgggctgc cccgggctcc tccctgccgc     60
```

```
ctcctctcag tggatggttc caggcaccct gtctggggca gggagggcac aggcctgcac    120

atcgaaggtg gggtgggacc aggctgcccc tcgccccagc atccaagtcc tcccttgggc    180

gcccgtggcc ctgcagactc tcagggctaa ggtcctctgt tgctttttgg ttccacctta    240

gaagaggctc cgcttgacta agagtagctt gaaggaggca ccatgcagga gctgcatctg    300

ctctggtggg cgcttctcct gggcctggct caggcctgcc ctgagccctg cgactgtggg    360

gaaaagtatg gcttccagat cgccgactgt gcctaccgcg acctagaatc cgtgccgcct    420

ggcttcccgg ccaatgtgac tacactgagc ctgtcagcca accggctgcc aggcttgccg    480

gagggtgcct tcagggaggt gcccctgctg cagtcgctgt ggctggcaca caatgagatc    540

cgcacggtgg ccgccggagc cctggcctct ctgagccatc tcaagagcct ggacctcagc    600

cacaatctca tctctgactt tgcctggagc gacctgcaca acctcagtgc cctccaattg    660

ctcaagatgg acagcaacga gctgaccttc atcccccgcg acgccttccg cagcctccgt    720

gctctgcgct cgctgcaact caaccacaac cgcttgcaca cattggccga gggcaccttc    780

accccgctca ccgcgctgtc ccacctgcag atcaacgaga acccctttcga ctgcacctgc    840

ggcatcgtgt ggctcaagac atgggccctg accacggccg tgtccatccc ggagcaggac    900

aacatcgcct gcacctcacc ccatgtgctc aagggtacgc cgctgagccg cctgccgcca    960

ctgccatgct cggcgccctc agtgcagctc agctaccaac ccagccagga tggtgccgag   1020

ctgcggcctg gttttgtgct ggcactgcac tgtgatgtgg acgggcagcc ggcccctcag   1080

cttcactggc acatccagat acccagtggc attgtggaga tcaccagccc caacgtgggc   1140

actgatgggc gtgccctgcc tggcacccct gtggccagct cccagccgcg cttccaggcc   1200

tttgccaatg gcagcctgct tatccccgac tttggcaagc tggaggaagg cacctacagc   1260

tgcctggcca ccaatgagct gggcagtgct gagagctcag tggacgtggc actggccacg   1320

cccggtgagg gtggtgagga cacactgggg cgcaggttcc atggcaaagc ggttgaggga   1380

aagggctgct atacggttga caacgaggtg cagccatcag ggccggagga caatgtggtc   1440

atcatctacc tcagccgtgc tgggaaccct gaggctgcag tcgcagaagg ggtccctggg   1500

cagctgcccc caggcctgct cctgctgggc caaagcctcc tcctcttctt cttcctcacc   1560

tccttctagc cccacccagg gcttccctaa ctcctcccct tgcccctacc aatgcccctt   1620

taagtgctgc aggggtctgg ggttggcaac tcctgaggcc tgcatgggtg acttcacatt   1680

ttcctacctc tccttctaat ctcttctaga gcacctgcta tccccaactt ctagacctgc   1740

tccaaactag tgactaggat agaatttgat cccctaactc actgtctgcg gtgctcattg   1800

ctgctaacag cattgcctgt gctctcctct caggggcagc atgctaacgg ggcgacgtcc   1860

taatccaact gggagaagcc tcagtggtgg aattccaggc actgtgactg tcaagctggc   1920

aagggccagg attgggggaa tggagctggg gcttagctgg gaggtggtct gaagcagaca   1980

gggaatggga gaggaggatg ggaagtagac agtggctggt atggctctga ggctccctgg   2040

ggcctgctca agctcctcct gctccttgct gttttctgat gatttggggg cttgggagtc   2100

cctttgtcct catctgagac tgaaatgtgg ggatccagga tggcttcctt cctcttaccc   2160

ttcctccctc agcctgcaac ctctatcctg gaacctgtcc tccctttctc cccaactatg   2220

catctgttgt ctgctcctct gcaaaggcca gccagcttgg gagcagcaga gaaataaaca   2280

gcatttctga tgcc                                                     2294
```

<210> SEQ ID NO 29
<211> LENGTH: 3644
<212> TYPE: DNA

<213> ORGANISM: Homo sapiens

<400> SEQUENCE: 29

```
cggcggcgca ggtgaggcgc ggggccgggg ccggaccggg aggcggggac cccccgcccc     60
accgcccgca cctgcggggc agccggcgct caggcgccgc agccgctcag cacctgcggc    120
gccctcaggg agccgggcgc ggggccctgc gcactcggag ctcggctcct ctccttcctt    180
ttcttttttt tcgggggggag gtgggggctg gtttggatgt tttccgagag ccggggacgg    240
tctcaagcta ttttcgcgga gggaagtctt tgaaatacga catctaaaag agtggccctc    300
ggcgacaatg ccgggcgttc ccggaccggg gcaacgctgg gattccgggg aagtggaggc    360
agagggagcg ggcacggggc cggcagccgc tccacggagt ccccggcagg ggcgagctta    420
gctgtccagc cgggtcccct gcccaccccg gcccgggccg cggtgacagc tgagggtcca    480
gagagccggc aggaggggac cctgccgatt gtctgccgcg atggggacgt gggcgtgccc    540
gcggaattca cctcctccgg ggaccagccg cccagggagg agccggcaca gaacgctggc    600
tcggagcgcc ggcaccctgg gcctttgcgt tgtttgtcgg ctgagcagct ggttcccgga    660
ccccgtgggc ctcctggcca atgcgagtga cagcgacctt ctgggtttat aataaagggc    720
ttgacgcgcc ggaaagtccc ctcgccgctg gccaccagcc ttccagccct tacggcccac    780
gccgtaatcc tggtgaccga gaagagagca gagccactgc cagaaggaag gggacaagac    840
ccagcaggac accttctttc cacgctttcc agcctgtggg agcggcaggg gcaacagaga    900
gaggatctgg agccaggatt aatgactcat ttatgaagca tcttattctg cgaccgaggc    960
tcagtggtca gtggcgacgt aaatggctcg actccccgct ggcattcgct tcatcatctc   1020
attctccagg gatcagtggt acagagcctt catttttatt ttgacatttc tgctgtatgc   1080
aagttttcac ttatctcgaa agcctatcag catagttaag ggtgagctcc acaagtactg   1140
cactgcttgg gatgaagctg acgtcaggtt cagcagccag aacaggaagt ctgggtccgc   1200
tgccccccac cagctccctg acaatgagac cgactgtggc tgggcaccgt ttgataagaa   1260
caactatcag cagctgcttg ggccctgga ctactccttc ctgtgcgcct atgccgtggg   1320
gatgtacctc agtggcatca ttggggagcg cctgccgatt aggtattacc taactttcgg   1380
gatgctcgcc agcggagcct tcaccgccct gttcggctta gggtatttct acaacatcca   1440
cagtttcgga ttctacgtgg taactcaggt catcaacggg ctggtgcaga ccaccggctg   1500
gcccagcgtc gtcacctgcc tcggcaactg gtttggaaaa ggaaggagag gtttgattat   1560
gggggtctgg aactcccaca cctccgtggg caacatcttg ggtcattga tcgctggcta   1620
ctgggtgtcc acatgctggg gcctgtcctt ggtcgtgcct ggagccatcg tggcagccat   1680
ggggatagtg tgctttctct tcctcattga acatccgaac gacgtcaggt gctcctccac   1740
cctggtgacg cactcaaaag gctatgagaa tggtacaaac agattgagac tccagaagca   1800
aatcttgaag agcgaaaaga acaagcctct ggacccagag atgcagtgcc tgctgctctc   1860
agatgggaag ggctccatcc acccgaacca ggtcgtcatt ctccccgggg acggtgggag   1920
tggcacggcc gccatcagct tcacaggggc cttgaaaatt ccaggcgtga tagagttctc   1980
actgtgtctg ctgtttgcca agctggtcag ctatactttc ctcttctggc tgcccctgta   2040
catcacgaat gtggatcacc ttgatgccaa aaaggcgggg gagctctcca ccctgtttga   2100
cgtgggcgga atctttggtg ggatcctggc aggtgtgatc tcagaccgac tggagaaaag   2160
ggcctccacc tgcggcctga tgctgctgct cgcggccccc acgctctaca tcttctccac   2220
catcagcaag atggggcttg aggccaccat cgccatgctg ctgctcagcg gagccctggt   2280
```

```
cagtgggccc tacacactca tcaccaccgc cgtctccgcc gacctgggga ctcataaaag   2340

tctgaaaggc aacgcgcacg ccctctccac cgtgacggcc atcattgacg ggacgggctc   2400

tgtaggagca gccctgggcc ccctgctggc tgggctcctc tccccgtccg gctggagcaa   2460

tgtgttttac atgctgatgt ttgcagatgc ctgtgcctta ctgttcctga tccgcctcat   2520

acacaaggag ctgagctgcc cagggtcagc tacgggggac caagttccat ttaaggaaca   2580

gtgacacccc accccagtcc cgtggagggg gtctgggccc acccttcaca actgcctttc   2640

aaggacagtt cagacaaagg gccctgcatg gaaagagtga cctccctttg ccttttgcac   2700

acgcacctgg aaaagacaca gaagccaacc tgagaacccc tggtgctatt ttaaaggaga   2760

catattgctg aacagcagtg agaaaagtct gcaggaactg ctgcctgagc caagccagag   2820

aaccgaagac ccggccggcc ctggcctcac aggcgtgtgc ccatgcagcc acccaaatgc   2880

acgcgtgaca acaaggccgg gagggtgggg ggggtgcaca ggtagccccg accctctcag   2940

gcattccagc cacagaacat caaagtgagc gagtactgcg ctggctgtgg cttcagagaa   3000

cctgtatgtg ccacgtggaa aaacaggaca ccagagccca ccagacagtg ccggccagca   3060

gagaagcaga gagccagcgc cacacaacat caagaaggcc gacaaccagg ttggaaacca   3120

agacggagct cagacccacc acatcgcccc agaggctttt ccagcaccca tgatgttccg   3180

gactgaccta aaaactaatt gtcgagaagc caagggtgag gaggcaggaa gcacctccgg   3240

ttggaggcac ccaggcttgc cagccacaga gcgccccgaa gtcaccgtca tcccagcccc   3300

tggccttcct gccgccctcc ggggccatgg cgctgctgtt cagctcaggc acaggggcac   3360

agcagaggtt tgggaagcgg tctccccacc ggcactggga ttggcgggtc caagcccagc   3420

aaccggcttc gctccacaac acacaccaca cctgggactg tttttaatac atagcaacag   3480

actgggttat ttatttaaga tgtgtattgt gtcatatgaa gtttaagaga cataaatggc   3540

attttgttat ttattaagac aaactccaat tgttctctgg ctgttttttt cagttgtgtc   3600

tagcaaaata cttatctgcc ctttgaaata aaatgttttt gttt                    3644
```

<210> SEQ ID NO 30
<211> LENGTH: 7568
<212> TYPE: DNA
<213> ORGANISM: Homo sapiens

<400> SEQUENCE: 30

```
gcgcggaggc agggaaccgg agccttggag cgacccaacc cctcgtctcg ctgccctccc     60

gcgcctgcaa cggtgcgcgg agactccggc gaactcagac acccaacggc ggagaacaga    120

agcggcaggc ggcggacgtg gcccggaagc tgcgcgccga acgcagcgca cccgctgccg    180

agcagaggag ccgcgccttt ccccgaccct cggctccagc ccccggcgcc tgccgcctcg    240

cagcccctct gcgtcctcgg ctcgggggcc ggcaccggcg atgccgagcg gacgctccag    300

tcctccgacc cgctgaagaa gcagcagccg ctcgcccgga gcctacgggg attgtgcgag    360

cggatcgtgc tcggtggagg ctcgggctgc ggggcgcggg gactccgggg ggcgggggga    420

gggaccgctc tgtcggtgcc cggcgccagc cgcggctttg aagggtctcc ctcccctgcc    480

cttagcagct ctgccacgga ctccgggagg ctgcgggcgg cgtcctgagg gctccccagc    540

agacccaatc ggacttgaga aggtgatcgc tctgctctcc caaccccctt ccctccccat    600

tccccccact taacttttg tctccgttca tccgcggctt cgtcccctcc ccggcagacc    660

cacccgcggc tgtgacaacc gcccggggca tgggcccccc aacacggctc ctagaggccc    720

cgcggcctcg caagatgtga gaggccctcc ccgggcagaa tcggagcttc aggagaggag    780
```

```
ctaataccccc gccccccgtc cctcacatca ggcggggtgg aggtgcgcgc tgagcccccg    840
cggtgctgag cgtcccggag cgcccaatcc tgggctggaa cgagtagctg gccggaggcg    900
cgccgcggag agccggctgt catgccctat tgatcccccct ctgccccccg ccaagtatgt    960
ttgggctgga ccaattcgag ccccaggtca acagcaggaa cgctggccag ggcgagagga   1020
actttaacga gaccggactg agcatgaaca cccactttaa ggccccggct ttccacactg   1080
gggggccccc tggccctgtg gatcctgcta tgagcgcgct ggggcaaccc ccgatcttgg   1140
gcatgaacat ggagccctac ggcttccacg cgcgcggcca ctcggagttg cacgcagggg   1200
ggctgcaagc gcagcctgtg cacggcttct ttggcggcca gcagcctcac cacggccacc   1260
cgggaagtca tcatccccac cagcatcacc cccactttgg gggcaacttc ggtggcccgg   1320
accccggggc ctcgtgcctg cacgggggtc gcctgctcgg ctacggcggc gcagccggag   1380
gcctgggcag ccagccgccc ttcgccgagg gctatgagca catggcggag agccaggggc   1440
ctgagagctt cggcccgcag cgaccgggga acctcccgga cttccacagt tcaggtgcct   1500
ccagccaccg cgtgccggcc ccatgcctgc cgctggacca gagccctaac cgagccgcct   1560
ccttccacgg cctgccgtcc tccagcggct ccgattccca cagtctggag ccacggaggg   1620
tgacgaacca aggagccgtc gactcgctgg aatacaatta ccgggcgagg cgccctcggg   1680
acattttgac atgttttcgc cctctgactc cgaagggcag ctgcctcatt atgcagcggg   1740
tcgccaggtt cctggggggc ggctttcccg gggcgccctc ggccatgccc agagctgcgg   1800
gcatggtggg cttgtccaaa atgcacgccc agccaccgca gcagcagccc cagcagcagc   1860
agcagcccca gcagcagcag cagcatggtg tgttctttga gaggttcagt ggggccagaa   1920
agatgcctgt gggtctggag ccctcagtgg gctccaggca cccgttaatg cagcctcccc   1980
agcaggcccc gccacccccct cagcagcagc ccccgcagca gccgccacag cagcagccgc   2040
cgccgccacc cgggcttcta gtccgacaaa attcgttgcc cgcctgcgct ccctcggccc   2100
cagcagggcg aggcgggcac gcccagcggc ggcctgcagg acggaggccc catgctgccc   2160
agccagcacg cgcaattcga gtatcccatc caccggctgg agaaccggag catgcaccct   2220
tattccgagc ctgttttcag catgcagcat cctcctccgc agcaggcgcc caaccagcgg   2280
ctgcagcatt tcgacgcgcc cccctacatg aacgtggcca agaggcgcgc ttcgactttc   2340
cgggcagcgc gggagtggac cgctgcgctt cgtggaacgg cagcatgcac aacggcgctc   2400
tggataatca cctctcccct tccgcctacc caggcctacc cggcgagttc acaccgcctg   2460
tgcccgacag cttcccttcg gggccgcccc tgcagcatcc ggccccggac caccagtccc   2520
tgcaacagca gcagcagcag cagcagcagc agcaacagca gcagcagcag cagcaacagc   2580
aacagcaaca gcagcagcag cagcagcgcc aaaacgcggc cctcatgatt aagcagatgg   2640
cgtcgcggaa tcagcagcag cggctgcgcc agcccaacct ggctcagcta ggccaccccg   2700
gggacgtggg ccagggcggc ctggtgcatg gcggcccggt gggcggcttg gcccagccga   2760
actttgagcg cgaaggcggc agcacgggcg ccgggcgtct gggcaccttc gagcagcagg   2820
cgccgcactt ggcgcaagag agcgcgtggt tctcaggtcc gcatccgccg cccggagacc   2880
tgctgccccg taggatgggc ggctcgggtc tgcccgctga ctgtggcccg cacgacccca   2940
gcctggcgcc ccctcctccg cctggtggct cgggggtgct gttccggggc cctctgcagg   3000
agccgatgag gatgcccgga gaggccacgt gccgcgctgc cttcaccggc ctgcagttcg   3060
gggcagtct gggaggcctg ggtcagctgc agtcgcccgg ggcgggcgtg gggctcccca   3120
gcgctgcttc ggagcgccgg cccccgccgc cggactttgc tacgtctgcg ctcgggggcc   3180
```

-continued

```
agccgggctt tccgtttggt gcagccggcc ggcagtccac gccgcacagc ggtccaggcg   3240

tgaactcgcc ccccagcgcg ggagggggcg gtggcagctc tggtggcggc ggtggcgggg   3300

gtgcctaccc gccgcagcct gatttccagc ccagccagcg cacctcggcc agtaaattgg   3360

gcgcgctctc gctgggctcc ttcaacaagc ccagctccaa ggacaacctg ttcggccaga   3420

gctgcctggc tgcgctctcc accgcttgcc agaacatgat cgccagcctc ggggccccca   3480

acctcaacgt gaccttcaac aagaagaacc cgccagaggg caagaggaaa ctgagccaga   3540

acgagaccga cggcgcggca gtggccggca acccgggctc ggattacttc ccaggaggga   3600

ctgctcctgg gggccccagg acccggaggc cgtccgggac cagtagcagc ggctccaaag   3660

cctcggggcc gcccaaccct ccagcccagg gggacggcac cagcctctcc cccaactaca   3720

ccctggaatc cacgtcgggg aatgacggca agccggtctc cgggggcggc ggccggggac   3780

ggggtcgcag aaaaagggac agtggtcacg tgagccctgg caccttcttt gacaagtact   3840

cggcggctcc ggacagcggg ggcgcacctg ggtgagcccc agggcagcag caagcgtcag   3900

gcgcagccgt cgggggaagc tccgcaggcg agacgcgcgg ggcaccgacg ccccacgaaa   3960

aggcgctcac gtcgccatcc tgggggaagg gggctgagtt gctcctgggg gatcagccgg   4020

acctcattgg gtccctggac ggcggggcca agtcggacag tagttcgcca aacgtgggtg   4080

agttcgcctc ggacgaggtg agcacgagct acgccaatga ggacgaggtg tcgtccagct   4140

ctgacaaccc ccaggcacta gttaaagcga gcaggagtcc cctggtgacc ggctcgccca   4200

aactccctcc ccgtggggta ggcgccgggg aacacggacc gaaggcgccc ccgcccgccc   4260

tcggcctggg catcatgtct aactctacct cgacccctga cagctacggc ggcggtgggg   4320

gcccgggcca tccgggcact ccgggcctgg agcaggtccg caccccgacg agcagcagcg   4380

gcgccccgcc acccgacgag atccaccccc tggagatcct tcaggcgcag atccagctac   4440

agaggcagca gttcagcatc tccgaggacc agcctctggg gctgaagggt ggcaagaagg   4500

gtgagtgcgc cgtcggggcc tcaggggcgc agaatggcga cagcgagctg ggcagctgct   4560

gctccgaggc ggtcaagagc gccatgagca ccattgacct ggactcgctg atggcagagc   4620

acagcgctgc ctggtacatg cccgctgaca aggccctggt ggacagcgcg gacgacgaca   4680

agacgttggc gccctgggag aaggccaaac cccagaaccc caacagcaaa gaagcccacg   4740

acctccctgc aaacaaggcc tcagcatccc agcctggcag ccacttgcag tgcctgtctg   4800

tccactgcac agacgacgtg ggtgacgcca aggctcgagc ctccgtgccc acctggcggt   4860

ccctgcattc tgacatctcc aacagatttg ggacattcgt ggctgcccta acttgaatga   4920

caagaaagat cccctcctct accaggccct tcctctcccc ctgtctgttt ccttccccct   4980

caaccttacc ccacccctct gttaatttga aagggccact attgctgagt ggatgagttt   5040

tttttttttc ctctaggttg gtacctgctt agtggcatat ggaccggaaa gggttaattt   5100

aaaggggggg aacctcaaaa gttttttttaa aaaagaaact tgtctgccac agtatgttac   5160

cagtgttaac ccttctgcag ttagcaaact tttgcttaag cctttttcct ctagatactc   5220

cccatgtttc ggtaatcttg gcatacattt tttagatgac ctctttcctt gttttgtttt   5280

catgctgctg tatgtccaag tattgttatt tcataataag acaagagttg ctttcttttt   5340

tattcttttt ccttttctta ccccctcccc ttttattttc tttttgcttt gttcactgct   5400

tattaaaatg gaaatcctgg agaatagtag ttctggaata ttgccgggtg aaagtccaat   5460

tgtcatcaca atgttatata ttgacacccc agtgtcatca gtcaggcagg agccaaacaa   5520

tgaatgcccc tcttaggtat tccgcctggg attttgtttt gtctgttccc taagaaaata   5580
```

```
tattttcatt cctgcaaaca cagtgctcag ccttcagttc ccttccactt gagttctctc   5640

ttctcctgct ggaagccgcc cctctctgcg atggacgtga ggacgtgtcc agctctgctc   5700

tgtgggaagg agttggaatg ttcgacagca gtgttttctc tccttttctg ggcctcctcg   5760

caaatgccca ggccctgcat tttcacgctg tgctaagcag cctttggtct gcatgggga    5820

tggtgtgctc ccagcctgca gtctttggag caaggctgct gcccgtgcct tgggtgctgg   5880

agttggagga ggctgttctc agccctttcc cttttctgaa agctgttcct ggccgggcat   5940

cccagggaag aaggagggga ctgcgtgtat ctcctccacc tctcccattc catccccagt   6000

ccagcctggg caaccccacc cctgggaggg atgaggcacc ctcttgctca gcctgctcag   6060

ccttctctga gcctttgcag ggatctgcag actcctgagg gctagaggac agagaaagag   6120

aatagaatga aatgactttg attcctgcgc cttttagttt tgaactctgg aattcctctg   6180

ccccctcccc aacatttttt tggaatctca ccctgttgca aaactagagc catgtcccaa   6240

gcatctcaca aaggaataac tgctctgagc agagatgagt ggtggttggc aggggcaggc   6300

aactttgggt gctgctgatg cctgcaaaag ccatttatgg cttgtggtgg ggggcacata   6360

gattccccgg tgggttagac aggaagtaac tgatatcact tcacccaaat atataaccgt   6420

gatggttatc tatttaattt cagtttttgt taacgagcgt gtcttactaa aacgctccac   6480

tttgagctcc cccacccct ccaggtcctc agagtttgca gatctgggct ttctaaagca    6540

agtgacctga aggctctggg ctcaccatac aacacccacg ttgtttattt caaagaactt   6600

ttcagcgaag ggagaggagc tttcagaaaa acctcactct ttcccctccc ttctcccctc   6660

tttccttctg ccggtccttt tggctggggt ctgagtctgc ggttctcgcc tgggcagtct   6720

tgacgaggag caaaccccgc cttcagaggg cagacaaagc aggtggcatg aattgatcag   6780

cgagaaaggt gtgagccgag gcagttcctg cgttctgcta caaaaggaat ggaaagggaa   6840

gggaatttcc ccccaccatg ggctgtggga gagttgaccg tattctgggc aagactccat   6900

gacccctctg attctgcagt gtacagctgt ttgagagcct catcatttta cttttgaaac   6960

aggaatgatt tctccttaat tgcttaaggc cggggagcaa agtgtcttaa cttctgtctt   7020

tgactttccc agcgttgagt catcaacact ttgccaatta gctcatggtc ctggcaacct   7080

cagaaacccc tgaagtttta aaaactttct cgctccccac gaccccagaa tgaaacagct   7140

ttaaaaatag ccttaagcaa aaggatgtta tttcattaaa tttggtttaa tggaaagaat   7200

aaaagtaaat gaaaaacaca ccctacacac tagactccga acactggtaa tcagtactgc   7260

atagcaaact ctttgggaaa gaaaacgaaa atgttattgc acatgtaaaa tatgaaaact   7320

taactctgct gtgtgttagg caatcctgta atcttttttg actcttaaaa gaaattcatt   7380

tctgaaatgc ttggttggaa gactgtgaca atagctcatg aaattgagtg ttattttttt   7440

ctttcttttt taaaaaaata tgtaaagtgc agtcttctgt attcctgcat attgtatata   7500

cctgtatatg ttttcctgag cagttaaata acaataaata tgacgttaat ggtgaaaaaa   7560

aaaaaaaa                                                             7568
```

```
<210> SEQ ID NO 31
<211> LENGTH: 2149
<212> TYPE: DNA
<213> ORGANISM: Homo sapiens

<400> SEQUENCE: 31

ccgcgggaac ccggaaacgc ctgggctgca ccgagctggc ggtggctacg gcgacgggag     60

ccggcggcgc tgcgggtcag cggtcgcgta ggacccagcg gactcggcag cctggggcgc    120
```

```
ccggcggagc tgaaccgcgg cccccggtgg tgggctcagc cggtcgagct gcgcgggagg    180

caaatgaaga taaaacaatg ttcgccaacc taaaatacgt ttccctggga attttggtct    240

ttcagactac cagtttggtt ctaacaatgc gttattccag aactttaaaa gaagaaggac    300

ctcgttatct atcttctaca gcagtggttg ttgctgaact tttgaagata atggcctgca    360

ttttattggt ctacaaagac agcaaatgta gtctaagagc actgaatcga gtactacatg    420

atgaaattct taataaacct atggaaacac ttaaacttgc tattccatca gggatctata    480

ctcttcagaa taatttactg tatgtggcac tatcaaatct agatgcagct acttatcagg    540

tcacgtatca gttaaaaatt cttacaacag cattattttc tgtgtctatg cttagtaaaa    600

aattgggtgt ataccagtgg ctgtccctag taattttgat gacaggagtt gcttttgtac    660

agtggccctc agattctcag cttgattcta aggaactttc agctggttct caatttgtag    720

gactcatggc agttctcaca gcatgttttt caagtggctt tgctggggtt tactttgaga    780

aaatcttaaa agaaacaaaa caatcagtgt ggataagaaa tattcagctt ggtttctttg    840

gaagtatatt tggattaatg ggtgtataca tttatgatgg agaactggta tcaaagaatg    900

gatttttca gggatataac cgactgacct ggatagtagt tgttcttcag gcacttggag    960

gccttgtaat agctgctgtt attaagtatg cagataatat tttaaaagga tttgcaacct   1020

ctttatcgat aatattatca acattgatct cctatttttg gcttcaagat tttgtgccaa   1080

ccagtgtctt tttccttgga gccatccttg taataacagc tacttttttg tatggttatg   1140

atcccaaacc tgcaggaaat cccactaaag catagttgta tactatcttt aactggtttt   1200

tcacgatggg gcactaggaa tctcgacatt aatcttgcac agaggacttc tacagagtct   1260

gagaagatat catcatgctg aatctgatca tactgttttt taaaagttta aggataagac   1320

atgtgtatat gtaacaaaac acattgcatc tagaaatcaa aacttgaaag tatttccagg   1380

gattaggatt agaaggaata ttagaggaaa cttgaaatct gagtttaaaa agattttacc   1440

tttttgattg ctgcagaaat gtcctatgca ctctttgcaa gagcacacaa caaatgtcag   1500

ataccaattt ttgcaaatta gatttaatct tattaaatgt ttttatctta ctctttctgt   1560

acagatatat caaatcacat gaaatattta aagtttgaaa attataatta cctataaagc   1620

tgtgaaaaat agaagtataa tttgaaaaaa catttcactt atcagagatt tttatattta   1680

tacaaaagat tactaaatga aggattgcta aatgtttttg gttcaattac ataaaaatta   1740

atattctggg tctgatctgt cagagaataa atatcaaatc taaatttaat gtagagatac   1800

atactatttc tccatatgaa ttttaagata ttttagtgct tcaagactgc tgaaagcaat   1860

ccagttgctc ctgtgctaga tggtagccag agaattttat agtaatggag gttagccctt   1920

aatctcttca ttgcatttca tttctgtaaa tcagattaag tccttaatat tattttaaat   1980

taaaatttgt gtgtaattgc cattaaattt tcaaaatgta atttaaaagg attaaatact   2040

catttaataa tttaaaataa ttattgtata atatctacat ttggagaatt ttgaactatc   2100

aagcatatac tgtatacagt tagaaagtta ttaaatgaac attttactc               2149
```

<210> SEQ ID NO 32
<211> LENGTH: 5080
<212> TYPE: DNA
<213> ORGANISM: Homo sapiens

<400> SEQUENCE: 32

```
cggacgtccg gcgcgggaga gaaaggtccc gaagatggca tattcataaa gacatcttct     60

gatgattgtg aacatcttta cctctgggtg ccaggccggg ccagtgactt cgtgttgagc    120
```

```
tgaaggaact tgtctaccgc ttccctgaaa acctttcttt cctaattcat gagccagcaa    180
gatgcggtcg ctgcactttc agagcgcctt ctcgtagctg cgtacaaagg ccaaacagag    240
aatgtggttc agctcatcaa caagggcgcc agggtagcgg ttaccaagca tggccggact    300
cccctgcatc ttgctgccaa taagggccat cttcctgtgg tccagatctt gctgaaggct    360
ggctgcgacc ttgatgtcca ggatgatggg gaccagaccg ccttgcaccg ggccacagtg    420
gtggggaaca cggagatcat cgcggcgctc atccacgaag ggtgtgccct ggacagacaa    480
gacaaggatg ggaatacagc cttgcatgaa gcatcctggc atggtttcag ccagtcagcc    540
aagctgctcg ttaaagcagg agccaacgtg cttgccaaga acaaggcggg gaacacagct    600
ctgcacctgg cctgccagaa cagccactcc cagagcacgc gcgtcctcct gctggccggg    660
tcccgcgctg acctcaaaaa taatgcagga gacacctgtt tgcacgttgc tgcgcgctat    720
aatcacttgt ccatcattag gctcctcctc actgctttct gttctgtcca tgaaaagaac    780
caggctggag acacagcact tcacgttgct gctgccctaa atcacaagaa ggtggccaaa    840
atcttactgg aagccggagc agatacgacc attgttaaca atgcaggcca gactccgctg    900
gagactgccc gctaccacaa taacccggaa gttgctcttc tccttactaa agctccccag    960
ggcagtgtct cagcaggaga cacccccagc agtgaacagg ctgtggccag aaaagaagaa   1020
gccagagaag agttcctgtc agcctcccca gaacccagag caaaggatga caggaggaga   1080
aagtcaaggc ccaaggtgtc agcgttttct gaccccaccc caccagccga ccaacagcct   1140
ggacaccaga agaacctgca tgctcataat caccctaaaa agaggaacag gcatcggtgt   1200
tcatccccac ccccacccca tgagttcagg gcgtatcagc tctacacatt gtaccggggc   1260
aaggatggga aagtgatgca ggcaccaata aatggttgtc gatgtgaacc tctaatcaac   1320
aagctggaga atcagttgga ggctactgtg gaggagataa aagcagagct gggatcggtt   1380
caggacaaaa tgaatacaaa gctggggcag atggagaata agacccagca ccaaatgcgt   1440
gttttggaca agctgatggt tgagcgactt tctgcagaga ggacggagtg cctgaaccgc   1500
ctgcaacagc actcagacac agagaagcat gagggggaga aacgacagat atccttggtg   1560
gatgaattaa aaacctggtg catgttaaag attcagaatc tggagcagaa gctttctgga   1620
gattctaggg cctgcagagc taaatccaca ccatctactt gtgagtcctc tacaggtgtg   1680
gaccaattag tggtgactgc aggtccagca gcagcttccg acagctcccc tccagtggtt   1740
aggcccaaag agaaggccct caactccact gctacccaga gactccagca ggagctgtcg   1800
tcttctgact gtacaggctc ccgactgaga aacgtcaagg tccagacagc cttgctaccc   1860
atgaatgagg cagccagatc tgatcagcag gctgggccct gcgtcaacag aggcactcaa   1920
actaagaagt ctgggaagag tgggccaaca aggcatcgtg cccagcaacc cgcagccagc   1980
agcacctgtg ggcagccgcc accagccaca ggcagcgagc agactggccc tcacattcgg   2040
gacacctccc aagctctgga gcttacccag tatttttttg aggctgtttc tacccagatg   2100
gaaaagtggt atgaaaggaa gattgaagaa gcacgaagcc aagccaatca gaaagcccag   2160
caagataagg ctacattgaa ggaacacatt aaaagtttag aagaggaact tgccaaacta   2220
aggactaggg tgcagaagga aaattagcac caataaagag gaaatatgaa aggattcttg   2280
aagatttcca gttttgcaac tgcataatag ctatgcccaa ggagtcaact attgtatata   2340
ttgcagattt gcctttttaa aaaaatcact aattctacaa tgtgccagat acatgtttcc   2400
tatgcccagg aagttatgaa gacttcaaca attaaactga aaccagggga agcttgctta   2460
gttttgggtt tcattataaa ctcttagcct cagtccaggt taatctgaag tttgaaagct   2520
```

```
cagattaagc aagccatgcc aagaaactgg acgatgtgta agcctagact ctaaaattca   2580
agatgtgtga aataatataa gtcaaaagca gaaaaacgta atcccgtctg aactcaagta   2640
gtcattcata taaatttgaa cacacctgct gtgcctagac aagtgtcttt ctgtaagagc   2700
tgtaactctg agatgtgcta aataaaccct ctttctcaaa ttcgtaattc tccaactgtt   2760
gacattttaa tcacatgaaa agttatcaga tttttgagga gaaatatttt catgatgtca   2820
caagatccaa tatatcttat gataaaattt attgaaaagt cagtttattt aaataatgaa   2880
taattggcta acagctctgg aaacaatgag atcaaatgag aaagattcaa attgtttgtt   2940
attttctgta ttttcagtca aaaaatcagt tatatagtga ttttaaagca gattaatgga   3000
aaaaaattca tgtaacaatt acctgaaaat ttataaccta ttcctaatca aacccaatta   3060
tatcagaata cctttctgaa tttgagattt ttgctctaca ttttataatg aataaggcta   3120
tttttttgaaa gtatttcatt ttgaattctg tcattaacct caaaagcttt ctactgcttt   3180
gcggtgaagg caaaatattc gataactcaa cttaggcccc actgttcccc aacttcatgg   3240
aggccagaag actttacttt gttccataat gaaatataaa cacagaacaa agttgtaaaa   3300
gtagcatgga tatgttgaaa ctttggacaa gcttcttgtc ctttggaata tgggatttat   3360
attcatctcc tcaatatccc atgtatgcac agaaacttca gttctatttc tatagacaca   3420
ggaacctagt gactattgaa cgtaattgta ataaaatgct gctcattgag ccaaagagaa   3480
gaaatgattt attaacatgg ggacaccaag aaaaacaaag tatgctttta ttccctttgt   3540
taagctcagt tttagggttt tttcttttttt tgatagtgac aatccataga tatagacatt   3600
cctaaaagaa aaataaataa ttcagtagat atatgtcact gttacctgaa tatggaatga   3660
atttgatgtt ttttattttg ttgagacagg gtcttgctct gtcacccaga ctggagtgca   3720
gtggcatgat cacacctcac tgcagccttg gcctctcagg ctcgtgatcc tcctgcctca   3780
acctcgcaag tagcttggga ctacaggcgt gtgccaccag tcctggctaa ttttttgtag   3840
atataaggtc tcatgatatt gcccaggctg aatttgatgt tatttcaagt tgattttcat   3900
gtgtttggga gcttgtcttg ttctcaacta ctacgcaggt agacagtctt cccccagaga   3960
ctcattagat tgcaatatag aggcactttc tcatttccct attgttccta atacagaatt   4020
gtagagctgg agagtacctt cagttttcta aatctattct caaacaggat atcactaacc   4080
tctttagaat cattcctcag tatacatcaa tttattgaga actgcctaat actcaagaaa   4140
ttaaatcctg agttcagtag gctgtgttcc aagcaggaat tattttcact taccaaaata   4200
tctcctatta cctcaaggta tccttgttga ggaatgctga aaactaaatt ttaagtatca   4260
agtctagacc atagagtgct ttggtgggag tattttgatt acctcctacc catcagaagc   4320
aggcagctaa tattgtgaac tgagtatttt tgtcaaaagt cacagggaag agactacaga   4380
agaatgagaa gggtcaaaag gacctagtgt ggcttactac atggatcttg tctcttggag   4440
gtctgtcgta gaagaagaaa caaatagagg tgatgaagac acagaacagg ctcagtcagc   4500
atcctcaccc agagatggca acatctatta agaccaatgc aataccttttt catcttcagc   4560
aaatgttgtt tcatctgttt ttgatccttg gcattgtcaa aaacttaact gcaggtccag   4620
tgtatatttt tccttatttt tcccttttag ctatctgcta aagcgagtaa atgccacaac   4680
tgtacttttc caaagaaaaa gaactattga caacttatag cctgtcatgc aggtcatgtt   4740
tcaaatcaag gctgaaattt tcaacagctg tgggaaaaac taaaacacag aaatactgta   4800
cagtattagt gttttttttaa agaaattgtt agtgcattat tgagtatact aaatatctgt   4860
gattaaataa attagttcta acttttgatt ttgggagccc aaaataaagg gagtgttgtt   4920
```

```
ttcatggtta tgccttgttt gtggagtcaa gtgttgatat acttgaggca tgttatgtgt   4980

cttctaatta atatttttat caccttgaat ttgtgtctct tccaagcatt aaagatacta   5040

tggatcttaa attccttatt aaaaaaatgc aagtgtgaat                         5080
```

<210> SEQ ID NO 33
<211> LENGTH: 2634
<212> TYPE: DNA
<213> ORGANISM: Homo sapiens

<400> SEQUENCE: 33

```
attcggctgc ggtacatctc ggcactctag ctgcagccgg gagaggcctt gccgccaccg     60

ctgtcgccca agcctccact gccgctgcca cctcagcgcc ggcctctgca tccccagctc    120

cagctccgct ctgcgccgct gctgccatcg ccgctgccac ctccgcagcc cgggcctccg    180

ccgccgccac tcaagcatcc gtgagtcatt ttctgcccat ctctggtcgc gcggtctccc    240

tggtagagtt tgtaggcttg caagatggca gaagcagatt ttaaaatggt ctcggaacct    300

gtcgcccatg ggttgccga agaggagatg gctagctcga ctagtgattc tggggaagaa     360

tctgacagca gtagctctag cagcagcact agtgacagca gcagcagcag cagcactagt    420

ggcagcagca gcggcagcgg cagcagcagc agcagcagcg gcagcactag cagccgcagc    480

cgcttgtata gaaagaagag ggtacctgag ccttccagaa gggcgcggcg ggccccgttg    540

ggaacaaatt tcgtggatag gctgcctcag gcagttagaa atcgtgtgca agcgcttaga    600

aacattcaag atgaatgtga caaggtagat accctgttct taaaagcaat tcatgatctt    660

gaaagaaaat atgctgaact caacaagcct ctgtatgata ggcggtttca aatcatcaat    720

gcagaatacg agcctacaga agaagaatgt gaatggaatt cagaggatga ggagttcagc    780

agtgatgagg aggtgcagga taacacccct agtgaaatgc ctcccttaga gggtgaggaa    840

gaagaaaacc ctaaagaaaa cccagaggtg aaagctgaag agaaggaagt tcctaaagaa    900

attcctgagg tgaaggatga agaaaaggaa gttcctaaag aaattcctga ggtaaaggct    960

gaagaaaaag cagattctaa agactgtatg gaggcaaccc ctgaagtaaa agaagatcct   1020

aaagaagtcc cccaggtaaa ggcagatgat aaagaacagc ctaaagcaac agaggctaag   1080

gcaagggctg cagtaagaga gactcataaa agagttcctg aggaaaggct tcaggacagt   1140

gtagatctta aaagagctag gaagggaaag cctaaaagag aagaccctaa aggcattcct   1200

gactattggc tgattgtttt aaagaatgtt gacaagctcg ggcctatgat tcagaagtat   1260

gatgagccca ttctgaagtt cttgtcggat gttagcctga agttctcaaa acctggccag   1320

cctgtaagtt acacctttga atttcatttt ctacccaacc catacttcag aaatgaggtg   1380

ctggtgaaga catatataat aaaggcaaaa ccagatcaca atgatccctt cttttcttgg   1440

ggatgggaaa ttgaagattg caaaggctgc aagatagact ggagaagagg aaaagatgtt   1500

actgtgacaa ctacccagag tcgcacaact gctactggag aaattgaaat ccagccaaga   1560

gtggttccta atgcatcatt cttcaacttc tttagtcctc ctgagattcc tatgattggg   1620

aagctggaac cacgagaaga tgctatcctg gatgaggact ttgaaattgg gcagatttta   1680

catgataatg tcatcctgaa atcaatctat tactatactg gagaagtcaa tggtacctac   1740

tatcaatttg gcaaacatta tggaaacaag aaatacagaa aataagtcaa tctgaaagat   1800

ttttcaagaa tcttaaaatc tcaagaagtg aagcagattc atacagcctt gaaaaaagta   1860

aaaccctgac ctgtaacctg aacactatta ttccttatag tcaagttttt gtggtttctt   1920

ggtagtctat attttaaaaa tagtcctaaa aagtgtctaa gtgccagttt attctatcta   1980
```

```
ggctgttgta gtataatatt cttcaaaata tgtaagctgt tgtcaattat ctaaagcatg   2040

ttagtttggt gctacacagt gttgattttt gtgatgtcct ttggtcatgt ttctgttaga   2100

ctgtagctgt gaaactgtca gaattgttaa ctgaaacaaa tatttgcttg aaaaaaaaag   2160

ttcatgaagt accaatgcaa gtgttttatt tttttctttt ttccagccca taagactaag   2220

ggtttaaatc tgcttgcact agctgtgcct tcattagttt gctatagaaa tccagtactt   2280

atagtaaata aaacagtgta ttttgaagtt tgactgcttg aaaaagatta gcatacatct   2340

aatgtgaaaa gaccacattt gattcaactg agaccttgtg tatgtgacat atagtggcct   2400

ataaatttaa tcataatgat gttattgttt accactgagg tgttaatata acatagtatt   2460

tttgaaaaag tttcttcatc ttatattgtg taattgtaaa ctaaagatac cgtgttttct   2520

ttgtattgtg ttctaccttc cctttcactg aaaatgatca cttcatttga tactgttttt   2580

catgttcttg tattgcaacc taaaataaat aaatattaaa gtgtgttata ctat         2634


<210> SEQ ID NO 34
<211> LENGTH: 2624
<212> TYPE: DNA
<213> ORGANISM: Homo sapiens

<400> SEQUENCE: 34

tatttataat atgtggagga gagagagctc accatgctca ggtaaaggga tgaagcctct     60

ggtatgtcag aaccatgctg tcttccatga gacttccttt gtgaagagca tccatttaaa    120

agacttttat gaatacatgg tttcaatcaa gtccccagag aacacatttg tcttctgagc    180

tgctggcagt tttgagaatc tgatgacctc cgaggggacc ctgcactcag ccatcaaagt    240

gttcctgccc ctctggacac tcataattca atggtagatg caggtggagt tgagaacatc    300

acccagcttc cccaggagct tcctcagatg atggctgcag cagccgatgg tttggggagt    360

atagcgatag acacgaccca gctcaacatg tccgtgacag atcccacagc ctgggctaca    420

gccatgaata acctgggcat ggttcccgta gggttgcctg gacagcagct cgtgtctgac    480

tcaatctgtg tcccaggctt tgatccaagc ctcaacatga tgactggaat caccccccatt    540

aacccaatga taccaggcct tggactggta cctcccccac caccaacaga agtggctgtt    600

gtcaaagaaa taatccactg caaaagctgt actctttttc ctcaaaatcc aaatcttcca    660

cctccttcca caagagaacg acctcctggg tgtaagaccg tgtttgtcgg aggattacca    720

gaaaatgcta ctgaggaaat tattcaagaa gtctttgaac agtgcggtga tattacagca    780

attcggaaaa gcaagaagaa tttttgtcac attcgctttg cagaggaatt catggttgat    840

aaagccattt acctttctgg ttataggatg cgattagggt ctagcaccga caaaaaggat    900

tcaggccgcc ttcatgtgga ctttgcccag gccagggatg acttctatga gtgggaatgc    960

aagcagagga tgcgtgcccg ggaggagcgg caccggcgca agctggagga ggaccggctc   1020

aggcccccat ccccgcctgc cataatgcac tactcggagc acgaagccgc tctgctggct   1080

gaaaagctga aagatgatag caagtcttca gaggctatca cagtgctgct ttcctggatt   1140

gaacgagggg aagtgaatcg gcgctctgca aaccagttct attccatggt gcagtcggcc   1200

aacagccacg tccgccggct aatgaatgaa aaagccaccc atgagcaaga gatggaggaa   1260

gccaaggaga attttaaaaa tgccttaact gggattctca ctcaatttga gcagattgtg   1320

gccgttttca acgcttctac cagacaaaaa gcttgggacc atttctcgaa agcccagcgc   1380

aagaacatag acatttggcg aaagcattct gaggagctcc ggaatgctca aagtgagcag   1440

ctcatgggca tccgccgcga agaagaaatg gaaatgtctg atgatgagaa ctgtgacagc   1500
```

cctacaaaga aaatgagagt cgatgaatca gccctggctg cccaggccta cgctctgaaa 1560
gaggagaatg acagtctccg ctggcagctg gatgcctaca ggaatgaggt ggagctgctg 1620
aaacaagaaa aagaacagct tttccgaaca gaagaaaacc tcaccaagga ccagcaactg 1680
cagtttctgc agcaaaccat gcaaggcatg cagcagcaat tgctaaccat ccaggaggag 1740
ttaaacaaca aaaagtcaga attggaacaa gcaaaggaag agcagtccca tacacaagcg 1800
ttactaaaag tcctgcagga acaattaaaa ggtaccaagg aattggtcga gaccaatggc 1860
cacagccatg aggattcaaa tgaaatcaat gtgttgacag ttgcattagt caaccaagac 1920
cgagagaaca atattgagaa aagaagccaa ggcttaaaat cagagaaaga agctctgcta 1980
ataggtatca tatcaacgtt tcttcacgtc catccttttg gagccaacat agaatatctt 2040
tggtcataca tgcagcagct ggactccaag atatctgcaa atgaaataga aatgcttttg 2100
atgaggctgc cacgcatgtt caaacaggaa ttcacgggtg tgggagccac gctggaaaaa 2160
agatggaagt tgtgtgcctt tgaaggaatt aaaaccacct aactgcgaag agcaaagcat 2220
ctctggaaat gaaaccatgt gaacctggcc agggcggtgc gacggggaag caggaggtgt 2280
ggggttggtc ccgcacgcaa cctttgtgga gccatcgaag cctgccttta gttatatctg 2340
tggcgttctc ttgtaagtgg aaatgtaatt gtgtaccagt ttcttaaaat aaacaaagct 2400
tcatactgtg acagatctgt ttcctatgaa aaccaaacaa tgattccaca gtcataatga 2460
tggcaaaatc ttaaaatgtg ctacatttga gaatagctca ccaagcaaaa tatttaaagt 2520
taatgatggt gtagcaatga ttgttgctag gctacagagt tgtatatgta atgtatagct 2580
gaaatcatta aatgacattt tcctgaaagt ctttctgttt tagt 2624

<210> SEQ ID NO 35
<211> LENGTH: 2719
<212> TYPE: DNA
<213> ORGANISM: Homo sapiens

<400> SEQUENCE: 35
gagcctacca aacctttggt tcgcagggct ggagctaagt ctcgctccag gagaaagaag 60
cagaagaaga actccaggca ggaagcagtg ccctggaaaa aacccaaagg catcaattcc 120
aacagcacag ctaacttgga ggatcctgag gtgggtgatg ctgaaagcat ggcgatctca 180
gagccgatca agggcagcag aaagccctgt gtgaataagg aggagttggc tttgaagaag 240
cccatggcga aatgtgcctg gaagggtccc agagagccac ctcaggatgc ccgggcagaa 300
gccgagagcc caggaggcgc ctctgagtca gaccaagatg gtggccatga aagcccacca 360
aagaagaagg ccgtggcctg ggtgtctgcc aagaaccccg ctcccatgag gaagaagaag 420
aaggtgagct tgggccctgt ctcctacgtc ttggttgact cagaagatgg caggaagaag 480
ccggtgatgc caaagaaagg gccaggctca agaagggagg catcagatca gaaggcccct 540
cggggccagc agcctgccga ggcaacagcc tcaacctcta ggggtccgaa ggccaagcca 600
gaaggctctc ctcggcgtgc caccaatgaa tccagaaagg tttgatctgg gggaccaccc 660
atactgagga gttgaaagaa caaggaagac gtaccaagtc aaccaagttc tctcttgtca 720
ctgaataaga ctttggactc tcttagggcc cctgttgata gagatctggc cctgaggtaa 780
acgataggtg aggtcttggg tgggagggag ttggggaagg gaggtggatc tctatgccct 840
tttctctacc aggcctgccg tttcaccgcc ttctctactc accttctctt cggaggcagg 900
agagttggta agaggattgg gaaaattcta gaacattcat tccccttat gcatgagcag 960 ggtcactgtt acactcatcc atgttcagct tttctccccc acgccttgct ccctcctcgg 1020

```
aatggtcagc gacctctgca ggccctggca tttggaagag ctgggtggcc ctgccatatt   1080

cttcctcccg ccttcctctt gtgtaaccag cggggtaagt taagccagga ccttcgctgc   1140

aaacctggtt ttattgctcc ttcagtctcc agcttccatc ctccagttat ctagccagga   1200

ggtcccaaga gttagtttta gggaaaaaga atgtctgcct agacctcaaa gtctttgagt   1260

tttagagtct gttagtaaaa atggcacttt gattcccatt tgggatgagc cctctcagga   1320

atcctgtggg gaaggggggt gattataggg aaggacgcag gcattcctag gtccccagct   1380

ctaattccat ccatctaccc aactgtcacc atctttgcac caaactgtca ccatctttgc   1440

agcagaaggt cactactcac attatagtaa gaggggaaaa aaatctttta aaacttggct   1500

gttggccggg cacggtggct cacgcctgta atcccagcac tttgggaggc tgaggcaggt   1560

cgatcacgag gtcaggcgtt taagaccagc ttgaccaaca tggtgaaacc ccatctctac   1620

aaaaattagc tgggcgtggt ggcgcgcgcc tgtaatccca gctactcagg aggctgaggc   1680

ggatgaattg cttgaatcca ggaggcagag gttgcaatga gccaagattg tgccacggca   1740

ctccagcctg ggcagcagag tgagactctc tctcaaaaaa acaaaacttg gctgttaatg   1800

tctgccctct gaattcagac acactatatt agaccagacc accatgtgtc attgtgtgtg   1860

tgtgtgtgtg tgtgtgtgtt tgcgtgcgca tgtgtagagg agagagcagg gtccctgaga   1920

taatggtttc caaactgtat cgtagccgtc cacaaagatg taatccaaat ctatttttct   1980

cacgtgttta aaaaactgaa aagtgactac tcagatatgt tggaagtcac atcgaagact   2040

atcagaatat taccttgtgt tcataggtta acttgttttt gtacacgtct tagttatttc   2100

aggcatctct ttgcttaaaa ttgagtttct tgtaaatgtg actgatgagc gaggttagaa   2160

gtggaagaaa ttcctgtgca tgttctataa tctgacaccc tgaaagcaag tttcctttcg   2220

tcattcacat gctcttgttc tgccgtgact gttcaggtgt atggtagtaa gtaaatgtat   2280

taacatggtg aacagtagta atattctatc atagagtatt agcccttgca agttttcagg   2340

gcgtcttttc cgacttcagt tttgtgata aagaatgtga acagttgtta gatgttctca   2400

gtgattcaac tttaaaacaa atttctcgtg atgattcatt tcaaaatcct gagtgagtct   2460

gactgaaaaa tacgagagaa aagagagtgg tttccgtttg cagctacaca gctgtgtgca   2520

tcgacgttct cctggggtgt gtgccaagcg aaacccaggg gtgaattgga ttcttgaaga   2580

gaccaaagcc tgtaactgtc cagcttctaa tttcaaaacg ggtccattag ggcttcgttg   2640

tgttaacaag ttgacaccat gactagtaaa tgtaaacgtg tatgtataaa ataaagttta   2700

gcaaattaag tgtcctgtt                                                2719
```

<210> SEQ ID NO 36
<211> LENGTH: 1935
<212> TYPE: DNA
<213> ORGANISM: Homo sapiens

<400> SEQUENCE: 36

```
acacaacctt ggacattaga gcctgtccgt ctgatctaga gaaggaatgt tgctggggaa     60

ggaaaactca gggcgaggtg agagaggaca gaacctctaa ccaggaagag gctgtccccg    120

ccaagctccg gagaggcgcg gaagcatgac cctcaggtgg taacagaaaa caatccagat    180

ggggtgcagg tgctgtaaaa taatacaaag ctatctcttt gatccagtcc aagtgccctc    240

tcctggctat gtcaatgaag tcaacagctg caagctagat gaagacgaca ctgataaatt    300

aaaaggcaaa tggagcagtg aagtcttggt gcagaaaaat gaccctcaga ggcagggctc    360

aaagaagact gagagcagca gcaggacagc tgatccatgg gagccctgct ggcctcacca    420
```

```
agggccgctc ccacaggggg acgctggagg ggaacaccat gcctgcggtg tcaacggcat    480

cggccctgct gccactccac agcccactgg gaattccagc cccacccagg atgacagggg    540

ctcctgggcc agtactgcaa atactgttcc cccaactcaa cccttcctgg aaggaggggg    600

caccaggaaa caggactgtg tgctgctggc ctcagaaggg acccaagtca tgagaaatgg    660

agactccaga gctccttctg aggcagaaag ttttgccttg gaagtacaag accatgtctt    720

ccagatacca gccccagatt accttcagca ctggggccca gctggagaca acgttgatca    780

taatgaaaag gactgtgttt tcaagaacca tactgaggat gaatccctag agggaattca    840

gcccccagtg gggagcatgg gtttgaatac gcccttctct gtgaggagaa gctgggattc    900

attgaatgag gatgtggaaa cagaagttct aagcatctgc tttaatgaga agggtcctgt    960

tcatgccatg cctgtggttg actcaggaaa caggcagggg gatacccatg gctccgatgg   1020

agatggggat ggggagattg tggacgagga tgcagcggtg gcggaggccc ttgcagcttt   1080

agaagctgct actgcaggag aagatttgga tgagactgat taggggaggg gatttgcaca   1140

gggaggtaag ctggtgtcat gctgagcatg cagatgcatt tgctccctgg atgcatagca   1200

ggtgattctg ccagcatgca ccagtgcagc cttaccagtt gtttacatcc agcatctgtt   1260

ctgattgtca gcatctgtcc catgctgctt gtcacatatc tggagtttca ctctgtgtag   1320

atgagctgtc attcaggaca ctaggagaaa aatctgagtg ggtcattgtg cccatatcca   1380

cagaaaatgc agaagttgaa cagcttgctt gacaaccctc aaacatcttt gagcacctgg   1440

tacagatgtt tatgagaata ctctaagatc tcaacccttg atcccaaagg cacacaatca   1500

cagagcattc cttttgactg taaactgttt accttgcttt tgagagccaa acattgtacc   1560

caacctggaa aaagtaacta ccccaattaa agtgcctcat gtgtccccag agcatggctt   1620

aacttcaggg acaatcaccc agggaactaa taactaacca gttgttcaac agcgggttaa   1680

gctcagcagt tttcacagta gagcagaagt ccccaggaaa caaagggtta gtcattagct   1740

gagatgttga ttttaaaaca ccttgacctt aacttttta cattattact tttaaatctc    1800

ctttgggatt ggggaggctg gccaaaataa gtcttaaaac tgcttatgtc atatttggat   1860

tttaagttca tgacattcgg aacagcaaag ccatatatgc aatgttttta tgccattaaa   1920

tgtctgattc caatt                                                    1935
```

```
<210> SEQ ID NO 37
<211> LENGTH: 1640
<212> TYPE: DNA
<213> ORGANISM: Homo sapiens

<400> SEQUENCE: 37
```

```
cagatcttct agctggctct ctgctgccac agctccgccg aagggagggg gtggaagagg     60

aggactaaac tcagagctga gaggagaggc aggtgtgtgc aggtgcatca cctggatcat    120

gaggtcaccc ctctgctggc tcctcccact tctcatcttg gcctcagtgg cccaaggcca    180

gccaacaaga cgaccaagac ccgggactgg gcccgggcgc agacccaggc ccaggcccag    240

gcccacaccc agctttcctc agcctgatga accagcagag ccaacagacc tgcctcctcc    300

cctccctcca ggccctccat ctatcttccc tgactgtccc cgcgaatgct actgcccccc    360

tgatttccca tctgccctct actgtgatag ccgcaacctg cgaaaggtcc ctgtcatccc    420

gccccgcatc cattacctct atctccagaa caacttcatc actgagctcc cggtggagtc    480

cttccagaat gccacaggcc tgcgatggat taacctggac aacaaccgaa tccgcaagat    540

agaccagagg gtgctggaga aactgcccgg cctggtgttc ctctacatgg agaagaacca    600
```

```
gttggaagag gtcccctcgg ccctgccccg gaacctggag cagctgaggc tgagccagaa    660

ccacatctcc agaatcccgc ctggtgtctt cagcaagctg gagaacctgc tgctcctgga    720

tctccagcac aacaggctga gcgacggcgt cttcaagccc gacaccttcc atggcctcaa    780

gaacctcatg cagctcaacc tggcccacaa catcctgaga aagatgccgc ccagggtccc    840

caccgccatt caccagctct acctggacag taacaagatt gagaccatcc ctaacggata    900

cttcaagagc tttcccaatc ttgccttcat tcggcttaac tacaacaagc tgacagacag    960

gggactcccc aagaactcct ttaatatctc caacctgctt gtgctccacc tgtcccacaa   1020

caggatcagc agtgtgcccg ccatcaacaa caggctggaa cacctgtacc tcaacaacaa   1080

tagcatcgag aaaatcaacg gaacccagat ttgccccaac gacctagtgg cgttccatga   1140

cttctcctcg gacctggaga acgtgccaca cctgcgctac ctgcggctgg atggaaacta   1200

cttgaagccg cccatcccgc tggacctcat gatgtgcttc cgcctcctgc agtccgtggt   1260

catctaggcc ctactccgcc accggatctg ctctgaccgc acttgaaggc tggggcccag   1320

gcacctgtgc cggccattcg ttttctctct ctccctttct ttctcccagc tttgcctccc   1380

ttatcccacc ctcgaggcag ggaaaagcca tctattcttc tgcagcctca ggagcgagac   1440

ttcaaggact cagtttggtt ccacccagtt gaaagacacc cagtgcacac ccaaactcct   1500

ggccttctgt ggtttccctt tgctccagaa acacagatgt gtctaaagaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa                                               1640
```

<210> SEQ ID NO 38
<211> LENGTH: 5511
<212> TYPE: DNA
<213> ORGANISM: Homo sapiens

<400> SEQUENCE: 38

```
tctctgtctg ccagggtctc cgactgtccc agacgggctg gtgtgggctt gggatcctcc     60

tggtgacctc tcccgctaag gtccctcagc cactctgccc caagatgggc cgtggggctg    120

gccgtgagta ctcacctgcc gccaccacgg cagagaatgg gggcggcaag aagaaacaga    180

aggagaagga actggatgag ctgaagaagg aggtggcaat ggatgaccac aagctgtcct    240

tggatgagct gggccgcaaa taccaagtgg acctgtccaa gggcctcacc aaccagcggg    300

ctcaggacgt tctggctcga gatgggccca acgccctcac accacctccc acaacccctg    360

agtgggtcaa gttctgccgt cagcttttcg gggggttctc catcctgctg tggattgggg    420

ctatcctctg cttcctggcc tacggcatcc aggctgccat ggaggatgaa ccatccaacg    480

acaatctata tctgggtgtg gtgctggcag ctgtggtcat tgtcactggc tgcttctcct    540

actaccagga ggccaagagc tccaagatca tggattcctt caagaacatg gtacctcagc    600

aagcccttgt gatccgggag ggagagaaga tgcagatcaa cgcagaggaa gtggtggtgg    660

gagacctggt ggaggtgaag ggtggagacc gcgtccctgc tgacctccgg atcatctctt    720

ctcatggctg taaggtggat aactcatcct taacaggaga gtcggagccc cagacccgct    780

cccccgagtt cacccatgag aaccccctgg agacccgcaa tatctgtttc ttctccacca    840

actgtgttga aggcactgcc aggggcattg tgattgccac aggagaccgg acggtgatgg    900

gccgcatagc tactctcgcc tcaggcctgg aggttgggcg gacacccata gcaatggaga    960

ttgaacactt catccagctg atcacagggg tcgctgtatt cctgggggtc tccttcttcg   1020

tgctctccct catcctgggc tacagctggc tggaggcagt catcttcctc atcggcatca   1080
```

```
tagtggccaa cgtgcctgag ggcttctgg ccactgtcac tgtgtgcctg accctgacag   1140
ccaagcgcat ggcacggaag aactgcctgg tgaagaacct ggaggcggtg gagacgctgg   1200
gctccacgtc caccatctgc tcggacaaga cgggcaccct cacccagaac cgcatgaccg   1260
tcgcccacat gtggttcgac aaccaaatcc atgaggctga caccaccgaa gatcagtctg   1320
gggccacttt tgacaaacga tcccctacgt ggacggccct gtctcgaatt gctggtctct   1380
gcaaccgcgc cgtcttcaag gcaggacagg agaacatctc cgtgtctaag cgggacacag   1440
ctggtgatgc ctctgagtca gctctgctca agtgcattga gctctcctgt ggctcagtga   1500
ggaaaatgag agacagaaac cccaaggtgg cagagattcc tttcaactct accaacaagt   1560
accagctgtc tatccacgag cgagaagaca gcccccagag ccacgtgctg gtgatgaagg   1620
gggccccaga gcgcattctg gaccggtgct ccaccatcct ggtgcagggc aaggagatcc   1680
cgctcgacaa ggagatgcaa gatgcctttc aaaatgccta catggagctg gggggacttg   1740
gggagcgtgt gctgggattc tgtcaactga atctgccatc tggaaagttt cctcggggct   1800
tcaaattcga cacggatgag ctgaactttc ccacggagaa gctttgcttt gtggggctca   1860
tgtctatgat tgaccctccc cggctgctg tgccagatgc tgtgggcaag tgccgaagcg   1920
caggcatcaa ggtgatcatg gtaaccgggg atcaccctat cacagccaag gccattgcca   1980
aaggcgtggg catcatatca gagggtaacg agactgtgga ggacattgca gcccggctca   2040
acattcccat gagtcaagtc aaccccagag aagccaaggc atgcgtggtg cacggctctg   2100
acctgaagga catgacatcg gagcagctcg atgagatcct caagaaccac acagagatcg   2160
tctttgctcg aacgtctccc cagcagaagc tcatcattgt ggagggatgt cagaggcagg   2220
gagccattgt ggccgtgacg ggtgacgggg tgaacgactc ccctgcattg aagaaggctg   2280
acattggcat tgccatgggc atctctggct ctgacgtctc taagcaggca gccgacatga   2340
tcctgctgga tgacaacttt gcctccatcg tcacgggggt ggaggagggc cgcctgatct   2400
ttgacaactt gaagaaatcc atcgcctaca ccctgaccag caacatcccc gagatcaccc   2460
ccttcctgct gttcatcatt gccaacatcc ccctacctct gggcactgtg accatccttt   2520
gcattgacct gggcacagat atggtccctg ccatctcctt ggcctatgag gcagctgaga   2580
gtgatatcat gaagcggcag ccacgaaact cccagacgga caagctggtg aatgagaggc   2640
tcatcagcat ggcctacgga cagatcggga tgatccaggc actgggtggc ttcttcacct   2700
actttgtgat cctggcagag aacggtttcc tgccatcacg gctactggga atccgcctcg   2760
actgggatga ccggaccatg aatgatctgg aggacagcta tggacaggag tggacctatg   2820
agcagcggaa ggtggtggag ttcacgtgcc acacggcatt ctttgccagc atcgtggtgg   2880
tgcagtgggc tgacctcatc atctgcaaga cccgccgcaa ctcagtcttc cagcagggca   2940
tgaagaacaa gatcctgatt tttgggctcc tggaggagac ggcgttggct gcctttctct   3000
cttactgccc aggcatgggt gtagccctcc gcatgtaccc gctcaaagtc acctggtggt   3060
tctgcgcctt cccctacagc ctcctcatct tcatctatga tgaggtccga aagctcatcc   3120
tgcggcggta tcctggtggc tgggtggaga aggagacata ctactgaccc cattggaaga   3180
agaaccaggc atggaaagat ggggagctct ggaggtgttg tggggatggt gatggagagg   3240
gatggaaata acgggtggca ttgggtggca acatttgggg agagataatg aggcaactca   3300
gcaggctaag ttgcggggta tataaattgg ggtgatgacc ccatagacct aactgtgaac   3360
aatcagatta gacactatgt gttagagtcc ccccgaccag atccttttcc atcccactcc   3420
actatgttgt ctatttttc tgaggaatta agggttaccc caccctgccc actcccatcc   3480
```

```
cttcaacccc acttcctact gtaatagatc agcatccaaa agcaggaacc catctaaacc   3540

agaaggaagc cctctcagat caccccagcc tcactccatt tcccacttcc acccccgtta   3600

gcttcctgca ggactctatc cctggcttcc ccttcagacc ttgcaatcac aaaaggttct   3660

tctggtgagt gcaagagcct gagactggaa aaggtggact tgtctcccag tcgaggctgg   3720

taagggacct tcagggagag ctgggcagac aggtgggaga tggaggtagg gctggctgga   3780

ggaaggaaac aacaaaggaa gtgaggtagt gccaatgaca ggacatttga catgagtctc   3840

cagatagatg tcgtggactc cagctctacg tcccacattt tagaataccc caccagcaga   3900

acaaactcag atctcatcag ggtagcagca gaggcaggac cagaaggcaa tcaagagctt   3960

ccagaaatgc cacacttgtg tgccacagag ttccccgctg acccttggtt aggggtcctc   4020

ttagtccaca aggtccggat gtcactcatg tacttaataa cacttcacct tctgtaatac   4080

taagtcctca gagctccatg ctgttctgaa agggatggcc acaagttctt tcccagcctc   4140

ttccattccc tttcttttca tgcccatccc gatgaacctg catcattccc cgacactgcc   4200

aagccaaccc tggaaaagga gttcgctggc cattggctag aatcagggtg gagaagttcc   4260

ctgaaccttc ctgtctccca gggacatgta tgcttccagg gacaagctta ggtcatgaac   4320

atggtcagaa cctttggaca agaggaaaaa tactaagaga tttgcttttt ctgggtgcgg   4380

tggctcatgc ctgtaatccc agcactttgg gaggccgagg caggtggatc atgaggtcag   4440

gagttcgagg cgagcctggc caacatggtg aaaccctgtc tctactaaaa gtacaaaaaa   4500

ttagccagtc atggtggcac acgcctgtaa tctcagctac tcaggaggct gaggcaggag   4560

aattgcttga acctgtgagg aagaggttgc agtgagctga gatcgtgcca ttacactcca   4620

gcctgggcga aagggtgaga ctccatctca aaaaaaaaaa aaatgatttg cttttgacgt   4680

cttaggtggc agggctgttc cctccaggca aatgcccttc aaaccgacga tcattgtgcc   4740

cacttaccct gggctggaga gttggtttca ggttcctaca ggagatagct ttctttccct   4800

tactccctat ctaacacttt tgctctgcag gcagccttgc ccattctcta agcctggctt   4860

agaaggcact gggaatgtcc tgtagagaga gacctagata ggtcatgcaa gtgagaaaga   4920

catctgagga aaatggaaga cctaaggcag acaggaagga agcacaaaag acaagcattg   4980

ggtcagaccc ataaaccacc tcccaaaggc tgtcatttca ttgcactgga attttgcttt   5040

atcagaagca aggaagtaag ggagtcattg ccttgggcct gggaatctaa gtgggagaca   5100

atattaattt ggatccgatt aattggagat tactaactgt ggacaaaagt ttatctttgc   5160

acaatcaata aaaatggcat ttttttagta aattaagagc ataaacaata ttgctagagg   5220

tggcatgttt agtctaccaa aaacaatact tttcaggcac tttagaaata tccttttaga   5280

agcagcgagt gcatgggcta attatcatca atctttatgt atttgttaaa gaaacatcta   5340

caggatcttt attggtgacc ttttgtaaga cattagtttg aggtactacc tatctacttg   5400

aaaataataa agtggcattt ctttatgaaa aaaaaagaaa tctcttccat aattcagatt   5460

tctacacttt atacttgcct ccctcctaaa tcgtgatatt gaaatatggt g            5511
```

```
<210> SEQ ID NO 39
<211> LENGTH: 2165
<212> TYPE: DNA
<213> ORGANISM: Homo sapiens

<400> SEQUENCE: 39

atggctgtgc gcggcgccaa caccttgacg tccttctcca tccaggcgat cctcaacaag     60

aaagaggagc gcggcgggct ggccgcgcca gaggggcgcc cggcgcccgg gggcacagcg    120
```

```
gcatcggtgg ccgcggctcc cgctgtctgc tgttggcggc tctttgggga gagggacgcg    180
ggcgcgttgg ggggcgccga ggactctctg ctggcgtctc ctgccggtac cagaacagct    240
gcggggcgga ctgcggagag cccggaaggc tgggactcgg actccgcgct cagcgaggag    300
aacgagagca ggcggcgctg cgcggacgcg cggggggcca gcggggccgg ccttgcgggg    360
ggatccttga gcctcggcca gccggtctgt gagctggccg cttccaaaga cctagaggag    420
gaagccgcgg gccggagcga cagcgagatg tccgccagcg tctcaggcga ccgcagccca    480
aggaccgagg acgacggtgt tggccccaga ggtgcacacg tgtccgcgct gtgcagcggg    540
gccggcggcg gggcggcag cgggccggca ggcgtcgcgg aggaggagga ggagccggcg    600
gcgcccaagc cacgcaagaa gcgctcgcgg gccgctttct cccacgcgca ggtcttcgag    660
ctggagcgcc gctttaacca ccagcgctac ctgtccgggc ccgagcgcgc agacctggcc    720
gcgtcgctga agctcaccga gacgcaggtg aaaatctggt tccagaaccg tcgctacaag    780
acaaagcgcc ggcagatggc agccgacctg ctggcctcgg cgcccgccgc caagaaggtg    840
gccgtaaagg tgctggtgcg cgacgaccag agacaatacc tgcccggcga agtgctgcgg    900
ccaccctcgc ttctgccact gcagccctcc tactattacc cgtactactg cctcccaggc    960
tgggcgctct ccacctgcgc agctgccgca ggcacccagt gaacccgctt gggctgaggc   1020
agcgagtgat tcccgcgctc cggctccgga ccggcgctga cagctgtagg ctgtagcctg   1080
cacggggcgc cccgccaagg aggcacctgg aggtgaaacc cagctccagc tcccgttagc   1140
caggacttgt cccctggcag ctgggctgag tctgccctga gggggcgcct ttttctaatt   1200
tgaacagagg caccctatgg cctaggggcc ctgatcgccc acctgcctgg aagcccctgg   1260
gctctattta ttatcatgac aatgttggaa ttaaattttg attcgaatat gtctgcctgg   1320
gggtggggtt ttccctgagc ggcaactcct ggagaccaca tagcctgaat cctcagaatt   1380
tcaggcctgc tgggagcttt ctgcactagg ccacactagt tcatggtatc catgctacca   1440
atctatgtgt atctacatat cttttatttt tggaaattgc atttgtaacc aaggggtgcg   1500
aaaccctggc agtcccaggc agcaccaggc caggggttga tttgaaacgt gaaggattgg   1560
gttttcaggc cctctgctcc acccctcctg tgtgtcagag ctagggtggg ggtgcccgat   1620
tcgggtgctg aatgtaagga ggggagcctc caagtgtggt gcaagccggg ggtctccaca   1680
tcttccttct ctgaagtcca ggtacctgca caagcaggaa gcgcctggga gtcccggaag   1740
gaggagagcg cacacccagg cagccctctg cggaaacttt ccttggtttc tttttatttg   1800
tgtaaaggag gttaagacgt gtcgcacttt tcagttgttt gtattcaaat gacgattatt   1860
tttctactca atgtgaatat ccctggccag cctttccacg gcgcccaccg cagtgccgct   1920
gcctggccct cagtgtctac cttctgccct ctgcgactcc agtgctctgg cccgggactc   1980
ccctatccgc ccctcactta cccttaaaca ggtgatccca cctgtcttgt caacctcgcc   2040
gcttttcgcc tccttaatgg cactgtgcac tcaactagag tattaactgt aaaaagattt   2100
gtgaagtttg gaagctctat tcgctgtatt ttttctttaa tttataaact tttagtttaa   2160
catgc                                                                2165
```

<210> SEQ ID NO 40
<211> LENGTH: 2820
<212> TYPE: DNA
<213> ORGANISM: Homo sapiens

<400> SEQUENCE: 40

```
ggcgggttcg cgccccgaag gctgagagct ggcgctgctc gtgccctgtg tgccagacgg     60
```

```
cggagctccg cggccggacc ccgcggcccc gctttgctgc cgactggagt ttgggggaag    120
aaactctcct gcgccccaga agatttcttc ctcggcgaag ggacagcgaa agatgagggt    180
ggcaggaaga gaaggcgctt tctgtctgcc ggggtcgcag cgcgagaggg cagtgccatg    240
ttcctctcca tcctagtggc gctgtgcctg tggctgcacc tggcgctggg cgtgcgcggc    300
gcgccctgcg aggcggtgcg catccctatg tgccggcaca tgccctggaa catcacgcgg    360
atgcccaacc acctgcacca cagcacgcag gagaacgcca tcctggccat cgagcagtac    420
gaggagctgg tggacgtgaa ctgcagcgcc gtgctgcgct tcttcttctg tgccatgtac    480
gcgcccattt gcaccctgga gttcctgcac gaccctatca agccgtgcaa gtcggtgtgc    540
caacgcgcgc gcgacgactg cgagcccctc atgaagatgt acaaccacag ctggcccgaa    600
agcctggcct gcgacgagct gcctgtctat gaccgtggcg tgtgcatttc gcctgaagcc    660
atcgtcacgg acctcccgga ggatgttaag tggatagaca tcacaccaga catgatggta    720
caggaaaggc ctcttgatgt tgactgtaaa cgcctaagcc ccgatcggtg caagtgtaaa    780
aaggtgaagc caactttggc aacgtatctc agcaaaaact acagctatgt tattcatgcc    840
aaaataaaag ctgtgcagag gagtggctgc aatgaggtca caacggtggt ggatgtaaaa    900
gagatcttca agtcctcatc acccatccct cgaactcaag tcccgctcat tacaaattct    960
tcttgccagt gtccacacat cctgccccat caagatgttc tcatcatgtg ttacgagtgg   1020
cgttcaagga tgatgcttct tgaaaattgc ttagttgaaa aatggagaga tcagcttagt   1080
aaaagatcca tacagtggga agagaggctg caggaacagc ggagaacagt tcaggacaag   1140
aagaaaacag ccgggcgcac cagtcgtagt aatcccccca aaccaaaggg aaagcctcct   1200
gctcccaaac cagccagtcc caagaagaac attaaaacta ggagtgccca gaagagaaca   1260
aacccgaaaa gagtgtgagc taactagttt ccaaagcgga gacttccgac ttccttacag   1320
gatgaggctg ggcattgcct gggacagcct atgtaaggcc atgtgcccct tgccctaaca   1380
actcactgca gtgctcttca tagacacatc ttgcagcatt tttcttaagg ctatgcttca   1440
gtttttcttt gtaagccatc acaagccata gtggtaggtt tgccctttgg tacagaaggt   1500
gagttaaagc tggtggaaaa ggcttattgc attgcattca gagtaacctg tgtgcatact   1560
ctagaagagt agggaaaata atgcttgtta caattcgacc taatatgtgc attgtaaaat   1620
aaatgccata tttcaaacaa aacacgtaat ttttttacag tatgttttat taccttttga   1680
tatctgttgt tgcaatgtta gtgatgtttt aaaatgtgat gaaaatataa tgtttttaag   1740
aaggaacagt agtggaatga atgttaaaag atctttatgt gtttatggtc tgcagaagga   1800
tttttgtgat gaaaggggat tttttgaaaa attagagaag tagcatatgg aaaattataa   1860
tgtgtttttt taccaatgac ttcagtttct gtttttagct agaaacttaa aaacaaaaat   1920
aataataaag aaaaataaat aaaaaggaga ggcagacaat gtctggattc ctgtttttttg   1980
gttacctgat ttccatgatc atgatgcttc ttgtcaacac cctcttaagc agcaccagaa   2040
acagtgagtt tgtctgtacc attaggagtt aggtactaat tagttggcta atgctcaagt   2100
attttatacc cacaagagag gtatgtcact catcttactt cccaggacat ccaccctgag   2160
aataatttga caagcttaaa aatggccttc atgtgagtgc caaattttgt tttcttcat   2220
ttaaatattt tctttgccta aatacatgtg agaggagtta aatataaatg tacagagagg   2280
aaagttgagt tccacctctg aaatgagaat tacttgacag ttgggatact ttaatcagaa   2340
aaaaagaact tatttgcagc attttatcaa caaatttcat aattgtggac aattggaggc   2400
atttatttta aaaaacaatt ttattggcct tttgctaaca cagtaagcat gtattttata   2460
```

```
aggcattcaa taaatgcaca acgcccaaag gaaataaaat cctatctaat cctactctcc   2520

actacacaga ggtaatcact attagtattt tggcatatta ttctccaggt gtttgcttat   2580

gcacttataa aatgatttga acaaataaaa ctaggaacct gtatacatgt gtttcataac   2640

ctgcctcctt tgcttggccc tttattgaga taagttttcc tgtcaagaaa gcagaaacca   2700

tctcatttct aacagctgtg ttatattcca tagtatgcat tactcaacaa actgttgtgc   2760

tattggatac ttaggtggtt tcttcactga caatactgaa taaacatctc accggaattc   2820


<210> SEQ ID NO 41
<211> LENGTH: 2305
<212> TYPE: DNA
<213> ORGANISM: Homo sapiens

<400> SEQUENCE: 41

cgagcccagg cgtctgagac ctactgactg gccgcgggca gggctgacag gcggtggggc     60

ggctcggccc ctggcggagt cggcggcggg cggggacgcg gcgctgggag gacgcggcgg    120

cgctgggaac ggacgcctgg gcgccccgag gcgccgggat gtggagcggc ccaccccagc    180

cagaccaggg cctcccgccg ccccttgcag ctgtcccggt cccctggaag agcacggacc    240

cctgccaagg ccacagggag tccccaggag ccctggtgga gacctctgca ggggaggagg    300

cccaaggcca ggagggcccc gcagccgccc agctggacgt gttgcgcctg cgcagctctt    360

ccatggagat ccgagagaag ggctccgagt tcctgaagga ggagctgcac agagcgcaga    420

aggagctgaa gctaaaggac gaggaatgtg agcggctgtc caaggtgcgg gagcagctag    480

aacaggagct ggaagagctg acggccagcc tgtttgagga agctcacaag atggttcgag    540

aagccaacat gaagcaggcg gcatcagaaa agcagctgaa ggaggctcgg ggcaagatcg    600

acatgctgca ggcagaggtg acagccttga agacactggt catcacgtcc acaccagcct    660

ctcccaaccg cgagcttcac ccccagctgc tgagccccac caaggccggg ccccgaaagg    720

gccactctcg ccacaagagc accagcagca ccctctgccc cgccgtgtgt cccgctgcgg    780

gacacaccct caccccagac agagagggca aggaggtgga cacaatcctg tttgcagagt    840

tccaggcctg gagggaatcc cccaccctgg acaagacctg ccccttcctg gaaagggtgt    900

accgagagga cgtgggcccc tgcctggact tcacaatgca ggagctctcg gtgctggtac    960

gggccgccgt ggaggacaac acgctcacca ttgagccggt ggcttcgcag acgctgccca   1020

cagtgaaggt ggccgaggtt gactgtagca gcaccaacac atgtgccctg agcgggctga   1080

cccgcacctg ccgccaccga atccggctcg gggactccaa aagccattac tacatctcgc   1140

catcttcccg ggccaggatc accgcagtgt gcaacttctt cacctacatc cgctacatcc   1200

agcaaggcct ggtgcggcag gacgcagagc ccatgttctg ggagatcatg aggttgcgga   1260

aggagatgtc actggccaag ctcggcttct tcccccagga ggcttagggc gcggcccagg   1320

cctgaagggg agctctgaga cagagcaaac acccaccccca gaacaagccg acacacaggg   1380

agacgggggc ctggagccag ccctgagcca gaggcagaat ggatggacag acaggccatg   1440

gaggcagcac tgagccagca ccacacgtcc atcctgggac agacgggcct ggacttcacg   1500

gcaagacccc cctctcttcc ccactgggtt ctgccaccac caggaggatt tcaagaaagc   1560

accaaagacc agggagctcg gatccatact cggggggcct cagcccttgg gaggggacac   1620

ctgaggcagc cagcgccccc tccccagtcc ccagaactgc ctgcaggtgc cttgttgctg   1680

gcttgtcttc agaaagggac tgttctgggt ggctggatct ccagggtacc ctccacccca   1740

gctgccaagc cctgggccag cagcaccccc ttgtggccat cctgtgcctt gttcccggtg   1800
```

```
gcctccctat tggactacta ggaggggctg gcagggcctc catagcacag aattgcccca   1860

aagccttgtt aagatgagtc aagacccctc ccccgcttcc tcccttcctt tccccccttcc   1920

tccctccccc ttcataaagg cctcccttgt caccttccct cccaccccgt ctcagccctg   1980

tgctcctgga ggccctgctc ccaaaaccgc tggaaggact ggggcacttt ctgccacagt   2040

agaacacaga cagggcttca gatcacccac gcctgttttc agctgtgggt ggccatgcag   2100

acacgcgccc tggcatgtgg ggcctgggtg ggcaggcagg acctgggccc tcccacccat   2160

cagagcccac tcaggaccag cgttcggagc tcccacctgg acgcatccct caccacgtcc   2220

ggatttcctt ctttggatgg aatgtaacgc gatctctatt taataaaggc aggctttgtt   2280

ggtaaaaaaa aaaaaaaaaa aaaaa                                          2305
```

<210> SEQ ID NO 42
<211> LENGTH: 1679
<212> TYPE: DNA
<213> ORGANISM: Homo sapiens

<400> SEQUENCE: 42

```
agacttggaa accccaaagt gtccgcgacc ctgcacggca gctcccttcc agcttcatgg     60

gcaaagtgtg gaaacagcag atgtaccctc agtacgccac ctactattac ccccagtatc    120

tgcaagccaa gtttggaagg cattcgggaa taccaagtga aaaggaagag tgaagaacag    180

aaaaatgtta gtgggatggc aaacactgtg aacattgctg tttctagtgg gccagaaaaa    240

tcagtctctg gtcccagccc accccatggc cctcccagt cccagcacca ccagcagtaa     300

taacaacagt agcagcagta gcaactcagg atgggatcag ctcagcaaaa cgaacctcta    360

tatccgagga ctgcctcccc acaccaccga ccaggacctg gtgaagctct gtcaaccata    420

tgggaaaata gtctccacaa aggcaatttt ggataagaca acgaacaaat gcaaaggtta    480

tggttttgtc gactttgaca gccctgcagc agctcaaaaa gctgtgtctg ccctgaaggc    540

cagtggggtt caagctcaaa tggcaaagca acaggaacaa gatcctacca acctctacat    600

ttctaatttg ccactctcca tggatgagca agaactagaa aatatgctca aaccatttgg    660

acaagttatt tctacaagga tactacgtga ttccagtggt acaagtcgtg gtgttggctt    720

tgctaggatg gaatcaacag aaaaatgtga agctgttatt ggtcatttta atggaaaatt    780

tattaagaca ccaccaggag tttctgcccc cacagaacct ttattgtgta agtttgctga    840

tggaggacag aaaaagagac agaacccaaa caaatacatc cctaatggaa gaccatggca    900

tagagaagga gaggtgagac ttgctggaat gacacttact tacgacccaa ctacagctgc    960

tatacagaac ggattttatc cttcaccata cagtattgct acaaaccgaa tgatcactca   1020

aacttctatt acaccctata ttgcatctcc tgtatctgcc taccaggtgg caaaggaaac   1080

cagagaaaac aagtatcggg gctctgctat caaggtgcaa agtccttcgt ggatgcaacc   1140

tcaaccatat attctacagc accctggtgc cgtgttaact ccctcaatgg agcacaccat   1200

gtcactacag cccgcatcaa tgatcagccc tctggcccag cagatgagtc atctgtcact   1260

aggcagcacc ggaacataca tgcctgcaac gtcagctatg caaggagcct acttgccaca   1320

gtatgcacat atgcagacga cagcggttcc tgttgaggag gcaagtggtc aacagcaggt   1380

ggctgtcgag acgtctaatg accattctcc atataccttt caacctaata agtaactgtg   1440

agatgtacag aaaggtgttc ttacatgaag aagggtgtga aggctgaaca atcatggatt   1500

tttctgatca attgtgcttt aggaaattat tgacagtttt gcacaggttc ttgaaaacgt   1560

tatttataat gaaatcaact aaaactattt ttgctataag ttctataagg tgcataaaac   1620
```

ccttaaattc atctagtagc tgttcccccg aacaggttta ttttagtaaa aaaaaaaaa 1679

<210> SEQ ID NO 43
<211> LENGTH: 905
<212> TYPE: DNA
<213> ORGANISM: Homo sapiens

<400> SEQUENCE: 43
tctcccgaat tcggcacgag gcggcgtctc gaggcgagtt ggcggagctg tgcgcgcggc 60
ggggcgatgg ggggctcggg cagtcgcctg tccaaggagc tgctggccga gtaccaggac 120
ttgacgttcc tgacgaagca ggagatcctc ctagcccaca ggcggttttg tgagctgctt 180
ccccaggagc agcggaccgt ggagtcgtca cttcgggcac aagtgccctt cgagcagatt 240
ctcagccttc cagagctcaa ggccaacccc ttcaaggagc gaatctgcag ggtcttctcc 300
acatccccag ccaaagacag ccttagcttt gaggacttcc tggatctcct cagtgtgttc 360
agtgacacag ccacgccaga catcaagtcc cattatgcct tccgcatctt tgactttgat 420
gatgacggaa ccttgaacag agaagacctg agccggctgg tgaactgcct cacgggagag 480
ggcgaggaca cacggcttag tgcgtctgag atgaagcagc tcatcgacaa catcctggag 540
gagtctgaca ttgacaggga tggaaccatc aacctctctg agttccagca cgtcatctcc 600
cgttctccag actttgccag ctcctttaag attgtcctgt gacagcagcc ccagcgtgtg 660
tcctggcacc ctgtccaaga acctttctac tgctgagctg tggccaaggt caagcctgtg 720
ttgccagtgc gggccaagct ggcccagcct ggagctggcg ctgtgcagcc tcaccccggg 780
caggggcggc cctcgttgtc agggcctctc ctcactgctg ttgtcattgc tccgtttgtg 840
tttgtactaa tcagtaataa aggtttagaa gtttgaccct aaaaaaaaaa aaaaaaaaaa 900
aaaaa 905

<210> SEQ ID NO 44
<211> LENGTH: 2010
<212> TYPE: DNA
<213> ORGANISM: Homo sapiens

<400> SEQUENCE: 44
gccacagccc agctgttccc tccgcggatt ctccggggct ggttcatcac ctccgaatat 60
tcctgtgaca ggagacgctt gcaaaacccg cctccagcct ccagcagcaa ataaatagaa 120
ggcttgcagc ccagaaggag ccagaagaag tttctaggca cgaggccctg ggtttattaa 180
gctcctggct ccgctctaga cctcagcggt tctggctgcc agcctgggca gcctgggaag 240
cctgggagga cggtggcttg ccggtctgtc gtgaggcagt gcggacgggg accctctggg 300
attctgctgg atctgccccg ggggttacct ttgggggctg ggaccccagt cgaggggaca 360
caaccgtccc tggcagtggt tggttctgct tctccctgca gaaaagcagc attttcggaa 420
gctgaagaat aagctagccc agccacacca ccttgttgtg tgaccttggg caggtggttc 480
tgtctctctg agcctctgtt tctctctgag ctgagcagcc accatggctg acggtcagat 540
gcccttctcc tgccactacc caagccgcct gcgccgagac cccttccggg actctcccct 600
ctcctctcgc ctgctggatg atggctttgg catggacccc ttcccagacg acttgacagc 660
ctcttggccc gactgggctc tgcctcgtct ctcctccgcc tggccaggca ccctaaggtc 720
gggcatggtg ccccggggcc ccactgccac cgccaggttt ggggtgcctg ccgagggcag 780 gacccccccca cccttccctg gggagccctg gaaagtgtgt gtgaatgtgc acagcttcaa 840
gccagaggag ttgatggtga agaccaaaga tggatacgtg gaggtgtctg gcaaacatga 900

```
agagaaacag caagaaggtg gcattgtttc taagaacttc acaaagaaaa tccagcttcc     960

tgcagaggtg gatcctgtga cagtatttgc ctcactttcc ccagagggtc tgctgatcat    1020

cgaagctccc caggtccctc cttactcaac atttggagag agcagtttca acaacgagct    1080

tccccaggac agccaggaag tcacctgtac ctgagatgcc agtactggcc catccttgtt    1140

ttgtccccaa ccctagggct tctctgattc caggatacat tactttagct gaactcagat    1200

ttagtgcaag taaaatgtta gagggtgcgg gggtgaggac tgaccacaga ttccctggat    1260

agtgtagtgg tagatttctc cacaggatag cgcaattggc aaatcatgct tggttgtgtt    1320

aggccaaaat actagttttg ctttctttac cttttctatc ttgatgaaaa tgttgcacat    1380

tctatagttg caaaacacat aaaaggggac ttaacatttc acgttgtatc ttacttgcag    1440

tgaatgcaag ggttactttt ctctggggac ctccccccatc acccaggttc ctactctggg   1500

ctcccgattc ccatggctcc caaaccatgc cgcatggttt ggttaatgaa acccagtagc    1560

taaccccact gtgcttccac atgcctggcc taaaatgggt gatatacagg tcttatatcc    1620

ccatatggaa tttatccatc aaccacataa aaacaaacag tgccttctgc cctctgccca    1680

gatgtgtcca gcacgttctc aaagtttcca cattagcact ccctaaggac gctgggagcc    1740

tgtcagttta tgatctgacc taggtccccc ctttcttctg tcccctgtgt ttaagtcggg    1800

atttttacag agggagctgt ctccagacag ctccatcagg aaccaagcaa aggccagata    1860

gcctgacaga taggctagtg gtattgtgta tatgggcggg acgtgtgtgt cattattatt    1920

tgagttatgc tgttgtttag ggtaaataa cagtaaataa ttaataataa taataataat    1980

aataataaag gagctgacgt tcttaaaaaa                                     2010
```

<210> SEQ ID NO 45
<211> LENGTH: 1509
<212> TYPE: DNA
<213> ORGANISM: Homo sapiens

<400> SEQUENCE: 45

```
agacttggaa accccaaagt gtccgcgacc ctgcacggca gctcccttcc agcttcatgg      60

gcaaagtgtg gaaacagcag atgtaccctc agtacgccac ctactattac ccccagtatc     120

tgcaagccaa gcagtctctg gtcccagccc accccatggc cctcccagt cccagcacca      180

ccagcagtaa taacaacagt agcagcagta gcaactcagg atgggatcag ctcagcaaaa     240

cgaacctcta tatccgagga ctgcctcccc acaccaccga ccaggacctg gtgaagctct     300

gtcaacccata tgggaaaata gtctccacaa aggcaatttt ggataagaca acgaacaaat    360

gcaaaggtta tggttttgtc gactttgaca gccctgcagc agctcaaaaa gctgtgtctg     420

ccctgaaggc cagtggggtt caagctcaaa tggcaaagca acaggaacaa gatcctacca     480

acctctacat ttctaatttg ccactctcca tggatgagca agaactagaa aatatgctca     540

aaccatttgg acaagttatt tctacaagga tactacgtga ttccagtggt acaagtcgtg     600

gtgttggctt tgctaggatg gaatcaacag aaaaatgtga agctgttatt ggtcatttta     660

atggaaaatt tattaagaca ccaccaggag tttctgcccc cacagaacct ttattgtgta     720

agtttgctga tggaggacag aaaaagagac agaacccaaa caaatacatc cctaatggaa     780

gaccatggca tagagaagga gaggtgagac ttgctggaat gacacttact tacgacccaa     840

ctacagctgc tatacagaac ggattttatc cttcaccata cagtattgct acaaaccgaa     900

tgatcactca aacttctatt acaccctata ttgcatctcc tgtatctgcc taccaggtgc     960

aaagtccttc gtggatgcaa cctcaaccat atattctaca gcaccctggt gccgtgttaa    1020
```

```
ctccctcaat ggagcacacc atgtcactac agcccgcatc aatgatcagc cctctggccc   1080

agcagatgag tcatctgtca ctaggcagca ccggaacata catgcctgca acgtcagcta   1140

tgcaaggagc ctacttgcca cagtatgcac atatgcagac gacagcggtt cctgttgagg   1200

aggcaagtgg tcaacagcag gtggctgtcg agacgtctaa tgaccattct ccatatacct   1260

ttcaacctaa taagtaactg tgagatgtac agaaaggtgt tcttacatga agaagggtgt   1320

gaaggctgaa caatcatgga tttttctgat caattgtgct ttaggaaatt attgacagtt   1380

ttgcacaggt tcttgaaaac gttatttata atgaaatcaa ctaaaactat ttttgctata   1440

agttctataa ggtgcataaa acccttaaat tcatctagta gctgttcccc cgaacaggtt   1500

tattttagt                                                            1509
```

```
<210> SEQ ID NO 46
<211> LENGTH: 344
<212> TYPE: DNA
<213> ORGANISM: Homo sapiens

<400> SEQUENCE: 46

attcccaacc aagtttgacc ccgccgcagt ggagattgtg gcagatgggt cagatagcat     60

gtgtcctgtc gctgtcacaa ctttttaata agggctgggg gtcctcttga agagcccagg    120

aactgcagtc cctcctctat gccttcccct gaacacagtg cgccctcact aataaattct    180

gagggctgac actgcctgag ccggctggtc tttgccctca atttcattga gatgggccat    240

tgaaaactca ttacaagctg tttagactct gactttgact tttgctcggc agcgaacaaa    300

attaacagct cttggaggta ggaaaaaagg cgctcagcca aatt                     344
```

```
<210> SEQ ID NO 47
<211> LENGTH: 401
<212> TYPE: DNA
<213> ORGANISM: Homo sapiens

<400> SEQUENCE: 47

ctcccaacgg cttgttagtg tctgggcagt gcggtgagac agaaagccca ggggtgtctg     60

gaatcagata ggtccaggtt tgaattctgc tcctgcccct tactgatcca gtgacttgga    120

ataagttacc caaggaagaa agaacattaa cttgattgag tgccttctgg agccaaaggc    180

tttatcgatg ctatctcatt aacatagctt cttgaggccc aattacttca cctgtcaagt    240

ggggatgata aaatcatcct tgaagggtta tagtgaagat taaataggat gaggcattga    300

aagtgtttgg cacatcacga gagaccttct ttcctcactc taaactcttc agagtttgta    360

cctgtatatc tgccaaatca acattatttt atctctcacg a                        401
```

```
<210> SEQ ID NO 48
<211> LENGTH: 493
<212> TYPE: DNA
<213> ORGANISM: Homo sapiens

<400> SEQUENCE: 48

aataccaaag ggaggaatcg tatgggttct tctgcccacc gttgtgacta agaatgcaca     60

gggacttggt tctcgttgca ccttttttta gtaacatgtt tcatggggac ccactgtaca    120

gcccttcatt ctgctgtgtc agtttggcct ggcctgacac tggctgcccc agcggggacc    180

acggaagcag agtgagagcc ttcgctgagt caatgctacc ttcagcccca gacgcatccc    240

atttccatgt cttccatgct cactgctcat gcacttttta cacggtttct tccaaacagc    300

ccggtcttga tgcaggagag tctggaaaag gaagaaaatg gtttcagttt caaaattcaa    360
```

aggaaaaagt tgaggactta ttttgtcctg tcaagattgc aagaacatgt aaaatgtacg 420
gagcttcata atacgttata ttgttccgaa gcagctcgtt gagaaacatt tgttttcaat 480
aacattttag ctt 493

<210> SEQ ID NO 49
<211> LENGTH: 416
<212> TYPE: DNA
<213> ORGANISM: Homo sapiens

<400> SEQUENCE: 49
atatgtctct ctccaacttt ccaccaaata aaatggttag agtgaatgcc cagtttcaca 60
tctgcctttt ggagtttgga aagcttaaac aagtcagtta agagaatgag aagaatctca 120
ctgtgggtga taaggagtgt gtagtttgct gtaagggcca ctgatatgac aagaatgatt 180
atcccacagt aagaatgggt aaaacttaat aaagttttct aactttatta aactcacatt 240
atttaatgaa aaaataactg caaaggacca atgagatcat gcatgctgct gtattcttgt 300
gatggaatct accaggatta agttgtattt aaatgaaaaa acaggtacac atttagagat 360
cattgaccaa gaaatgtaaa tatatttgat taataaaacg tttttatgat gactcg 416

<210> SEQ ID NO 50
<211> LENGTH: 469
<212> TYPE: DNA
<213> ORGANISM: Homo sapiens

<400> SEQUENCE: 50
ctgtgtgcat gtgtgtgtgt atatatatag ttagaagtta gaaactgaaa ctctttttttg 60 tctaccatca tttcatattt ttcttgctat ttcaaaccta taatttttaa agaaacgact 120
aacgtaatca ttcatagaat atgctgtcag taacttaaca atataaatgt taacatggag 180
gcatttagtt cagcatttgc tttacttaat agagtgcaga aaatgtggcc cttttctcag 240
ttagggtgta tgtgaagata aatttagaat ttctagacta gtaaatactt ctctgataat 300
aacttaatta tagctatttc aaaccaaatt gtttaattgt ggtgaatcat atgtaaattg 360
ttcagatgta ggtcaacacc cacgcccaca ttctagcacc tctttcctaa ttcaagacaa 420
ctttgcagtg cctaaaagag ctgaacagtg cagattagag acataagac 469

<210> SEQ ID NO 51
<211> LENGTH: 840
<212> TYPE: DNA
<213> ORGANISM: Homo sapiens

<400> SEQUENCE: 51
gaggttgtaa acgttataag cagtttttat atataactta tttaatacaa atgtgactta 60
attaagcgta accttttctc tggagttgtg gtgaaactaa tcacgtctgt gagagatcag 120
aaagaaagag acttagggaa gtggaagaga aagggaattt tggaatttat ttctttaaaa 180
ataatgcaat ggaaatatat caaaacatgt aaacgcccac cttaaaccaa atgttatttg 240
gtcatgaggc accttgctgg agtctcagat tccaaaagtc tcttcttcag actgggtagg 300
gaatatgata ttttagggac aaagctgagg actggtttta aataggcttt aaaataaaag 360
atcaatatta tcataatgct atcattctgc taaacggccc caaaacagta gaatttctgc 420
tcatgtccta gcaggttcag aagactgcag ccaagttcag atgtaaaaac aagaagtagc 480
acttttccaa aggaaaacaa caaaacaaat gggaaaaaga taatggaccg catttcacct 540
attttaatac tattttaaca attttttcat ctaccaatat atccccaata aataaatata 600

```
aaaggggggg agggtcaatc tggggaatct taattttta tgttttaaga aaacaaaaaa    660

aactgcatta tttttgtaaa gtatttattg agtcacggat tattgtgcat caagcaattg    720

ttaatatgac ctggtcctat ggggtagaac ttaggaaaaa taaagttggt tcttattcaa    780

tattttactt tgcaaaattc tagtaaaaga gagtatataa taaaatcata ataaaaggtg    840
```

<210> SEQ ID NO 52
<211> LENGTH: 493
<212> TYPE: DNA
<213> ORGANISM: Homo sapiens

<400> SEQUENCE: 52

```
ggaataaact ggataaccca gacagtcccc acagaatttc tttcaggtca cagatttctt     60

aaaactcacc cccaaaatgt gcctgcttgg ttgtttgaat cttgcataat taatgtcaca    120

ggcgcaagcc gctgaactta gttgagatgc agaaaacaaa caaatgcaat gacatatctg    180

agaagcattt atgtaactcc ggttaagtgg tgaggagggg tgtgtgaaga cagtgtgcat    240

gcatgagtgt gtattcatat atatgtgtat acatatgaat ttcactgtta ttttccaggg    300

tctatggaca atgtggcagt aagagtctat gatgttctga aacttttcac agtaaatcca    360

aagattacag accttacaag gtgcttgcat tctgttgctt ttccatctgt cacttctcag    420

gttatttgac tgtgttcaaa ccttcttttc tttttcattg agtttcattt tttaagcttg    480

ttaaatgctt ttg                                                       493
```

<210> SEQ ID NO 53
<211> LENGTH: 1372
<212> TYPE: DNA
<213> ORGANISM: Homo sapiens

<400> SEQUENCE: 53

```
tttgtggtgt ctcaatgaca aatatgcaga tgccaccctc ctttgtctaa tgtacggtgc     60

tttagggcaa ctatttaata taaagcaact cagaacttgt ttcaggaagt gttgctcttt    120

cgccttacat gccaaggttc tagggaaaaa gctgaccata tgtaaaaaca ttgatgctca    180

agcacataaa gaattacatt ctttaaacat agagtacata ggatcaagtc tctgcacaat    240

aattgagatg tgttataggg aaaagtgagc acagtgctat tgtccactta gtcttggtga    300

atgtgcagta ggctcacccc taaggaatct catgttgcct gcagtaaaaa taaaaatgga    360

ctgctacaat gacatactga gagagtttta aatcatgctt tacaaactga cattctgagc    420

tctgagacag cagaaaatgt atcaccagag caagggagga ggcaaatgtt ctgaacaata    480

attgaaatgg ttgtgatttt atttggagtt ggcacagatc caagtgacca aaggagttca    540

aggcccaaaa tttagttatg ctggattaat tctgagagta acaagcacat agattataat    600

ctaagaaaac cctttgtagc tatgcatgtc gggagagcat ctaacactaa tggtgatgtt    660

tcccatgcag agactcagat tacagtgact cttccagtga agacagatga aagccattgg    720

gcattgtacc tttgttaatc caagctaaac taaccaagga tataggggtg tgtatgtgtc    780

tgtgtgtgtg tgtttgtgtg tgtgtacaca tacatctata ggtatgaatg agccaaaaag    840

ctgctgactt acagcttagg aaatgcaaag tcaagttttt cttttcaccc tgaggcactc    900

agtgcataaa ggttcaagtt ttaaaactaa gaatgtttcc aaaagaccag caatgttaaa    960

agagtatttc gtgtatacta gacgtgcctt taagcaataa aaattccaag agctgatcat   1020

tattgtgctt ccattttaga aaagtttatt tagtaacaaa cttcccagtg tagggaggtt   1080

tttccttgcc cttttgaaca tgttaggtta ttttcttcct atcctggggc cttaccaatg   1140
```

tgtaatgctt tcaaagtttc tatgaagcct gtgtggattc tattttagct tatttatata 1200
ttctcattta ttttgaagga tattatactt aatttggttc agagtagtcg ccaggttttg 1260
cacctgacaa tggcacatat tttttgtata actttttcta ggtccttacc cttttccaca 1320
ctttacattt gtacagtgaa agcaactgcc agtggaggcc tgaaatgtcc aa 1372

<210> SEQ ID NO 54
<211> LENGTH: 784
<212> TYPE: DNA
<213> ORGANISM: Homo sapiens

<400> SEQUENCE: 54
cacgctgctt gcccgctgtt gatgtgcagt tcccagtgcc tgtgtgagcc gacatctgct 60
cagtcctatc cctcgtcagc gtgtggagac ccagctcctg cagccctcct gctcccacgc 120
ccccagacag cttggtggag ggtcctgcat ctgggccagg ctggggtgca cccagcaaag 180
acaaagctgc ctccacgtgc ccaaggattc agatggtgca ctggccccgg gaggagtctg 240
accaaaaatg gagcccgctc tgtgggaagc cccgactccc ccacgagaaa cggtcccacg 300
gtgcggatct ccccccttccc ttgtggggca cagctggcct gggcctccaa tcctgcggag 360
ctttcctggg tgtggctttg acctcagaag tggctctggt ttggcctcag gagtgtggcc 420
tggcccagcc tgctgcagcc tcctgggggg cccttgatgc cactaatccc ccgacccccc 480
gcatctgcca aactgcacag acacacgcat tgtaaggccg cttgtggcct ccagcgtgca 540
ctcttgttta cgtcattgtc atcttcaaga ccagtccttt gtgattagtt ttgcttcgcg 600
agccctggtg tggactgtgg tctgtatgaa tcgtgtgtaa ctgtggtgag ggcttgtcc 660 tgtatgtgag tctgtaccca ggtggggtct gtgccctgca caccgggccc ctctgtattt 720
atcgctgcct gaatgcaaca gtaatttata tccaggacaa atacagtctg ggcgtcacta 780
tcct 784

<210> SEQ ID NO 55
<211> LENGTH: 703
<212> TYPE: DNA
<213> ORGANISM: Homo sapiens

<400> SEQUENCE: 55
agcagcagcc caggaggcct cccgcccgta ctttcccgcg tccatccctc tgtcccacgg 60
tcggtgagtc agcggacgct gatggaggcc ttgggctctg ggcactatgt gggaggcagc 120
atcaggtcca tggcggcggc ggccctgtct ggcctggcgg tgcggctgtc gcgcccgcag 180
gggacccgcg gctcttacgg cgccttctgc aagacgctca cgcgcacgct gctcaccttc 240
ttcgacctgg cctggcggct gcgcaagaac ttcttttact tctatattct ggcctcggtg 300
attctcaacg tccacctgca ggtatatatt tagagccact aactttgtgg catttggggg 360
ctcctcgtca ggatggctga cttccaccca cctgctcacc caccctagag caaagcgacc 420
aactccgctc ctgcatgcag acttgccact cattctttcc attgcctcat cttttagtat 480
aaatgggtgg caaaaaaaga aaaaaacagc atttgtggaa agcctgaaat ataacccaaa 540
tcgtctaaga tagaatgaaa aattgactct caaggaaata tttgaaggaa cagaatacag 600
cttaaaaatt tgaaaatcct taaaaatatc tgagaagttt ttgcatccgt aaaacagaaa 660
acagcacgaa ctttaggaaa tgacaatggg cacagaatgc aat 703

<210> SEQ ID NO 56
<211> LENGTH: 545
<212> TYPE: DNA

<213> ORGANISM: Homo sapiens

<400> SEQUENCE: 56

```
aatttaaaag gcaagctcac cacaatgtaa gcctatggtc tggccaacct tgcttttggg     60
aactgtgaca ccaaagcccc caggactatc tgcctctcca ggagccagat agaatgacat    120
gcctttttcc taattgtcca cattccaccc ccaacccact gccactgtgg gccaagccat    180
ccatcttgca atcttcatct aaaacagctc tcatttcatg ccagttttgc tcaaacctgc    240
accgtcacaa gatattcaga agatgaaaac gtagaagaca cccctgaatt aaaaacactt    300
acatagcagt ggctggaatt actccaaaac gtgcccagtg atcgcactgt aacatgggat    360
tttctcaccc aaataggcaa ctcatgcttc ctgagtgtaa tcaaagcatg tggtgttttg    420
gggccatatg caccaggttt ctattttaga aaccttcagc tgtcttgctt atgtaccgta    480
tgtaaattta ttctttttaa aaatcacttt tatttgattt tgacttatta aatgctttaa    540
aagcc                                                                 545
```

<210> SEQ ID NO 57
<211> LENGTH: 791
<212> TYPE: DNA
<213> ORGANISM: Homo sapiens

<400> SEQUENCE: 57

```
gcttcccctg tttgcgtggc agcaagggtt ccacgtgcat ttgcaatttg cacagctaaa     60
attgcagcat ttccccagct gggctgtccc aaatgttacc atttgagatg ctcccaggcg    120
tcctaagaga atccaccctc tctggccctg ggacattgca agctgctaca aataaattct    180
gtgttctttt gacaatagcg tcattgccaa gtgcacatca gtgagcctct tgaatctgtt    240
tagtctcctt tttcaacaaa ggagtgtgtt cagaaaagga gagagaggct gagatcattc    300
aggagtttgt tgggcagcaa gcatggagct tcttgcacaa attctgggtc cataaacaac    360
ccccaaagtc cctgctgatc cagtagccct ggaggttccc caggtaggga gagccagagg    420
tgccagcctt cctgaagggc cagaaaattt agcctggatc tcctctttta cctgctagga    480
ctggaaagag ccagaagtgg ggtggcctga agccctctct ctgcttgagg tattgcccct    540
gtgtggaatt gagtgctcat gggttggcct catatcagcc tgggagttat ttttgatatg    600
tagaatgcca gatcttccag attaggctaa atgtaatgaa aacctcttag gattatctgt    660
ggagcatcag tttgggaaga attattgaat tatcttgcaa gaaaaaagta tgtctcactt    720
tttgttaatg ttgctgcctc attgacctgg gaaaaatgaa aaaaaaaaat aaagcaaatg    780
gtaagaccct t                                                          791
```

<210> SEQ ID NO 58
<211> LENGTH: 649
<212> TYPE: DNA
<213> ORGANISM: Homo sapiens

<400> SEQUENCE: 58

```
caggcctgct gcggccatcc gcaaacgggc atttccttga acttttgaga gtgcctttga     60
ccagctgttc gcagctggga aactccaact tttgaagtca gagcttggag cggccccccgc    120
aagggcgtgg ctcaaaccct ccccagagct gggagccatt gcttatgcaa gcccgtttct    180
tttgatgtaa agatggaagt cgttactata ttttaataat gcaaatacat cttttaaaat    240
aagttaacat ttcttaccac cagatggatc aggctttgaa tttaatcatg taaatgtttg    300
taattttatg tcattttgtt aaaatgggac gctttcaatt ggtttccaag aaagatgata    360
```

```
cctctgcatt ttctggtgga aaaggtgtaa tacccttaat gagatcaaag tgttagggga    420

aaaaaattcc aaaagtagtt acaagctata tcaatgtcaa agtaaatgca cttcatcaaa    480

gctaagaagt cacaggaatt gttctcaggt ttttaaaaaa atttttcctg aattcaggaa    540

gtgtcttctg aatagcagct agccaaataa agcggtgtgt gtgtactgca gctgtaggtg    600

aacttaaaaa taataataaa aagaacaaat aaagcagtgt gtaccagcc               649
```

<210> SEQ ID NO 59
<211> LENGTH: 515
<212> TYPE: DNA
<213> ORGANISM: Homo sapiens

<400> SEQUENCE: 59

```
aaaaatattc agtcatttcc tactataatc ctcatgtatc catgtaactg actcaaaaat     60

acttcagcca cagaaagcta aaactgagca aatctcattc ttcttttcca tccccttt gc    120

atgtggctgg catttagtaa tgattaataa tatggccagc tgaataacag aggtttgaga    180

cacaattctt tctcaaagga gtcagctaag ctgggtctac ttatggacaa acatctaaat    240

gtgtggaagt atctgatatt tgacaatggt aaatttccac ttagctagct agcattgtca    300

gacttcaatc tcctcatggc tctggccgtc ctgttttaag catgataatt gttggccaca    360

tctcacatag ttctcattga gtgagttcat aaataaacag ggtttttttt tttttttaaa    420

gagcagccaa gcacaaagtg tgactttgtt gacattttat gtgactttgt catatgttcc    480

taacccccaa taaaagcaat gttgcatcaa ctgtg                               515
```

<210> SEQ ID NO 60
<211> LENGTH: 687
<212> TYPE: DNA
<213> ORGANISM: Homo sapiens

<400> SEQUENCE: 60

```
tattgaaaaa aagtggggtg tatgcatgtg gtttaattcc agattgcttt tgggtttaag     60

tggtatcaaa tttcagtata tttctgtctt atgtgaaaga aatatattac taaaacgtca    120

gtgacgcaat aatgtcagct gtcaagcact agatttattt ttgcaggata tggagtgcaa    180

tgaactgagt caatatggca aggtgtatgt gatctgtggg agttatgcca tttaacatag    240

gaagtgcatg ggactttccc tctctgcact ccagctctta ctgtaccatt agaagatgca    300

gaattctgtt ggtgtgcaaa aagtatagcc ttacattcaa gcagaatgga tctgaagaaa    360

gcagcaatat ctgttactag agaacattcc catgtgttta aactcttcac ttcttagatg    420

catttaaatt cttaatgcaa atgacgtagc aatttgaaaa cttctccgta ttacttgtgt    480

ttaaaatgtc ttgctttaaa tacaaaacaa atggtaaagg ggattatctt ttgtttagat    540

ggttaaatat tatttttgcc ttagatagct ttgtaataat ttttctccag acagttcaac    600

acttttgaaa aatgacatga attttcatta aaaacccttt tcctatgttt attgtataca    660

agaattatgc aataaaattt ctttata                                         687
```

<210> SEQ ID NO 61
<211> LENGTH: 1384
<212> TYPE: DNA
<213> ORGANISM: Homo sapiens

<400> SEQUENCE: 61

```
agggtttgtt tttttgtttg tttgtttgtt tttgagacag agtttcgctc ttgttgccca     60

ggctggagtg caatggcccg atctcagctc accgcaacct ccacctcccg gattccagcg    120
```

```
attctcctgc ctcatcctac attaagggtt ttgtcagaca attgtcacac gaagaatagt    180
gtcacttatc tgctcttgac acacagaact ggcctggcat atagctttcc agattttact    240
caaacttggt actccagttt gaaaatttaa attttgactg ctgattagct ggaaagccta    300
gttttaatgg aaagaaagtt tgcttttaaa actgaaagta gtttcttttt gctaacaaat    360
ctaacttcat acataattgg ccatattagt aaaacacctc atgatagcag tgtatatata    420
gtcttgtttg tagttggaag tcatctttta ggagttattc tcaaatatat ataatagcta    480
cccatgcatc attattaaaa tccccaaatt caaaaaacct ctgatatata tatataattt    540
tttttttttg tttttttggc caactgagat tgaaatccaa gtgctggttt ctagttctga    600
acatcaacta aagagttttg gaaatgacag caatttataa caagttcata ttgacttcct    660
ctctatggca ggaagacatt ctgtgctgtt ttgaacagat taaagatttg tgtagtttgt    720
gggaaattga cgtttttgtt taaattccac ccgcgtttgt cttttcctac cacctgtggc    780
caggtgctcg ctggccatca cagttgcgat tccatgagta gctgctttat gactgctttt    840
tgtactatct ggatgtgccc agagttactt ctgtacaagc tctgtatctg tgtccgttga    900
gaacattatt ttaacaagaa gaacaccaac agtagcatga aatataatac tgttttataa    960
ttctaaagct gctgttaatt tatgaagtac ataataatct aatgtaaact gcagaagtca   1020
gagcaagtgc ctacattttg ttatttttgg cattactaca gagccatgta caatagaaag   1080
caatgcaaga cttgtaaact ctcaccactt cttgtaatat caaatgttcc ccctcaggtt   1140
attttgctta tggtacccat gagttgcctc tctctgtaca tagataaatt gttccaatat   1200
tttcctttga tgtttggaac tacagatagt caagggctgg aaattttagt tttcaatata   1260
agcttccagc ttagcaatta cctctagtcc aagacaatat ttgattccta gttctgtttg   1320
gggcaaattt tcatttatct aaataaaatg caatctaatt aaatgccatg gattttcttt   1380
ctgt                                                                1384
```

<210> SEQ ID NO 62
<211> LENGTH: 1823
<212> TYPE: DNA
<213> ORGANISM: Homo sapiens

<400> SEQUENCE: 62

```
tttaagagtg gaggtgttca tgattctaag ctcaggaatc ttgtgatcat gtattaaata     60
tgttatctca tactataatg ataaaaaagc ttaatgatgt gggttgggat ggatattaac    120
ataaataatt gagtccgctg cttctatagc aatgctgtag gatagaacaa taatgtaagt    180
gatatatgta attaaaaaat tctagaagcc acattaaaaa ataaaaataa acagctgaag    240
ttaattttaa tattttattt aactcaatac atccaaaatg ttatcatttt aacatgtaat    300
tgatgtaaag atttattctg atagtttgta ctatttcttg tactaatttt ttgaaatctg    360
gtatgcattt tacaaatttg ggcaagccac attttaagtg ctcattagcc acatgaggcc    420
agtggatact gtattgaata gcacagtcct atagcatatt tattaatttg tcttgtagta    480
agatgaaata gacaataata cggaataata tcttaaatgg aaatctttgt tagtctctag    540
agccttcatt gcttgataaa taggacatct aaactttaga tataaatcag ttgtcaatga    600
gataaaatta ttgccagcaa atattttcct tcaaagataa gtaacttttg atatggcagt    660
tggtgaaatg aaagaatata atctgccttc ttgttaaatg gttgactatt ctgtagcttg    720
taggtagtac gtattagaaa cttgtgtatg tgggaaatat ttggcataat actgttttca    780
gtatatagta gctatttttt aaggaaatta gtttcataca agaaaaagat tattataaaa    840
```

-continued

```
gtgatacttt tgcatgaaat attagtttgt gttgataact cttagttaac ccttaaagtt    900

taaaacagta ctcaaaaaaa aataatgaga atctagtatt ctgtagttaa ctaatctata    960

agataaattg ctaaagtact agggagcttg taaatcttaa aaatcttttt atttcagtgt   1020

tcattcaggt tggatatatt tgaaattgta gatttctatc tgtacaacat ctcctagtta   1080

atagaatttt tttccttccc ctcccttctc tctcctcctc cttttctaac caaagggcat   1140

tttatcaaca atcatgctga attcaattaa tatctcaagc taaaaaacta tgtaattgag   1200

gttgtatctg gagaagatgg gaaaacattg tataatttaa gcccttaatt gtctgttgag   1260

cttttagggc tgagtaattg cctttcatac aaataaaagc tttaactctt ttctcaagag   1320

tgtaccaccg tccttagaat caggtgtttt aaatccagtt tcttttaatt aaatgggact   1380

gtagtgatcc ctaccctgta gagaaatcaa cagaactaga gaagctaagg gcttgatcag   1440

gtttccccta gaacctgtgt tgcctgcctg ctgtatcttc catgtctttc ttattcaact   1500

tctagaagta gagaaggttg ggacttgagt gtagaagaaa catcagaata atttcaaaaa   1560

acaggaagtt ggaactataa tttttaaatt attgtattgt ttttacggat tttacatgta   1620

tagttaaata ttaaaattca tctcttgcag ttcaataaaa gctatagtat agattttatt   1680

tttaagaagt ttatataatt cttttgtgaa ccaatatgta aaactagaat atttattaaa   1740

ctaataatat gtattagtat caataaaata tgtatttatt tttaaattgg tatgaaacaa   1800

aataaaaatt tgtagacact ctt                                           1823
```

```
<210> SEQ ID NO 63
<211> LENGTH: 404
<212> TYPE: DNA
<213> ORGANISM: Homo sapiens

<400> SEQUENCE: 63

gacctgctct attctcatac taatagacta tttttagatt tttttaaagt aatcacaata     60

aattcagtat atcttaagtc ttttggcttc ctgtgaactt cttcccttga cagtttatct    120

tagcactgaa acatcaaata tattgtatct gctttatcta atactcagaa acaaagaacc    180

tacatgacca atatcaaatt ttattttta gttctgactc ctaaagtctt gctgtcctat     240

cctcaatgct gttaaaaact tctgaggttc cagttttgtt atgtggtgac tccattggct    300

cctgtcttcg tcagtctgct tcttcttggg tagcttggga attctgtgct atggtgatat    360

gtctggatac aatttgtaag tcagcctaca cagccagacc atgt                     404
```

```
<210> SEQ ID NO 64
<211> LENGTH: 5111
<212> TYPE: DNA
<213> ORGANISM: Homo sapiens

<400> SEQUENCE: 64

cacacacaca cggaccgctt actccgctct gcctgctcgc tcccactgtc cccaagcccg     60

ccccgcccgc ggcaagtgcg tgcccaggcg cagccaccgg cgagatcagg agcgcagcgc    120

ccgcagcctg agggaaccgg cgcagggcag cagcggctgc agctggattc gcgcgcccca    180

gcgctcagtg gcggcggccg ggacaccctg ggcagcaccc cgcaccgcag caccccagac    240

tacgagcaat cgtgcccgtc cccgccgggg ctggagggcg cagggccgcc accctgcaag    300

ttcgtgggcc cccggccacc cttatgagag aaggcgaagc cgggcgaagg agcaggacgc    360

tcggcagcag gactcctccg caagccccgc gggccctctg ttcccgcgcc ccccgggcgc    420

ccaagaagca aaatgcaacc accgcgctac agctgagagg ggaaggggcc agcgccatcc    480
```

-continued

```
gctcgcccgg aatccggtcc ccgcggcggc tgcgcgtccc ggccgcggcc cctccggccc    540
gggagtgagc agcagcagga ggagaggcag cggcccgggg ttggccgggg ctggggagga    600
gggacgggac ggagggaggg cgcgggggcg gggagggggc cccggcggat aaagatggca    660
atgtctctca tccaagcgtg ctgcagtctg gctctctcaa catggctgct ttcctttttgt   720
ttcgtgcatc tgctctgcct ggactttacc gtggccgaga aggaggaatg gtacaccgcc    780
ttcgtgaaca tcacctacgc cgagcccgcg ccggaccccg gggccggggc ggcgggcggc    840
ggcggcgcgg agctgcacac ggagaagacg gagtgcgggc gctacggaga gcactcgccc    900
aagcaggacg cccgcgggga ggtggtcatg gccagctcgg cccacgaccg cctggcctgc    960
gaccccaaca ccaagttcgc cgccccgacc cgcggcaaga actggatagc cctcatcccc   1020
aagggcaact gcacgtacag ggataagatc cggaacgcgt tcctgcagaa cgcctcagcc   1080
gtggtcatct tcaacgtggg ctccaacacc aacgagacca tcaccatgcc ccacgcgggt   1140
gtagaagaca tcgtggccat aatgattcct gagccaaaag ggaaggagat agtaagcctg   1200
ctggaaagaa acatcaccgt gacaatgtac atcaccatcg gaacccggaa cttgcagaaa   1260
tatcgccgac tgggggatgc agcaaagaaa gccatcagca aactccagat caggaccatc   1320
aagaagggtg acaaggaaac agagtctgat tttgacaact gtgcagtttg tattgaaggg   1380
tacaagccca atgacgttgt ccggatcctg ccctgccggc atcttttcca caagtcctgt   1440
gttgacccct ggcttctaga ccatcgtacc tgtcccatgt gcaagatgaa cattcttaaa   1500
gccctaggga tcccgcccaa tgccgactgc atggacgact tgcccactga cttcgagggc   1560
tctctgggag gtccacccac caaccagatc acaggtgcca gcgacacaac agtgaatgaa   1620
agttcagtca ctttggaccc tgctgtccgg actgtgggag ccttgcaggt ggtccaggat   1680
acagacccca tcccccagga gggagacgtc atctttacta ctaacagtga gcaggagcca   1740
gctgtaagca gtgattctga catttccttg atcatggcaa tggaggttgg actgtctgat   1800
gtagaacttt ccactgacca ggactgtgaa gaagtgaaat cttgaaacga caaatccaga   1860
agcaaagaga tagtaggacc caagggaaag gaagggaaga gtgctccaag acttggacca   1920
ggcacacaca cacctccaga tcaccttggc aactccaggg cgctccgttc aagaatgctg   1980
acgaaaagca atatccaaag tcttgtcaat caggatgcag tttctccatc ggtatggcag   2040
tctgtggcct tggcagctgg gaagttgaaa gctgatttcc actcctatgt ccatgtagac   2100
atacacttca gaagctccta aaacagagac tgaaaggcca cctttaggat ttcttagttt   2160
catttcaatt ctttccatgt ctcatcattc ttgtttttgg catgttgttt gatttctttg   2220
gcaatttttt taaagattat ttgtagttta ctttccatct attcctttgt ttttcctttg   2280
atgcactcca gcttttgtat aggtttctgt ttagaagcac cagttcctgc tatgatcagt   2340
ttgtattcca tctctgagat atgtggtctt gacctcccag catgaagtgt gcatggcttt   2400
gagaagtgcc tcagcaccct gaaatggact aaggccagct ttcattaaga atctaagttc   2460
ttctaagtgg gccttagtgc tccaagactt ggaccaggca cacacacacc tccagatcac   2520
cttggcaact ccagggcgct ccgttcaaga atgctgacga aaagcaatat ccaaagtctt   2580
gtcaatcagg atgcagtttc tccatcggta tggcagtctg tggccttggc agctgggaag   2640
ttgaaagctg atttccactc ctatgtccat gtagacatac acttcagaag ctcctaaaac   2700
agagactgaa aggccacctt taggatttct tagtttcatt tcaattcttt ccatgtctca   2760
tcattcttgt ttttggcatg ttgtttgatt tctttggcaa ttttttttaaa gattatttgt  2820
agtttacttt ccatctattc ctttgttttt cctttgatgc actccagctt ttgtataggt   2880
```

```
ttctgtttag aagcaccagt tcctgctatg atcagtttgt attccatctc tgagatatgt   2940

ggtcttgacc tcccagcatg aagtgtgcat ggctttgaga agtgcctcag caccctgaaa   3000

tggactaagg ccagctttca ttaagaatct aagttcttct aagtgggcct ttaaaaaccc   3060

cagctgccag agaccccaac actaagccct aaatctgctg aggccactgc tggttatttt   3120

aagccacatc acacttgctt ccacttgccg ggcttgatta agggcccacg tgacatgaga   3180

agggagctct agggaagccg tttcattctt ctgggtctta cagtctttgg ctgaaattct   3240

gaactcagaa gtcccctcca aggcatccag tctttggtgg ttgtagggct ggttttaaaa   3300

ccagatacca cattttcttc ctattgaaaa caaaatgcca gttgcattgg tttcccctgg   3360

gctagaacag tttttttctt acctctgtaa gtgggttctg taaaaaatgg aggctttaga   3420

gaaaagccaa tcatttttaa gtccaatggc aaacatagtg gggctgcag tagcacctag    3480

cttttacctt aatttcgaca cacttctgtt gaatctcacc agaccatgtg ggaggattta   3540

ggtgaatccc tagcagattg cttcccaggg ctccctgagt gtgtccagat accaagtgag   3600

gaatgaggtg tgatttgctg tatcatttga accaaaaagt atgcagcatg agaatttgct   3660

agatcgttta tcctgactga aatagacaaa gtaagaggga aaggaaaaga ggtatcaagt   3720

aaatactgaa acccaatggt gtttttaaac tgtttctgtt tttattcatc ttttgtaact   3780

atgacagaaa tgtgctattt tttcagtggg caattttgta atatattcag actatccaga   3840

tacagagatg actaaggtca ttgatagcgt ctctgaacaa tcagacggat caccttatct   3900

ctacacagct ggcaaacacc aggctgcggc ttggattaac caggaaagaa agcttttctc   3960

actgagttgt ttttatgtat tgatggggac ttttccacct cattagacta atactcattc   4020

aaaaagagtt tggttctgct gtaaatcctt gccgcctgct gaaacatggt gtgcaggtca   4080

acggagaata ctagctgctc ctttttcacc acctttacca atttcctatt tgatggtttg   4140

taagtagaca gtaaggcaag gcagatgatt attaccctca gaaaggttgc atctccctag   4200

gagtccaatg cttcctgtaa tgaaatccac tctctatgtg tgggaaaaga ggcagggagg   4260

aatgaagaga gctctgaatc gagaatccta gatgaaccac acgctttact aagcctcggc   4320

ttcttcatct ataatgtgaa gggtttaata acatgagtcc ccaagctcct ctggctgtgg   4380

gaccacagat gagtctttca gaggcaggat ccatttttgc agatagctat gacttgtggc   4440

aatcaggctt cgtagcttgg ggaggtagag ttacttgaca tgtatcatgt aataacagcc   4500

tttgagactt ggcacaacta tggtgctgag aatgaaaatc taaatgattg aagttttaag   4560

tccaagtagg agttggtttg ttttgccttg tttaaaaatt gctgttagtc acagagtttg   4620

caatctctgg ataccttcaa atcctagctc tcactgtggg attcttgatc tcagaggtgt   4680

ttatttttca cagtcagcat aggcttgcgc cactgactcc tccttcagtc ggctttgccc   4740

aaaacaaatt ttagtattac tggtattaag tttagtccag tggaattaga aggataattc   4800

aatagcaaca gaaatataaa ttatattcca ttcccagaga gagaatgcgc tttggattgt   4860

ttagtcctct gattaacgag tattttctct tcctgccaag aactaggtga atcaggaatt   4920

gattgcatat gcaagccctg gccacagctg cacttacagg atgcctcata gacgatgagg   4980

ggtctgaaag gccaacccga ggctggcaga tctgacccca aggaggtcct gctgcaaacc   5040

ccctgagcct ttgccattca ctacttacca aagtttgttt ctggaggatt ttcctgtagc   5100

tttgatagtt t                                                        5111
```

<210> SEQ ID NO 65
<211> LENGTH: 1577
<212> TYPE: DNA

<213> ORGANISM: Homo sapiens

<400> SEQUENCE: 65

```
gtctcgccct cttgcagtct gcagcttctc ctgtcatcgg aaatgccagg ccaaggtggc     60
tgccccctgc gttcctccat ccaaccatga gctggtgccc atcaccactg agaatgcacc    120
aaagaatgta gtggacaagg gagaaggagg ctcccggggt ggaaacacac ggaaaagcct    180
cgaggacaac ggctccacca gggtcacccc gagtgtccag ccccacctcc agcccatcag    240
aaacatgagt gtgagccgga ccatggagga cagctgtgag ctggacctgg tgtacgtcac    300
agagaggatc atcgctgtct ccttccccag cacagccaat gaggagaact tccggagcaa    360
cctctctgag cggagacctg acatcacgag ctccatgcca aggtacagga atttggctgg    420
cccgacctcc acaccccagc cctggagaag atctgcagca tctgtaaggc catggacaca    480
tggctcaatg cagaccctca caatgtcgtt gttctacaca acaagggaaa ccgaggcagg    540
ataggagttg tcatcgcggc ttacatgcac tacagcaaca tttctgccag tgcggaccag    600
gctctggacc ggtttgcaat gaagcggttc tatgaggata agattgtgcc cattggccag    660
ccatcccaaa gaaggtacgt gcattacttc agtggcctgc tctccggctc catcaaaatg    720
aacaacaagc ccttgtttct gcaccacgtg atcatgcacg gcatccccaa ctttgagtct    780
aaaggaggat gtcggccgtt tctccgcatc taccaggcca tgcaacctgt gtacacatct    840
ggcatctaca acatcccagg agacagccag actagcgtct gcatcaccat cgagccagga    900
ctgctcttga agggagacat cttgctgaag tgctaccaca agaagttccg aagcccagcc    960
cgagacgtca tcttccgtgt gcagttccac acctgtgcca tccatgacct ggggggttgtc  1020
tttgggaagg aggaccttga tgatgctttc aaagatgatc gatttccaga gtatggcaaa   1080
gtggagtttg tattttctta tggccagag aaaattcaag gcatggagca cctggagaac    1140
gggccgagcg tgtctgtgga ctataacacc tctgaccccc tcatccgctg ggactcctac   1200
gacaacttca gtgggcatcg agatgacggc atggaggagg tggtgggaca cacgcagggg   1260
ccactagatg ggagcctgta tgctaaggtg aagaagaaag actccctgca cggcagcacc   1320
ggggctgtta atgccacacg tcctacactg tcggccaccc ccaacacgtg gaacacacgc   1380
tttctgtgta tttatataga tggaaatata ctttatattt tgtatcatcg tgcctatagc   1440
cgctgccacc gtgtataaat cctggtgtat gctccttatc ctggacatga atgtattgta   1500
cactgacgcg tccccactcc tgtacagctg ctttgtttct ttgcaatgca ttgtatggct   1560
ttataaatga taaagtt                                                  1577
```

<210> SEQ ID NO 66
<211> LENGTH: 954
<212> TYPE: DNA
<213> ORGANISM: Homo sapiens

<400> SEQUENCE: 66

```
cgcgcaggga ccatgtcggc ggagacggag cgccccacag aggaccaggt ggaaatcctg     60
gagtacaact tcaacaaggt cgacaagcac ccggattcca ccacgctgtg cctcatcgcg    120
gccgaggcag gcctttccga ggaggagacc cagaaatggt ttaagcagcg cctggcaaag    180
tggcggcgct cagaaggcct gccctcagag tgcagatccg tcacagacta aggagatggc    240
aggcattgac agcttcactc catgaaggcc atctctgttt ctctcctccg cttaaccaag    300
ctgttgtggt ttttcagcat agtgttgtat gttccattgc tagctgtcct gctgtttaac    360
acagtgttgt attttttttc taaatgtaca taattagaaa agaaaataac aataggaagc    420
```

```
tatgtgtatc ttctgtgtaa agcagtggct tcactggaaa aatggtgtgg ctagcatttc    480

cctttgagtc atgatgacag atggtgtgaa aaccatctaa gtttgctttt gaccatcacc    540

tcccagtagc aatttgcttt cataatccat ttagcaatcc aggcctctgt tgaaaagata    600

atatgaggga gaagggaaca catttccttc tgaacttact tccctaagtc actttcctta    660

tgtatcatct aatacaatga tggttgagtg aaaatacaga aggggtgttt gagtattcag    720

atttcataaa acacttcctt ggaatatagc tgcattaact tggaaagaag cctgttgggc    780

cagaagacag aaactccaac tggcaaaaaa gcaagcatct aagaaaaaaa accaccaaag    840

ttcttgaatt tactatattt aaatgcattg gttaagttta ttttgctaaa taaagtgaac    900

tgctttttgt ctctaaaatg atattctaaa taaaacctta actttttgtt gaaa          954


<210> SEQ ID NO 67
<211> LENGTH: 378
<212> TYPE: DNA
<213> ORGANISM: Homo sapiens

<400> SEQUENCE: 67

tcatccttag caaattgcca attagcaaag aagagagggc agatgaagta ccagccaatt     60

tgaaattggt gtggacttcc atcaaggtat attaattcat tttacctaga tgattcgaaa    120

ttagttgctt ttttctttta atcctaaaag gataattttc ttcatgttct tcttgtcatg    180

tcagccaaat cctatagtgt caactttcag taaatgtatc ttagaaataa ctatggacca    240

atctagatct ttctctctct atcatctata cagtttagag attttaaaac tcttaccact    300

tagtttgaaa ttttatttta atttataaaa tgatatattc ttatgtaaaa aattcagaca    360

ataaagatgt atttaaag                                                  378


<210> SEQ ID NO 68
<211> LENGTH: 369
<212> TYPE: DNA
<213> ORGANISM: Homo sapiens

<400> SEQUENCE: 68

tgtaacaagt ggtgcttctt tagaaagttg tcattagaat gttctgagga agttaagcag     60

ctgcttcatc aatcccatga cacatgcctt gttagcatgc ccatcaaata atcagatcaa    120

acacctgctc cttattgtca tacccacgaa ctgttaaata taaaaaaatt caaagtattt    180

gacatcttaa gcaaatatcc agaatatttt taagtaaaaa accatcttaa gtattcaaaa    240

tttccttggc tttttaaagg tgataatttt gctttgtgtt actttttttgc tcttgaatgt    300

atcgttatga tggtctctta taatcatggt atctttcaca gaataaaaat taaaaataat    360

gccagggtg                                                            369


<210> SEQ ID NO 69
<211> LENGTH: 363
<212> TYPE: DNA
<213> ORGANISM: Homo sapiens

<400> SEQUENCE: 69

ctgtgtgtaa gatctttctc ttttgaccca ctattgataa gtccatatat gctattagta     60

tatttactaa tttatcaaat actatgctaa tattagttag acaatagtca aaatagatac    120

ggtccctgtc ctcatggccc tcttttaatc ttacagataa ggatattttt tgacatgtcg    180

tcttgagttt aaggtgatag gttttctcta gcctgtagta gagaacatca gaaatttacc    240

tatacagact ttcttttgcc tgacttatac acaaaagata atttttcacc gaagttgatc    300
```

taatttacaa attgccgtat gtttcaaaga aaacttttgg gcatctaaaa gaattcataa 360
tac 363

<210> SEQ ID NO 70
<211> LENGTH: 348
<212> TYPE: DNA
<213> ORGANISM: Homo sapiens

<400> SEQUENCE: 70
ctatcaaccg tggatggttt ctttttagct tgtccttccc gttctacagc atggaggtta 60
agagctctgg ctttggttcc aatcgtgtcc cctttcctcc ctgtgtgtta ttgattgacc 120
tctctgagcc cattgataaa tggagttaaa aatttatact cactggggtg gtgagaaggt 180
taagggcaat gatgtataca agacattagc atttgctata aggaggatgt atctcagttg 240
ccatatttgt atcactaacc atttgaagat tttgtgttca agatttggaa gagaatcttc 300
ttcccaagcc agcattttat attttgcatt aaaaaaaacc acaaaaga 348

<210> SEQ ID NO 71
<211> LENGTH: 391
<212> TYPE: DNA
<213> ORGANISM: Homo sapiens

<400> SEQUENCE: 71
atgccatcga agacatggtg gccagcgtgg aggaccaggg cctgtctgtc cactgggccc 60
tggacctgta agacctggat atcattgggt ttccatgcac aggccagcac ctcagtaatg 120
tggttctgaa agattaacag gtttaaggga cagaagcaat gaaagaagca atgtgaattt 180
tccatttgct ttcatattat tacctggatt agccattacc agaggaaaaa taaacatttc 240
tcagtaactt tgcctttatg gggaaagggt tgactattga tgtattatat gtttttgtat 300
ttgatgcatc attaggcata atttttaaaa tgataagtac ctttcaagcc aagtttgcat 360
aacctacttt caataaaaac cctctatctt g 391

<210> SEQ ID NO 72
<211> LENGTH: 373
<212> TYPE: DNA
<213> ORGANISM: Homo sapiens

<400> SEQUENCE: 72
tatatataat aaaaatttat atataaataa atacataaac aaactcaagt gtccaacagg 60
gctagataag gagcttacaa gaatgaagca gttgtgatgt gattcaatag ggaataggtg 120
gggccttggc aaaccaaaga acatattctg tctaaagtgg atggccacaa cttgctccag 180
ctgtggaaac ttgggccatg tactgctaga tctaaggatt ttcttttgag agatgctaga 240
tatatacgtt ttttaaaaat aaaattatcc tgattttaac aacattgcct tattatataa 300
aacatacctt ggagggtgtg ggtaagacac aatgtccttg aaattatatt tcactgggtt 360
aatgaaattg gct 373

<210> SEQ ID NO 73
<211> LENGTH: 412
<212> TYPE: DNA
<213> ORGANISM: Homo sapiens

<400> SEQUENCE: 73
cgtgcgagac acgtgtgcgt ttactgttat gtcggtcata tgtctgtacg tgtcgtgggc 60
caacctcgtt ctgcctccag ctttcctggt tagcgcaacg cggctccacg accacacgca 120

```
cttcagggtg gaagctggaa gctgagacac aggttaggtg gcgcgaggct gccctgcgct    180

ccgctttgct ttgggattaa tttattctgc atctgctgag aggggcaccc cagccatatc    240

ttacactttg gtaaagcaga aaaccaggaa aattttctta aaatatccac aatattcctt    300

gagtgagtca gaatctatag ccggttagtg atggtttcag acagaatcgt gttcgtgtct    360

gttttgctcg attcctttcc taagttaaat aaatgcaagc ctctgaactc tg            412
```

<210> SEQ ID NO 74
<211> LENGTH: 364
<212> TYPE: DNA
<213> ORGANISM: Homo sapiens

<400> SEQUENCE: 74

```
gactggagtc tatttttaat tgttttcctt actaaataga gtttttctgt ttcctgcttc     60

taacttgaaa agcagatgaa taaaacattt tctttcactt cagatctttc cactaaaatc    120

ttaaggttgt tttagtagtt ttgtattttt tttcactatg tgtggctcct gtattaattt    180

tcacccatga atctgggttc ttaataaaaa gggccccagc tcccacacgg aaccatgcag    240

gagcccattc tccttcagcg gtgccatgcc ccttactggc agtggctctc cttgcccaga    300

aagtgtctgt aatgtgggac aaagtgaaat tttgtttctc tgaacttcct tgtgactcat    360

attt                                                                  364
```

<210> SEQ ID NO 75
<211> LENGTH: 551
<212> TYPE: DNA
<213> ORGANISM: Homo sapiens

<400> SEQUENCE: 75

```
gatcttgagg ctcaggggag gctaggagtc cactcgagtc ctgggctcct gccctgtttg     60

gcctgtgccc atgctgggct tcagaacaga agctgcataa gctccccaaa tgagcttatt    120

ctcctttgcc tttcaactct cttcttccgt tatcctccca ggtatttagg attatattag    180

gttttcagtt cttatcacct ttcttctcaa ggttctaaga agtccttcat gcagatttgt    240

agtctctgag ctttcatttc caggagctgt ttgtgaagca ctattaccta ctcgccctta    300

cctcacagcc ctctctcctc tagttttccc tgtcacacag gtgacttttc tccattcctg    360

tgttcaaact gtctggattt cacagtgctt gacagaatca ataagaagaa aagctttctt    420

gtttttctct ctttgccaaa ggacagatga agacatcttg gaaaagaaga aaagattgtt    480

gaggtgatgt ttaaaagtgg aactcgtgct gtgaagaaag cagcgggtag ccatcctaga    540

gtacaggaac c                                                         551
```

<210> SEQ ID NO 76
<211> LENGTH: 436
<212> TYPE: DNA
<213> ORGANISM: Homo sapiens

<400> SEQUENCE: 76

```
ctgggtccag gcctcagaca cggagaagct gctctggtga cctagacggg tcgggggatc     60

ctggcggctt aggggactgg ttgctggaag tcgagtttgg tcagggtccc acaggctgct    120

ctcatgtgga gagctttaaa gtaggtaaga actggcagaa gaacctgagg ttgatctacc    180

agcgtttcgt ttggagtggg accccagaga ctaggaaacg taaagcaaag tcatgcatct    240

gtcacgtatg tagtacccat atgaacagac tccactcttg tctctcctgt gtctttttg     300

gctgcttcac tgagaaacat attcacaaac atgcagaaac aaagcagcac catttagctg    360
```

tagacottta tcatggggtc atatattgct tcatgtgtaa ggattatgta tatgacaaag 420
acatagaaca gattgc 436

<210> SEQ ID NO 77
<211> LENGTH: 412
<212> TYPE: DNA
<213> ORGANISM: Homo sapiens

<400> SEQUENCE: 77
cctttatcgg ctgaatattc tcgatgtcaa cagtatgagc aacagaaaat aaaaacttgg 60
aattcagtga cagcttttta tgtaactgcc tcagttttct tagggtaatc aagccaaaga 120
gaaaatcaga gatgccaagg atagagtggt tgagagaggc ccatattgaa ataggcacac 180
gattgtcacc atttctcact ttacaagctg tataatcagt aagctgattc tttttatact 240
tcaaattata tgaacttgac ctcatatttg gctgcaaata ccctgatgat tctcaaatct 300
aatgctacat cttagcttat tccctcgagc tccagacaat gtgtctaacc aaatgtttgc 360
atttgaatgt cccacaggca tttaaattta gcttgtttaa aatctttttc tg 412

<210> SEQ ID NO 78
<211> LENGTH: 500
<212> TYPE: DNA
<213> ORGANISM: Homo sapiens

<400> SEQUENCE: 78
ctgaaaactc taaaactggg aagtatgtat aatgtcatta tttgactttg gcaattattt 60
agtataaaac atgatttctg agccttccag cacctttaag gatggcaccc ttacaaatgc 120
ttaatgagcc tatgggtttg tttggtactg taatgacaag ccatcgcaag tgacctctat 180
atacagggtc actcagagcc cttaaaaaga taaagtcttg gcattgttaa ttgcattaga 240
ggtatgtctc cttttgtatt tagtacacca aatacttaat atttcagaat gcttattcct 300
tcaatgattt cctaagtgta tcagttgaga ttatgttcag ttgtatggga cgagtgtttt 360
atacaaatag aggcttattt acctcttatg taaaagaagt ctggagttag tgatccaggg 420
tggtagagaa tgtatcactg gcccgtgtat caatgaccca catatcaatg acccacgtat 480
caatgacccg catatgaatg 500

<210> SEQ ID NO 79
<211> LENGTH: 441
<212> TYPE: DNA
<213> ORGANISM: Homo sapiens

<400> SEQUENCE: 79
agggtgcttt gtatttttgt tcggggctgt gttttcagcc ttactgcttg ccgttcccat 60
atgtggactc ttgcctgtcg cactgatttc tgtcttccca atccaatgct catagagatc 120
actaaggata atcctgctta ttaagtgatg agttggtttg aattgtctct ggtggtagtc 180
taggaaagtg ggatttcttt ttaattttgg ggttttgttt ttgatttgtg gtaccaatga 240
ggattttatt tgagacagtg taatgggggc cagatgagag aaccattttc tttgtaagct 300
tagcatggct gggctctagc cagctccaga tgaaattttg gctaattatc cctttagaaa 360
agtcaggctt aagcagaact gggctctagg tcaattaacc aaaagccagt tcacccaatg 420
accagttcat ttatttaaaa a 441

<210> SEQ ID NO 80
<211> LENGTH: 793
<212> TYPE: DNA

<213> ORGANISM: Homo sapiens

<400> SEQUENCE: 80 atttagata gcatttccca cttgatgctc cttgccctca tcaccattca tcttattact 60
acagtcagtt tctgtggact accaagataa tagcgctttc ccaaacacaa gcactcattt 120
taaagcagtt atcttttaat gtgaattctc tttgttaaaa tgtcaatgtt gtgagatttg 180
gtagcatatt cctatttaaa ctagtgaata tgattttgat atgaaccttg aaagatgggg 240
aatttgagtg cttttaacgt gttgaaagtg taacacttga aactttggag gctgggaaat 300
cgaggcgatg aagtgttcta taagataggt tttctgccct tttaaatata gtggtgctgt 360
ctttgtttcc aattggaatt tcagtgtaat gcactgttct cacttcagat gcagaggaag 420
gataaaatag tgaagttgat atggccctgt tcagccaaat ttccgaatca taaagtgaca 480
tgctaatagg atatactgtg gcatttctgt gtattacagc ttgtatggtt tgagttactt 540
ttccacacat aattttttct cctccacaca agtcattaaa tatgttttcc tgagagatag 600
tcaagctttg ttgtatagga aagtttcgtt tgtggaaata aatgagtttc actgtaagct 660
aatgtaattc tattacgtga ggaaatgttc cttaaaaaat aaagaatatt atatactgtt 720
gttttcctga atatttttta aaagacacat taactatttc ctatttcatc cttcatggac 780
atcccacaat aga 793

<210> SEQ ID NO 81
<211> LENGTH: 813
<212> TYPE: DNA
<213> ORGANISM: Homo sapiens

<400> SEQUENCE: 81
ttggatgcta cttgtggttg aattgtgttc ccccaaaata tatggtgaag tcttaacccc 60
catccccgtg aatgggacct tgtttggaaa tagggtcttt gcagatatag tcaagatgag 120
gtcacattgg attagggtgg gccccaaatc caatgactgg catccttagg agaagagaga 180
gttttggtaa tagacacaaa tgcagtggga agaagaccag gggacaagag gcaagttgga 240
gtgatgcagc cggaagggaa gggacaccaa ggatctccgg ccaccagcag aagccagcag 300
agaggcatgg gacaggttcc ccacaagcct tagaaggaag catggccctg acttcagaat 360
tccagactcc agaactggaa gaataaatgt ctgttgtttt aagctgctta gttcatgctg 420
agttcatgct gacttgttac tatagcccca gaaagctaat acagtcgttt atgtaattac 480
ataacctgac acacaagatc gacccattca ctgctgccca gtccaccatt ttcataatga 540
agtagaaatg ggaggtaaga aaaacattcc agccagttct gtttagccct gggacacata 600
tttgtcccgt caggaatctt atgccctcct ggaacccccg cccacctcag tccagtccca 660
gtcaggcgaa cggcctctgg acagggactg aggtggctct gagccactgg agatcatttt 720
tcttggagga tggagattgg ctagtacctc tggcctaact gtgtaggtca atactctttt 780
acattgcctt ctaataaaag cagaatgata cag 813

<210> SEQ ID NO 82
<211> LENGTH: 866
<212> TYPE: DNA
<213> ORGANISM: Homo sapiens

<400> SEQUENCE: 82
agccctttct ttgatgttca tttgaaccat agcgttgttg atattcagag tattttgacc 60
tacaaacata aacattttat atggttcaaa ctaacagtta atttgcttca gtttaccagg 120

```
catggatgag tacagtttca atgctaatag caaatatttt acttatttta ctttcctgag    180

cactttacat gttttcactg ttttcctcct cacatcaaca accccaatga attttatctc    240

tcatttataa ataaagaaat aggtgtaaag agataaagta atatgcccaa gtaagtggga    300

aactcaggat ttgaacccaa ctcctcttgc tccagagtct acacgctgaa caacaatgct    360

attccgccct ctacccttga tctagtcccc tcttggccat ctggtagttt tgtaaattca    420

agcatagctc cttctatggc cttgagcccc tcctttccct gcacagtaga gaggggttgg    480

acttttattg gattgtgttt gtattgtaat tgtgtgtttt tccagatgtg ttttctagcc    540

acaggaagag atactcaaat aagtctttca acagtatcta ttatgctgac attcacactt    600

gtttgtgtta ttttgtacgt tttggaagcc ttctgtagtt aagtattagt tgagctaatt    660

ccttactgtt tttgtgtcat actttgttat ggagcaacgt aatatgtgta tgttgttaac    720

tgaatcgata gaaatctaag aatcaacttg gtctatatca tctgatgatt caggggctgg    780

tttggatcat tgataaagta aattattccc tgttttactt aactccttag tggcagtttt    840

ctagattccc attattggct tgcatc                                          866
```

```
<210> SEQ ID NO 83
<211> LENGTH: 474
<212> TYPE: DNA
<213> ORGANISM: Homo sapiens

<400> SEQUENCE: 83

cattcctcct ttccttgccc agctatggcc ccctctcatt cacaaagtgc cccctccatg     60

tccctggacc cttaagatat ccccttggca ccctggtcag agactctgtg tctgactcag    120

gtggtccctg cagagtgccc tgggaaggga aggagcactg atttgggggt tttgagggtc    180

aagtaggggt tggtaacacc tggaaagaag gactctttca cttcgatccc tggacaatta    240

tggaggattc ggaggtagaa gaggggaagg aagatggttt ctatctcatg acccccactc    300

cctgtgagag ggaatggggg aagcctgatg accctcagct gttccaatct agtatttttt    360

ttcttttta aaattactgt atttattatg acgatggtga ctccccagtg caaagggggg    420

ccagattctg tgtgtttctc taacctcttt gtaaataaat gcacagtgta acat          474
```

```
<210> SEQ ID NO 84
<211> LENGTH: 476
<212> TYPE: DNA
<213> ORGANISM: Homo sapiens

<400> SEQUENCE: 84

tgccactgga taaacaggcc cttggtgaca tcccccaggc tccccatgac tctcctccag     60

tctctccaac tccaaaaacc cctccctgcc aagccagact tgccaagctg gatgaagatg    120

agctgtaact ggtgaaaacc atgggggtgg tgctgactca gccgcctatt ccccaaggag    180

cttcagggca gtccttctgg cactgctcca gaattcctcc ttcttggtgt gtctggaggg    240

tgggcaaggc tgggagggat atcaacttgg aggagaacac ctagacccaa ggactttttt    300

ctgcccaagg aacacagttt ccttcagctc ccatccctat gcatgcatca tggtcccccc    360

aaaaggagga tatgtgggtg ggtgggaggg ctggggcagg ggccagatag aaattattgg    420

ttttgttttt taattttgtt tttcctgttt tctgagaata aaggttttgt tatatc        476
```

```
<210> SEQ ID NO 85
<211> LENGTH: 491
<212> TYPE: DNA
<213> ORGANISM: Homo sapiens
```

<400> SEQUENCE: 85

```
cagtccaaaa gacaagcaaa ttaagaatgg agcttaacca tgcctccatt gggaagtcta     60

gactttgagc caggtacagt aagaaaaatt agcctctgat tcattaagtt tgccacatga    120

cttattttga tattttggat acattaactc acttaggaga attcagaaaa gaatgggtga    180

ttaaagttca ttacagctga ataaatgtgt ctaaaacaga ctcttgtatt ctgaaagtac    240

agtctacaac tgataaaacc ttatgattct tttctccccc attatgcccc tatatatatc    300

aagatttggg tactttattt tagtagaaaa tatatatctt ttacatatgt atgtatttat    360

aaatgcatag atatatgtat aaaaatttgt aagcgttagc ggcattaatt caccaatgca    420

tttggacaac ttgatgtaac tgactttatt ttatgtgact ataataaaaa gcataatttt    480

ctcattctgt c                                                         491
```

<210> SEQ ID NO 86
<211> LENGTH: 745
<212> TYPE: DNA
<213> ORGANISM: Homo sapiens

<400> SEQUENCE: 86

```
agggcctact taccaagtgt aaatcacaac ataggctacc aaaatatttc ttatttgcta     60

ggagaacaaa gctgtcacgg tgcatgatag ttggacagag atggctaaaa aagaggcaaa    120

ttcagatttg gaaacagggt ggcctcttca ttatttattg ccaagatctg aaaatcttca    180

acatcttata agacaacaat gaagtagccc ctgaacagca tggagttgct gtgagtttgt    240

tcgttgcaga cctttgtgtt gggtcctggg aatctgagct ttgttccctg tgcatggtgg    300

ataattgaaa ccaagaggac atgggataga ccttgtgaca gaccaattct gtgacccctg    360

tcttctgggt cacattattc attgttgatt taaatacagg actaccaaac agtacaaatc    420

tatcatgagt ctggtagaaa agtaaaagta aaagctgcac acgttacata ctgtttattg    480

ttctaatgta caactaacta tttgcatata atgtgattta atttattgct gttttgtgta    540

gaaaaggaga actaatgact gtggatataa cccatgtttt gtataatata ttttatttct    600

tgtgcgaact ggtcatttaa aatatctact tcatttgatg tttggatata aatgtgtatg    660

tgtccttgta aatgtttcta tcaagcaaga atgccacgta ctcagagtat aacaatgtgt    720

tctcattaaa aaatacatcc cacgg                                          745
```

<210> SEQ ID NO 87
<211> LENGTH: 1548
<212> TYPE: DNA
<213> ORGANISM: Homo sapiens

<400> SEQUENCE: 87

```
agacttggaa accccaaagt gtccgcgacc ctgcacggca gctcccttcc agcttcatgg     60

gcaaagtgtg gaaacagcag atgtaccctc agtacgccac ctactattac ccccagtatc    120

tgcaagccaa gcagtctctg gtcccagccc accccatggc ccctcccagt cccagcacca    180

ccagcagtaa taacaacagt agcagcagta gcaactcagg atgggatcag ctcagcaaaa    240

cgaacctcta tatccgagga ctgcctcccc acaccaccga ccaggacctg gtgaagctct    300

gtcaaccata tgggaaaata gtctccacaa aggcaatttt ggataagaca acgaacaaat    360

gcaaaggtta tggttttgtc gactttgaca gccctgcagc agctcaaaaa gctgtgtctg    420

ccctgaaggc cagtggggtt caagctcaaa tggcaaagca acaggaacaa gatcctacca    480

acctctacat ttctaatttg ccactctcca tggatgagca agaactagaa aatatgctca    540
```

```
aaccatttgg acaagttatt tctacaagga tactacgtga ttccagtggt acaagtcgtg    600

gtgttggctt tgctaggatg gaatcaacag aaaaatgtga agctgttatt ggtcatttta    660

atggaaaatt tattaagaca ccaccaggag tttctgcccc cacagaacct ttattgtgta    720

agtttgctga tggaggacag aaaaagagac agaacccaaa caaatacatc cctaatggaa    780

gaccatggca tagagaagga gaggctggaa tgacacttac ttacgaccca actacagctg    840

ctatacagaa cggattttat ccttcaccat acagtattgc tacaaaccga atgatcactc    900

aaacttctat tacaccctat attgcatctc ctgtatctgc ctaccaggtg gcaaaggaaa    960

ccagagaaaa caagtatcgg ggctctgcta tcaaggtgca aagtccttcg tggatgcaac   1020

ctcaaccata tattctacag caccctggtg ccgtgttaac tccctcaatg gagcacacca   1080

tgtcactaca gcccgcatca atgatcagcc ctctggccca gcagatgagt catctgtcac   1140

taggcagcac cggaacatac atgcctgcaa cgtcagctat gcaaggagcc tacttgccac   1200

agtatgcaca tatgcagacg acagcggttc ctgttgagga ggcaagtggt caacagcagg   1260

tggctgtcga gacgtctaat gaccattctc catatacctt tcaacctaat aagtaactgt   1320

gagatgtaca gaaaggtgtt cttacatgaa gaagggtgtg aaggctgaac aatcatggat   1380

ttttctgatc aattgtgctt taggaaatta ttgacagttt tgcacaggtt cttgaaaacg   1440

ttatttataa tgaaatcaac taaaactatt tttgctataa gttctataag gtgcataaaa   1500

cccttaaatt catctagtag ctgttccccc gaacaggttt attttagt                1548
```

<210> SEQ ID NO 88
<211> LENGTH: 1500
<212> TYPE: DNA
<213> ORGANISM: Homo sapiens

<400> SEQUENCE: 88

```
agacttggaa accccaaagt gtccgcgacc ctgcacggca gctcccttcc agcttcatgg     60

gcaaagtgtg gaaacagcag atgtaccctc agtacgccac ctactattac ccccagtatc    120

tgcaagccaa gcagtctctg gtcccagccc accccatggc ccctcccagt cccagcacca    180

ccagcagtaa taacaacagt agcagcagta gcaactcagg atgggatcag ctcagcaaaa    240

cgaacctcta tatccgagga ctgcctcccc acaccaccga ccaggacctg gtgaagctct    300

gtcaaccata tgggaaaata gtctccacaa aggcaatttt ggataagaca acgaacaaat    360

gcaaaggtta tggttttgtc gactttgaca gccctgcagc agctcaaaaa gctgtgtctg    420

ccctgaaggc cagtggggtt caagctcaaa tggcaaagca acaggaacaa gatcctacca    480

acctctacat ttctaatttg ccactctcca tggatgagca agaactagaa aatatgctca    540

aaccatttgg acaagttatt tctacaagga tactacgtga ttccagtggt acaagtcgtg    600

gtgttggctt tgctaggatg gaatcaacag aaaaatgtga agctgttatt ggtcatttta    660

atggaaaatt tattaagaca ccaccaggag tttctgcccc cacagaacct ttattgtgta    720

agtttgctga tggaggacag aaaaagagac agaacccaaa caaatacatc cctaatggaa    780

gaccatggca tagagaagga gaggctggaa tgacacttac ttacgaccca actacagctg    840

ctatacagaa cggattttat ccttcaccat acagtattgc tacaaaccga atgatcactc    900

aaacttctat tacaccctat attgcatctc ctgtatctgc ctaccaggtg caaagtcctt    960

cgtggatgca acctcaacca tatattctac agcaccctgg tgccgtgtta actccctcaa   1020

tggagcacac catgtcacta cagcccgcat caatgatcag ccctctggcc cagcagatga   1080

gtcatctgtc actaggcagc accggaacat acatgcctgc aacgtcagct atgcaaggag   1140
```

```
cctacttgcc acagtatgca catatgcaga cgacagcggt tcctgttgag gaggcaagtg   1200

gtcaacagca ggtggctgtc gagacgtcta atgaccattc tccatatacc tttcaaccta   1260

ataagtaact gtgagatgta cagaaaggtg ttcttacatg aagaagggtg tgaaggctga   1320

acaatcatgg atttttctga tcaattgtgc tttaggaaat tattgacagt tttgcacagg   1380

ttcttgaaaa cgttatttat aatgaaatca actaaaacta tttttgctat aagttctata   1440

aggtgcataa aacccttaaa ttcatctagt agctgttccc ccgaacaggt ttattttagt   1500


<210> SEQ ID NO 89
<211> LENGTH: 2675
<212> TYPE: DNA
<213> ORGANISM: Homo sapiens

<400> SEQUENCE: 89

aaaacattca acaaattaat gggtgtaagg aactggaaaa cctggactcc taccacatgc     60

agataaaacc aatagagtgc agaataagac tcaagtcaag taagtaacgt taaacaccat    120

aaagacacat ggccttcttt gtgtacatga catgcattct caacaatgca ctgacggata    180

tgagtgggat cctgtgagac agcaatgcaa agatattgat gaatgtgaca ttgtcccaga    240

cgcttgtaaa ggtggaatga agtgtgtcaa ccactatgga ggatacctct gccttccgaa    300

aacagcccag attattgtca ataatgaaca gcctcagcag gaaacacaac cagcagaagg    360

aacctcaggg gcaaccaccg ggttgtagc tgccagcagc atggcaacca gtggagtgtt    420

gcccgggggt ggttttgtgg ccagtgctgc tgcagtcgca ggccctgaaa tgcagactgg    480

ccgaaataac tttgtcatcc ggcggaaccc agctgaccct cagcgcattc cctccaaccc    540

ttcccaccgt atccagtgtg cagcaggcta cgagcaaagt gaacacaacg tgtgccaaga    600

catagacgag tgcactgcag ggacgcacaa ctgtagagca gaccaagtgt gcatcaattt    660

acggggatcc tttgcatgtc agtgccctcc tggatatcag aagcgagggg agcagtgcgt    720

agacatagat gaatgtacca tccctccata ttgccaccaa agatgcgtga atacaccagg    780

ctcattttat tgccagtgca gtcctgggtt tcaattggca gcaaacaact atacctgcgt    840

agatataaat gaatgtgatg ccagcaatca atgtgctcag cagtgctaca acattcttgg    900

ttcattcatc tgtcagtgca atcaaggata tgagctaagc agtgacaggc tcaactgtga    960

agacattgat gaatgcagaa cctcaagcta cctgtgtcaa tatcaatgtg tcaatgaacc   1020

tgggaaattc tcatgtatgt gcccccaggg ataccaagtg gtgagaagta gaacatgtca   1080

agatataaat gagtgtgaga ccacaaatga atgccgggag gatgaaatgt gttggaatta   1140

tcatggcggc ttccgttgtt atccacgaaa tccttgtcaa gatccctaca ttctaacacc   1200

agagaaccga tgtgtttgcc cagtctcaaa tgccatgtgc cgagaactgc cccagtcaat   1260

agtctacaaa tacatgagca tccgatctga taggtctgtg ccatcagaca tcttccagat   1320

acaggccaca actatttatg ccaacaccat caatactttt cggattaaat ctggaaatga   1380

aaatggagag ttctacctac gacaaacaag tcctgtaagt gcaatgcttg tgctcgtgaa   1440

gtcattatca ggaccaagag aacatatcgt ggacctggag atgctgacag tcagcagtat   1500

agggaccttc cgcacaagct ctgtgttaag attgacaata atagtggggc cattttcatt   1560

ttagtctttt ctaagagtca accacaggca tttaagtcag ccaaagaata ttgttacctt   1620

aaagcactat tttatttata gatatatcta gtgcatctac atctctatac tgtacactca   1680

cccataacaa acaattacac catggtataa agtgggcatt taatatgtaa agattcaaag   1740

tttgtcttta ttactatatg taaattagac attaatccac taaactggtc ttcttcaaga   1800
```

```
gagctaagta tacactatct ggtgaaactt ggattctttc ctataaaagt gggaccaagc   1860

aatgatgatc ttctgtggtg cttaaggaaa cttactagag ctccactaac agtctcataa   1920

ggaggcagcc atcataacca ttgaatagca tgcaagggta agaatgagtt tttaactgct   1980

ttgtaagaaa atggaaaagg tcaataaaga tatatttctt tagaaaatgg ggatctgcca   2040

tatttgtgtt ggtttttatt ttcatatcca gcctaaaggt ggttgtttat tatatagtaa   2100

taaatcattg ctgtacaaca tgctggtttc tgtagggtat ttttaatttt gtcagaaatt   2160

ttagattgtg aatattttgt aaaaaacagt aagcaaaatt ttccagaatt cccaaaatga   2220

accagatacc ccctagaaaa ttatactatt gagaaatcta tggggaggat atgagaaaat   2280

aaattccttc taaaccacat tggaactgac ctgaagaagc aaactcggaa aatataataa   2340

catccctgaa ttcaggcatt cacaagatgc agaacaaaat ggataaaagg tatttcactg   2400

gagaagtttt aatttctaag taaaatttaa atcctaacac ttcactaatt tataactaaa   2460

atttctcatc ttcgtacttg atgctcacag aggaagaaaa tgatgatggt ttttattcct   2520

ggcatccaga gtgacagtga acttaagcaa attaccctcc tacccaattc tatggaatat   2580

tttatacgtc tccttgttta aaatctgact gctttacttt gatgtatcat atttttaaat   2640

aaaaataaat attcctttag aagatcactc taaaa                              2675
```

<210> SEQ ID NO 90
<211> LENGTH: 1528
<212> TYPE: DNA
<213> ORGANISM: Homo sapiens

<400> SEQUENCE: 90

```
aggaaacctt taaaaattcc agttaagcaa tgttgaaatc agtttgcatc tcttcaaaag     60

aaacctctca ggttagcttt gaactgcctc ttcctgagat gactaggaca gtctgtaccc    120

agaggccacc cagaagccct cagatgtaca tacacagatg ccagtcagct cctggggttg    180

cgccagggcc cccgctctag ctcactgttg cctcgctgtc tgccaggagg ccctgccatc    240

cttgggccct ggcagtggct gtgtcccagt gagctttact cacgtggccc ttgcttcatc    300

cagcacagct ctcaggtggg cactgcaggg acactggtgt cttccatgta gcgtcccagc    360

tttgggctcc tgtaacagac ctctttttgg ttatggatgg ctcacaaaat agggccccca    420

atgctatttt tttttttaa gtttgtttaa ttatttgtta agattgtcta aggccaaagg    480

caattgcgaa atcaagtctg tcaagtacaa taacattttt aaaagaaaat ggatcccact    540

gttcctcttt gccacagaga aagcacccag acgccacagg ctctgtcgca tttcaaaaca    600

aaccatgatg gagtggcggc cagtccagcc ttttaaagaa cgtcaggtgg agcagccagg    660

tgaaaggcct ggcggggagg aaagtgaaac gcctgaatca aaagcagttt tctaattttg    720

actttaaatt tttcatccgc cggagacact gctcccattt gtggggggac attagcaaca    780

tcactcagaa gcctgtgttc ttcaagagca ggtgttctca gcctcacatg ccctgccgtg    840

ctggactcag gactgaagtg ctgtaaagca aggagctgct gagaaggagc actccactgt    900

gtgcctggag aatggctctc actactcacc ttgtctttca gcttccagtg tcttgggttt    960

tttatacttt gacagctttt ttttaattgc atacatgaga ctgtgttgac tttttttagt   1020

tatgtgaaac actttgccgc aggccgcctg gcagaggcag gaaatgctcc agcagtggct   1080

cagtgctccc tggtgtctgc tgcatggcat cctggatgct tagcatgcaa gttccctcca   1140

tcattgccac cttggtagag agggatggct ccccaccctc agcgttgggg attcacgctc   1200

cagcctcctt cttggttgtc atagtgatag ggtagcctta ttgccccctc ttcttatacc   1260
```

ctaaaacctt ttacactagt gccatgggaa ccaggtctga aaaagtagag agaagtgaaa 1320
gtagagtctg ggaagtagct gcctataact gagactagac ggaaaaggaa tactcgtgta 1380
ttttaaaata tgaatgtgac tcaagactcg aggccgatac gaggctgtga ttctgccttt 1440
ggatggatgt tgctgtacac aaatgctaca gacttgtact aacaccccgt aatttggcat 1500
ttgtttaacc tcatttataa aagcttca 1528

<210> SEQ ID NO 91
<211> LENGTH: 732
<212> TYPE: DNA
<213> ORGANISM: Homo sapiens

<400> SEQUENCE: 91
gaatcacaaa atcaaaatat ttattttgtt ctttttcata tgacactgtt aaaacattcc 60
tactacagca atactgctct ccaggagctt acaatctaaa acagtcaaca ttaattgtag 120
acccagtaat taaggcatta tatcaaatgc agactttgta tctttttttt tttttttttg 180
aaacggagtt ttgctcttgt cgcccaggct ggagtgcaat ggcgccatct tggctcactg 240
caacctccgc ctcctgggtt caagcgattc tcctgcctca gcctcccgag tagctgggat 300
tacaggcatg caccaccacg cccagctaat tttgtattt ttagtagagg cattgattaa 360
agattcacag caaatcacta gttaagcaga ttttttttct atttcctact tcaaagttct 420
gggtgccaca tagtggtcag aaatggaaca gagaagctgt cttaagcctt gttcaagaag 480
caggaaaggc atcagaagaa gtaacagttg gcagagggtc tcgggaaaaa catcttcctt 540
ctgatctttt gcatagcacc ttttggaatt ttcatcatgt ttgcttatta aacaaagctc 600
ctactgccat catactaatc atgcaaaaag attgccaaat catgtttggt aggaggactt 660
ttgaggtagc ttttgaacaa atgttttttt ctttttttctt ttttttgca ataaagaaaa 720 caaattaatc at 732

<210> SEQ ID NO 92
<211> LENGTH: 6993
<212> TYPE: DNA
<213> ORGANISM: Homo sapiens

<400> SEQUENCE: 92
gtgtgggagg tcgttcagtg tcatctcaga atttgttgag caccagatca tgcatactag 60
agagaacctc tatgagtatg gtgagtcctt tatccacagt gtggctgtca gtgaagttca 120
gaaaagtcag gttggaggga aacgttttga atgtaaggac tgtggagaga ccttcaataa 180
gagtgccgcc ttggctgaac atcggaagat tcatgctaga ggttatcttg tggaatgtaa 240
gaatcaggaa tgtgaggaag ccttcatgcc tagccccacc tttagtgagc ttcagaaaat 300
atatggcaaa gacaaattct acgagtgcag ggtgtgtaag gaaaccttcc ttcatagttc 360
tgccctgatt gagcaccaga aatccactt tggggatgac aaagataatg agcgtgaaca 420
tgaacgtgaa cgtgaacgtg agcgcgggga aacctttagg cccagcccag cccttaatga 480
gtttcagaaa atgtatggta aagagaaaat gtacgaatgt aaggtgtgtg gggagacttt 540
ccttcatagc tcatccctga aagaacatca gaaaatccat actagaggga acccatttga 600
aaacaagggt aaagtgtgtg aggaaacctt tattcctggt cagtccctta aaaggcgtca 660
gaaaacttac aataaggaga agctctgtga ctttacagat ggccgggatg ccttcatgca 720
aagctcagag ctcagtgagc atcagaaaat tcattctcga aagaacctct ttgaaggcag 780
agggtatgag aaatctgtca ttcatagtgg gccattcact gaatctcaga agagtcatac 840

```
tataacaaga cctcttgaaa gtgatgagga cgaaaaggcg ttcaccatta gctctaaccc    900
ctatgaaaac cagaagattc ccactaagga aaatgtctat gaggcaaaat catatgagag    960
gtctgttatt catagcttag cctctgtgga agctcagaaa agtcacagtg tagcagggcc   1020
cagtaaacca aaagtaatgg cagagtctac cattcagagc ttcgatgcta tcaaccatca   1080
gagagttcgt gctggaggga acacctctga aggaagggaa tacagtaggt ctgttatcca   1140
tagcttagtg gcttccaaac ctccaagaag tcacaatgga aatgaattgg tggaatctaa   1200
tgagaaggga gaatcctcca tttatatctc agaccttaat gataagcgac agaagattcc   1260
tgccagagag aacccttgtg aagggggcag taagaatcgc aactatgaag actctgtcat   1320
acagagtgta ttccgtgcca aacctcagaa aagtgttcct ggagagggat ctggtgagtt   1380
taagaaggat ggcgaattct ctgttcccag ctcaaatgtc cgtgaatacc agaaggctcg   1440
tgctaaaaag aaatacattg agcataggag caatgagacc tctgtaattc actctctgcc   1500
ttttggtgaa caaacatttc gccctcgagg gatgctctat gaatgtcagg agtgtgggga   1560
gtgctttgct catagctctg acctcactga gcaccagaag attcatgata gggagaagcc   1620
ctctggaagc agaaactatg aatggtctgt cattcgcagc ttggccccta ctgaccctca   1680
aacaagttac gcccaagagc agtatgctaa agagcaagcg cggaacaaat gtaaggactt   1740
cagacaattt tttgctacca gcgaagacct caacacaaac cagaaaatct atgaccaaga   1800
gaagtctcat ggcgaggagt ctcaaggcga gaatactgat ggggaggaga cccacagcga   1860
ggagacccat ggtcaggaga caattgaaga ccctgtcatt caaggctcag acatggaaga   1920
ccctcagaag gatgaccctg atgacaaaat ctatgaatgt gaggactgtg gcctgggctt   1980
tgtggatctc acagacctca cagaccatca gaaagtccac agcaggaagt gcctggttga   2040
cagtcgggag tacacacatt ctgtaattca cacccattcc atcagcgagt atcagagaga   2100
ttacactgga gagcagctgt atgaatgtcc aaagtgtggg gaatctttta ttcatagctc   2160
attccttttc gagcatcaga gaatccatga acaagaccag ttgtattcca tgaaggggtg   2220
tgatgatggt tttattgccc tcttgcccat gaagccacgg aggaatcgtg ctgcagagag   2280
gaatcctgct cttgctgggt cggccattcg atgccttttg tgtggacaag gcttcattca   2340
tagctctgcc cttaatgagc atatgagact tcatagggaa gatgatttac tggagcagag   2400
ccagatggct gaggaagcta tcattccagg cttagccctc actgagtttc agagaagtca   2460
gaccgaagag agactctttg aatgtgcagt ctgtggagaa tctttcgtca acccagcaga   2520
acttgcagat cacgtaactg ttcataagaa tgagccctat gagtacgggt cctcctatac   2580
tcacacctca tttcttactg agcccctcaa aggagctata ccattctatg aatgcaagga   2640
ttgtggtaag tcctttattc atagcacagt cctcactaaa cataaggagc ttcatctgga   2700
agaagaagaa gaagatgaag cagcagcagc tgcagcagca gcagcccagg aagttgaagc   2760
caatgtccat gttccacaag tagttctgag gattcagggc ttaaacgtag aggctgctga   2820
gccagaagtg gaggctgccg agccagaagt ggaggctgct gagccagaag tggaggctgc   2880
tgagccaaac ggagaggctg aagggccaga tggagaggct gcagagccca ttggagaggc   2940
tggacagcca aatggagagg ccgagcagcc aaatggggat gctgatgagc cagatggtgc   3000
aggtattgaa gacccagaag aaagagctga agagccagag ggaaaagctg aagagccaga   3060
gggagatgcc gacgagcctg acggtgtggg aattgaagac ccagaagaag gtgaagatca   3120
agagattcag gtagaagaac catactatga ctgccatgaa tgcacagaaa ccttcacttc   3180
cagcacagca ttcagtgaac acctgaaaac tcatgccagc atgatcatat ttgagcctgc   3240
```

```
aaatgccttt ggggagtgct caggctacat cgaacgtgcc agcaccagca caggtggtgc   3300
caatcaagct gatgagaagt acttcaaatg tgacgtctgt gggcagctct tcaatgaccg   3360
cctgtccctc gccagacacc agaataccca cactggctga gggcatgggg taaaggttag   3420
aaaaccttca cctaggactt gacccttacc aaaccacaga gaatccaaac caatccatga   3480
taatgtcagt aggagactta accttagtgt gttacacacc tgacttaaca tctctaaact   3540
cagattgaaa agagaccgaa tgtgcagatt ccacagtctt aagctttccc cttcagatgt   3600
cagtgtctgc atgtgggaaa gccatagcac acatcttacc tttccaagta atcagattga   3660
gaaaacccta tgagtattcc agactacaga gtttgcccaa atcaactgta aatgacactt   3720
gtgtaacgta tatatagtgt ttcatgaggt gtatataaaa tagcaaatta tgacagaaca   3780
gtgatcacat atatttggat ttatatgata tacagttaca gtttactctg cagaggtacc   3840
ttacctggta ttctttgaat ttttttttt tttggaggag gaagagagca acaaatttga   3900
ttatattttt aagtgtctta gatcctgaga aagatttatt gtgcattatt tgaaccctgt   3960
caatatcttt ttgagtaatt gttttgtttc ttacccttaa atagtcttgt gaagctgtag   4020
gcatgataga taacatggct tttactcctt actgtttgaa aagataagta ctttagcttc   4080
tttctgcagc catttcatct gcaccaacac tttggaacct aatactgtgt aaggctttac   4140
aatatacgga ttggcttttt gtgacccaga ttgattggtt gccacatgtt atgtttgttg   4200
aagtggttct catgcaaaaa tattacacat ttgtgttctg ggttttttt tttttttta     4260
accaactcaa tatgtgtttg atgatagtga attgataaaa cccgaagctt ttccctgtaa   4320
atcttacatc tttgccttta aagaatgggt tacaaccatc actagatcac agtagtgcct   4380
aatgaaggtt gagaaccgta ggagaggctc tcatgctgta aataatgttg caggctaata   4440
acctttcatc acttcctttg tgcgcttcct gccttaagtg acaagtagca acatggcttg   4500
ggtcccctgt gcagcatcag cttatgctgc cacaagtcag tttgcaccct aggtgcccag   4560
gagctagtat ccttagatct ttctatcgct aacttaattc tcttcgttag ttatctgacc   4620
ctctaactcc atgtctaact tgcattaaaa aaaaaaaaat tctttacagt caacccaagc   4680
ttaacatgga ctcaggttcc ccagcagcct taatttgttt tgttaacatc tgttccttct   4740
ttttcagctc tcctagagta tttctgagtg ttgtgttcat ctaatcttag tattctttta   4800
attacaaatt gacctcacag cttgaggttt cttgtgtctt attctgtgga ctacctgtgc   4860
tcctttgctt cccctcccct cgcataataa ctatattaag aaattttttt tggccttgag   4920
ttggctggaa aaaaaatata aaatttaaaa aatttaaaaa aaaagatttg caaaatgtaa   4980
gtgtagatca tttgaacaag caaaattaaa gtacccactg gggaaatgt gtctgaatct    5040
tactcttctg gatctgcagg attagggctt ggaagtatgt caaagatgga gggagtgtca   5100
aagtttagga agattgtaga gctgagagca agaagcagaa atgagtgagt caaagaaggg   5160
agtcctaata catcaccaga tctaggaggg gagaggagac agacagaaga aaacaccaga   5220
ggcaagaact gtagaaggcc aggtttctga gaatgaattg agcggggtgt cctgagcagt   5280
ttggaaaagg agtttttgat ggtatggtgt aggtgagggc tggctgcata ggaaggactg   5340
aggttggaac ggacatcggg aaagctgagg ggcagtgagg tttactacat gggaaaagga   5400
ctcttgaaac gagaatcagt gttgatgtca gggtgaactt tgtgggtaca ttacttggtg   5460
ttaacattgt tggcagtggt agcccctttt cagaaagcaa cttgctgtaa gtcagggtgt   5520
ccgttccaac cttcagctag tgaaaaggta gtaacaaatg gtaaacaaga gaatgattgt   5580
ttaaacctat ctgtggacac ttaatgcaac tgtttaaaaa tgataatcac gagttatgta   5640
```

```
gcaacgtgga aatatattta cagaacatta agtggagaaa gcaggacacg aaagtatatt   5700

tatactacag ttataactca acagttcatt tatatgctgt tcatttaaca gttcatttaa   5760

acagttcatt ataactgttt aaaaatatat atgcttatag tcaaaagctg ttgtggtgtt   5820

gttgttgtag gcttatagtt gagcattatt ttcttaaatt tcttgaatgt tctttatggt   5880

agtgttacta aaaagtttat gatcacattt tcattgtgaa cataatttga actcattatc   5940

acacacttgg aaaatacaga aaagtggagg aaaaaaaatc atatccccac catccaaaga   6000

catatactct cctcttatct tgttcattct tgtttctgtg cacaggttta tgattataac   6060

tgtgtcaaaa tgtatattca aaatagctgt tacattacct ttgtggaatt atggttaaat   6120

actttcactt taattttttc aaatgttccc tataataatg tcctgataac agtgtattat   6180

gtgtgtctcc attggtgtgc ataatacata cccagaggaa aaattagaaa ataaagtaaa   6240

ttattttaaa aaattaccta tattcccaac acctaacaac tactgctaac atcttgatct   6300

gtttcctcta tcttgtttca gtgcacacgc ttgtgataac agtgttaaat atgtgtgcat   6360

aaagtcttaa atgaaaagat gtggaaaata actaaaatag tgttgtcatt gtgggaattt   6420

ggttaaatat tttgtctcaa attccttaaa taatctttgg tgttttggta ataaatttta   6480

tgtatgtatt ttccattaca aatataatac atactcatac aaaactttgg aaattcagta   6540

aagaaaattc acacatattc ccaacaccca acaacaatta actgttaaca tcttgatctg   6600

tgcactagtc tgtgattatt agggtgttag tgataagtat gcataaatgt caaagatggg   6660

aagaaagatg aaaaacaaga aatagttgtg tggttgttgt gggattatgg ttattttgtt   6720

tcggtttcct tgaaaggtca tcattctagt gttttggtag tccaccttta ctacatatat   6780

ttccattata tatgaaatgt gttcattata gaaactttga agttacagaa atgtagaaga   6840

gaaactcacc catgttttca ccatccaaag agtgtggtta acatcttgat atattttctt   6900

catcttgttt ctgtgcacag gtttttggtt tgttaatatg gttgtggtca ttctatctgt   6960

aatagtgtca acaataaaaa taaagttaaa aat                                6993
```

<210> SEQ ID NO 93
<211> LENGTH: 1182
<212> TYPE: DNA
<213> ORGANISM: Homo sapiens

<400> SEQUENCE: 93

```
ggcactgccc caatgtgagt ctccttccca ggctacgaat actcggacca gaagtcggga     60

aagtcaaagg ggaaggatgt taacttggcg gagttcgctg tggctgcagg ggaccagatg    120

ctttacagga gtgaggacat ccagctagat tacaaaaaca acatcctgaa ggagagggcg    180

gagctggccc acagcccccct gcctgccaag tacatcgacc tagacaaagg gttccggaag    240

gagaactgca aatagggagg ccctgggctc ctggctgggc cagcagctgc acctctcctg    300

tctgtgctcc tcggggcatc tcctgatgct ccggggctca ccccccttcc agcggctggt    360

cccgctttcc tggaatttgg cctgggcgta tgcagaggcc gcctccacac ccctccccca    420

ggggcttggt ggcagcatag cccccacccc tgcggccttt gctcacgggt ggccctgccc    480

acccctggca caaccaaaat cccactgatg cccatcatgc cctcagaccc ttctgggctc    540

tgcccgctgg gggcctgaag acattcctgg aggacactcc catcagaacc tggcagcccc    600

aaaactgggg tcagcctcag ggcaggagtc ccactcctcc agggctctgc tcgtccgggg    660

ctgggagatg ttcctggagg aggacactcc catcagaact tggcagcctt gaagttgggg    720

tcagcctcgg caggagtccc actcctcctg gggtgctgcc tgccaccaag agctccccca    780
```

```
cctgtaccac catgtgggac tccaggcacc atctgttctc cccagggacc tgctgacttg    840

aatgccagcc cttgctcctc tgtgttgctt tgggccacct ggggctgcac cccctgccct    900

ttctctgccc catccctacc ctagccttgc tctcagccac cttgatagtc actgggctcc    960

ctgtgacttc tgaccctgac acccctccct tggactctgc ctgggctgga gtctagggct   1020

ggggctacat ttggcttctg tactggctga ggacagggga gggagtgaag ttggtttggg   1080

gtggcctgtg ttgccactct cagcacccca catttgcatc tgctggtgga cctgccacca   1140

tcacaataaa gtccccatct gatttttaga aaaaaaaaaa aa                      1182


<210> SEQ ID NO 94
<211> LENGTH: 2626
<212> TYPE: DNA
<213> ORGANISM: Homo sapiens

<400> SEQUENCE: 94

gggtacggct gcgagaagac gacagaaggg gatgtcacct gctttatttc tggctttggc     60

ctgtggtctg tgataccat cctgcttgat gttctgcaga atggcacttg actgctgggc    120

atgcatgaag ttaagggcaa gaaacagtat gccatgtgtt ctgtaccatc atgtgtctct    180

tcttgcttct gggcccttct actggtgaac tttcatcaag atctgcgcca tgccgtgtca    240

ctatcaagcc attaagtttt gtctgggttg ctgtcagccc cagttggctt cctggtcaac    300

aaggacctca agaactgcct gtggaccgag gccccctacc agtgcatgag acacacacct    360

accctcccca gctttccagg aaccctactg gctgccagac tgatgggcgg gctggtatgt    420

gtggacatgt gttcactgtc attatgctgt ggctccaggt gagggtgagg actgggccta    480

tatagaatcc agataccatt gtcaacttcc cttattcccg tctaagatgt gagcagagtg    540

ccatagtagg ggttctggga agaggtattt ctgatttgtg ggcctctgct tgcttgactt    600

caggtcactt atacttctta ttttgcttgc ctgccttcat ccctcatttc ctccctctca    660

ttcttctttc ctccctccct ttcctggtag cctcctttcc tccccttctg ccttcccctt    720

ccttctttcc ttattctttt ttattttgtt taaatagtac cacagagaaa acaactgaaa    780

aaccacattt ttctacatac agctggggag gtagctgaga acttggcact gcgcacacat    840

actaggttga aagagagttg aggaaaccag aaggccaagt ggatctgctg gcaaaccctg    900

aacctgtctc ctgcgcttgc tctacagttc tgaagttgaa aatcgttttc atgcctagca    960

tctgcttgag ttataaaccc caaggcagcc atgtcataga ctagtgttta ctcttgtttt   1020

gactttgttt taatgcttcc taagacccaa gtgcctcctg ctgtttcctc ctttgtggta   1080

gcctctggcc atctggacct caatccccag ctttcccact ttcagcagtc ctttgctctc   1140

tttgcttcta cctcaaatag ccccaggagt gggctttagt ctccaatatg gagcatctca   1200

agcttctcct gggggatggg gattgggatg ggcggaatct gttttggatc tccgggttat   1260

ttccagtggg tgtaaaagca gagctgggcc tttccctctc ttatccctga gggtgggtaa   1320

gaaggactgt atctacacct gttcttccct accttctctt ttgttaggga ggcctcattc   1380

taagttcctc aagagagtcc ttggcttaaa gctgtagcaa gggtgtgcta ggtgggggat   1440

ttggagcaaa accgtcgagt aggcatgata ctggtatgga gtgggcctgc aaaatcagac   1500

agaaatggct tgagaagccg cagggggagc atgcctgtct ctcagtgata gagtatggga   1560

gggacctccc tagcttggaa aatgagaatt gaaggggtta tgaacaaata ggatgcctag   1620

ttgaggatgt tcccaaagtt ttgtccaatc ttatcattag tagattttat aagccacaga   1680

gacaaaccag aaacggaata atgttacttt ggatgcttta tttttttgtt ctaggtgtgg   1740
```

```
ctttgtacat gcagaagaat gctatatgct gcacattttg cctttaaagt cttacgactt   1800

tccccatttt agtctaatgg gaagatacag atgtgcaagt ctgctttttt gtttttttgtt   1860

attatttttt tttttgctct gtgttatgga cattttcaga catgcacaga agtggagagg   1920

atggtccttg gaccccatgt gtccatcacc tagctgcatc acttatcagc tatggtcaac   1980

ctggtttcat ctgtatctct ctcttttcac ctgtattgtt tattgaaaat ccaagacact   2040

atgccaatgc aaccgtgact actttgggag attggtagtc tcttttgatg gtgatagtga   2100

tggggtgcac tatcataatc acatcaggtc tgctttttgc ttttaatgtt aactaatgaa   2160

gttccagaga tgggccttag aaatgtgttt taagaattaa caaggagtct caaaaagaaa   2220

tgagagggat gcttcctttc ccttgcatct acaaaacaag agagagactg ttctgttgta   2280

aaactctttc aaaaattctg atatggtaag gtacttgaga cccttcacca gaatgtcaat   2340

cttttttctt gtgtaacatg gaaacttgtg tgaccattag cattgttatc agcttgtact   2400

ggtctcataa ctctggtttt ggaagaataa tttggaaatt gttgctgtgt tctgtgaaaa   2460

taacctcccc aaaataatta gtaactggtt gttctacttg gtaatttgac accctgttaa   2520

taacgcaatt atttctgtgt tcttaaacag tataaatagt tgtaagtttg catgcatgat   2580

ggaaaaataa aaacctgtat ctctgtcaaa aaaaaaaaaa aaaaaa                  2626
```

<210> SEQ ID NO 95
<211> LENGTH: 1347
<212> TYPE: DNA
<213> ORGANISM: Homo sapiens

<400> SEQUENCE: 95

```
gacttggcac ttttaaaggt aacttcacca aagaccgaag agccagtaac cagtagctcc     60

aacttgtctc agcatcacat cttctgtgct ctttattttt gccggaccag tttgcggtta    120

ggagaatgtg cctttttttgt acctttgcat ttaggtttta taattttaat tgatgtatgg   180

acacacacaa acaaaaaagc atgaaggaag atttggatcc aagcagtgcc acactttaca    240

tcatcactac aagtgttcaa gtgtaaagaa aaccaatttt gaaactatga aattcctgat    300

tcataaatac acagttattt ctactttagt acatataaga taattcactg ttattaaagc    360

tcttttatta aggcaattgc atatgtttta aaagcaatgg taaattaagt tgtcttccaa    420

aactgtgtac ttgtctggtc agctgtgtat gatcagttat ctacctcaga gtctattttc    480

ttttgtgctg ggacaggttg ctggccctcc ctgtttccac agaccaaatc ctcctagctc    540

aggagctagg gctaagcagt tatttctttc aagtattttt tagttcttaa attttatgct    600

tgtatttgat gatagatgtc agtgacattt catagtttca aaagtccttg ctgctctgag    660

gagtgtagat tctagtgaaa attacatagt cataagagaa atgtgttttt gtttttgttt    720

ttgtttcatt tttttaaagt tgtggtatta ttggttctat gctccctgga atattactgc    780

tttgtgaaag tccagactga acgcagcacc ctctgtgtac ctagtacagt tataaacctg    840

ggtctctcac tacttgatat ttttgcatta gttaagacag aaatttgata gctcggttag    900

aggggagggg aaatctgctg ctggaaatgt ctgaactaag tgccatactc gtctgggtaa    960

gatttgggaa acataacctc tgtacataaa aaaaaaaaat cagttaaaca tcacatagta   1020

gacagccatt aaattataaa aaaattaatt tatgaagaaa gaccttttgt acagattgaa   1080

aaaaaaaaga ttttcataga gatatctata tgatcaagag agttaatttt ttatttttgt   1140

tttactagtg ccacagactt gccagtggta acttatttgt ccggttcaag ataactctgt   1200

agttttcttt cctaggactt gttgttaaac gccaaaagac atttttgaac tgtacattttg   1260
```

atcagattgt tagcttttct gttttatttc ttttgagaac ctttgaataa aaaacatctg 1320
aaattttaaa aaaaaaaaaa aaaaaaa 1347

<210> SEQ ID NO 96
<211> LENGTH: 1643
<212> TYPE: DNA
<213> ORGANISM: Homo sapiens

<400> SEQUENCE: 96
atggccctgc tgccccgagc cctgagcgcc ggcgcgggac cgagctggcg gcgggcggcg 60
cgcgccttcc gaggcttcct gctgcttctg cccgagcccg cggccctcac gcgcgccctc 120
tcccgtgcca tggcctgcag gcaggagccg cagccgcagg gcccgccgcc cgctgctggc 180
gccgtggcct cctatgacta cctggtgatc gggggcggct cgggcgggct ggccagcgcg 240
cgcagggcgg ccgagctggg tgccagggcc gccgtggtgg agagccacaa gctgggtggc 300
acttgcgtga atgttggatg tgtacccaaa aaggtaatgt ggaacacagc tgtccactct 360
gaattcatgc atgatcatgc tgattatggc tttccaagtt gtgagggtaa attcaattgg 420
cgtgttatta aggaaaagcg ggatgcctat gtgagccgcc tgaatgccat ctatcaaaac 480
aatctcacca agtcccatat agaaatcatc cgtggccatg cagccttcac gagtgatccc 540
aagcccacaa tagaggtcag tgggaaaaag tacaccgccc cacacatcct gatcgccaca 600
ggtggtatgc cctccacccc tcatgagagc cagatccccg gtgccagctt aggaataacc 660
agcgatggat tttttcagct ggaagaattg cccggccgca gcgtcattgt tggtgcaggt 720
tacattgctg tggagatggc agggatcctg tcagccctgg gttctaagac atcactgatg 780
atacggcatg ataaggtact tagaagtttt gattcaatga tcagcaccaa ctgcacggag 840
gagctggaga acgctggcgt ggaggtgctg aagttctccc aggtcaagga ggttaaaaag 900
actttgtcgg gcttggaagt cagcatggtt actgcagttc ccggtaggct accagtcatg 960
accatgattc cagatgttga ctgcctgctc tgggccattg ggcgggtccc gaataccaag 1020
gacctgagtt taaacaaact ggggattcaa accgatgaca agggtcatat catcgtagac 1080
gaattccaga ataccaacgt caaaggcatc tatgcagttg gggatgtatg tggaaaagct 1140
cttcttactc cagttgcaat agctgctggc cgaaaacttg cccatcgact tttgaatat 1200 aaggaagatt ccaaattaga ttataacaac atcccaactg tggtcttcag ccaccccct 1260 attgggacag tgggactcac ggaagatgaa gccattcata aatatggaat agaaaatgtg 1320
aagacctatt caacgagctt taccccgatg tatcacgcag ttaccaaaag gaaaacaaaa 1380
tgtgtgatga aaatggtctg tgctaacaag gaagaaaagg tggttgggat ccatatgcag 1440
ggacttgggt gtgatgaaat gctgcagggt tttgctgttg cagtgaagat gggagcaacg 1500
aaggcagact ttgacaacac agtcgccatt caccctacct cttcagaaga gctggtcaca 1560
cttcgttgag aaccaggaga cacgtgtggc gggcagtggg acccatagat cttctgaaat 1620
gaaacaaata atcacattga ctt 1643

<210> SEQ ID NO 97
<211> LENGTH: 2099
<212> TYPE: DNA
<213> ORGANISM: Homo sapiens

<400> SEQUENCE: 97
aactctggga attgaagttt ctgtggaagg aagcgtgagc cgtaaccagg ccaacccaga 60
aaggctttct ttctgagatt tcacttccct gtcaactctt cagctcgagg caccaaataa 120

```
tgtcatctga aatgttgcca gcatttattg aaacttctaa tgttgacaaa aagcaaggca    180

taaatgaaga tcaagaggag agccagaagc caagattagg tgaagggtgt gaaccaatat    240

ctaaacgaca aatgaaaaaa ctaataaaac agaaacaatg ggaagagcaa cgggaactcc    300

gcaaacaaaa gcgaaaagaa aaacgcaaga ggaaaaaatt agagcgacaa tgtcaaatgg    360

aaccaaactc agatggacat gacagaaaac gtgttcgaag agatgttgtt catagcaccc    420

ttcgccttat tattgactgt agttttgatc acttgatggt attaaaggac attaagaaac    480

ttcataagca gattcaacga tgttacgcag aaaaccgacg ggcactgcat cctgtgcagt    540

tttacttgac aagccacgga ggccagctga aaaagaacat ggatgaaaat gacaaaggat    600

gggtcaactg gaaggatatc catatcaaac cagagcacta tagtgaactc ataaagaaag    660

aagacctgat ttaccttacg tcagattcac ctaatatact gaaggaatta gatgaatcag    720

aggcctatgt gattggagga ttagtagatc acaaccatca caagggactc acatataaac    780

aagcgtcaga ttatggaatc aatcatgcac agctcccact tggaaatttt gtgaagatga    840

atagtcgaaa agttttggca gttaatcatg tgtttgaaat tattctggaa tacctggaaa    900

caagagactg gcaagaagca tttttacta tcttgcccca acggaaagga gctgttccca    960

cagacaaagc ctgtgaaagt gcttctcatg acaatcagtc tgtcaggatg gaggaaggtg   1020

gatcggacag tgattccagt gaggaggaat atagcagaaa tgaactagat tcaccacatg   1080

aagaaaagca ggataaggaa aatcacactg aatctacagt gaactctctg ccacactaat   1140

gttacctggt ttcctttag tttaaggaaa aattaggaga aagtgaggtg ctatatagaa   1200

tattgaaatt ggaagaacat tttattttct cttatttctg ttgtgatttt taaaaacttt   1260

tttttggacc taaataataa taaaaaaaaa agccctttaa actttgtaag gaaatatttt   1320

ttgattttgc gtaagaagat ttaaatgtgt atgtgatttt ttttgttttt gtttttaaag   1380

cctcagtagt ttctagataa ttttactgta ttagtatatt ttcattttct ttcattttat   1440

attctttaga atgtgccttc tgacctttca gtttttaat tttatagtca catcaacatc   1500

tttatgatct attgcctata tatctgtgag ggcacatatt cataaatata ctgtcaatct   1560

atcagcattt gtgtatggta ggttaccctc tatttgcagc ttttatgttt aaattagtta   1620

cttgaaagaa tgtagtaatt ttaggaagaa gtatcagttt gatagactta ataattcatt   1680

tcttttggac tatggagcgc atatctgttc cttctttatg atgccttttt atggttctga   1740

agtaattact gaagagttga gaatctcttt aatgcatttt cttaattctt acaatggtga   1800

taagttactt caattataaa attgaatttt gcagactaaa ttattttata aggctgttgc   1860

tattgaaaga tcaattttgt cttacctgca tttaaaatgg aacagctctt agcagctgtg   1920

gttttttttt ccatattttt tttaaatttg ttggctctta agatgaataa agtttatagg   1980

tgcatctgcc tcctcttctc taagaatatg catactaatg tttgtttcta taaatcaaat   2040

acacatgtga taatatgcat gtaaatacat aactatcctc atcaaaaaaa aaaaaaaaa    2099
```

<210> SEQ ID NO 98
<211> LENGTH: 1027
<212> TYPE: DNA
<213> ORGANISM: Homo sapiens

<400> SEQUENCE: 98

```
aggcccgtgg atctcatcga agatggcggc gcgatctgtg tcgggcatta ccagaagagt     60

cttcatgtgg acagtctcag ggacaccatg tagagaattt tggtctcgat tcagaaaaga    120

gaaagagcca gtggttgttg agacagtaga agagaaaaag gaacctatcc tagtgtgtcc    180
```

```
acctttacga agccgagcat acacaccacc tgaagatctc cagagtcgtt tggaatctta    240
cgttaaagaa gtttttggtt catctcttcc tagtaattgg caagacatct ccctggaaga    300
tagtcgtcta aagttcaatc ttctggctca tttagctgat gacttgggtc atgtagtccc    360
taactccaga ctccaccaga tgtgcagggt tagagatgtt cttgatttct ataatgtccc    420
tattcaagat agatctaaat ttgatgaact cagtgccagt aatctgcccc ccaatttgaa    480
aatcacttgg agttactaag caattcggaa gagaaacaca ttgaaatcac tgtctttccc    540
tgagcaaggg ggctgctcat tagatctttt gatactttac catgtgaaat actaccagaa    600
ctgttctcta aacccacttt ttctgtagag gaatgtatca tcttttttt tctcatatta     660
caaatggaca aataacggac tttctatttt catatttgct gaaaccattt tttaaatgaa    720
attaggtcat tatttatgaa aagttttgag agggcactgt caacttgggt ttaagacagg    780
aggacattgc aagttcacac ctttcataag cataaagtag ttgcaagaaa gtattttcat    840
cctgttagga ttcatatcta agatagagtt atgcattgca catacacaaa taaactttta    900
ttagatagat acctataaaa gaaacataaa agtatgttgt gtattactga cagttctaga    960
ttaatttctt ttagaattaa agcagatttg ttaaagtgaa aaaaaaaaaa aaaaaaaaaa   1020
aaaaaaa                                                             1027
```

<210> SEQ ID NO 99
<211> LENGTH: 3658
<212> TYPE: DNA
<213> ORGANISM: Homo sapiens

<400> SEQUENCE: 99

```
ccaggatctc ctctggggga gttttctatt accagaaact tcattacatc agaatccaaa     60
ctcatgatcc tctcttgaaa acagacactc ctcttgagct cctgggcttt ctcgtttcct    120
cctttggtgg tgccatgacg ctcccagctg ccctggcctg ccatccttgc tttgttgtgt    180
ccccagacac ccacagtcag caagtcctgc tgaatcttct tccagagagt tgttgaattc    240
cagcctgggt gacagaacga gactctgtct gaaaaaaaaa aaaggaggaa tgatactacc    300
tgttaatgat actacctgtt aggattattg gggtattaaa tgagatgatt tgacaaagtg    360
ccatttaaag tatatagcat tagataaata ttttatcttt tgtggacttt aacaaatagt    420
ttattgatgg aaattttttta aaaaagcttt taagttacac attttaagtt cctgctactg   480
aaagcaggat taactagtct gtagaataat agtaattttt taattttgtc tccttagctc    540
attacctaaa ggacttattg taaataagct atttaagatc ttaagaaata ctgtattttt    600
ttaaatggaa ggctaagaaa aacataaaca gcctaagcat gtgcattaaa actttgttga    660
cttataagat tattcaaaat atgttatttt aattttggaa ttatattgtt tactttaggc    720
agcagaactt gctgaattca ctgccaagat tgcacttcta gaggaagcca agaagaaaaa    780
ggaagaggaa gctactgagt ggcaacacaa agcttttgca gcccaggaag acttggaaaa    840
gaccaaagaa gagttaaaaa ctgtgatgtc tgcccccccct ccacctccac caccaccagt   900
cattcctcca acagaaaacg aacatgatga acacgatgag aataatgctg aagctagtgc    960
tgaattatca aatgaagggg taatgaacca tagaagcgag gaagaacgtg taaccgaaac   1020
acagaaaaat gagcgtgtta agaagcaact tcaggcatta agttcagaat tagcccaagc   1080
cagagatgaa accaagaaaa cacaaaatga tgttcttcat gctgagaatg ttaaagcagg   1140
ccgtgataag tacaagactc tgcgacagat tcgacaaggc aatacaaagc agcgtatcga   1200
tgagtttgaa gcaatgtgag agctgttatt ttgcatatat gttcttcata agctgaacca   1260
```

-continued

```
ccaacagaga aaagcaggcc tttgcagata tgatggaatg catcccacct tgccaaagca   1320
cttacaccag tttgactgtg ctagctaaaa gacaaattta aggggagctc ttcaacatta   1380
aggcagtatg atatcatgct tggttttctt ttttcttttg gtccagggaa tggagaatgg   1440
tgttccattg cctcttttca catttttttt ctttttcttt ttttttctg ttgaagatta    1500
acactaatta tcacgtctga caaatgtgta tgtgtggttt cagttctgtg tacattttaa   1560
aggataatgg tgaacatttt aatgggtttc ccttgccctt tccatattta acctatttcc   1620
acattctctc tcactcacat tttctcagtg tgcccttctc ttatctgcca tgtccatagc   1680
cataattcca ccatcataca gatcaggcag tgtttaaaat gatggtaggt agcacagtgg   1740
acagtctttg atcatcatgt agaatatggc tatgaatcag gaaagagatt agaacattta   1800
ataatgtatg tacagctggt gcttagtttt tttttaatct aaatttaatt accttattgg   1860
atatttgata tttggttatt taatcacagt catctttaac agcttacact gattggtgtt   1920
ttatctcctg tgatcctttg atggcttttt ttgcctacca tttcacagag gtttagacag   1980
cagtagtagc tccctaggag agtttactga tgaaacagcc tctgcaagat tttaaaagtt   2040
ttgttctttt atagactgat ttagaaaaac aaatgattag ttaaaaaaag aaaatataca   2100
tttgttggta actaatgtta ttttttaaaa cctggacctt tctggaaggg cagcatataa   2160
aaacatcagt cccgaggagg ggacaacaat actacctcac tactacatct gtgatgactg   2220
gttgttcaaa cacaatggag tgtgtaaggt atatgtttta taattcataa ccatagcctc   2280
gatcatcaag aaatactttc gaaatttcat tttccttcag aatatcttaa gagtgctaaa   2340
tttttaactg ccttttgtc gagtcaaact gtgggattct gatttgtatt aaaattgtaa    2400
gctcctcact ggtatactat catcctggag ggtgttgta tggctgagca agagagagag    2460
agaatgagag agagactgtg tgtgtgtgtg tgtgtgtgtg tactctgtgt gtgtatgaga   2520
gagagagaga aatgctaacc ttgtagcatg tgaagaatgt ctgtaccttg atacgatagt   2580
tacataatca gtatatttgg tttctagatc actgtgctta ttttgtttca atctctgact   2640
aaaaatactt aaatttggtt tgttaattct tattttagaa attataattt tagtttatat   2700
taatttcggt tatagcttac tgaagaaatc tttccagtta gaaggaggtt ctaatattca   2760
catgttctaa tactttgttt attgtaaaac agctaaattt ggagatacgt aaagccttgt   2820
tttctctgtg tggttcagct actttccatt tggtattaca cagtcaaatt tacatttatc   2880
tattaaaatt gccattttat taaacatttt catgcacagt agattcaagt tgtgtctgaa   2940
aatatctctt gtgcttttt gattttgctg actttaaaag gattaatctg ggcagacatt     3000
atgtaaaaga aaggttgcgt ttaatatatt ttttgaactt tgtaggacaa aacatagctg   3060
gttaaccttg aagtgactgt tgtaccatgg ttgtgcacat gcttcagaat cctatggaag   3120
agaatattcc tacttgcagt acatcaaagg aatggatggt ggaccctact attcatgttt   3180
tgagacataa atgttcactt taaagcaatt gcataataga taaaaacctg aactttcatt   3240
ggatttttgt taattttcct cattttgaat tatgtgcact accatagcta catcagtttg   3300
atacagtatt gaaaaattat cagttatatt ttgctgttta tgatctattt gtagattagg   3360
attaaaatgg atttaatcca tttttaaggc tgtgtgaatt tttctaaaca agaaccattt   3420
gcaatatgga tttcttagag attaaaccaa ttataactta ttagcagtcg cgagcacatg   3480
ttcatatagt caatgtaaaa atacactaat gagtatttgg taaatcccag taggctttta   3540
ccattagcat aattttgtgt tgtacaatta agttacaatt acatctctaa ttttggataa   3600
tattcattgg ttaacaataa agtgacaaaa gctcatgcaa aaaaaaaaaa aaaaaaa      3658
```

<210> SEQ ID NO 100
<211> LENGTH: 1460
<212> TYPE: DNA
<213> ORGANISM: Homo sapiens

<400> SEQUENCE: 100
cctccacagg cgtcatggcc ctccgattcc tcttgggctt tctgcttgcc ggtgttgacc 60
tgggtgtcta cctgatgcgc ctggagctgt gcgacccaac ccagaggctt cgggtggccc 120
tggcagggga gttggtgggg gtgggagggc acttcctgtt cctgggcctg gcccttgtct 180
ctaaggattg gcgattccta cagcgaatga tcaccgctcc ctgcatcctc ttcctgtttt 240
atggctggcc tggtttgttc ctggagtccg cacggtggct gatagtgaag cggcagattg 300
aggaggctca gtctgtgctg aggatcctgg ctgagcgaaa ccggccccat gggcagatgc 360
tgggggagga ggcccaggag gccctgcagg acctggagaa tacctgccct ctccctgcaa 420
catcctcctc ttcctttgct tccctcctca actaccgcaa catctggaaa aatctgctta 480
tcctgggctt caccaacttc attgcccatg ccattcgcca ctgctaccag cctgtgggag 540
gaggagggag cccatcggac ttctacctgt gctctctgct ggccagcggc accgcagccc 600
tggcctgtgt cttcctgggg gtcaccgtgg accgatttgg ccgccggggc atccttcttc 660
tctccatgac ccttaccggc attgcttccc tggtcctgct gggcctgtgg gattatctga 720
acgaggctgc catcaccact ttctctgtcc ttgggctctt ctcctcccaa gctgccgcca 780
tcctcagcac cctccttgct gctgaggtca tccccaccac tgtccggggc cgtggcctgg 840
gcctgatcat ggctctaggg gcgcttggag gactgagcgg cccggcccag cgcctccaca 900
tgggccatgg agccttcctg cagcacgtgg tgctggcggc ctgcgccctc ctctgcattc 960
tcagcattat gctgctgccg gagaccaagc gcaagctcct gcccgaggtg ctccgggacg 1020
gggagctgtg tcgccggcct tccctgctgc ggcagccacc ccctacccgc tgtgaccacg 1080
tcccgctgct tgccaccccc aaccctgccc tctgagcggc ctctgagtac cctggcggga 1140
ggctggccca cacagaaagg tggcaagaag atcgggaaga ctgagtaggg aaggcagggc 1200
tgcccagaag tctcagaggc acctcacgcc agccatcgcg gagagctcag agggccgtcc 1260
ccaccctgcc tcctccctgc tgctttgcat tcacttcctt ggccagagtc aggggacagg 1320 gaggggagctc cacactgtaa ccactgggtc tgggctccat cctgcgccca aagacatcca 1380
cccagacctc attatttctt gctctatcat tctgtttcaa taaagacatt tggaataaac 1440
gagcatatca tagcctggac 1460

<210> SEQ ID NO 101
<211> LENGTH: 60
<212> TYPE: DNA
<213> ORGANISM: Homo sapiens

<400> SEQUENCE: 101
gataggttgg agacaattga ttgctcgatg atataaaatg ttaagtacca tgaatgatgc 60

<210> SEQ ID NO 102
<211> LENGTH: 60
<212> TYPE: DNA
<213> ORGANISM: Homo sapiens

<400> SEQUENCE: 102
gaagtgctgg atttgtgtat cactggctat cagttcctca tgttgttaag cctcacacag 60

<210> SEQ ID NO 103

<211> LENGTH: 60
<212> TYPE: DNA
<213> ORGANISM: Homo sapiens

<400> SEQUENCE: 103
aagttgttgt gcaatactta attcagacat gtaccacaag ttaatggtag actaacactg 60

<210> SEQ ID NO 104
<211> LENGTH: 60
<212> TYPE: DNA
<213> ORGANISM: Homo sapiens

<400> SEQUENCE: 104
atcatgggga taaccggaat tgatacaatg tcttgattca agattcagag ctcatttttt 60

<210> SEQ ID NO 105
<211> LENGTH: 60
<212> TYPE: DNA
<213> ORGANISM: Homo sapiens

<400> SEQUENCE: 105
acaacattta cctaatgtca ttcactaaca tggaagagtt gtgaaaattc tagagtgctg 60

<210> SEQ ID NO 106
<211> LENGTH: 60
<212> TYPE: DNA
<213> ORGANISM: Homo sapiens

<400> SEQUENCE: 106
ctgagagaca accacagtga catcgtcaac gccatcatgg aactgaccat gtagccactg 60

<210> SEQ ID NO 107
<211> LENGTH: 60
<212> TYPE: DNA
<213> ORGANISM: Homo sapiens

<400> SEQUENCE: 107
gaactggatg aatcatacca gaaagtaatt gaactcttct ctgtatgcac taatgaagac 60

<210> SEQ ID NO 108
<211> LENGTH: 60
<212> TYPE: DNA
<213> ORGANISM: Homo sapiens

<400> SEQUENCE: 108
tggtctagaa ataagcatag cacagttaat ggacattacc acaatggaat cctcaatggc 60

<210> SEQ ID NO 109
<211> LENGTH: 60
<212> TYPE: DNA
<213> ORGANISM: Homo sapiens

<400> SEQUENCE: 109
ctttggacca aagatctctt tcgtgattcc ttgcaacaat caatgagaat cttcatgtat 60

<210> SEQ ID NO 110
<211> LENGTH: 60
<212> TYPE: DNA
<213> ORGANISM: Homo sapiens

<400> SEQUENCE: 110
tgcatgtaaa ttgcagagaa aacaaaacca aagctgattg gaaacaatta attgtgggtg 60

<210> SEQ ID NO 111

<211> LENGTH: 60
<212> TYPE: DNA
<213> ORGANISM: Homo sapiens

<400> SEQUENCE: 111
aacaagagac cacttcctta acagctgtat tatcttaaac ccacataaac acttctcctt 60

<210> SEQ ID NO 112
<211> LENGTH: 60
<212> TYPE: DNA
<213> ORGANISM: Homo sapiens

<400> SEQUENCE: 112
ttcaagtgct ctcatagttc tatcctctaa ttccattaaa tccatactag gagcgtcagt 60

<210> SEQ ID NO 113
<211> LENGTH: 60
<212> TYPE: DNA
<213> ORGANISM: Homo sapiens

<400> SEQUENCE: 113
gaggagatcc cgcccgactg gaggatagag aagacgtacc tctacctgtg ctatgtgtga 60

<210> SEQ ID NO 114
<211> LENGTH: 60
<212> TYPE: DNA
<213> ORGANISM: Homo sapiens

<400> SEQUENCE: 114
gagtgcgcga gaaacagaag ctcttccagg aggacaatga catcccgttg tacctgaagg 60

<210> SEQ ID NO 115
<211> LENGTH: 60
<212> TYPE: DNA
<213> ORGANISM: Homo sapiens

<400> SEQUENCE: 115
ccccaagaaa tagatgccct ttcttgaatt gcatttttta aaacaagaaa gtttccccac 60

<210> SEQ ID NO 116
<211> LENGTH: 60
<212> TYPE: DNA
<213> ORGANISM: Homo sapiens

<400> SEQUENCE: 116
ttaatcgatc agatttttcc agaattccgt atcagtcacc attttaatat ggggacaatg 60

<210> SEQ ID NO 117
<211> LENGTH: 60
<212> TYPE: DNA
<213> ORGANISM: Homo sapiens

<400> SEQUENCE: 117
gcaagaactc tgggcttggg taatgagcag gaagaaaatt ttctgatctt aagcccagct 60

<210> SEQ ID NO 118
<211> LENGTH: 60
<212> TYPE: DNA
<213> ORGANISM: Homo sapiens

<400> SEQUENCE: 118
gagtttaaat agaatgcatt taggcattgt agagatctga aatagttttc ttccactgcg 60

<210> SEQ ID NO 119

<211> LENGTH: 60
<212> TYPE: DNA
<213> ORGANISM: Homo sapiens

<400> SEQUENCE: 119
caaaatgaac cagatacccc ctagaaaatt atactattga gaaatctatg gggaggatat 60

<210> SEQ ID NO 120
<211> LENGTH: 60
<212> TYPE: DNA
<213> ORGANISM: Homo sapiens

<400> SEQUENCE: 120
gcatatgtga ctgtcatgag atcctactta gtatgatcct ggctagaatg ataattaaaa 60

<210> SEQ ID NO 121
<211> LENGTH: 60
<212> TYPE: DNA
<213> ORGANISM: Homo sapiens

<400> SEQUENCE: 121
cacggagtgt gccaaaacta aaaagcattt tgaaacatac agaatgttct attgtcattg 60

<210> SEQ ID NO 122
<211> LENGTH: 60
<212> TYPE: DNA
<213> ORGANISM: Homo sapiens

<400> SEQUENCE: 122
ttgttatgta tatagatgtg caagtcttgt cagaattggc ctcagtgtag ttaaagggca 60

<210> SEQ ID NO 123
<211> LENGTH: 60
<212> TYPE: DNA
<213> ORGANISM: Homo sapiens

<400> SEQUENCE: 123
tgtccacatt gtgatgttca gtatttgagc ttatagtgaa ctgagcaatc ataaataagc 60

<210> SEQ ID NO 124
<211> LENGTH: 60
<212> TYPE: DNA
<213> ORGANISM: Homo sapiens

<400> SEQUENCE: 124
tgtgatccag ggaatgaaaa gaaatttgac cctggattgg ttctctcctt ggacttaagg 60

<210> SEQ ID NO 125
<211> LENGTH: 60
<212> TYPE: DNA
<213> ORGANISM: Homo sapiens

<400> SEQUENCE: 125
cgatacaata ttgttaagct gtattataag tattgttaca cagggttatg caattcccgg 60

<210> SEQ ID NO 126
<211> LENGTH: 60
<212> TYPE: DNA
<213> ORGANISM: Homo sapiens

<400> SEQUENCE: 126
gatgaagcca ttcataaata tggaatagaa aatgtgaaga cctattcaac gagctttacc 60

<210> SEQ ID NO 127

<211> LENGTH: 60
<212> TYPE: DNA
<213> ORGANISM: Homo sapiens

<400> SEQUENCE: 127
tgcagtgagg gtcaaaggag agtcaacata tgtgattgtt ccataataaa cttctggtgt 60

<210> SEQ ID NO 128
<211> LENGTH: 60
<212> TYPE: DNA
<213> ORGANISM: Homo sapiens

<400> SEQUENCE: 128
acttctagac ctgctccaaa ctagtgacta ggatagaatt tgatccccta actcactgtc 60

<210> SEQ ID NO 129
<211> LENGTH: 60
<212> TYPE: DNA
<213> ORGANISM: Homo sapiens

<400> SEQUENCE: 129
ccacacctgg gactgttttt aatacatagc aacagactgg gttatttatt taagatgtgt 60

<210> SEQ ID NO 130
<211> LENGTH: 60
<212> TYPE: DNA
<213> ORGANISM: Homo sapiens

<400> SEQUENCE: 130
tggtttaatg gaaagaataa aagtaaatga aaaacacacc ctacacacta gactccgaac 60

<210> SEQ ID NO 131
<211> LENGTH: 60
<212> TYPE: DNA
<213> ORGANISM: Homo sapiens

<400> SEQUENCE: 131
tcctgtgcta gatggtagcc agagaatttt atagtaatgg aggttagccc ttaatctctt 60

<210> SEQ ID NO 132
<211> LENGTH: 60
<212> TYPE: DNA
<213> ORGANISM: Homo sapiens

<400> SEQUENCE: 132
gtaaatgcca caactgtact tttccaaaga aaaagaacta ttgacaactt atagcctgtc 60

<210> SEQ ID NO 133
<211> LENGTH: 60
<212> TYPE: DNA
<213> ORGANISM: Homo sapiens

<400> SEQUENCE: 133
gcttgaaaaa gattagcata catctaatgt gaaaagacca catttgattc aactgagacc 60

<210> SEQ ID NO 134
<211> LENGTH: 60
<212> TYPE: DNA
<213> ORGANISM: Homo sapiens

<400> SEQUENCE: 134
gtggcgttct cttgtaagtg gaaatgtaat tgtgtaccag tttcttaaaa taaacaaagc 60

<210> SEQ ID NO 135

<211> LENGTH: 60
<212> TYPE: DNA
<213> ORGANISM: Homo sapiens

<400> SEQUENCE: 135
tcctgagtga gtctgactga aaaatacgag agaaaagaga gtggtttccg tttgcagcta 60

<210> SEQ ID NO 136
<211> LENGTH: 60
<212> TYPE: DNA
<213> ORGANISM: Homo sapiens

<400> SEQUENCE: 136
ggaaacaaag ggttagtcat tagctgagat gttgatttta aaacaccttg accttaactt 60

<210> SEQ ID NO 137
<211> LENGTH: 60
<212> TYPE: DNA
<213> ORGANISM: Homo sapiens

<400> SEQUENCE: 137
aggctggaac acctgtacct caacaacaat agcatcgaga aaatcaacgg aacccagatt 60

<210> SEQ ID NO 138
<211> LENGTH: 60
<212> TYPE: DNA
<213> ORGANISM: Homo sapiens

<400> SEQUENCE: 138
agaaacatct acaggatctt tattggtgac cttttgtaag acattagttt gaggtactac 60

<210> SEQ ID NO 139
<211> LENGTH: 60
<212> TYPE: DNA
<213> ORGANISM: Homo sapiens

<400> SEQUENCE: 139
gtgcactcaa ctagagtatt aactgtaaaa agatttgtga agtttggaag ctctattcgc 60

<210> SEQ ID NO 140
<211> LENGTH: 60
<212> TYPE: DNA
<213> ORGANISM: Homo sapiens

<400> SEQUENCE: 140
acaaactgtt gtgctattgg atacttaggt ggtttcttca ctgacaatac tgaataaaca 60

<210> SEQ ID NO 141
<211> LENGTH: 60
<212> TYPE: DNA
<213> ORGANISM: Homo sapiens

<400> SEQUENCE: 141
ccctcaccac gtccggattt ccttctttgg atggaatgta acgcgatctc tatttaataa 60

<210> SEQ ID NO 142
<211> LENGTH: 60
<212> TYPE: DNA
<213> ORGANISM: Homo sapiens

<400> SEQUENCE: 142
agacgtctaa tgaccattct ccatatacct ttcaacctaa taagtaactg tgagatgtac 60

<210> SEQ ID NO 143

<211> LENGTH: 60
<212> TYPE: DNA
<213> ORGANISM: Homo sapiens

<400> SEQUENCE: 143
cattatgcct tccgcatctt tgactttgat gatgacggaa ccttgaacag agaagacctg 60

<210> SEQ ID NO 144
<211> LENGTH: 60
<212> TYPE: DNA
<213> ORGANISM: Homo sapiens

<400> SEQUENCE: 144
ggcctaaaat gggtgatata caggtcttat atccccatat ggaatttatc catcaaccac 60

<210> SEQ ID NO 145
<211> LENGTH: 60
<212> TYPE: DNA
<213> ORGANISM: Homo sapiens

<400> SEQUENCE: 145
aaacttctat tacaccctat attgcatctc ctgtatctgc ctaccaggtg caaagtcctt 60

<210> SEQ ID NO 146
<211> LENGTH: 60
<212> TYPE: DNA
<213> ORGANISM: Homo sapiens

<400> SEQUENCE: 146
tgagatgggc cattgaaaac tcattacaag ctgtttagac tctgactttg acttttgctc 60

<210> SEQ ID NO 147
<211> LENGTH: 60
<212> TYPE: DNA
<213> ORGANISM: Homo sapiens

<400> SEQUENCE: 147
aaatcatcct tgaagggtta tagtgaagat taaataggat gaggcattga aagtgtttgg 60

<210> SEQ ID NO 148
<211> LENGTH: 60
<212> TYPE: DNA
<213> ORGANISM: Homo sapiens

<400> SEQUENCE: 148
agattgcaag aacatgtaaa atgtacggag cttcataata cgttatattg ttccgaagca 60

<210> SEQ ID NO 149
<211> LENGTH: 60
<212> TYPE: DNA
<213> ORGANISM: Homo sapiens

<400> SEQUENCE: 149
gtaagggcca ctgatatgac aagaatgatt atcccacagt aagaatgggt aaaacttaat 60

<210> SEQ ID NO 150
<211> LENGTH: 60
<212> TYPE: DNA
<213> ORGANISM: Homo sapiens

<400> SEQUENCE: 150
ccaaattgtt taattgtggt gaatcatatg taaattgttc agatgtaggt caacacccac 60

<210> SEQ ID NO 151

<211> LENGTH: 60
<212> TYPE: DNA
<213> ORGANISM: Homo sapiens

<400> SEQUENCE: 151
aaagtattta ttgagtcacg gattattgtg catcaagcaa ttgttaatat gacctggtcc 60

<210> SEQ ID NO 152
<211> LENGTH: 60
<212> TYPE: DNA
<213> ORGANISM: Homo sapiens

<400> SEQUENCE: 152
ggcagtaaga gtctatgatg ttctgaaact tttcacagta aatccaaaga ttacagacct 60

<210> SEQ ID NO 153
<211> LENGTH: 60
<212> TYPE: DNA
<213> ORGANISM: Homo sapiens

<400> SEQUENCE: 153
agacgtgcct ttaagcaata aaaattccaa gagctgatca ttattgtgct tccattttag 60

<210> SEQ ID NO 154
<211> LENGTH: 60
<212> TYPE: DNA
<213> ORGANISM: Homo sapiens

<400> SEQUENCE: 154
ctgcctgaat gcaacagtaa tttatatcca ggacaaatac agtctgggcg tcactatcct 60

<210> SEQ ID NO 155
<211> LENGTH: 60
<212> TYPE: DNA
<213> ORGANISM: Homo sapiens

<400> SEQUENCE: 155
atctgagaag tttttgcatc cgtaaaacag aaaacagcac gaactttagg aaatgacaat 60

<210> SEQ ID NO 156
<211> LENGTH: 60
<212> TYPE: DNA
<213> ORGANISM: Homo sapiens

<400> SEQUENCE: 156
agatattcag aagatgaaaa cgtagaagac acccctgaat taaaaacact tacatagcag 60

<210> SEQ ID NO 157
<211> LENGTH: 60
<212> TYPE: DNA
<213> ORGANISM: Homo sapiens

<400> SEQUENCE: 157
agaatgccag atcttccaga ttaggctaaa tgtaatgaaa acctcttagg attatctgtg 60

<210> SEQ ID NO 158
<211> LENGTH: 60
<212> TYPE: DNA
<213> ORGANISM: Homo sapiens

<400> SEQUENCE: 158
agttacaagc tatatcaatg tcaaagtaaa tgcacttcat caaagctaag aagtcacagg 60

<210> SEQ ID NO 159

<211> LENGTH: 60
<212> TYPE: DNA
<213> ORGANISM: Homo sapiens

<400> SEQUENCE: 159
tggaagtatc tgatatttga caatggtaaa tttccactta gctagctagc attgtcagac 60

<210> SEQ ID NO 160
<211> LENGTH: 60
<212> TYPE: DNA
<213> ORGANISM: Homo sapiens

<400> SEQUENCE: 160
agcagcaata tctgttacta gagaacattc ccatgtgttt aaactcttca cttcttagat 60

<210> SEQ ID NO 161
<211> LENGTH: 60
<212> TYPE: DNA
<213> ORGANISM: Homo sapiens

<400> SEQUENCE: 161
gtgcctacat tttgttattt ttggcattac tacagagcca tgtacaatag aaagcaatgc 60

<210> SEQ ID NO 162
<211> LENGTH: 60
<212> TYPE: DNA
<213> ORGANISM: Homo sapiens

<400> SEQUENCE: 162
agggctgagt aattgccttt catacaaata aaagctttaa ctcttttctc aagagtgtac 60

<210> SEQ ID NO 163
<211> LENGTH: 60
<212> TYPE: DNA
<213> ORGANISM: Homo sapiens

<400> SEQUENCE: 163
tgactcctaa agtcttgctg tcctatcctc aatgctgtta aaaacttctg aggttccagt 60

<210> SEQ ID NO 164
<211> LENGTH: 60
<212> TYPE: DNA
<213> ORGANISM: Homo sapiens

<400> SEQUENCE: 164
ctatggtgct gagaatgaaa atctaaatga ttgaagtttt aagtccaagt aggagttggt 60

<210> SEQ ID NO 165
<211> LENGTH: 60
<212> TYPE: DNA
<213> ORGANISM: Homo sapiens

<400> SEQUENCE: 165
gtgtataaat cctggtgtat gctccttatc ctggacatga atgtattgta cactgacgcg 60

<210> SEQ ID NO 166
<211> LENGTH: 60
<212> TYPE: DNA
<213> ORGANISM: Homo sapiens

<400> SEQUENCE: 166
gtattcagat ttcataaaac acttccttgg aatatagctg cattaacttg gaaagaagcc 60

<210> SEQ ID NO 167

<211> LENGTH: 60
<212> TYPE: DNA
<213> ORGANISM: Homo sapiens

<400> SEQUENCE: 167
gtcagccaaa tcctatagtg tcaactttca gtaaatgtat cttagaaata actatggacc 60

<210> SEQ ID NO 168
<211> LENGTH: 60
<212> TYPE: DNA
<213> ORGANISM: Homo sapiens

<400> SEQUENCE: 168
tgtaacaagt ggtgcttctt tagaaagttg tcattagaat gttctgagga agttaagcag 60

<210> SEQ ID NO 169
<211> LENGTH: 60
<212> TYPE: DNA
<213> ORGANISM: Homo sapiens

<400> SEQUENCE: 169
ttctctagcc tgtagtagag aacatcagaa atttacctat acagactttc ttttgcctga 60

<210> SEQ ID NO 170
<211> LENGTH: 60
<212> TYPE: DNA
<213> ORGANISM: Homo sapiens

<400> SEQUENCE: 170
agcatttgct ataaggagga tgtatctcag ttgccatatt tgtatcacta accatttgaa 60

<210> SEQ ID NO 171
<211> LENGTH: 60
<212> TYPE: DNA
<213> ORGANISM: Homo sapiens

<400> SEQUENCE: 171
gggacagaag caatgaaaga agcaatgtga attttccatt tgctttcata ttattacctg 60

<210> SEQ ID NO 172
<211> LENGTH: 60
<212> TYPE: DNA
<213> ORGANISM: Homo sapiens

<400> SEQUENCE: 172
gggtgtgggt aagacacaat gtccttgaaa ttatatttca ctgggttaat gaaattggct 60

<210> SEQ ID NO 173
<211> LENGTH: 60
<212> TYPE: DNA
<213> ORGANISM: Homo sapiens

<400> SEQUENCE: 173
tttcttaaaa tatccacaat attccttgag tgagtcagaa tctatagccg gttagtgatg 60

<210> SEQ ID NO 174
<211> LENGTH: 60
<212> TYPE: DNA
<213> ORGANISM: Homo sapiens

<400> SEQUENCE: 174
tgcccagaaa gtgtctgtaa tgtgggacaa agtgaaattt tgtttctctg aacttccttg 60

<210> SEQ ID NO 175

<211> LENGTH: 60
<212> TYPE: DNA
<213> ORGANISM: Homo sapiens

<400> SEQUENCE: 175
aagacatctt ggaaaagaag aaaagattgt tgaggtgatg tttaaaagtg gaactcgtgc 60

<210> SEQ ID NO 176
<211> LENGTH: 60
<212> TYPE: DNA
<213> ORGANISM: Homo sapiens

<400> SEQUENCE: 176
gacctttatc atggggtcat atattgcttc atgtgtaagg attatgtata tgacaaagac 60

<210> SEQ ID NO 177
<211> LENGTH: 60
<212> TYPE: DNA
<213> ORGANISM: Homo sapiens

<400> SEQUENCE: 177
attgaaatag gcacacgatt gtcaccattt ctcactttac aagctgtata atcagtaagc 60

<210> SEQ ID NO 178
<211> LENGTH: 60
<212> TYPE: DNA
<213> ORGANISM: Homo sapiens

<400> SEQUENCE: 178
atgggacgag tgttttatac aaatagaggc ttatttacct cttatgtaaa agaagtctgg 60

<210> SEQ ID NO 179
<211> LENGTH: 60
<212> TYPE: DNA
<213> ORGANISM: Homo sapiens

<400> SEQUENCE: 179
caatccaatg ctcatagaga tcactaagga taatcctgct tattaagtga tgagttggtt 60

<210> SEQ ID NO 180
<211> LENGTH: 60
<212> TYPE: DNA
<213> ORGANISM: Homo sapiens

<400> SEQUENCE: 180
ttcctgagag atagtcaagc tttgttgtat aggaaagttt cgtttgtgga aataaatgag 60

<210> SEQ ID NO 181
<211> LENGTH: 60
<212> TYPE: DNA
<213> ORGANISM: Homo sapiens

<400> SEQUENCE: 181
tctggcctaa ctgtgtaggt caatactctt ttacattgcc ttctaataaa agcagaatga 60

<210> SEQ ID NO 182
<211> LENGTH: 60
<212> TYPE: DNA
<213> ORGANISM: Homo sapiens

<400> SEQUENCE: 182
taactgaatc gatagaaatc taagaatcaa cttggtctat atcatctgat gattcagggg 60

<210> SEQ ID NO 183

<211> LENGTH: 60
<212> TYPE: DNA
<213> ORGANISM: Homo sapiens

<400> SEQUENCE: 183
tggtaacacc tggaaagaag gactctttca cttcgatccc tggacaatta tggaggattc 60

<210> SEQ ID NO 184
<211> LENGTH: 60
<212> TYPE: DNA
<213> ORGANISM: Homo sapiens

<400> SEQUENCE: 184
ttggttttgt tttttaattt tgtttttcct gttttctgag aataaaggtt ttgttatatc 60

<210> SEQ ID NO 185
<211> LENGTH: 60
<212> TYPE: DNA
<213> ORGANISM: Homo sapiens

<400> SEQUENCE: 185
acagctgaat aaatgtgtct aaaacagact cttgtattct gaaagtacag tctacaactg 60

<210> SEQ ID NO 186
<211> LENGTH: 60
<212> TYPE: DNA
<213> ORGANISM: Homo sapiens

<400> SEQUENCE: 186
tttattgcca agatctgaaa atcttcaaca tcttataaga caacaatgaa gtagcccctg 60

<210> SEQ ID NO 187
<211> LENGTH: 60
<212> TYPE: DNA
<213> ORGANISM: Homo sapiens

<400> SEQUENCE: 187
ccaaacaaat acatccctaa tggaagacca tggcatagag aaggagaggc tggaatgaca 60

<210> SEQ ID NO 188
<211> LENGTH: 60
<212> TYPE: DNA
<213> ORGANISM: Homo sapiens

<400> SEQUENCE: 188
tgtatctgcc taccaggtgc aaagtccttc gtggatgcaa cctcaaccat atattctaca 60

<210> SEQ ID NO 189
<211> LENGTH: 60
<212> TYPE: DNA
<213> ORGANISM: Homo sapiens

<400> SEQUENCE: 189
ccagaattcc caaaatgaac cagatacccc ctagaaaatt atactattga gaaatctatg 60

<210> SEQ ID NO 190
<211> LENGTH: 60
<212> TYPE: DNA
<213> ORGANISM: Homo sapiens

<400> SEQUENCE: 190
ctacagactt gtactaacac cccgtaattt ggcatttgtt taacctcatt tataaaagct 60

<210> SEQ ID NO 191

<211> LENGTH: 60
<212> TYPE: DNA
<213> ORGANISM: Homo sapiens

<400> SEQUENCE: 191
tcatgcaaaa agattgccaa atcatgtttg gtaggaggac ttttgaggta gcttttgaac 60

<210> SEQ ID NO 192
<211> LENGTH: 60
<212> TYPE: DNA
<213> ORGANISM: Homo sapiens

<400> SEQUENCE: 192
ctagtctgtg attattaggg tgttagtgat aagtatgcat aaatgtcaaa gatgggaaga 60

<210> SEQ ID NO 193
<211> LENGTH: 60
<212> TYPE: DNA
<213> ORGANISM: Homo sapiens

<400> SEQUENCE: 193
gcatctgctg gtggacctgc caccatcaca ataaagtccc catctgattt ttagaaaaaa 60

<210> SEQ ID NO 194
<211> LENGTH: 60
<212> TYPE: DNA
<213> ORGANISM: Homo sapiens

<400> SEQUENCE: 194
cctccccaaa ataattagta actggttgtt ctacttggta atttgacacc ctgttaataa 60

<210> SEQ ID NO 195
<211> LENGTH: 60
<212> TYPE: DNA
<213> ORGANISM: Homo sapiens

<400> SEQUENCE: 195
ctcactactt gatatttttg cattagttaa gacagaaatt tgatagctcg gttagagggg 60

<210> SEQ ID NO 196
<211> LENGTH: 60
<212> TYPE: DNA
<213> ORGANISM: Homo sapiens

<400> SEQUENCE: 196
tggaatagaa aatgtgaaga cctattcaac gagctttacc ccgatgtatc acgcagttac 60

<210> SEQ ID NO 197
<211> LENGTH: 60
<212> TYPE: DNA
<213> ORGANISM: Homo sapiens

<400> SEQUENCE: 197
taaggctgtt gctattgaaa gatcaatttt gtcttacctg catttaaaat ggaacagctc 60

<210> SEQ ID NO 198
<211> LENGTH: 60
<212> TYPE: DNA
<213> ORGANISM: Homo sapiens

<400> SEQUENCE: 198
gcaagttcac acctttcata agcataaagt agttgcaaga aagtattttc atcctgttag 60

<210> SEQ ID NO 199

```
<211> LENGTH: 60
<212> TYPE: DNA
<213> ORGANISM: Homo sapiens

<400> SEQUENCE: 199

catgcttcag aatcctatgg aagagaatat tcctacttgc agtacatcaa aggaatggat     60


<210> SEQ ID NO 200
<211> LENGTH: 60
<212> TYPE: DNA
<213> ORGANISM: Homo sapiens

<400> SEQUENCE: 200

ttgctctatc attctgtttc aataaagaca tttggaataa acgagcatat catagcctgg     60
```